(12) United States Patent
Eriksson et al.

(10) Patent No.: US 8,092,804 B2
(45) Date of Patent: Jan. 10, 2012

(54) BINDING MEMBERS FOR INTERLEUKIN-4 RECEPTOR ALPHA (IL-4Rα)-173

(75) Inventors: Per-Olof Fredrik Eriksson, Lund (SE);
Karin Von Wachenfeldt, Lund (SE);
Suzanne Cohen, Cambridge (GB);
Claire Louise Dobson, Cambridge (GB); Deborah Louise Lane, Cambridge (GB)

(73) Assignee: MedImmune Limited, Cambridge (GB)

( * ) Notice: Subject to any disclaimer, the term of this patent is extended or adjusted under 35 U.S.C. 154(b) by 0 days.

(21) Appl. No.: 12/338,161

(22) Filed: Dec. 18, 2008

(65) Prior Publication Data

US 2009/0202568 A1    Aug. 13, 2009

Related U.S. Application Data

(60) Provisional application No. 61/015,869, filed on Dec. 21, 2007.

(51) Int. Cl.
*A61K 39/395* (2006.01)
*C07K 16/00* (2006.01)
*C07K 16/18* (2006.01)
*C07K 16/28* (2006.01)
*C12N 15/13* (2006.01)

(52) U.S. Cl. ............ 424/143.1; 424/133.1; 424/135.1; 424/139.1; 424/141.1; 424/130.1; 530/387.1; 530/387.3; 530/387.9; 530/388.1; 530/388.15; 530/388.2; 536/23.1; 536/23.53; 435/69.1; 435/326; 435/328; 435/331; 435/334; 435/252.3; 435/254.11

(58) Field of Classification Search .................. None
See application file for complete search history.

(56) References Cited

U.S. PATENT DOCUMENTS

| 5,717,072 | A * | 2/1998 | Mosley et al. | 530/388.22 |
| 6,716,587 | B2 * | 4/2004 | Mosley et al. | 435/7.1 |
| 2003/0190311 | A1 | 10/2003 | Dall'Acqua et al. | |
| 2005/0112694 | A1 * | 5/2005 | Carter et al. | 435/7.1 |

FOREIGN PATENT DOCUMENTS

| WO | WO 89/09621 | * | 10/1989 |
| WO | WO 97/28267 | | 8/1997 |
| WO | WO 00/64944 | * | 11/2000 |
| WO | WO 00/78336 | * | 12/2000 |
| WO | WO 00/78336 A1 | | 12/2000 |
| WO | WO 01/62272 | * | 8/2001 |
| WO | WO 01/62272 A2 | | 8/2001 |
| WO | WO 01/62287 | * | 8/2001 |
| WO | WO 01/62287 A1 | | 8/2001 |
| WO | WO 01/92340 | * | 12/2001 |
| WO | WO 01/92340 A2 | * | 12/2001 |
| WO | WO 02/04009 | * | 1/2002 |
| WO | WO 02/04009 A2 | | 1/2002 |
| WO | WO 02/11767 | * | 2/2002 |
| WO | WO 02/11767 A2 | | 2/2002 |
| WO | WO 2005/047331 | * | 5/2005 |
| WO | WO 2005/047331 A2 | | 5/2005 |
| WO | WO 2007/082068 | * | 7/2007 |
| WO | WO 2007/082068 A2 | | 7/2007 |
| WO | WO 2008/054606 | * | 5/2008 |
| WO | WO 2008/054606 A2 | | 5/2008 |
| WO | WO 2008/076784 | * | 6/2008 |
| WO | WO 2008/076784 A2 | | 6/2008 |
| WO | WO 2009/081201 A2 | | 7/2009 |
| WO | WO 2010/070346 A2 | | 6/2010 |

OTHER PUBLICATIONS

De Maagd et al, The human thymus microenvironment: heterogeneity detected by monoclonal anti-epithelial cell antibodies, Immunology, 1985, 54, pp. 745-754.
Bielory, American Academy of Allergy, Asthma, and Immunology—2008 Annual Meeting, IDrugs, 2008, 11, 5, pp. 309-311.
Goebeler et al, Interleukin-13 selectively induces monocyte chemoattractant protien-1 synthesis and secretion by human endothelial cells. Involvement of IL-4R- alpha and Stat6 phosphorylation, Immunology, 1997, 3, pp. 450-457.
Horner et al, Toxicity and Pharmacodynamics of Cy317HuXCy, A Surrogate for AMG 317, in Cynomolgus Monkeys: 4-week and 13-week Repeated Dose Studies, Journal of Allergy and Clinical Immunology, 2008, 121, 2, p. S7.
Larche et al, Functional evidence for a monoclonal antibody that binds to the human IL-4 receptor, Immunology 1988, 65 617-622.
Angal, S. et al., 1993, "A Single Amino Acid Substitution Abolishes The Heterogeneity Of Chimeric Mouse/Human (IgG4) Antibody", Molecular Immunology 30(1):105-108.
International Search Report for corresponding PCT/GB2008/051212 dated Sep. 2, 2009.
International Search Report for corresponding PCT/GB2009/051728 dated Aug. 19, 2010.
Rudikoff, Stuart et al., 1982, "Single amino acid substitution altering antigen-binding specificity", Proc. Natl. Acad. Sci. USA, 79:1979-1983.

* cited by examiner

*Primary Examiner* — Elizabeth C Kemmerer

(57) ABSTRACT

Binding members, especially antibody molecules, for interleukin (IL)-4 receptor alpha (IL-4Rα), and their therapeutic use e.g. in treating or preventing disorders associated with IL-4Rα, IL-4 and/or IL-13, examples of which are asthma and COPD.

39 Claims, 25 Drawing Sheets

FIG 1A

| KABAT NUMBERING | FW 1 | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 |
| Antibody 1 | Q | V | Q | L | V | Q | S | G | A | E | V | K | K | P | G | A | S | V | K | V | S | C | K | A | S | G | Y | A | F | T |
| Antibody 2 | | | | | | | | | | | | | | | | | | | | | | | | | | | | | | |
| Antibody 3 | | | | | | | | | | | | | | | | | | | | | | | | | | | | | | |
| Antibody 4 | | | | | | | | | | | | | | | | | | | | | | | | | | | | | | |
| Antibody 5 | | | | | | | | | | | | | | | | | | | | | | | | | | | | | | |
| Antibody 6 | | | | | | | | | | | | | | | | | | | | | | | | | | | | | | |
| Antibody 7 | | | | | | | | | | | | | | | | | | | | | | | | | | | | | | |
| Antibody 8 | | | | | | | | | | | | | | | | | | | | | | | | | | | | | | |
| Antibody 9 | | | | | | | | | | | | | | | | | | | | | | | | | | | | | | |
| Antibody 10 | | | | | | | | | | | | | | | | | | | | | | | | | | | | | | |
| Antibody 11 | | | | | | | | | | | | | | | | | | | | | | | | | | | | | | |
| Antibody 12 | | | | | | | | | | | | | | | | | | | | | | | | | | | | | | |
| Antibody 13 | | | | | | | | | | | | | | | | | | | | | | | | | | | | | | |
| Antibody 14 | | | | | | | | | | | | | | | | | | | | | | | | | | | | | | |
| Antibody 15 | | | | | | | | | | | | | | | | | | | | | | | | | | | | | | |
| Antibody 16 | | | | | | | | | | | | | | | | | | | | | | | | | | | | | | |
| Antibody 17 | | | | | | | | | | | | | | | | | | | | | | | | | | | | | | |
| Antibody 18 | | | | | | | | | | | | | | | | | | | | | | | | | | | | | | |
| Antibody 19 | | | | | | | | | | | | | | | | | | | | | | | | | | | | | | |
| Antibody 20 | | | | | | | | | | | | | | | | | | | | | | | | | | | | | | |
| Antibody 21 | | | | | | | | | | | | | | | | | | | | | | | | | | | | | | |
| Antibody 22 | | | | | | | | | | | | | | | | | | | | | | | | | | | | | | |
| Antibody 23 | | | | | | | | | | | | R | | | | | | | | | | | | | | | | | | |
| Antibody 24 | | | | | | | | | | | | | | | | | | | | | | | | | | | | | | |
| Antibody 24FGL | | | | | | | | | | | | | | | | | | | | | | | | | | | | | | |
| Antibody 24PGL | | | | | | | | | | | | | | | | | | | | | | | | | | | | | | |
| Antibody 25 | | | | | | | | | | | | | | | | | | | | | | | | | | | | | | |
| Antibody 26 | | | | | | | | | | | | | | | | | | | | | | | | | | | | | | |
| Antibody 27 | | | | | | | | | | | | R | | | | | | | | | | | | | | | | | | |
| Antibody 28 | | | | | | | | | | | | | | | | | | | | | | | | | | | | | | |
| Antibody 29 | | | | | | | | | | | | | | | | | | | | | | | | | | | | | | |
| Antibody 30 | | | | | | | | | | | | | | | | | | | | | | | | | | | | | | |
| Antibody 31 | | | | | | | | | | | | | | | | | | | | | | | | | | | | | | |
| Antibody 32 | | | | | | | | | | | | | | | | | | | | | | | | | | | | | | |
| Antibody 33 | | | | | | | | | | | E | | | | | | | | | | | | | | | | | | | |
| Antibody 34 | | | | | | | | | | | | | | | | | | | | | | | | | | | | | | |
| Antibody 35 | | | | | | | | | | | | | | | | | | | | | | | | | | | | | | |
| Antibody 36 | | | | | | | | | | | | | | | | | | | | | | | | | | | | | | |
| Antibody 37 | | | | | | | | | | | | | | | | | | | | | | | | | | | | | | |
| Antibody 37 GL | | | | | | | | | | | | | | | | | | | | | | | | | | | | | | |
| Antibody 38 | | | | | | | | | | | | | | | | | | | | | | | | | | | | | | |
| Antibody 39 | | | | | | | | | | | | | | | | | | | | | | | | | | | | | | |
| Antibody 40 | | | | | | | | | | | | | | | | | | | | | | | | | | | | | | |
| Antibody 41 | | | | | | | | | | | | R | | | | | | | | | | | | | | | | | | |
| Antibody 42 | | | | | | | | | | | | | | | | | | | | | | | | | | | | | | |

FIG 1B

| | CDR 1 | | | | | FW 2 | | | | | | | | | | | | | | CDR 2 | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|
| | 31 | 32 | 33 | 34 | 35 | 36 | 37 | 38 | 39 | 40 | 41 | 42 | 43 | 44 | 45 | 46 | 47 | 48 | 49 | 50 | 51 | 52 | 52A | 53 | 54 | 55 | 56 | 57 | 58 | 59 | 60 | 61 | 62 | 63 | 64 | 65 |
| | S | Y | Y | M | H | W | A | R | Q | A | P | G | Q | G | L | E | W | M | G | I | I | N | P | S | G | G | S | T | S | Y | A | Q | K | F | Q | G |
| | | | | | | | | | | | | | | | | | | | | | | | | | | | | A | | | | | | | | |
| | | | | | | | | | | | | | | | | | | | | | | | | | | | | R | | | | | | | | |
| | | | | | | | | V | | | | | | | | | | | | | | | | | | | | R | | | | | | | | |
| | | | | | | | | V | | | | | | | | | | | | | | | | | | | | R | | | | | | | | |
| | | | | | | | | | | | | | | | | | | | | | | | | | | | | R | | A | | | | | | |
| | | | | | | | | | | | | | | | | | | | | | | | | | | | | A | | | | | | | | |
| | | | | | | | | | | | | | | | | | | | | | | | | | | | | R | | | | | | | | |
| | | | | | | | | V | | | | | | | | | | | | | | | | | | | | R | | | | | | | | |
| | | | | | | | | | | | | | | | | | | | | | | | | | | | | | | A | | | | | | |
| | | | | | | | | | | | | | | | | | | | | | | | | | | | | R | | | | | | | | |
| | | | | | | | | | | | | | | | | | | | V | | | | | | | | | | | | | | | | | |

FIG 1C

| | | | | | | | | | | | | | | | | | | FW 3 | | | | | | | | | | | | | | |
|---|---|---|---|---|---|---|---|---|---|---|---|---|---|---|---|---|---|---|---|---|---|---|---|---|---|---|---|---|---|---|---|---|
| 66 | 67 | 68 | 69 | 70 | 71 | 72 | 73 | 74 | 75 | 76 | 77 | 78 | 79 | 80 | 81 | 82 | 82A | 82B | 82C | 83 | 84 | 85 | 86 | 87 | 88 | 89 | 90 | 91 | 92 | 93 | 94 |
| R | V | T | M | T | R | D | T | S | T | S | T | V | Y | M | E | L | S | S | L | R | S | E | D | T | A | V | Y | Y | C | A | R |
| | | S | | | | | | | | | | | | | | | | | | | | | | | | | | | | | |
| | | | | | | | | | | | | | | | | | | | | | | P | | | | | | | | | |
| | | S | | | | | | | | | | | | | | | | | | | | | | | | | | | | | |
| | | A | | | | | | | | | | | | | | | | | | | | P | | | | | | | | | |
| | | | | | | | | | | | | | | | | | | | | | | P | | | | | | | | | |
| | | | | | | | | | | | | | | | | | | | | | | | G | | | | | | | | |

FIG 1D

| | CDR 3 | | | | | | | FW 4 | | | | | | | | | | |
|---|---|---|---|---|---|---|---|---|---|---|---|---|---|---|---|---|---|---|
| | 95 | 96 | 97 | 98 | 99 | 101 | 102 | 103 | 104 | 105 | 106 | 107 | 108 | 109 | 110 | 111 | 112 | 113 |
| | G | K | W | W | L | D | Y | W | G | K | G | T | L | V | T | V | S | S |
| | | | | | | Y | N | | | | | | | | | | | |
| | | | L | L | K | N | P | | | | | | | | | | | |
| | | | | | | Y | N | | | | | | | | | | | |
| | | | | | | Y | D | | | | | | | | | | | |
| | | | Y | | M | Y | D | | | | | | | | | | | |
| | | | | | W | Q | | | | | | | | | | | | |
| | | | | | W | Q | | | | | | | | | | | | |
| | | | | | | Y | N | | | | | | | | | | | |
| | | | | | | Y | D | | | | | | | | | | | |
| | | | | | F | Y | D | | | | | | | | | | | |
| | | | | | F | Y | D | | | | | | | | | | | |
| | | | | | | Y | D | | | | | | | | | | | |
| | | | | | | Y | N | | | | | | | | | | | |
| | | | | | | Y | N | | | | | | | | | | | |
| | | | | | | Y | N | | | | | | | | | | | |
| | | | | | W | Q | H | | | | | | | | | | | |
| | | | | | W | Q | H | | | | | | | | | | | |
| | | | | | W | Q | H | | | | | | | | | | | |
| | | | Y | | M | Y | D | | | | | | | | | | | |
| | | | Y | | M | Y | D | | | | | | | | | | | |
| | | | Y | | M | Y | D | | | | | | | | | | | |
| | | | Y | | M | Y | D | | | | | | | | | | | |
| | | | Y | | M | Y | D | | | | | | | | | | | |
| | | | Y | | M | Y | D | | | | | | | | | | | |
| | | | Y | | M | Y | D | | | | | | | | | | | |
| | | | Y | | M | Y | D | | | | | | | | | | | |
| | | | Y | | M | Y | D | | | | | | | Q | | | |
| | | | Y | | M | Y | D | | | | N | | | | | | |
| | | | Y | | M | Y | D | | | | | | | R | | | |
| | | | Y | | M | Y | D | | | | | | | | | | |
| | | | Y | | M | Y | D | | | | | | | | | | |
| | | | Y | | M | Y | D | | | | | | | | | | |
| | | | Y | | M | Y | D | | | | | | | | | | |
| | | | Y | | M | Y | D | | | | | | | | | | |
| | | | Y | | M | Y | D | | | | | | | | | | |
| | | | Y | | M | Y | D | | | | | | | | | | |
| | | | Y | | M | Y | D | | | | | | | | | | |
| | | | Y | | M | Y | D | | | | | | | | | | |
| | | | Y | | M | Y | D | | | | | | | | | | |
| | | | Y | | M | Y | D | | | | | | | | | | |
| | | | Y | | M | Y | D | | | | | | | | | | G |
| | | | Y | | M | Y | D | | | | | | | | | | |

FIG 2A

| KABAT NUMBERING | FW1 | | | | | | | | | | | | | | | | | | | | | | | CDR1 | | | | | | | | | | | |
|---|---|---|---|---|---|---|---|---|---|---|---|---|---|---|---|---|---|---|---|---|---|---|---|---|---|---|---|---|---|---|---|---|---|---|---|
| | 1 | 2 | 3 | 4 | 5 | 6 | 7 | 8 | 9 | 11 | 12 | 13 | 14 | 15 | 16 | 17 | 18 | 19 | 20 | 21 | 22 | 23 | 24 | 25 | 26 | 27 | 27A | 27B | 28 | 29 | 30 | 31 | 32 | 33 | 34 |
| Antibody 1 | Q | S | V | L | T | Q | P | P | S | V | S | A | A | P | G | Q | K | V | T | I | S | C | S | G | G | S | S | N | I | G | N | S | Y | V | S |
| Antibody 2 | | | | | | | | | | | | | | | | | | | | | | | | | | | | | | | | | | | |
| Antibody 3 | | | | | | | | | | | | | | | | | | | | | | | | | | | | | | | | | | | |
| Antibody 4 | | | | | | | | | | | | | | | | | | | | | | | | | | | | | | | | | | | |
| Antibody 5 | | | | | | | | | | | | | | | | | | | | | | | | | | | | | | | | | | | |
| Antibody 6 | | | | | | | | | | | | | | | | | | | | | | | | | | | | | | | | | | | |
| Antibody 7 | | | | | | | | | | | | | | | | | | | | | | | | | | | | | | | | | | | |
| Antibody 8 | | | | | | | | | | | | | | | | | | | | | | | | | | | | | | | | | | | |
| Antibody 9 | | | | | | | | | | | | | | | | | | | | | | | | | | | | | | | | | | | |
| Antibody 10 | | | | | | | | | | | | | | | | | | | | | | | | | | | | | | | | | | | |
| Antibody 11 | | | | | | | | | | | | | | | | | | | | | | | | | | | | | | | | | | | |
| Antibody 12 | | | | | | | | | | | | | | | | | | | | | | | | | | | | | | | | | | | |
| Antibody 13 | | | | | | | | | | | | | | | | | | | | | | | | | | | | | | | | | | | |
| Antibody 14 | | | | | | | | | | | | | | | | | | | | | | | | | | | | | | | | | | | |
| Antibody 15 | | | | | | | | | | | | | | | | | | | | | | | | | | | | | | | | | | | |
| Antibody 16 | | | | | | | | | | | | | | | | | | | | | | | | | | | | | | | | | | | |
| Antibody 17 | | | | | | | | | | | | | | | | | | | | | | | | | | | | | | | | | | | |
| Antibody 18 | | | | | | | | | | | | | | | | | | | | | | | | | | | | | | | | | | | |
| Antibody 19 | | | | | | | | | | | | | | | | | | | | | | | | | | | | | | | | | | | |
| Antibody 20 | | | | | | | | | | | | | | | | | | | | | | | | | | | | | | | | | | | |
| Antibody 21 | | | | | | | | | | | | | | | | | | | | | | | | | | | | | | | | | | | |
| Antibody 22 | | P | | | | | | | | | | | | | | | | | | | | | | | | | | | | | | | | | |
| Antibody 23 | | | | | | | | | | | | | | | | | | | | | | | | | | | | | | | | N | | | |
| Antibody 24 | | | | | | | | | | | | | | | | | | | | | | | | | | | | | | | | | | | |
| Antibody 24FGL | | | | | | | | | | | | | | | | | | | | | | | | | | | | | | | | | | | |
| Antibody 24PGL | | | | | | | | | | | | | | | | | | | | | | | | | | | | | | | | | | | |
| Antibody 25 | | | | | | | | | | | | | | | | | | | | | | | | | | | | | | | | | | | |
| Antibody 26 | | | | | | | | | | | | | | | | | | | | | | | | | | | | | | | | | | | |
| Antibody 27 | | | | | | | | | L | | | | | | | | | | | | | | | | | | | | | | | | | | |
| Antibody 28 | L | P | | | | | | | | | | | | | | | | | | | | | | | | | | S | | | | | | | |
| Antibody 29 | | | | | | | | | | | | | | | | | | | | | | | | | | | | | | | | | | | |
| Antibody 30 | | | | | | | | | | | | | | | | | | | | | | | | | | | | | | | | | | | |
| Antibody 31 | | | | | | | | | | | | | | | | | | | | | | | | | | | | S | | | | | | | |
| Antibody 32 | | | | | | | | | | | | | | | | | | | | | | | | | | | | | | | | | | | |
| Antibody 33 | | | A | | | | | | | | | | | | | | | | | | | | | | | | | | | | | | | | |
| Antibody 34 | | | | | | | | | | | | | | | | | | | | | | | | | | | | | | | | | | | |
| Antibody 35 | | | | | | | | | | | | | | | | | | | | | | | | | | | | | | | | | | | |
| Antibody 36 | | | | | | | | | | | | | | | | | | | | | | | | | | | | | | | | | | | |
| Antibody 37 | | | | | | | | | | | | | | | | | | | | | | | | | | | G | S | | | | | | | |
| Antibody 37 GL | | | | | | | | | | | | | | | | | | | | | | | | | | | G | S | | | | | | | |
| Antibody 38 | | | | | | | | | | | | | | | | | | | | | | | | | | | | | | | | | | | |
| Antibody 39 | | | | | | | | | | | | | | | | | | | | | | | | | | | | | | | | | | | |
| Antibody 40 | | | | | | | | | | | | | | | | | | | | | | | | | | | | | | | | | | | |
| Antibody 41 | | | | | | | | | | | | | | | | | | | | | | | | | | | T | | | | | | | | |
| Antibody 42 | | A | | | | | | | | | | | | | | | | | | | | | | | | | | | | | | | | | |

FIG 2B

| | FW2 | | | | | | | | | | | | | | | CDR2 | | | | | | |
|---|---|---|---|---|---|---|---|---|---|---|---|---|---|---|---|---|---|---|---|---|---|---|
| | 35 | 36 | 37 | 38 | 39 | 40 | 41 | 42 | 43 | 44 | 45 | 46 | 47 | 48 | 49 | 50 | 51 | 52 | 53 | 54 | 55 | 56 |
| | W | Y | Q | Q | L | P | G | T | A | P | K | L | L | I | Y | D | N | N | K | R | P | S |
| | | | | | | | | | | | | | | | | | | | | | | |
| | | | | | | | | | | | | | | | | | | | | | | P |
| | | | | | | | | | | | | | | | | | | | | | | |
| | | | | R | | | | | | | | | | | | | | | | | | |
| | | | | | | | | A | | | | | | | | | | | | | | |
| | | | | R | | | | A | | | | | | | | | | | | | | |
| | | | | | | | | | | | | | | | | | | | | | | |
| | | | | R | | | | | | | | | | | | | | | | | | P |
| | | | | R | | | | A | | | | | | | | | | | | | | |

FIG 2C

| | | | | | | | | | | | | | | | FW3 | | | | | | | | | | | | | | | | |
|---|---|---|---|---|---|---|---|---|---|---|---|---|---|---|---|---|---|---|---|---|---|---|---|---|---|---|---|---|---|---|---|
| 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 | 85 | 86 | 87 | 88 |
| G | I | P | D | R | F | S | G | S | K | S | G | T | S | A | T | L | A | I | T | G | L | Q | T | G | D | E | A | D | Y | Y | C |
| | | | | | | | | | | | | | | | | | | | | | | | | | | | | | V | F | |
| | | | | | | | | | | | | | | | | | | | | | | | | | | | | | | F | |
| | | | | | | | | | | | | | | | | | | | | | | | | | | | | | | F | |
| | | | | | | | | | | | | | | | | | G | | | | | | | | | | | | | | |
| | | | | | | | | | | | | | | | | | G | | | | | | | | | | | | | F | |
| | | | | | | | | | | | | | T | | | | | | | | | | | | | | | | | | |
| | | | | | | | | | | | | | | | | | | | | | | | | | | | | | | F | |
| | | | | | | | | F | R | | | | | | | | | | | | | | | | | | | | | | |
| | | | | | | | | | | | | | | | | | | | | | | | | | | | | | | F | |
| | | | | | | | | | | | | | | | | | | | | | | | | | | | | | | F | |
| | | | | | | | | | | | | | | | | | | | | | | | | | | | | | | F | |
| | V | | | | | | | | | | | | | | | | | | | | | | | | | | | | | | |
| | | | | | | | | | | | | | | | | | | G | | | | | | | | | | | | | |
| | | | | | | | | | | | | | | | | | | | | | | | | | | | | | | F | |

FIG 2D

| | CDR3 | | | | | | | | | | | | FW4 | | | | | | | | | |
|---|---|---|---|---|---|---|---|---|---|---|---|---|---|---|---|---|---|---|---|---|---|---|
| | 89 | 90 | 91 | 92 | 93 | 94 | 95 | 95A | 95B | 95C | 96 | 97 | 98 | 99 | 100 | 101 | 102 | 103 | 104 | 105 | 106 | 107 |
| | G | T | W | D | T | S | L | S | A | N | Y | V | F | G | T | G | T | K | L | T | V | L |
| | | | | | | | Q | P | P | | P | L | | | | | | | | | | |
| | | | | F | G | T | P | A | S | | | | | | | | | | | | | |
| | | | | | | | S | P | P | Q | P | I | | | | | | | | | | |
| | | | | | | | S | P | P | Q | P | I | | | | | | | | | | |
| | | | | | | | T | T | Y | H | P | I | | | | | | | | | | |
| | | | | | | | S | P | P | Q | P | I | | | | | | | | | | |
| | | | | | | | T | T | Y | H | P | I | | | | | | | | | | |
| | | | | | | | T | T | M | Y | P | L | | | | | | | | | | |
| | | | | | | | T | V | L | T | P | I | | | | | | | | | | |
| | | | | | | | P | | M | I | P | L | | | | | | | | | | |
| | | | | | | | T | T | M | Y | P | L | | | | | | | | | | |
| | | | | | | | T | T | L | Q | P | L | | | | | | | | | | |
| | | | | | | | P | P | T | K | P | L | | | | | | | | | | |
| | | | | | | | T | H | R | H | P | L | | | | | | | | | | |
| | | | | | | | T | T | Y | H | P | I | | | | | | | | | | |
| | | | | | | | P | V | D | R | P | I | | | | | | | | | | |
| | | | | | | | T | T | P | M | P | | | | | | | | | | | |
| | | | | | | | T | T | Y | H | P | I | | | | | | | | | | |
| | | | | | | | T | V | W | E | W | P | | | | | | | | | | |
| | | | | | | | T | V | W | E | W | P | | | | | | | | | | |
| | | | | | | | T | V | W | E | W | P | | | | | | | | | | |
| | | | | | | | T | V | W | E | W | P | | | | | | | | | | |
| | | | | | | | T | V | W | E | W | P | | | | | | | | | | |
| | | | | | | | T | V | W | E | W | P | | | | | | | | | | |
| | | | | | | | T | V | W | E | W | P | | | | | | | | | | |
| | | | | | V | | T | V | W | E | W | P | | | | | | | | | | |
| | | | | | | | T | V | W | E | W | P | | | | | | | | | | |
| | | | | | | | T | V | W | E | W | P | | | | | | | | | | |
| | | | | | | | P | V | W | E | W | P | | | | | | | | | | |
| | | | | | | | P | V | W | E | W | P | | | | | | | | | | |
| | | | | | | | T | V | W | E | W | P | | | | | | | | | | |
| | | | | | A | | P | V | W | E | W | P | | | | | | | | | | |
| | | | | | | | T | A | W | E | W | P | | | | | | | | | | |
| | | | | | | | T | V | W | E | W | P | | | | | | | | | | |
| | | | | | | | T | V | W | E | W | P | | | | | | | | | | |
| | | | | | | | P | V | W | E | W | P | | | | | | | | | | |
| | | | | | | S | T | V | W | E | W | P | | | | | | | | | | |
| | | | | | | | P | V | W | E | W | P | | | | | | | | | | |
| | | | | | | | P | V | W | E | W | P | | | | | | | | | | |
| | | | | | | | T | V | W | E | W | P | | | | | | | | | | |
| | | | | | | | T | A | W | E | W | P | | | | | | | | | | |
| | | | | | | S | T | V | W | E | W | P | | | | | | | | | | |
| | | | | | | | T | V | W | E | W | P | | | | | | | | | | |
| | | | | | | | T | G | W | E | W | P | | | | | | | | | | |

FIG 3A

| KABAT NUMBERING | FW 1 | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 |
| Antibody 20 | Q | V | Q | L | V | Q | S | G | A | E | V | K | K | P | G | A | S | V | K | V | S | C | K | A | S | G | Y | A | F | T |
| Antibody 1 | | | | | | | | | | | | | | | | | | | | | | | | | | | | | | |
| Antibody 2 | | | | | | | | | | | | | | | | | | | | | | | | | | | | | | |
| Antibody 3 | | | | | | | | | | | | | | | | | | | | | | | | | | | | | | |
| Antibody 4 | | | | | | | | | | | | | | | | | | | | | | | | | | | | | | |
| Antibody 5 | | | | | | | | | | | | | | | | | | | | | | | | | | | | | | |
| Antibody 6 | | | | | | | | | | | | | | | | | | | | | | | | | | | | | | |
| Antibody 7 | | | | | | | | | | | | | | | | | | | | | | | | | | | | | | |
| Antibody 8 | | | | | | | | | | | | | | | | | | | | | | | | | | | | | | |
| Antibody 9 | | | | | | | | | | | | | | | | | | | | | | | | | | | | | | |
| Antibody 10 | | | | | | | | | | | | | | | | | | | | | | | | | | | | | | |
| Antibody 11 | | | | | | | | | | | | | | | | | | | | | | | | | | | | | | |
| Antibody 12 | | | | | | | | | | | | | | | | | | | | | | | | | | | | | | |
| Antibody 13 | | | | | | | | | | | | | | | | | | | | | | | | | | | | | | |
| Antibody 14 | | | | | | | | | | | | | | | | | | | | | | | | | | | | | | |
| Antibody 15 | | | | | | | | | | | | | | | | | | | | | | | | | | | | | | |
| Antibody 16 | | | | | | | | | | | | | | | | | | | | | | | | | | | | | | |
| Antibody 17 | | | | | | | | | | | | | | | | | | | | | | | | | | | | | | |
| Antibody 18 | | | | | | | | | | | | | | | | | | | | | | | | | | | | | | |
| Antibody 19 | | | | | | | | | | | | | | | | | | | | | | | | | | | | | | |
| Antibody 21 | | | | | | | | | | | | | | | | | | | | | | | | | | | | | | |
| Antibody 22 | | | | | | | | | | | | | | | | | | | | | | | | | | | | | | |
| Antibody 23 | | | | | | | | | | | | R | | | | | | | | | | | | | | | | | | |
| Antibody 24 | | | | | | | | | | | | | | | | | | | | | | | | | | | | | | |
| Antibody 24 PGL | | | | | | | | | | | | | | | | | | | | | | | | | | | | | | |
| Antibody 25 | | | | | | | | | | | | | | | | | | | | | | | | | | | | | | |
| Antibody 26 | | | | | | | | | | | | | | | | | | | | | | | | | | | | | | |
| Antibody 27 | | | | | | | | | | | | R | | | | | | | | | | | | | | | | | | |
| Antibody 28 | | | | | | | | | | | | | | | | | | | | | | | | | | | | | | |
| Antibody 29 | | | | | | | | | | | | | | | | | | | | | | | | | | | | | | |
| Antibody 30 | | | | | | | | | | | | | | | | | | | | | | | | | | | | | | |
| Antibody 31 | | | | | | | | | | | | | | | | | | | | | | | | | | | | | | |
| Antibody 32 | | | | | | | | | | | | | | | | | | | | | | | | | | | | | | |
| Antibody 33 | | | | | | | | | | | E | | | | | | | | | | | | | | | | | | | |
| Antibody 34 | | | | | | | | | | | | | | | | | | | | | | | | | | | | | | |
| Antibody 35 | | | | | | | | | | | | | | | | | | | | | | | | | | | | | | |
| Antibody 36 | | | | | | | | | | | | | | | | | | | | | | | | | | | | | | |
| Antibody 37 | | | | | | | | | | | | | | | | | | | | | | | | | | | | | | |
| Antibody 37 GL | | | | | | | | | | | | | | | | | | | | | | | | | | | | | | |
| Antibody 38 | | | | | | | | | | | | | | | | | | | | | | | | | | | | | | |
| Antibody 39 | | | | | | | | | | | | | | | | | | | | | | | | | | | | | | |
| Antibody 40 | | | | | | | | | | | | | | | | | | | | | | | | | | | | | | |
| Antibody 41 | | | | | | | | | | | | R | | | | | | | | | | | | | | | | | | |
| Antibody 42 | | | | | | | | | | | | | | | | | | | | | | | | | | | | | | |

FIG 3B

| | CDR 1 | | | | | FW 2 | | | | | | | | | | | | | | CDR 2 | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|
| | 31 | 32 | 33 | 34 | 35 | 36 | 37 | 38 | 39 | 40 | 41 | 42 | 43 | 44 | 45 | 46 | 47 | 48 | 49 | 50 | 51 | 52 | 52A | 53 | 54 | 55 | 56 | 57 | 58 | 59 | 60 | 61 | 62 | 63 | 64 | 65 |
| | S | Y | Y | M | H | W | A | R | Q | A | P | G | Q | G | L | E | W | M | G | I | I | N | P | S | G | G | S | T | S | Y | A | Q | K | F | Q | G |
| | | | | | | | | | | | | | | | | | | | | | | | | | | | | A | | | | | | | | |
| | | | | | | | | | | | | | | | | | | | | | | | | | | | | R | | | | | | | | |
| | | | | | | | | V | | | | | | | | | | | | | | | | | | | | R | | | | | | | | |
| | | | | | | | | | | | | | | | | | | | | | | | | | | | | R | | A | | | | | | |
| | | | | | | | | | | | | | | | | | | | | | | | | | | | | | | | | | | | | |
| | | | | | | | | | | | | | | | | | | | | | | | | | | | | | | A | | | | | | |
| | | | | | | | | | | | | | | | | | | | | | | | | | | | | R | | | | | | | | |
| | | | | | | | | V | | | | | | | | | | | | | | | | | | | | R | | | | | | | | |
| | | | | | | | | | | | | | | | | | | | | | | | | | | | | | | A | | | | | | |
| | | | | | | | | | | | | | | | | | | | | | | | | | | | | R | | | | | | | | |
| | | | | | | | | | | | | | | | | | | | V | | | | | | | | | | | | | | | | | |

FIG 3C

| | | | | | | | | | | | | | | | FW 3 | | | | | | | | | | | | | | |
|---|---|---|---|---|---|---|---|---|---|---|---|---|---|---|---|---|---|---|---|---|---|---|---|---|---|---|---|---|---|
| 66 | 67 | 68 | 69 | 70 | 71 | 72 | 73 | 74 | 75 | 76 | 77 | 78 | 79 | 80 | 81 | 82 | 82A | 82B | 82C | 83 | 84 | 85 | 86 | 87 | 88 | 89 | 90 | 91 | 92 | 93 | 94 |
| R | V | T | M | T | R | D | T | S | T | S | T | V | Y | M | E | L | S | S | L | R | S | E | D | T | A | V | Y | Y | C | A | R |
| | | S | | | | | | | | | | | | | | | | | | | | | | | | | | | | | |
| | | | | | | | | | | | | | | | | | | | | | | | | | | P | | | | | |
| | | S | | | | | | | | | | | | | | | | | | | | | | | | | | | | | |
| | | A | | | | | | | | | | | | | | | | | | | | | | | | P | | | | | |
| | | | | | | | | | | | | | | | | | | | | | | | | | | P | | | | | |
| | | | | | | | | | | | | | | | | | | | | | | | | | | G | | | | | |

FIG 3D

|  | CDR 3 | | | | | | | FW 4 | | | | | | | | | | |
|---|---|---|---|---|---|---|---|---|---|---|---|---|---|---|---|---|---|---|
| 95 | 96 | 97 | 98 | 99 | 101 | 102 | 103 | 104 | 105 | 106 | 107 | 108 | 109 | 110 | 111 | 112 | 113 |
| G | K | Y | W | M | Y | D | W | G | K | G | T | L | V | T | V | S | S |
|   |   | W |   | L | D | Y |   |   |   |   |   |   |   |   |   |   |   |
|   |   | W |   | L |   | N |   |   |   |   |   |   |   |   |   |   |   |
|   |   | L | L | K | N | P |   |   |   |   |   |   |   |   |   |   |   |
|   |   | W |   | L |   | N |   |   |   |   |   |   |   |   |   |   |   |
|   |   | W |   | L |   |   |   |   |   |   |   |   |   |   |   |   |   |
|   |   |   |   |   |   |   |   |   |   |   |   |   |   |   |   |   |   |
|   |   | W |   | W | Q | Y |   |   |   |   |   |   |   |   |   |   |   |
|   |   | W |   | W | Q | Y |   |   |   |   |   |   |   |   |   |   |   |
|   |   | W |   | L |   | N |   |   |   |   |   |   |   |   |   |   |   |
|   |   | W |   | L |   |   |   |   |   |   |   |   |   |   |   |   |   |
|   |   | W |   | F |   |   |   |   |   |   |   |   |   |   |   |   |   |
|   |   | W |   | F |   |   |   |   |   |   |   |   |   |   |   |   |   |
|   |   | W |   | L |   |   |   |   |   |   |   |   |   |   |   |   |   |
|   |   | W |   | L |   | N |   |   |   |   |   |   |   |   |   |   |   |
|   |   | W |   | L |   | N |   |   |   |   |   |   |   |   |   |   |   |
|   |   | W |   | L |   | N |   |   |   |   |   |   |   |   |   |   |   |
|   |   | W |   | W | Q | H |   |   |   |   |   |   |   |   |   |   |   |
|   |   | W |   | W | Q | H |   |   |   |   |   |   |   |   |   |   |   |
|   |   | W |   | W | Q | H |   |   |   |   |   |   |   |   |   |   |   |
|   |   |   |   |   |   |   |   |   |   |   |   |   |   |   |   |   |   |
|   |   |   |   |   |   |   |   |   |   |   |   |   |   |   |   |   |   |
|   |   |   |   |   |   |   |   |   |   |   |   |   |   |   |   |   |   |
|   |   |   |   |   |   |   |   |   |   |   |   |   |   |   |   |   |   |
|   |   |   |   |   |   |   |   |   |   |   |   |   |   |   |   |   |   |
|   |   |   |   |   |   |   |   |   |   |   |   |   |   |   |   |   |   |
|   |   |   |   |   |   |   |   |   |   |   |   |   |   | Q |   |   |   |
|   |   |   |   |   |   |   |   |   | N |   |   |   |   |   |   |   |   |
|   |   |   |   |   |   |   |   |   |   |   |   | R |   |   |   |   |   |
|   |   |   |   |   |   |   |   |   |   |   |   |   |   |   |   |   |   |
|   |   |   |   |   |   |   |   |   |   |   |   |   |   |   |   |   |   |
|   |   |   |   |   |   |   |   |   |   |   |   |   |   |   |   |   |   |
|   |   |   |   |   |   |   |   |   |   |   |   |   |   |   |   |   |   |
|   |   |   |   |   |   |   |   |   |   |   |   |   |   |   |   |   |   |
|   |   |   |   |   |   |   |   |   |   |   |   |   |   |   |   |   |   |
|   |   |   |   |   |   |   |   |   |   |   |   |   |   |   |   |   |   |
|   |   |   |   |   |   |   |   |   |   |   |   |   |   |   |   | G |   |

FIG 4A

| Kabat numbering | FW1 | | | | | | | | | | | | | | | | | | | | | | | CDR1 | | | | | | | | | | | |
|---|---|---|---|---|---|---|---|---|---|---|---|---|---|---|---|---|---|---|---|---|---|---|---|---|---|---|---|---|---|---|---|---|---|---|---|
| | 1 | 2 | 3 | 4 | 5 | 6 | 7 | 8 | 9 | 11 | 12 | 13 | 14 | 15 | 16 | 17 | 18 | 19 | 20 | 21 | 22 | 23 | 24 | 25 | 26 | 27 | 27A | 27B | 28 | 29 | 30 | 31 | 32 | 33 | 34 |
| Antibody 20 | Q | S | V | L | T | Q | P | P | S | V | S | A | A | P | G | Q | K | V | T | I | S | C | S | G | G | S | S | N | I | G | N | S | Y | V | S |
| Antibody 1 | | | | | | | | | | | | | | | | | | | | | | | | | | | | | | | | | | | |
| Antibody 2 | | | | | | | | | | | | | | | | | | | | | | | | | | | | | | | | | | | |
| Antibody 3 | | | | | | | | | | | | | | | | | | | | | | | | | | | | | | | | | | | |
| Antibody 4 | | | | | | | | | | | | | | | | | | | | | | | | | | | | | | | | | | | |
| Antibody 5 | | | | | | | | | | | | | | | | | | | | | | | | | | | | | | | | | | | |
| Antibody 6 | | | | | | | | | | | | | | | | | | | | | | | | | | | | | | | | | | | |
| Antibody 7 | | | | | | | | | | | | | | | | | | | | | | | | | | | | | | | | | | | |
| Antibody 8 | | | | | | | | | | | | | | | | | | | | | | | | | | | | | | | | | | | |
| Antibody 9 | | | | | | | | | | | | | | | | | | | | | | | | | | | | | | | | | | | |
| Antibody 10 | | | | | | | | | | | | | | | | | | | | | | | | | | | | | | | | | | | |
| Antibody 11 | | | | | | | | | | | | | | | | | | | | | | | | | | | | | | | | | | | |
| Antibody 12 | | | | | | | | | | | | | | | | | | | | | | | | | | | | | | | | | | | |
| Antibody 13 | | | | | | | | | | | | | | | | | | | | | | | | | | | | | | | | | | | |
| Antibody 14 | | | | | | | | | | | | | | | | | | | | | | | | | | | | | | | | | | | |
| Antibody 15 | | | | | | | | | | | | | | | | | | | | | | | | | | | | | | | | | | | |
| Antibody 16 | | | | | | | | | | | | | | | | | | | | | | | | | | | | | | | | | | | |
| Antibody 17 | | | | | | | | | | | | | | | | | | | | | | | | | | | | | | | | | | | |
| Antibody 18 | | | | | | | | | | | | | | | | | | | | | | | | | | | | | | | | | | | |
| Antibody 19 | | | | | | | | | | | | | | | | | | | | | | | | | | | | | | | | | | | |
| Antibody 21 | | | | | | | | | | | | | | | | | | | | | | | | | | | | | | | | | | | |
| Antibody 22 | | P | | | | | | | | | | | | | | | | | | | | | | | | | | | | | | | | | |
| Antibody 23 | | | | | | | | | | | | | | | | | | | | | | | | | | | | | | | | N | | | |
| Antibody 24 | | | | | | | | | | | | | | | | | | | | | | | | | | | | | | | | | | | |
| Antibody 24PGL | | | | | | | | | | | | | | | | | | | | | | | | | | | | | | | | | | | |
| Antibody 25 | | | | | | | | | | | | | | | | | | | | | | | | | | | | | | | | | | | |
| Antibody 26 | | | | | | | | | | | | | | | | | | | | | | | | | | | | | | | | | | | |
| Antibody 27 | | | | | | | | L | | | | | | | | | | | | | | | | | | | | | | | | | | | |
| Antibody 28 | L | P | | | | | | | | | | | | | | | | | | | | | | | | | | S | | | | | | | |
| Antibody 29 | | | | | | | | | | | | | | | | | | | | | | | | | | | | | | | | | | | |
| Antibody 30 | | | | | | | | | | | | | | | | | | | | | | | | | | | | | | | | | | | |
| Antibody 31 | | | | | | | | | | | | | | | | | | | | | | | | | | | | S | | | | | | | |
| Antibody 32 | | | | | | | | | | | | | | | | | | | | | | | | | | | | | | | | | | | |
| Antibody 33 | | | A | | | | | | | | | | | | | | | | | | | | | | | | | | | | | | | | |
| Antibody 34 | | | | | | | | | | | | | | | | | | | | | | | | | | | | | | | | | | | |
| Antibody 35 | | | | | | | | | | | | | | | | | | | | | | | | | | | | | | | | | | | |
| Antibody 36 | | | | | | | | | | | | | | | | | | | | | | | | | | | G | S | | | | | | | |
| Antibody 37 | | | | | | | | | | | | | | | | | | | | | | | | | | | G | S | | | | | | | |
| Antibody 37 GL | | | | | | | | | | | | | | | | | | | | | | | | | | | G | S | | | | | | | |
| Antibody 38 | | | | | | | | | | | | | | | | | | | | | | | | | | | | | | | | | | | |
| Antibody 39 | | | | | | | | | | | | | | | | | | | | | | | | | | | | | | | | | | | |
| Antibody 40 | | | | | | | | | | | | | | | | | | | | | | | | | | | | | | | | | | | |
| Antibody 41 | | | | | | | | | | | | | | | | | | | | | | | | | | | | T | | | | | | | |
| Antibody 42 | | A | | | | | | | | | | | | | | | | | | | | | | | | | | | | | | | | | |

FIG 4B

| | FW2 | | | | | | | | | | | | | | | CDR2 | | | | | | |
|---|---|---|---|---|---|---|---|---|---|---|---|---|---|---|---|---|---|---|---|---|---|---|
| 35 | 36 | 37 | 38 | 39 | 40 | 41 | 42 | 43 | 44 | 45 | 46 | 47 | 48 | 49 | 50 | 51 | 52 | 53 | 54 | 55 | 56 |
| W | Y | Q | Q | L | P | G | T | A | P | K | L | L | I | Y | D | N | N | K | R | P | S |
| | | | | | | | | | | | | | | | | | | | | | |
| | | | | | | | | | | | | | | | | | | | | | |
| | | | | | | | | | | | | | | | | | | | | | |
| | | | | | | | | | | | | | | | | | | | | | |
| | | | | | | | | | | | | | | | | | | | | | |
| | | | | | | | | | | | | | | | | | | | | | |
| | | | | | | | | | | | | | | | | | | | | | |
| | | | | | | | | | | | | | | | | | | | | | |
| | | | | | | | | | | | | | | | | | | | | | |
| | | | | | | | | | | | | | | | | | | | | | |
| | | | | | | | | | | | | | | | | | | | | | |
| | | | | | | | | | | | | | | | | | | | | | |
| | | | | | | | | | | | | | | | | | | | | | |
| | | | | | | | | | | | | | | | | | | | | | |
| | | | | | | | | | | | | | | | | | | | | | |
| | | | | | | | | | | | | | | | | | | | | | |
| | | | | | | | | | | | | | | | | | | | | | |
| | | | | | | | | | | | | | | | | | | | | | |
| | | | | | | | | | | | | | | | | | | | | | |
| | | | | | | | | | | | | | | | | | | | | | P |
| | | | | | | | | | | | | | | | | | | | | | |
| | | | | | | | | | | | | | | | | | | | | | |
| | | | | | | | | | | | | | | | | | | | | | |
| | | | | | | | | | | | | | | | | | | | | | |
| | | | R | | | | | | | | | | | | | | | | | | |
| | | | | | | | A | | | | | | | | | | | | | | |
| | | | | | | | | | | | | | | | | | | | | | |
| | | | R | | | | A | | | | | | | | | | | | | | |
| | | | | | | | | | | | | | | | | | | | | | |
| | | | | | | | | | | | | | | | | | | | | | |
| | | | | | | | | | | | | | | | | | | | | | |
| | | | | | | | | | | | | | | | | | | | | | |
| | | | | | | | | | | | | | | | | | | | | | |
| | | | | | | | | | | | | | | | | | | | | | |
| | | | | | | | | | | | | | | | | | | | | | |
| | | | | | | | | | | | | | | | | | | | | | |
| | | | | | | | | | | | | | | | | | | | | | |
| | | | R | | | | | | | | | | | | | | | | | | P |
| | | | R | | | | A | | | | | | | | | | | | | | |

FIG 4C

| | | | | | | | | | | | | | | | FW3 | | | | | | | | | | | | | | | | |
|---|---|---|---|---|---|---|---|---|---|---|---|---|---|---|---|---|---|---|---|---|---|---|---|---|---|---|---|---|---|---|---|
| 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 | 85 | 86 | 87 | 88 |
| G | I | P | D | R | F | S | G | S | K | S | G | T | S | A | T | L | A | I | T | G | L | Q | T | G | D | E | A | D | Y | Y | C |
| | | | | | | | | | | | | | | | | | | | | | | | | | | | | | V | F | |
| | | | | | | | | | | | | | | | | | | | | | | | | | | | | | | F | |
| | | | | | | | | | | | | | | | | | | | | | | | | | | | | | | F | |
| | | | | | | | | | | | | | | | | | G | | | | | | | | | | | | | F | |
| | | | | | | | | | | | | | | T | | | | | | | | | | | | | | | | | |
| | | | | | | | | | | | | | | | | | | | | | | | | | | | | | | F | |
| | | | | | | | | | | | | | | | | | | | | | | | | | | | | | | | |
| | | | | | | | F | R | | | | | | | | | | | | | | | | | | | | | | | |
| | | | | | | | | | | | | | | | | | | | | | | | | | | | | | | F | |
| | | | | | | | | | | | | | | | | | | | | | | | | | | | | | | F | |
| | | | | | | | | | | | | | | | | | | | | | | | | | | | | | | F | |
| | | | V | | | | | | | | | | | | | | | | | | | | | | | | | | | | |
| | | | | | | | | | | | | | | | | | G | | | | | | | | | | ' | | | | |
| | | | | | | | | | | | | | | | | | | | | | | | | | | | | | | F | |

FIG 4D

| | | | | | | CDR3 | | | | | | FW4 | | | | | | | | | |
|---|---|---|---|---|---|---|---|---|---|---|---|---|---|---|---|---|---|---|---|---|---|
| 89 | 90 | 91 | 92 | 93 | 94 | 95 | 95A | 95B | 95C | 96 | 97 | 98 | 99 | 100 | 101 | 102 | 103 | 104 | 105 | 106 | 107 |
| G | T | W | D | T | S | T | V | W | E | W | P | F | G | T | G | T | K | L | T | V | L |
| | | | | | | L | S | A | N | Y | V | | | | | | | | | | |
| | | | | | | Q | P | P | N | P | L | | | | | | | | | | |
| | | | F | G | T | P | A | S | N | Y | V | | | | | | | | | | |
| | | | | | | S | P | P | Q | P | I | | | | | | | | | | |
| | | | | | | S | P | P | Q | P | I | | | | | | | | | | |
| | | | | | | | T | Y | H | P | I | | | | | | | | | | |
| | | | | | | S | P | P | Q | P | I | | | | | | | | | | |
| | | | | | | | T | Y | H | P | I | | | | | | | | | | |
| | | | | | | | T | M | Y | P | L | | | | | | | | | | |
| | | | | | | | | L | T | P | I | | | | | | | | | | |
| | | | | | | P | S | M | I | P | L | | | | | | | | | | |
| | | | | | | | T | M | Y | P | L | | | | | | | | | | |
| | | | | | | | T | L | Q | P | L | | | | | | | | | | |
| | | | | | | P | P | T | K | P | L | | | | | | | | | | |
| | | | | | | | H | R | H | P | L | | | | | | | | | | |
| | | | | | | | T | Y | H | P | I | | | | | | | | | | |
| | | | | | | P | | D | R | P | I | | | | | | | | | | |
| | | | | | | | T | P | M | P | V | | | | | | | | | | |
| | | | | | | | T | Y | H | P | I | | | | | | | | | | |
| | | | | | | | | | | | | | | | | | | | | | |
| | | | | | | | | | | | | | | | | | | | | | |
| | | | | | | | | | | | | | | | | | | | | | |
| | | | V | | | | | | | | | | | | | | | | | | |
| | | | | | | | | | | | | | | | | | | | | | |
| | | | | | | | P | | | | | | | | | | | | | | |
| | | | | | | | P | | | | | | | | | | | | | | |
| | | | | A | | | P | | | | | | | | | | | | | | |
| | | | | | | | | A | | | | | | | | | | | | | |
| | | | | | | | | | | | | | | | | | | | | | |
| | | | | | | | P | | | | | | | | | | | | | | |
| | | | | | S | | | | | | | | | | | | | | | | |
| | | | | | | | P | | | | | | | | | | | | | | |
| | | | | | | | P | | | | | | | | | | | | | | |
| | | | | | | | | | | | | | | | | | | | | | |
| | | | | | | | | A | | | | | | | | | | | | | |
| | | | | | S | | | | | | | | | | | | | | | | |
| | | | | | | | | | | | | | | | | | | | | | |
| | | | | | | | | G | | | | | | | | | | | | | |

FIG 5A

|  | Antibody 1 | Antibody 2 | Antibody 3 | Antibody 4 | Antibody 5 | Antibody 6 | Antibody 7 | Antibody 8 | Antibody 9 | Antibody 10 | Antibody 11 | Antibody 12 | Antibody 13 | Antibody 14 | Antibody 15 |
|---|---|---|---|---|---|---|---|---|---|---|---|---|---|---|---|
| Antibody 1 | - |  |  |  |  |  |  |  |  |  |  |  |  |  |  |
| Antibody 2 | 88% | - |  |  |  |  |  |  |  |  |  |  |  |  |  |
| Antibody 3 | 81% | 78% | - |  |  |  |  |  |  |  |  |  |  |  |  |
| Antibody 4 | 86% | 95% | 77% | - |  |  |  |  |  |  |  |  |  |  |  |
| Antibody 5 | 86% | 93% | 77% | 77% | - |  |  |  |  |  |  |  |  |  |  |
| Antibody 6 | 83% | 86% | 77% | 98% | 98% | - |  |  |  |  |  |  |  |  |  |
| Antibody 7 | 86% | 90% | 77% | 88% | 88% | 90% | - |  |  |  |  |  |  |  |  |
| Antibody 8 | 86% | 86% | 77% | 95% | 95% | 90% | 95% | - |  |  |  |  |  |  |  |
| Antibody 9 | 86% | 93% | 77% | 91% | 91% | 86% | 86% | 86% | - |  |  |  |  |  |  |
| Antibody 10 | 86% | 90% | 77% | 91% | 91% | 88% | 88% | 93% | 90% | - |  |  |  |  |  |
| Antibody 11 | 86% | 90% | 78% | 88% | 88% | 88% | 93% | 93% | 86% | 91% | - |  |  |  |  |
| Antibody 12 | 85% | 90% | 77% | 88% | 88% | 90% | 91% | 88% | 90% | 88% | 90% | - |  |  |  |
| Antibody 13 | 86% | 91% | 77% | 91% | 91% | 88% | 91% | 91% | 86% | 93% | 86% | 96% | - |  |  |
| Antibody 14 | 86% | 95% | 78% | 93% | 93% | 90% | 95% | 88% | 90% | 91% | 86% | 91% | 95% | - |  |
| Antibody 15 | 86% | 93% | 77% | 91% | 91% | 90% | 91% | 93% | 90% | 90% | 91% | 95% | 91% | 91% | - |
| Antibody 16 |  |  |  |  |  |  |  |  |  |  | 90% | 91% | 95% | 90% | 90% |
| Antibody 17 |  |  |  |  |  |  |  |  |  |  |  | 95% | 91% | 91% | 91% |
| Antibody 18 |  |  |  |  |  |  |  |  |  |  |  |  | - | 90% | 93% |
| Antibody 19 |  |  |  |  |  |  |  |  |  |  |  |  |  | 91% | 93% |
| Antibody 20 |  |  |  |  |  |  |  |  |  |  |  |  |  |  | - |
| Antibody 21 |  |  |  |  |  |  |  |  |  |  |  |  |  |  |  |
| Antibody 22 |  |  |  |  |  |  |  |  |  |  |  |  |  |  |  |
| Antibody 23 |  |  |  |  |  |  |  |  |  |  |  |  |  |  |  |
| Antibody 24 |  |  |  |  |  |  |  |  |  |  |  |  |  |  |  |
| Antibody 24 PGL |  |  |  |  |  |  |  |  |  |  |  |  |  |  |  |
| Antibody 24 GL |  |  |  |  |  |  |  |  |  |  |  |  |  |  |  |
| Antibody 25 |  |  |  |  |  |  |  |  |  |  |  |  |  |  |  |
| Antibody 26 |  |  |  |  |  |  |  |  |  |  |  |  |  |  |  |
| Antibody 27 |  |  |  |  |  |  |  |  |  |  |  |  |  |  |  |
| Antibody 28 |  |  |  |  |  |  |  |  |  |  |  |  |  |  |  |
| Antibody 29 |  |  |  |  |  |  |  |  |  |  |  |  |  |  |  |
| Antibody 30 |  |  |  |  |  |  |  |  |  |  |  |  |  |  |  |
| Antibody 31 |  |  |  |  |  |  |  |  |  |  |  |  |  |  |  |
| Antibody 32 |  |  |  |  |  |  |  |  |  |  |  |  |  |  |  |
| Antibody 33 |  |  |  |  |  |  |  |  |  |  |  |  |  |  |  |
| Antibody 34 |  |  |  |  |  |  |  |  |  |  |  |  |  |  |  |
| Antibody 35 |  |  |  |  |  |  |  |  |  |  |  |  |  |  |  |
| Antibody 36 |  |  |  |  |  |  |  |  |  |  |  |  |  |  |  |
| Antibody 37 |  |  |  |  |  |  |  |  |  |  |  |  |  |  |  |
| Antibody 37 GL |  |  |  |  |  |  |  |  |  |  |  |  |  |  |  |
| Antibody 38 |  |  |  |  |  |  |  |  |  |  |  |  |  |  |  |
| Antibody 39 |  |  |  |  |  |  |  |  |  |  |  |  |  |  |  |
| Antibody 40 |  |  |  |  |  |  |  |  |  |  |  |  |  |  |  |
| Antibody 41 |  |  |  |  |  |  |  |  |  |  |  |  |  |  |  |
| Antibody 42 |  |  |  |  |  |  |  |  |  |  |  |  |  |  |  |

FIG 5B

| | Antibody 16 | Antibody 17 | Antibody 18 | Antibody 19 | Antibody 20 | Antibody 21 | Antibody 22 | Antibody 23 | Antibody 24 | Antibody 24 PGL | Antibody 24 GL | Antibody 25 | Antibody 26 | Antibody 27 | Antibody 28 |
|---|---|---|---|---|---|---|---|---|---|---|---|---|---|---|---|
| Antibody 1 | 86% | 85% | 86% | 85% | 83% | 81% | 83% | 80% | 81% | 81% | 81% | 78% | 83% | 83% | 81% |
| Antibody 2 | 91% | 86% | 88% | 86% | 85% | 83% | 85% | 81% | 83% | 83% | 83% | 80% | 85% | 85% | 83% |
| Antibody 3 | 77% | 78% | 78% | 77% | 77% | 75% | 77% | 73% | 75% | 75% | 75% | 73% | 77% | 77% | 77% |
| Antibody 4 | 93% | 88% | 88% | 88% | 85% | 83% | 85% | 81% | 83% | 83% | 83% | 80% | 85% | 85% | 83% |
| Antibody 5 | 91% | 88% | 88% | 88% | 86% | 85% | 86% | 83% | 85% | 85% | 85% | 81% | 86% | 86% | 85% |
| Antibody 6 | 95% | 86% | 88% | 93% | 91% | 90% | 91% | 88% | 90% | 90% | 90% | 86% | 91% | 91% | 88% |
| Antibody 7 | 88% | 91% | 91% | 91% | 83% | 81% | 83% | 80% | 81% | 81% | 81% | 78% | 83% | 83% | 81% |
| Antibody 8 | 95% | 91% | 93% | 98% | 85% | 83% | 85% | 81% | 83% | 83% | 83% | 80% | 85% | 85% | 81% |
| Antibody 9 | 95% | 86% | 90% | 90% | 86% | 85% | 86% | 83% | 85% | 85% | 85% | 81% | 86% | 86% | 83% |
| Antibody 10 | 93% | 90% | 88% | 90% | 90% | 88% | 90% | 86% | 88% | 88% | 88% | 85% | 90% | 90% | 86% |
| Antibody 11 | 88% | 88% | 86% | 86% | 86% | 85% | 86% | 83% | 85% | 85% | 85% | 81% | 86% | 86% | 86% |
| Antibody 12 | 91% | 86% | 90% | 90% | 88% | 86% | 88% | 85% | 86% | 86% | 86% | 83% | 88% | 88% | 85% |
| Antibody 13 | 93% | 86% | 90% | 90% | 88% | 86% | 88% | 85% | 86% | 86% | 86% | 83% | 88% | 88% | 85% |
| Antibody 14 | 91% | 88% | 86% | 86% | 85% | 83% | 85% | 81% | 83% | 83% | 83% | 80% | 85% | 85% | 85% |
| Antibody 15 | 95% | 86% | 88% | 90% | 86% | 85% | 86% | 83% | 85% | 85% | 85% | 81% | 86% | 86% | 83% |
| Antibody 16 | | 88% | 90% | 95% | 86% | 85% | 86% | 83% | 85% | 85% | 85% | 81% | 86% | 86% | 83% |
| Antibody 17 | | | 91% | 93% | 85% | 83% | 85% | 81% | 83% | 83% | 83% | 80% | 85% | 85% | 85% |
| Antibody 18 | | | | 95% | 85% | 83% | 85% | 81% | 83% | 83% | 83% | 80% | 85% | 85% | 81% |
| Antibody 19 | | | | | 85% | 83% | 85% | 81% | 83% | 83% | 83% | 80% | 85% | 85% | 81% |
| Antibody 20 | | | | | | 98% | 100% | 96% | 98% | 98% | 98% | 95% | 100% | 100% | 96% |
| Antibody 21 | | | | | | | 98% | 95% | 96% | 96% | 96% | 96% | 98% | 98% | 95% |
| Antibody 22 | | | | | | | | 96% | 98% | 98% | 98% | 95% | 100% | 100% | 96% |
| Antibody 23 | | | | | | | | | 95% | 95% | 95% | 91% | 96% | 96% | 93% |
| Antibody 24 | | | | | | | | | | 100% | 100% | 96% | 98% | 98% | 95% |
| Antibody 24 PGL | | | | | | | | | | | 100% | 96% | 98% | 98% | 95% |
| Antibody 24 GL | | | | | | | | | | | | 96% | 98% | 98% | 95% |
| Antibody 25 | | | | | | | | | | | | | 95% | 95% | 91% |
| Antibody 26 | | | | | | | | | | | | | | 100% | 96% |
| Antibody 27 | | | | | | | | | | | | | | | 96% |
| Antibody 28 | | | | | | | | | | | | | | | |
| Antibody 29 | | | | | | | | | | | | | | | |
| Antibody 30 | | | | | | | | | | | | | | | |
| Antibody 31 | | | | | | | | | | | | | | | |
| Antibody 32 | | | | | | | | | | | | | | | |
| Antibody 33 | | | | | | | | | | | | | | | |
| Antibody 34 | | | | | | | | | | | | | | | |
| Antibody 35 | | | | | | | | | | | | | | | |
| Antibody 36 | | | | | | | | | | | | | | | |
| Antibody 37 | | | | | | | | | | | | | | | |
| Antibody 37 GL | | | | | | | | | | | | | | | |
| Antibody 38 | | | | | | | | | | | | | | | |
| Antibody 39 | | | | | | | | | | | | | | | |
| Antibody 40 | | | | | | | | | | | | | | | |
| Antibody 41 | | | | | | | | | | | | | | | |
| Antibody 42 | | | | | | | | | | | | | | | |

FIG 5C

| | Antibody 29 | Antibody 30 | Antibody 31 | Antibody 32 | Antibody 33 | Antibody 34 | Antibody 35 | Antibody 36 | Antibody 37 | Antibody 37 GL | Antibody 38 | Antibody 39 | Antibody 40 | Antibody 41 | Antibody 42 |
|---|---|---|---|---|---|---|---|---|---|---|---|---|---|---|---|
| Antibody 1 | 83% | 83% | 80% | 83% | 83% | 83% | 83% | 80% | 78% | 78% | 81% | 81% | 81% | 80% | 83% |
| Antibody 2 | 85% | 85% | 81% | 85% | 85% | 85% | 85% | 81% | 80% | 80% | 83% | 83% | 83% | 81% | 85% |
| Antibody 3 | 78% | 77% | 77% | 78% | 77% | 77% | 78% | 75% | 73% | 73% | 75% | 77% | 77% | 73% | 77% |
| Antibody 4 | 85% | 85% | 81% | 85% | 85% | 85% | 85% | 81% | 80% | 80% | 83% | 83% | 83% | 81% | 85% |
| Antibody 5 | 86% | 86% | 83% | 86% | 86% | 86% | 86% | 83% | 81% | 81% | 85% | 85% | 85% | 83% | 86% |
| Antibody 6 | 90% | 91% | 86% | 91% | 91% | 91% | 90% | 88% | 85% | 85% | 90% | 90% | 90% | 88% | 91% |
| Antibody 7 | 83% | 83% | 80% | 83% | 83% | 83% | 83% | 80% | 78% | 78% | 81% | 83% | 81% | 80% | 83% |
| Antibody 8 | 83% | 85% | 80% | 85% | 85% | 85% | 83% | 81% | 78% | 78% | 83% | 83% | 83% | 81% | 85% |
| Antibody 9 | 85% | 86% | 81% | 86% | 86% | 86% | 85% | 83% | 80% | 80% | 85% | 85% | 85% | 83% | 86% |
| Antibody 10 | 88% | 90% | 85% | 88% | 90% | 86% | 88% | 86% | 83% | 83% | 88% | 86% | 88% | 86% | 88% |
| Antibody 11 | 88% | 86% | 85% | 86% | 86% | 86% | 88% | 85% | 83% | 83% | 85% | 85% | 85% | 83% | 86% |
| Antibody 12 | 86% | 88% | 83% | 88% | 88% | 88% | 86% | 85% | 81% | 81% | 86% | 86% | 86% | 85% | 88% |
| Antibody 13 | 86% | 88% | 83% | 88% | 88% | 88% | 86% | 85% | 81% | 81% | 86% | 86% | 86% | 85% | 88% |
| Antibody 14 | 86% | 85% | 83% | 85% | 85% | 85% | 86% | 81% | 81% | 81% | 83% | 83% | 83% | 81% | 85% |
| Antibody 15 | 85% | 86% | 81% | 86% | 86% | 86% | 85% | 83% | 80% | 80% | 85% | 85% | 85% | 83% | 86% |
| Antibody 16 | 85% | 86% | 81% | 86% | 86% | 86% | 85% | 83% | 80% | 80% | 85% | 85% | 85% | 83% | 86% |
| Antibody 17 | 86% | 85% | 83% | 83% | 85% | 85% | 86% | 81% | 81% | 81% | 83% | 81% | 83% | 81% | 83% |
| Antibody 18 | 83% | 85% | 80% | 85% | 85% | 85% | 83% | 81% | 78% | 78% | 83% | 83% | 83% | 81% | 85% |
| Antibody 19 | 83% | 85% | 80% | 85% | 85% | 85% | 83% | 81% | 78% | 78% | 83% | 83% | 83% | 81% | 85% |
| Antibody 20 | 98% | 100% | 95% | 98% | 100% | 100% | 98% | 96% | 93% | 93% | 98% | 96% | 98% | 96% | 98% |
| Antibody 21 | 96% | 98% | 93% | 96% | 98% | 98% | 96% | 93% | 91% | 91% | 100% | 95% | 96% | 95% | 96% |
| Antibody 22 | 98% | 100% | 95% | 98% | 100% | 100% | 98% | 96% | 93% | 93% | 98% | 96% | 98% | 96% | 98% |
| Antibody 23 | 95% | 96% | 91% | 95% | 96% | 96% | 95% | 93% | 90% | 90% | 95% | 93% | 95% | 93% | 95% |
| Antibody 24 | 96% | 98% | 93% | 96% | 98% | 98% | 96% | 95% | 95% | 95% | 96% | 98% | 96% | 95% | 96% |
| Antibody 24 PGL | 96% | 98% | 93% | 96% | 98% | 98% | 96% | 95% | 95% | 95% | 96% | 98% | 96% | 95% | 96% |
| Antibody 24 GL | 96% | 98% | 93% | 96% | 98% | 98% | 96% | 95% | 95% | 95% | 96% | 98% | 96% | 95% | 96% |
| Antibody 25 | 93% | 95% | 91% | 93% | 95% | 95% | 93% | 91% | 91% | 91% | 93% | 95% | 93% | 91% | 93% |
| Antibody 26 | 98% | 100% | 95% | 98% | 100% | 100% | 98% | 96% | 93% | 93% | 98% | 96% | 98% | 96% | 98% |
| Antibody 27 | 98% | 100% | 95% | 98% | 100% | 100% | 98% | 96% | 93% | 93% | 98% | 96% | 98% | 96% | 98% |
| Antibody 28 | 98% | 96% | 98% | 95% | 96% | 96% | 98% | 93% | 93% | 93% | 95% | 93% | 95% | 93% | 95% |
| Antibody 29 | - | 98% | 96% | 96% | 98% | 98% | 100% | 95% | 95% | 95% | 96% | 95% | 96% | 95% | 96% |
| Antibody 30 | 98% | - | 95% | 98% | 100% | 100% | 98% | 96% | 93% | 93% | 98% | 96% | 98% | 96% | 98% |
| Antibody 31 | 95% | | - | 93% | | | 96% | 91% | 91% | 91% | 93% | 91% | 93% | 91% | 93% |
| Antibody 32 | | | | - | 98% | 98% | 96% | 96% | 95% | 95% | 96% | 96% | 96% | 96% | 98% |
| Antibody 33 | | | | | - | 100% | 98% | 96% | 93% | 93% | 98% | 96% | 98% | 96% | 98% |
| Antibody 34 | | | | | | - | 98% | 96% | 93% | 93% | 98% | 96% | 98% | 96% | 98% |
| Antibody 35 | | | | | | | - | 95% | 96% | 96% | 96% | 95% | 96% | 95% | 96% |
| Antibody 36 | | | | | | | | - | 91% | 91% | 98% | 96% | 98% | 96% | 96% |
| Antibody 37 | | | | | | | | | - | 100% | 91% | 93% | 91% | 90% | 91% |
| Antibody 37 GL | | | | | | | | | | - | 91% | 93% | 91% | 90% | 91% |
| Antibody 38 | | | | | | | | | | | - | 95% | 96% | 95% | 96% |
| Antibody 39 | | | | | | | | | | | | - | 95% | 93% | 96% |
| Antibody 40 | | | | | | | | | | | | | - | 95% | 96% |
| Antibody 41 | | | | | | | | | | | | | | - | 95% |
| Antibody 42 | | | | | | | | | | | | | | | - |

FIG 6A

| | Antibody 1 | Antibody 2 | Antibody 3 | Antibody 4 | Antibody 5 | Antibody 6 | Antibody 7 | Antibody 8 | Antibody 9 | Antibody 10 | Antibody 11 | Antibody 12 | Antibody 13 | Antibody 14 | Antibody 15 |
|---|---|---|---|---|---|---|---|---|---|---|---|---|---|---|---|
| Antibody 1 | - | | | | | | | | | | | | | | |
| Antibody 2 | | 93% | | | | | | | | | | | | | |
| Antibody 3 | | - | 82% | | | | | | | | | | | | |
| Antibody 4 | | | 82% | 93% | | | | | | | | | | | |
| Antibody 5 | | | | 100% | 93% | | | | | | | | | | |
| Antibody 6 | | | | 82% | 96% | 86% | | | | | | | | | |
| Antibody 7 | | | | - | 82% | 82% | 93% | | | | | | | | |
| Antibody 8 | | | | | 96% | 89% | 89% | 93% | | | | | | | |
| Antibody 9 | | | | | - | 93% | 89% | 89% | 93% | | | | | | |
| Antibody 10 | | | | | | - | 86% | 86% | 100% | 93% | | | | | |
| Antibody 11 | | | | | | | - | 100% | 82% | 96% | 89% | | | | |
| Antibody 12 | | | | | | | | - | 100% | 82% | 93% | 89% | | | |
| Antibody 13 | | | | | | | | | 96% | 82% | 93% | 82% | 93% | | |
| Antibody 14 | | | | | | | | | 89% | 96% | 93% | 93% | 96% | 93% | |
| Antibody 15 | | | | | | | | | 89% | 100% | 96% | 96% | 100% | 100% | 93% |
| Antibody 16 | | | | | | | | | - | 93% | 93% | 93% | 93% | 96% | 96% |
| Antibody 17 | | | | | | | | | | 89% | 89% | 89% | 89% | 89% | 89% |
| Antibody 18 | | | | | | | | | | 89% | 89% | 89% | 89% | 89% | 89% |
| Antibody 19 | | | | | | | | | | 96% | 93% | 93% | 96% | 100% | 100% |
| Antibody 20 | | | | | | | | | | - | 96% | 96% | 100% | 96% | 96% |
| Antibody 21 | | | | | | | | | | | - | 100% | 96% | 93% | 93% |
| Antibody 22 | | | | | | | | | | | | - | 96% | 93% | 93% |
| Antibody 23 | | | | | | | | | | | | | - | 96% | 96% |
| Antibody 24 | | | | | | | | | | | | | | - | 100% |
| Antibody 24 PGL | | | | | | | | | | | | | | | - |
| Antibody 24 GL | | | | | | | | | | | | | | | |
| Antibody 25 | | | | | | | | | | | | | | | |
| Antibody 26 | | | | | | | | | | | | | | | |
| Antibody 27 | | | | | | | | | | | | | | | |
| Antibody 28 | | | | | | | | | | | | | | | |
| Antibody 29 | | | | | | | | | | | | | | | |
| Antibody 30 | | | | | | | | | | | | | | | |
| Antibody 31 | | | | | | | | | | | | | | | |
| Antibody 32 | | | | | | | | | | | | | | | |
| Antibody 33 | | | | | | | | | | | | | | | |
| Antibody 34 | | | | | | | | | | | | | | | |
| Antibody 35 | | | | | | | | | | | | | | | |
| Antibody 36 | | | | | | | | | | | | | | | |
| Antibody 37 | | | | | | | | | | | | | | | |
| Antibody 37GL | | | | | | | | | | | | | | | |
| Antibody 38 | | | | | | | | | | | | | | | |
| Antibody 39 | | | | | | | | | | | | | | | |
| Antibody 40 | | | | | | | | | | | | | | | |
| Antibody 41 | | | | | | | | | | | | | | | |
| Antibody 42 | | | | | | | | | | | | | | | |

FIG 6B

| | Antibody 16 | Antibody 17 | Antibody 18 | Antibody 19 | Antibody 20 | Antibody 21 | Antibody 22 | Antibody 23 | Antibody 24 | Antibody 24 PGL | Antibody 24 GL | Antibody 25 | Antibody 26 | Antibody 27 | Antibody 28 |
|---|---|---|---|---|---|---|---|---|---|---|---|---|---|---|---|
| Antibody 1 | 93% | 89% | 89% | 89% | 86% | 82% | 86% | 86% | 82% | 82% | 82% | 79% | 86% | 86% | 86% |
| Antibody 2 | 100% | 89% | 89% | 89% | 89% | 86% | 89% | 89% | 86% | 86% | 86% | 82% | 89% | 89% | 89% |
| Antibody 3 | 82% | 82% | 82% | 82% | 82% | 79% | 82% | 82% | 79% | 79% | 79% | 75% | 82% | 82% | 82% |
| Antibody 4 | 100% | 89% | 89% | 89% | 89% | 86% | 89% | 89% | 86% | 86% | 86% | 82% | 89% | 89% | 89% |
| Antibody 5 | 96% | 89% | 89% | 89% | 93% | 89% | 93% | 93% | 89% | 89% | 89% | 86% | 93% | 93% | 93% |
| Antibody 6 | 89% | 86% | 86% | 86% | 100% | 96% | 100% | 100% | 96% | 96% | 96% | 93% | 100% | 100% | 100% |
| Antibody 7 | 89% | 96% | 96% | 96% | 86% | 82% | 86% | 86% | 82% | 82% | 82% | 79% | 86% | 86% | 86% |
| Antibody 8 | 89% | 89% | 96% | 96% | 86% | 82% | 86% | 86% | 82% | 82% | 82% | 79% | 86% | 86% | 86% |
| Antibody 9 | 100% | 89% | 89% | 89% | 89% | 86% | 89% | 89% | 86% | 86% | 86% | 82% | 89% | 89% | 89% |
| Antibody 10 | 96% | 89% | 89% | 89% | 93% | 89% | 93% | 93% | 89% | 89% | 89% | 86% | 93% | 93% | 93% |
| Antibody 11 | 93% | 89% | 89% | 89% | 93% | 89% | 93% | 93% | 89% | 89% | 89% | 86% | 93% | 93% | 93% |
| Antibody 12 | 93% | 89% | 89% | 89% | 93% | 89% | 93% | 93% | 89% | 89% | 89% | 86% | 93% | 93% | 93% |
| Antibody 13 | 96% | 89% | 89% | 89% | 93% | 89% | 93% | 93% | 89% | 89% | 89% | 86% | 93% | 93% | 93% |
| Antibody 14 | 100% | 89% | 89% | 89% | 89% | 86% | 89% | 89% | 86% | 86% | 86% | 82% | 89% | 89% | 89% |
| Antibody 15 | 100% | 89% | 89% | 89% | 89% | 86% | 89% | 89% | 86% | 86% | 86% | 82% | 89% | 89% | 89% |
| Antibody 16 | - | 89% | 89% | 89% | 86% | 82% | 86% | 86% | 82% | 82% | 82% | 79% | 86% | 86% | 86% |
| Antibody 17 | | - | 100% | 100% | 86% | 82% | 86% | 86% | 82% | 82% | 82% | 79% | 86% | 86% | 86% |
| Antibody 18 | | | - | 100% | 86% | 82% | 86% | 86% | 82% | 82% | 82% | 79% | 86% | 86% | 86% |
| Antibody 19 | | | | - | 86% | 82% | 86% | 86% | 82% | 82% | 82% | 79% | 86% | 86% | 86% |
| Antibody 20 | | | | | - | 96% | 100% | 100% | 96% | 96% | 96% | 93% | 100% | 100% | 100% |
| Antibody 21 | | | | | | - | 96% | 96% | 93% | 93% | 93% | 96% | 96% | 96% | 96% |
| Antibody 22 | | | | | | | - | 100% | 96% | 96% | 96% | 93% | 96% | 100% | 100% |
| Antibody 23 | | | | | | | | - | 96% | 96% | 96% | 93% | 100% | 100% | 100% |
| Antibody 24 | | | | | | | | | - | 100% | 100% | 96% | 96% | 96% | 96% |
| Antibody 24 PGL | | | | | | | | | | - | 100% | 96% | 96% | 96% | 96% |
| Antibody 24 GL | | | | | | | | | | | - | 96% | 96% | 96% | 96% |
| Antibody 25 | | | | | | | | | | | | - | 93% | 93% | 93% |
| Antibody 26 | | | | | | | | | | | | | - | 100% | 100% |
| Antibody 27 | | | | | | | | | | | | | | - | 100% |
| Antibody 28 | | | | | | | | | | | | | | | - |
| Antibody 29 | | | | | | | | | | | | | | | |
| Antibody 30 | | | | | | | | | | | | | | | |
| Antibody 31 | | | | | | | | | | | | | | | |
| Antibody 32 | | | | | | | | | | | | | | | |
| Antibody 33 | | | | | | | | | | | | | | | |
| Antibody 34 | | | | | | | | | | | | | | | |
| Antibody 35 | | | | | | | | | | | | | | | |
| Antibody 36 | | | | | | | | | | | | | | | |
| Antibody 37 | | | | | | | | | | | | | | | |
| Antibody 37GL | | | | | | | | | | | | | | | |
| Antibody 38 | | | | | | | | | | | | | | | |
| Antibody 39 | | | | | | | | | | | | | | | |
| Antibody 40 | | | | | | | | | | | | | | | |
| Antibody 41 | | | | | | | | | | | | | | | |
| Antibody 42 | | | | | | | | | | | | | | | |

FIG 6C

| | Antibody 29 | Antibody 30 | Antibody 31 | Antibody 32 | Antibody 33 | Antibody 34 | Antibody 35 | Antibody 36 | Antibody 37 | Antibody 37GL | Antibody 38 | Antibody 39 | Antibody 40 | Antibody 41 | Antibody 42 |
|---|---|---|---|---|---|---|---|---|---|---|---|---|---|---|---|
| Antibody 1 | 86% | 86% | 86% | 86% | 86% | 86% | 86% | 82% | 82% | 82% | 82% | 82% | 86% | 86% | 86% |
| Antibody 2 | 89% | 89% | 89% | 89% | 89% | 89% | 89% | 86% | 86% | 86% | 86% | 86% | 89% | 89% | 89% |
| Antibody 3 | 82% | 82% | 82% | 82% | 82% | 82% | 82% | 79% | 79% | 79% | 79% | 79% | 82% | 82% | 82% |
| Antibody 4 | 89% | 89% | 89% | 89% | 89% | 89% | 89% | 86% | 86% | 86% | 86% | 86% | 89% | 89% | 89% |
| Antibody 5 | 93% | 93% | 93% | 93% | 93% | 93% | 93% | 89% | 89% | 89% | 89% | 89% | 93% | 93% | 93% |
| Antibody 6 | 100% | 100% | 100% | 100% | 100% | 100% | 100% | 96% | 96% | 96% | 96% | 96% | 100% | 100% | 100% |
| Antibody 7 | 86% | 86% | 86% | 86% | 86% | 86% | 86% | 82% | 82% | 82% | 82% | 82% | 86% | 86% | 86% |
| Antibody 8 | 86% | 86% | 86% | 86% | 86% | 86% | 86% | 82% | 82% | 82% | 82% | 82% | 86% | 86% | 86% |
| Antibody 9 | 89% | 89% | 89% | 89% | 89% | 89% | 89% | 86% | 86% | 86% | 86% | 86% | 89% | 89% | 89% |
| Antibody 10 | 93% | 93% | 93% | 93% | 93% | 93% | 93% | 89% | 89% | 89% | 89% | 89% | 93% | 93% | 93% |
| Antibody 11 | 93% | 93% | 93% | 93% | 93% | 93% | 93% | 89% | 89% | 89% | 89% | 89% | 93% | 93% | 93% |
| Antibody 12 | 93% | 93% | 93% | 93% | 93% | 93% | 93% | 89% | 89% | 89% | 89% | 89% | 93% | 93% | 93% |
| Antibody 13 | 93% | 93% | 93% | 93% | 93% | 93% | 93% | 89% | 89% | 89% | 89% | 89% | 93% | 93% | 93% |
| Antibody 14 | 89% | 89% | 89% | 89% | 89% | 89% | 89% | 86% | 86% | 86% | 86% | 86% | 89% | 89% | 89% |
| Antibody 15 | 89% | 89% | 89% | 89% | 89% | 89% | 89% | 86% | 86% | 86% | 86% | 86% | 89% | 89% | 89% |
| Antibody 16 | 89% | 89% | 89% | 89% | 89% | 89% | 89% | 86% | 86% | 86% | 86% | 86% | 89% | 89% | 89% |
| Antibody 17 | 86% | 86% | 86% | 86% | 86% | 86% | 86% | 82% | 82% | 82% | 82% | 82% | 86% | 86% | 86% |
| Antibody 18 | 86% | 86% | 86% | 86% | 86% | 86% | 86% | 82% | 82% | 82% | 82% | 82% | 86% | 86% | 86% |
| Antibody 19 | 86% | 86% | 86% | 86% | 86% | 86% | 86% | 82% | 82% | 82% | 82% | 82% | 86% | 86% | 86% |
| Antibody 20 | 100% | 100% | 100% | 100% | 100% | 100% | 100% | 96% | 96% | 96% | 96% | 96% | 100% | 100% | 100% |
| Antibody 21 | 96% | 96% | 96% | 96% | 96% | 96% | 96% | 100% | 93% | 93% | 100% | 93% | 96% | 96% | 96% |
| Antibody 22 | 100% | 100% | 100% | 100% | 100% | 100% | 100% | 96% | 96% | 96% | 96% | 96% | 100% | 100% | 100% |
| Antibody 23 | 100% | 100% | 100% | 100% | 100% | 100% | 100% | 96% | 96% | 96% | 96% | 96% | 100% | 100% | 100% |
| Antibody 24 | 96% | 96% | 96% | 96% | 96% | 96% | 96% | 93% | 100% | 100% | 93% | 100% | 96% | 96% | 96% |
| Antibody 24 PGL | 96% | 96% | 96% | 96% | 96% | 96% | 96% | 93% | 100% | 100% | 93% | 100% | 96% | 96% | 96% |
| Antibody 24 GL | 93% | 93% | 93% | 93% | 93% | 93% | 93% | 96% | 96% | 96% | 96% | 96% | 93% | 93% | 93% |
| Antibody 25 | 100% | 100% | 100% | 100% | 100% | 100% | 100% | 96% | 96% | 96% | 96% | 100% | 100% | 100% | 100% |
| Antibody 26 | 100% | 100% | 100% | 100% | 100% | 100% | 100% | 96% | 96% | 96% | 96% | 96% | 100% | 100% | 100% |
| Antibody 27 | 100% | 100% | 100% | 100% | 100% | 100% | 100% | 96% | 96% | 96% | 96% | 96% | 100% | 100% | 100% |
| Antibody 28 | 100% | 100% | 100% | 100% | 100% | 100% | 100% | 96% | 96% | 96% | 96% | 96% | 100% | 100% | 100% |
| Antibody 29 | - | 100% | 100% | 100% | 100% | 100% | 100% | 96% | 96% | 96% | 96% | 96% | 100% | 100% | 100% |
| Antibody 30 | | - | 100% | 100% | 100% | 100% | 100% | 96% | 96% | 96% | 96% | 96% | 100% | 100% | 100% |
| Antibody 31 | | | - | 100% | 100% | 100% | 100% | 96% | 96% | 96% | 96% | 96% | 100% | 100% | 100% |
| Antibody 32 | | | | - | 100% | 100% | 100% | 96% | 96% | 96% | 96% | 96% | 100% | 100% | 100% |
| Antibody 33 | | | | | - | 100% | 100% | 96% | 96% | 96% | 96% | 96% | 100% | 100% | 100% |
| Antibody 34 | | | | | | - | 100% | 96% | 96% | 96% | 96% | 96% | 100% | 100% | 100% |
| Antibody 35 | | | | | | | - | 96% | 96% | 96% | 96% | 96% | 100% | 100% | 100% |
| Antibody 36 | | | | | | | | - | 96% | 96% | 96% | 96% | 96% | 96% | 96% |
| Antibody 37 | | | | | | | | | - | 100% | 93% | 100% | 96% | 96% | 96% |
| Antibody 37GL | | | | | | | | | | - | 93% | 100% | 96% | 96% | 96% |
| Antibody 38 | | | | | | | | | | | - | 93% | 96% | 96% | 96% |
| Antibody 39 | | | | | | | | | | | | - | 96% | 96% | 96% |
| Antibody 40 | | | | | | | | | | | | | - | 100% | 100% |
| Antibody 41 | | | | | | | | | | | | | | - | 100% |
| Antibody 42 | | | | | | | | | | | | | | | - |

FIG 7A

| | Antibody 1 | Antibody 2 | Antibody 3 | Antibody 4 | Antibody 5 | Antibody 6 | Antibody 7 | Antibody 8 | Antibody 9 | Antibody 10 | Antibody 11 | Antibody 12 | Antibody 13 | Antibody 14 | Antibody 15 |
|---|---|---|---|---|---|---|---|---|---|---|---|---|---|---|---|
| Antibody 1 | - | 84% | 81% | 81% | 81% | 81% | 81% | 81% | 81% | 81% | 84% | 81% | 81% | 81% | 81% |
| Antibody 2 | 84% | - | 75% | 90% | 90% | 84% | 90% | 84% | 87% | 84% | 87% | 87% | 87% | 90% | 87% |
| Antibody 3 | | | - | 71% | 71% | 71% | 71% | 71% | 71% | 71% | 75% | 71% | 71% | 75% | 71% |
| Antibody 4 | | | | - | 100% | 87% | 100% | 87% | 84% | 87% | 84% | 84% | 87% | 87% | 84% |
| Antibody 5 | | | | | - | 87% | 100% | 87% | 84% | 87% | 84% | 84% | 87% | 87% | 84% |
| Antibody 6 | | | | | | - | 87% | 100% | 90% | 90% | 84% | 90% | 90% | 84% | 90% |
| Antibody 7 | | | | | | | - | 87% | 84% | 87% | 84% | 84% | 87% | 87% | 84% |
| Antibody 8 | | | | | | | | - | 90% | 90% | 84% | 90% | 90% | 84% | 90% |
| Antibody 9 | | | | | | | | | - | 87% | 90% | 100% | 93% | 87% | 90% |
| Antibody 10 | | | | | | | | | | - | 84% | 87% | 90% | 84% | 87% |
| Antibody 11 | | | | | | | | | | | - | 90% | 87% | 90% | 87% |
| Antibody 12 | | | | | | | | | | | | - | 93% | 87% | 90% |
| Antibody 13 | | | | | | | | | | | | | - | 87% | 90% |
| Antibody 14 | | | | | | | | | | | | | | - | 87% |
| Antibody 15 | | | | | | | | | | | | | | | - |
| Antibody 16 | | | | | | | | | | | | | | | |
| Antibody 17 | | | | | | | | | | | | | | | |
| Antibody 18 | | | | | | | | | | | | | | | |
| Antibody 19 | | | | | | | | | | | | | | | |
| Antibody 20 | | | | | | | | | | | | | | | |
| Antibody 21 | | | | | | | | | | | | | | | |
| Antibody 22 | | | | | | | | | | | | | | | |
| Antibody 23 | | | | | | | | | | | | | | | |
| Antibody 24 | | | | | | | | | | | | | | | |
| Antibody 24 PGL | | | | | | | | | | | | | | | |
| Antibody 25 | | | | | | | | | | | | | | | |
| Antibody 26 | | | | | | | | | | | | | | | |
| Antibody 27 | | | | | | | | | | | | | | | |
| Antibody 28 | | | | | | | | | | | | | | | |
| Antibody 29 | | | | | | | | | | | | | | | |
| Antibody 30 | | | | | | | | | | | | | | | |
| Antibody 31 | | | | | | | | | | | | | | | |
| Antibody 32 | | | | | | | | | | | | | | | |
| Antibody 33 | | | | | | | | | | | | | | | |
| Antibody 34 | | | | | | | | | | | | | | | |
| Antibody 35 | | | | | | | | | | | | | | | |
| Antibody 36 | | | | | | | | | | | | | | | |
| Antibody 37 | | | | | | | | | | | | | | | |
| Antibody 37 GL | | | | | | | | | | | | | | | |
| Antibody 38 | | | | | | | | | | | | | | | |
| Antibody 39 | | | | | | | | | | | | | | | |
| Antibody 40 | | | | | | | | | | | | | | | |
| Antibody 41 | | | | | | | | | | | | | | | |
| Antibody 42 | | | | | | | | | | | | | | | |

FIG 7B

| | Antibody 16 | Antibody 17 | Antibody 18 | Antibody 19 | Antibody 20 | Antibody 21 | Antibody 22 | Antibody 23 | Antibody 24 | Antibody 24 PGL | Antibody 24 GL | Antibody 25 | Antibody 26 | Antibody 27 | Antibody 28 |
|---|---|---|---|---|---|---|---|---|---|---|---|---|---|---|---|
| Antibody 1 | 81% | 81% | 84% | 81% | 81% | 81% | 81% | 75% | 81% | 81% | 81% | 78% | 81% | 81% | 78% |
| Antibody 2 | 84% | 84% | 87% | 84% | 81% | 81% | 81% | 75% | 81% | 81% | 81% | 78% | 81% | 81% | 78% |
| Antibody 3 | 71% | 75% | 75% | 71% | 71% | 71% | 71% | 65% | 71% | 71% | 71% | 71% | 71% | 71% | 71% |
| Antibody 4 | 87% | 87% | 87% | 87% | 81% | 81% | 81% | 75% | 81% | 81% | 81% | 78% | 81% | 81% | 78% |
| Antibody 5 | 87% | 87% | 87% | 87% | 81% | 81% | 81% | 75% | 81% | 81% | 81% | 78% | 81% | 81% | 78% |
| Antibody 6 | 100% | 87% | 90% | 100% | 84% | 84% | 84% | 78% | 84% | 84% | 84% | 81% | 84% | 84% | 78% |
| Antibody 7 | 87% | 87% | 87% | 87% | 81% | 81% | 81% | 75% | 81% | 81% | 81% | 78% | 81% | 81% | 78% |
| Antibody 8 | 100% | 87% | 90% | 100% | 84% | 84% | 84% | 78% | 84% | 84% | 84% | 81% | 84% | 84% | 78% |
| Antibody 9 | 90% | 84% | 90% | 90% | 84% | 84% | 84% | 78% | 84% | 84% | 84% | 81% | 84% | 84% | 78% |
| Antibody 10 | 90% | 90% | 87% | 90% | 87% | 87% | 87% | 81% | 87% | 87% | 87% | 84% | 87% | 87% | 81% |
| Antibody 11 | 84% | 87% | 84% | 84% | 81% | 81% | 81% | 75% | 81% | 81% | 81% | 78% | 81% | 81% | 81% |
| Antibody 12 | 90% | 84% | 90% | 90% | 84% | 84% | 84% | 78% | 84% | 84% | 84% | 81% | 84% | 84% | 78% |
| Antibody 13 | 90% | 84% | 90% | 90% | 84% | 84% | 84% | 78% | 84% | 84% | 84% | 81% | 84% | 84% | 78% |
| Antibody 14 | 84% | 87% | 84% | 84% | 81% | 81% | 81% | 75% | 81% | 81% | 81% | 78% | 81% | 81% | 81% |
| Antibody 15 | 90% | 84% | 87% | 90% | 84% | 84% | 84% | 78% | 84% | 84% | 84% | 81% | 84% | 84% | 78% |
| Antibody 16 | - | 84% | 90% | 100% | 84% | 84% | 84% | 78% | 84% | 84% | 84% | 81% | 84% | 84% | 78% |
| Antibody 17 | | - | 84% | 87% | 84% | 84% | 84% | 78% | 84% | 84% | 84% | 81% | 84% | 84% | 84% |
| Antibody 18 | | | - | 90% | 84% | 84% | 84% | 78% | 84% | 84% | 84% | 81% | 84% | 84% | 78% |
| Antibody 19 | | | | - | 84% | 84% | 84% | 78% | 84% | 84% | 84% | 81% | 84% | 84% | 78% |
| Antibody 20 | | | | | - | 100% | 100% | 93% | 100% | 100% | 100% | 96% | 100% | 100% | 93% |
| Antibody 21 | | | | | | - | 100% | 93% | 100% | 100% | 100% | 96% | 100% | 100% | 93% |
| Antibody 22 | | | | | | | - | 93% | 100% | 100% | 100% | 96% | 100% | 100% | 93% |
| Antibody 23 | | | | | | | | - | 93% | 93% | 93% | 90% | 93% | 93% | 87% |
| Antibody 24 | | | | | | | | | - | 100% | 100% | 96% | 100% | 100% | 93% |
| Antibody 24 PGL | | | | | | | | | | - | 100% | 96% | 100% | 100% | 93% |
| Antibody 24 GL | | | | | | | | | | | - | 96% | 100% | 100% | 93% |
| Antibody 25 | | | | | | | | | | | | - | 96% | 96% | 90% |
| Antibody 26 | | | | | | | | | | | | | - | 100% | 93% |
| Antibody 27 | | | | | | | | | | | | | | - | 93% |
| Antibody 28 | | | | | | | | | | | | | | | - |
| Antibody 29 | | | | | | | | | | | | | | | |
| Antibody 30 | | | | | | | | | | | | | | | |
| Antibody 31 | | | | | | | | | | | | | | | |
| Antibody 32 | | | | | | | | | | | | | | | |
| Antibody 33 | | | | | | | | | | | | | | | |
| Antibody 34 | | | | | | | | | | | | | | | |
| Antibody 35 | | | | | | | | | | | | | | | |
| Antibody 36 | | | | | | | | | | | | | | | |
| Antibody 37 | | | | | | | | | | | | | | | |
| Antibody 37 GL | | | | | | | | | | | | | | | |
| Antibody 38 | | | | | | | | | | | | | | | |
| Antibody 39 | | | | | | | | | | | | | | | |
| Antibody 40 | | | | | | | | | | | | | | | |
| Antibody 41 | | | | | | | | | | | | | | | |
| Antibody 42 | | | | | | | | | | | | | | | |

FIG 7C

| | Antibody 29 | Antibody 30 | Antibody 31 | Antibody 32 | Antibody 33 | Antibody 34 | Antibody 35 | Antibody 36 | Antibody 37 | Antibody 37 GL | Antibody 38 | Antibody 39 | Antibody 40 | Antibody 41 | Antibody 42 |
|---|---|---|---|---|---|---|---|---|---|---|---|---|---|---|---|
| Antibody 1 | 81% | 81% | 75% | 81% | 81% | 81% | 81% | 78% | 75% | 75% | 81% | 81% | 78% | 75% | 81% |
| Antibody 2 | 81% | 81% | 75% | 81% | 81% | 81% | 81% | 78% | 75% | 75% | 81% | 81% | 78% | 75% | 81% |
| Antibody 3 | 75% | 71% | 71% | 75% | 71% | 71% | 75% | 71% | 68% | 68% | 71% | 75% | 71% | 65% | 71% |
| Antibody 4 | 81% | 81% | 75% | 81% | 81% | 81% | 81% | 78% | 75% | 75% | 81% | 81% | 78% | 75% | 81% |
| Antibody 5 | 81% | 81% | 75% | 81% | 81% | 81% | 81% | 78% | 75% | 75% | 81% | 81% | 78% | 75% | 81% |
| Antibody 6 | 81% | 84% | 75% | 84% | 84% | 84% | 81% | 81% | 75% | 75% | 84% | 84% | 81% | 78% | 84% |
| Antibody 7 | 81% | 81% | 75% | 81% | 81% | 81% | 81% | 78% | 75% | 75% | 81% | 81% | 78% | 75% | 81% |
| Antibody 8 | 81% | 84% | 75% | 84% | 84% | 84% | 81% | 81% | 75% | 75% | 84% | 84% | 81% | 78% | 84% |
| Antibody 9 | 81% | 84% | 75% | 84% | 84% | 84% | 81% | 81% | 75% | 75% | 84% | 84% | 81% | 78% | 84% |
| Antibody 10 | 84% | 87% | 78% | 84% | 87% | 87% | 84% | 84% | 78% | 78% | 87% | 84% | 84% | 81% | 84% |
| Antibody 11 | 84% | 81% | 75% | 81% | 81% | 81% | 84% | 78% | 75% | 75% | 81% | 81% | 78% | 75% | 81% |
| Antibody 12 | 81% | 84% | 75% | 84% | 84% | 84% | 81% | 81% | 75% | 75% | 84% | 84% | 81% | 78% | 84% |
| Antibody 13 | 81% | 84% | 75% | 84% | 84% | 84% | 81% | 81% | 75% | 75% | 84% | 84% | 81% | 78% | 84% |
| Antibody 14 | 84% | 81% | 78% | 81% | 81% | 81% | 81% | 78% | 78% | 78% | 81% | 81% | 78% | 75% | 81% |
| Antibody 15 | 81% | 84% | 75% | 84% | 84% | 84% | 81% | 81% | 75% | 75% | 84% | 84% | 81% | 78% | 84% |
| Antibody 16 | 81% | 84% | 75% | 84% | 84% | 84% | 81% | 81% | 75% | 75% | 84% | 84% | 81% | 78% | 84% |
| Antibody 17 | 87% | 84% | 81% | 81% | 84% | 84% | 87% | 81% | 81% | 81% | 84% | 81% | 81% | 78% | 81% |
| Antibody 18 | 81% | 84% | 75% | 84% | 94% | 84% | 81% | 81% | 75% | 75% | 84% | 84% | 81% | 78% | 84% |
| Antibody 19 | 81% | 84% | 75% | 84% | 84% | 84% | 81% | 81% | 75% | 75% | 84% | 84% | 81% | 78% | 84% |
| Antibody 20 | 96% | 100% | 90% | 96% | 100% | 100% | 96% | 96% | 90% | 90% | 100% | 96% | 96% | 93% | 96% |
| Antibody 21 | 96% | 100% | 90% | 96% | 100% | 100% | 96% | 96% | 90% | 90% | 100% | 96% | 96% | 93% | 96% |
| Antibody 22 | 96% | 100% | 90% | 96% | 100% | 100% | 96% | 96% | 90% | 90% | 100% | 96% | 96% | 93% | 96% |
| Antibody 23 | 90% | 93% | 84% | 90% | 93% | 93% | 90% | 90% | 84% | 84% | 93% | 90% | 90% | 87% | 90% |
| Antibody 24 | 96% | 100% | 90% | 96% | 100% | 100% | 96% | 96% | 90% | 90% | 100% | 96% | 96% | 93% | 96% |
| Antibody 24 PGL | 96% | 100% | 90% | 96% | 100% | 100% | 96% | 96% | 90% | 90% | 100% | 96% | 96% | 93% | 96% |
| Antibody 24 GL | 96% | 100% | 90% | 96% | 100% | 100% | 96% | 96% | 90% | 90% | 100% | 96% | 96% | 93% | 96% |
| Antibody 25 | 93% | 96% | 93% | 93% | 96% | 96% | 93% | 93% | 87% | 87% | 96% | 93% | 93% | 90% | 93% |
| Antibody 26 | 96% | 100% | 90% | 96% | 100% | 100% | 96% | 96% | 90% | 90% | 100% | 96% | 96% | 93% | 96% |
| Antibody 27 | 96% | 100% | 90% | 96% | 100% | 100% | 96% | 96% | 90% | 90% | 100% | 96% | 96% | 93% | 96% |
| Antibody 28 | 96% | 93% | 96% | 90% | 93% | 93% | 96% | 90% | 96% | 96% | 93% | 90% | 90% | 87% | 90% |
| Antibody 29 | - | 96% | 93% | 93% | 96% | 96% | 100% | 93% | 93% | 93% | 96% | 93% | 93% | 90% | 93% |
| Antibody 30 | 96% | - | 90% | 96% | 100% | 100% | 96% | 96% | 90% | 90% | 100% | 96% | 96% | 93% | 96% |
| Antibody 31 | 93% | 90% | - | 87% | 90% | 90% | 93% | 87% | 93% | 93% | 90% | 87% | 87% | 84% | 87% |
| Antibody 32 | 93% | 96% | 87% | - | 96% | 96% | 93% | 93% | 87% | 87% | 96% | 93% | 93% | 90% | 93% |
| Antibody 33 | 96% | 100% | 90% | 96% | - | 100% | 96% | 96% | 90% | 90% | 100% | 96% | 96% | 93% | 96% |
| Antibody 34 | 96% | 100% | 90% | 96% | 100% | - | 96% | 96% | 90% | 90% | 100% | 96% | 96% | 93% | 96% |
| Antibody 35 | 100% | 96% | 93% | 93% | 96% | 96% | - | 93% | 93% | 93% | 96% | 93% | 93% | 90% | 93% |
| Antibody 36 | 93% | 96% | 87% | 93% | 96% | 96% | 93% | - | 87% | 87% | 96% | 93% | 93% | 90% | 93% |
| Antibody 37 | 93% | 90% | 93% | 87% | 90% | 90% | 93% | 87% | - | 100% | 90% | 87% | 87% | 84% | 87% |
| Antibody 37 GL | 93% | 90% | 93% | 87% | 90% | 90% | 93% | 87% | 100% | - | 90% | 87% | 87% | 84% | 87% |
| Antibody 38 | 96% | 100% | 90% | 96% | 100% | 100% | 96% | 96% | 90% | 90% | - | 96% | 96% | 93% | 96% |
| Antibody 39 | 93% | 96% | 87% | 93% | 96% | 96% | 93% | 93% | 87% | 87% | 96% | - | 93% | 90% | 93% |
| Antibody 40 | 93% | 96% | 87% | 93% | 96% | 96% | 93% | 93% | 87% | 87% | 96% | 93% | - | 90% | 93% |
| Antibody 41 | 90% | 93% | 84% | 90% | 93% | 93% | 90% | 90% | 84% | 84% | 93% | 90% | 90% | - | 90% |
| Antibody 42 | 93% | 96% | 87% | 93% | 96% | 96% | 93% | 93% | 87% | 87% | 96% | 93% | 93% | 90% | - |

BINDING MEMBERS FOR INTERLEUKIN-4 RECEPTOR ALPHA (IL-4Rα)-173

This application is entitled to priority pursuant to U.S.C. 35 §119(e) to U.S. Provisional Application Ser. No. 61/015,869, filed Dec. 21, 2007, which is incorporated herein by reference in its entirety.

This invention relates to binding members for interleukin (IL)-4 receptor alpha (IL-4Rα, also referred to as CD 124), especially antibody molecules, and their therapeutic use e.g. in treating or preventing disorders associated with IL-4Rα, IL-4 and/or IL-13, examples of which are asthma and COPD.

The human IL-4Rα subunit (Swiss Prot accession number P24394) is a 140 kDa type 1 membrane protein that binds human IL-4 with a high affinity (Andrews et al J. Biol. Chem. (2002) 277:46073-46078). The IL-4/IL-4Rα complex can dimerize with either the common gamma chain (γc, CD132) or the IL-13Ralpha1 (IL-13Rα1) subunit, via domains on IL-4, to create two different signalling complexes, commonly referred to as Type I and Type II receptors, respectively. Alternatively, IL-13 can bind IL-13Rα1 to form an IL-13/IL-13Rα1 complex that recruits the IL-4Rα subunit to form a Type II receptor complex. Thus, IL-4Rα mediates the biological activities of both IL-4 and IL-13 (reviewed by Gessner et al, Immunobiology, 201:285, 2000). In vitro studies have shown that IL-4 and IL-13 activate effector functions in a number of cell types, for example in T cells, B cells, eosinophils, mast cells, basophils, airway smooth muscle cells, respiratory epithelial cells, lung fibroblasts, and endothelial cells (reviewed by Steinke et al, Resp Res, 2:66, 2001, and by Willis-Karp, Immunol Rev, 202:175, 2004).

IL-4Rα is expressed in low numbers (100-5000 molecules/cell) on a variety of cell types (Lowenthal et al, J Immunol, 140:456, 1988), e.g. peripheral blood T cells, monocytes, airway epithelial cells, B cells and lung fibroblasts. The type I receptor predominates in hematopoietic cells, whereas the type II receptor is expressed on both hematopoietic cells and non-hematopoietic cells.

IL-4Rα polymorphisms in the human population have been described (reviewed by Gessner et al, Immunobiology, 201:285, 2000) and association with IgE levels or clinical atopy has been reported in some populations. For instance, V75R576 IL-4Rα is associated with allergic asthma and enhanced IL-4Rα function (Risma et al. J. Immunol. 169(3): 1604-1610, 2002).

Several lines of evidence support an important role for the IL-4/IL-13 pathway in asthma pathology (reviewed by Chatila, Trends in Molecular Med, 10:493, 2004), and also in a range of other conditions, as listed elsewhere herein. Increased secretion of IL-4 and IL-13 are believed to both initiate and maintain the disease process. IL-13 is thought to be the dominant partner in triggering airway hyperresponsiveness (AHR), mucus hypersecretion and airway remodelling, whereas IL-4 is has been suggested to be the main inducer of Th2 polarisation and IgE production (Wynn, Annu Rev Immunol, 21: 425, 2003).

The role of IL-4Rα in asthma is further supported by evidence from animal models of disease. Administration of a functional murine IL-4R antagonist (IL-4 mutant; C118 deletion) during allergen challenge with ovalbumin (OVA, a model allergen) inhibited the development of allergic airway eosinophilia and AHR in mice previously sensitized with OVA (Tomkinson et al J. Immunol. 166(9):5792-5800, 2001). Furthermore, a number of in vivo studies have demonstrated positive effects of blocking either IL-13 or IL-4 in animal models of asthma. For instance, therapeutic dosing with an anti-IL-13 mAb in a chronic model of OVA-induced persistent airway inflammation inhibited AHR, halted progression of subepithelial fibrosis and inflammation and restored mucus hyperplasia to basal levels (Yang et al., J. Pharmacol. Exp. Ther. 313(1):8-15, 2005). In a mouse OVA model, inhibition of IL-4 by an anti-IL-4 antibody showed a marked reduction in eosinophil infiltration when administered during immunization (Coyle et al., Am J Resp Cell Mol Biol, 13:54, 1995). In a similar model, IL-4-deficient mice had substantially fewer eosinophils in bronchoalveolar lavage and much less peribronchial inflammation after OVA challenge (Brusselle et al., Clin Exp Allergy, 24:73, 1994).

In humans, phase IIa studies showed that an IL-4Rα antagonist (a so-called IL-4 mutein) reduced an allergen-induced late asthmatic response and attenuated the resting inflammatory status of the lungs in asthma patients (Wenzel et al., Lancet, 370:1422, 2007). These human data further strengthen the notion that an IL-4Rα antagonist may provide clinical utility in asthma.

In addition to its role in asthma, IL-4Rα has been linked with a number of other pathologies, e.g. as follows:

Chronic Obstructive Pulmonary Disease (COPD) includes patient populations with varying degrees of chronic bronchitis, small airway disease and emphysema and is characterised by progressive irreversible lung function decline that responds poorly to current asthma based therapy. The underlying causes of COPD remain poorly understood. The "Dutch hypothesis" proposes that there is a common susceptibility to COPD and asthma and therefore, that similar mechanisms may contribute to the pathogenesis of both disorders (Sluiter et al., Eur Respir J, 4(4): p. 479-89, 1991). Zheng et al (J Clin Invest, 106(9):1081-93, 2000) have demonstrated that over-expression of IL-13 in the mouse lung caused emphysema, elevated mucus production and inflammation, reflecting aspects of human COPD. Furthermore, AHR, an IL-13 dependent response in murine models of allergic inflammation, has been shown to be predictive of lung function decline in smokers (Tashkin et al., Am J Respir Crit. Care Med, 153(6 Pt 1):1802-11, 1996). A link has also been established between an IL-13 promoter polymorphism and susceptibility to develop COPD (Van Der Pouw Kraan et al., Genes Immun, 3(7): 436-9, 2002). The signs are therefore that IL-4/IL-13 pathway, and in particular IL-13, plays an important role in the pathogenesis of COPD.

IL-13 may play a role in the pathogenesis of inflammatory bowel disease. Heller et al. (Heller et al., Immunity, 17(5): 629-38, 2002) report that neutralisation of IL-13 by administration of soluble IL-13R.alpha.2 ameliorated colonic inflammation in a murine model of human ulcerative colitis. Correspondingly, IL-13 expression was higher in rectal biopsy specimens from ulcerative colitis patients when compared to controls (Inoue et al., Am J Gastroenterol, 94(9): 2441-6, 1999).

In addition to asthma, the IL-4/Il-13 pathway has been linked to other fibrotic conditions, like systemic sclerosis (Hasegawa et al., J Rheumatol, 24(2):328-32, 1997), pulmonary fibrosis (Hancock et al., Am J Respir Cell Mol Biol, 18(1): 60-5, 1998), parasite-induced liver fibrosis (Fallon et al., J Immunol, 164(5): 2585-91, 2000; Chiaramonte et al, J Clin Invest, 104(6): 777-85, 1999; Chiaramonte Hepatology 34(2):273-82, 2001), and cystic fibrosis (Hauber et al., J. Cyst Fibr, 2:189, 2003).

IL-4 and to some extent IL-13, are crucial for B cell mediated activities, such as B cell proliferation, immunoglobulin secretion, and expression of FcepsilonR. Clinical applications of an IL-4Rα inhibitor include for example, use in allergy therapy to suppress IgE synthesis (including for example atopic dermatitis and food allergy), use in transplation therapy to prevent transplant rejection, as well as suppression of delayed-type hypersensitivity or contact hypersensitivity reactions.

Il-4R antagonists may also find use as adjuvants to allergy immunotherapy and as vaccine adjuvants.

Antibodies to IL-4Rα have been described. Two examples are the neutralizing murine anti-IL-4Rα monoclonal antibodies MAB230 (clone 25463) and 16146 (clone 25463.11) which are supplied by R&D Systems (Minneapolis, Minn.) and Sigma (St Louis, Mo.), respectively. These antibodies are of the IgG2a subtype and were developed from mouse hybridomas developed from mice immunised with purified recombinant human IL-4Rα (baculovirus-derived). Two further neutralizing murine anti-IL-4Rα antibodies M57 and X2/45-12 are supplied by BD Biosciences (Franklin Lakes, N.J.) and eBioscience (San Diego, Calif.), respectively. These are IgG1 antibodies and are also produced by mouse hybridomas developed from mice immunized with recombinant soluble IL-4Rα.

Fully human antibodies are likely to be of better clinical utility than murine or chimeric antibodies. This is because human anti-mouse antibodies (HAMA) directed against the FC part of the mouse immunoglobulin are often produced, resulting in rapid clearance and possible anaphylactic reaction (Brochier et al., Int. J. Immunopharm., 17:41-48, 1995). Although chimeric antibodies (mouse variable regions and human constant regions) are less immunogenic than murine mAbs, human anti-Chimeric antibody (HACA) responses have been reported (Bell and Kamm, Aliment. Pharmacol. Ther., 14:501-514, 2000).

WO 01/92340 (Immunex) describes human monoclonal antibodies against IL-4 receptor generated by procedures involving immunization of transgenic mice with soluble IL-4R peptide and the creation of hybridoma cell lines that secrete antibodies to IL-4R, the principal antibody 12B5 is disclosed as being an IgG1 antibody and fully human. WO 05/047331 (Immunex) discloses further antibodies derived from 12B5 (renamed H1L1) via oligonucleotide mutagenesis of the VH region. Each mutated VH chain was paired with one of 6 distinct VL chains to create a small repertoire of antibody molecules.

WO 07/082,068 (Aerovance) discloses a method of treating asthma comprising administering a mutant human IL-4 protein having substitutions of R121D and Y124D. The specification teaches that such IL4 mutein administered in a pharmaceutical composition can antagonise the binding of wild type huIL-4 and wild type huIL-13 to receptors.

WO 08/054,606 (Regeneron) discloses particular antibodies against human IL-4R that were raised in transgenic mice capable of producing human antibodies.

There are advantages and benefits in the discovery and development of an antibody to human IL-4Rα that also exhibits cross-reactivity to the orthologous protein from another species, for example cynomolgus monkey. Such an antibody would facilitate the characterization of such antibodies with respect to pharmacology and safety in vivo. Potency or affinity to another species, which is for example less than 10-fold different than the human activity may be appropriate for such an evaluation. However, the human IL-4Rα protein displays a relatively little similarity to the orthologous IL-4Rα protein from other species except chimpanzee. Therefore, the discovery of high affinity and potency antibodies appropriate for clinical use with cross-reactivity to a species widely considered suitable for safety and toxicological evaluation for clinical development would be very challenging.

Through appropriately designed selection techniques and assays, the inventors have developed binding members for IL-4Rα that inhibit the biological activity of human and cynomolgus monkey IL-4Rα.

As detailed in the Examples, from an initial lead identification program the inventors selected a single antibody molecule to human IL-4Rα that also exhibited some, but weak, binding to and functional neutralisation of, cynomolgus IL-4Rα. Following a planned and defined process of targeted and random mutagenesis and further selection of mutants from this parent antibody molecule, a larger panel of antibody molecules with greatly improved properties was developed. VH and VL regions, including the complementarity determining regions (CDRs) of the parent antibody (Antibody 1), and of the optimised antibodies, are shown in FIGS. 1, 2, 3 and 4. These antibody molecules, VH, VL, CDRs, and binding members comprising one or more of the CDRs, form aspects of the present invention.

In addition to wild-type IL-4Rα the binding members of the present invention have also been found to bind 175V IL-4Rα, a common human variant.

Described herein are binding members that neutralise the biological effects of IL-4Rα with high potency, bind IL-4Rα with high affinity and inhibit signalling induced by IL-4 and IL-13. Notably, the binding members inhibit signalling from the high affinity complexes e.g. IL-4:IL-4Rα:γc, IL-4:IL-4Rα:IL-13Rα1, IL-13 IL-13Rα1:IL-4Rα. Such action prevents signalling of both IL-4 and IL-13. Additionally, the data indicate that the binding members inhibit interaction and signalling of IL-4Rα type 1 and type 2 complexes. These and other properties and effects of the binding members are described in further detail below.

The binding members are useful for treating disorders in which IL-4Rα, IL-4 or IL-13 are expressed, e.g., one or more of the IL-4Rα-, IL-4- or IL-13-related disorders referred to elsewhere herein, such as asthma or COPD.

As described elsewhere herein, binding of a binding member to IL-4Rα may be determined using surface plasmon resonance e.g. BIAcore.

Surface plasmon resonance data may be fitted to a 1:1 Langmuir binding model (simultaneous ka kd) and an affinity constant KD calculated from the ratio of rate constants kd1/ka1. A binding member of the invention may have a monovalent affinity for binding human IL-4Rα that is less than 20 nM. In other embodiments the monovalent affinity for binding human IL-4Rα that is less than 10 nM, e.g. less than 8, less than 5 nM. In other embodiments the binding member also binds cynomolgus IL-4Rα. In one embodiment, a binding member of the present invention has a monovalent affinity for binding human IL-4Rα in the range 0.05 to 12 nM. In one embodiment, a binding member of the present invention has a monovalent affinity for binding human IL-4Rα in the range of 0.1 to 5 nM. In one embodiment, a binding member of the present invention has a monovalent affinity for binding human IL-4Rα in the range of 0.1 to 2 nM.

In one embodiment, a binding member of the invention may immunospecifically bind to human IL-4Rα and may have an affinity (KD) of less than 5000 pM, less than 4000 pM, less than 3000 pM, less than 2500 pM, less than 2000 pM, less than 1500 pM, less than 1000 pM, less than 750 pM, less than 500 pM, less than 250 pM, less than 200 pM, less than 150 pM, less than 100 pM, less than 75 pM as assessed using a method described herein or known to one of skill in the art (e.g., a BIAcore assay, ELISA) (Biacore International AB, Uppsala, Sweden).

In a specific embodiment, a binding member of the invention may immunospecifically bind to human IL-4Rα and may have an affinity (KD) of between 25 to 5000 pM, 25 to 4000 pM, 25 to 3500 pM, 25 to 3000 pM, 25 to 2500 pM, 25 to 2000 pM, 25 to 1500 pM, 25 to 1000 pM, 25 to 750 pM, 25 to 500 pM, 25 to 250 pM, 25 to 100 pM, 25 to 75 pM, 25 to 50 pM as assessed using a method described herein or known to one of skill in the art (e.g., a BIAcore assay, ELISA). In another embodiment, an anti-IL-4Rα binding member (including an antibody) of the invention may immunospecifically bind to bind to human IL-4Rα and may have an affinity (KD) of 500 pM, 100 pM, 75 pM or 50 pM as assessed using a method described herein or known to one of skill in the art (e.g., a BIAcore assay, ELISA).

As described in more detail in the Examples, binding members according to the invention neutralise IL-4Rα with high potency. Neutralisation means inhibition of a biological activity mediated by IL-4Rα. Binding members of the invention may neutralise one or more activities mediated by IL-4Rα. The inhibited biological activity is likely mediated by prevention of IL-4Rα forming a signalling complex with gamma chain (or IL-13Rα) and either of the associated soluble ligands, e.g. IL-4 or IL-13.

Neutralisation of IL-4 or IL-13 signalling through its IL-4Rα containing receptor complex may be measured by inhibition of IL-4 or IL-13 stimulated TF-1 cell proliferation.

The epitope of human IL4Rα to which the antibodies of the invention bind was located by a combination of mutagenesis and domain swapping. Whole domain swap chimeras localised the epitope to domain 1 (D1) of human IL4Rα (residues M1-E119). Human IL-4Rα contains five loop regions, which are in close proximity to IL4 in a crystal structure (Hage et al., Cell 97:271-281, 1999). Loop swap chimeras enabled the further localisation of the human IL-4Rα epitope bound by an antibody of the invention, to a major component in loop 3 (residues L89-N98) and a minor component in loop 2 (residues V65-H72). Chimeras without human loop 3 failed to inhibit human IL-4Rα binding to antibody and chimeras without loop 2 gave a 100 fold higher $IC_{50}$ than human IL-4Rα (Table 5). Consistent with the domain swap data both loop2 and loop3 are located in domain 1 (D1) (Hage et al., Cell 97:271-281, 1999).

The antibody epitope was located to a discontinuous epitope of 18 amino acids in two loop regions of human IL-4Rα; V65-H72 and L89-N98. The epitope can be further localised to amino acid residues L67 and L68 of loop 2 and D92 and V93 of loop3 (see SEQ ID NO: 454 or 460 for location of residues 67, 68, 92 and 93). The D92 residues was the most important, followed by V93, for the antibody tested was still capable of binding chimeric IL-4Rα that lacked the L67 and/or L68 residues in loop2. Of course it is likely that the antibodies of the invention will also bind residues of the human IL-4Rα protein in addition to one of L67, L68, D92 and V93.

According to one aspect of the invention there is provided an isolated binding member capable of binding to human interleukin-4 receptor alpha (hIL-4Rα) at least one amino acid residue selected from the amino acid at position 67, 68, 92 and 93, according to the position in SEQ ID NO: 460. According to one aspect of the invention there is provided an isolated binding member capable of binding to at least one of amino acid residues 67, 68, 92 and 93, according to the position in SEQ ID NO: 460, of native human interleukin-4 receptor alpha (hIL-4Rα). In a particular embodiment the isolated binding member is capable of binding to the amino acid at position 92 of hIL-4Rα, according to the position in SEQ ID NO: 460. In another embodiment the isolated binding member is capable of binding to D92 and at least one other residue selected from L67, L68 and V93. In another embodiment the isolated binding member is capable of binding to D92 and V93. In another embodiment the isolated binding member is capable of binding to D92, V93 and either of L67 or L68. In another embodiment the antibody is capable of binding to each of L67, L68, D92 and V93. Each of these embodiments refers to amino acid positions in hIL-4Rα whose locations can be identified according to the hIL-4Rα amino acid sequence (from positions 1-229) depicted in SEQ ID NO: 460. In one embodiment the binding member is able to bind to the recited epitope residues (i.e. at least one of positions 67, 68, 92 and 93) of full-length hIL-4Rα. In one embodiment the binding member is able to bind to the recited epitope residues (i.e. at least one of positions 67, 68, 92 and 93) of native hIL-4Rα expressed on the cell surface. In one embodiment the binding member is able to bind to the recited epitope residues (i.e. at least one of positions 67, 68, 92 and 93) of recombinantly expressed full-length (229 amino acid) hIL-4Rα.

According to a further aspect of the invention there is provided an isolated binding member capable of binding human interleukin-4 receptor alpha (hIL-4Rα). In a particular embodiment the binding member is a human antibody. In a further embodiment the binding member is also capable of binding cynomolgus monkey interleukin-4 receptor alpha (cyIL-4Rα).

According to another aspect of the invention there is provided an isolated binding member for human interleukin-4 receptor alpha (hIL-4Rα), which binding member has an $IC_{50}$ geomean for inhibition of human IL-4 (hIL-4) induced cell proliferation of less than 50 pM in TF-1 proliferation assay using 18 pM soluble human IL-4 protein and which binding member is also capable of binding cyIL-4Rα.

In particular embodiments of this aspect of the invention the binding member has an $IC_{50}$ geomean for inhibition of human IL-4 (hIL-4) induced cell proliferation of less than 50 pM, less than 35 pM, less than 25 pM, or less than 20 pM, in a TF-1 proliferation assay using 18 pM of soluble human IL-4. In particular embodiments the binding member of the invention has an $IC_{50}$ geomean for inhibition of human IL-4 (hIL-4) induced cell proliferation of between 1 to 50 pM, 1 to 35 pM, 2 to 30 pM, 2 to 25 pM, 2 to 12 pM, using 18 pM of soluble human IL-4 in a method described herein (e.g. Example 3.2.1) or known to one of skill in the art.

Binding to cyIL-4Rα can be measured by any suitable means.

Similarly, binding members within the scope of the invention have an $IC_{50}$ geomean for inhibition of human IL-13 (hIL-13)-mediated TF-1 proliferation (via neutralisation of hIL-4Rα) of less than 200 pM using 400 pM soluble human IL-13 (hIL-13). In a particular embodiment the $IC_{50}$ geomean for inhibition of human IL-13 (hIL-13)-mediated TF-1 proliferation (via neutralisation of hIL-4Rα) using 400 pM soluble human IL-13 (hIL-13) is between 5 and 75 pM or between 5 and 45 pM.

In particular embodiments, the binding members of the invention are substantially incapable of binding to murine IL-4Rα. By this we mean that a binding member of the invention is capable of at least 500-fold (such as at least 500-fold, at least 1000-fold, at least 1500-fold, at least 2000-fold, at least 3000-fold, at least 4000-fold) greater binding to human interleukin-4 receptor alpha than to murine IL-4Rα (i.e. binding to murine IL-4Rα is at least 500 fold weaker than to human IL-4Rα). This can be measured, for example, by the HTRF competition assay as disclosed in Example 5.1.2.

Geomean (also known as geometric mean), as used herein means the average of the logarithmic values of a data set, converted back to a base 10 number. This requires there to be at least two measurements, e.g. at least 2, preferably at least 5, more preferably at least 10 replicate. The person skilled in the art will appreciate that the greater the number of replicates the more robust the geomean value will be. The choice of replicate number can be left to the discretion of the person skilled in the art.

Inhibition of biological activity may be partial or total. In specific embodiments, binding members are provided that inhibit IL-4Rα biological activity by at least 95%, at least 90%, at least 85%, at least 80%, at least 75%, at least 70%, at least 60%, or at least 50% of the activity in the absence of the binding member. The degree to which a binding member neutralises IL-4Rα is referred to as its neutralising potency. Potency may be determined or measured using one or more assays known to the skilled person and/or as described or referred to herein. For example, potency may be assayed in:

Receptor-ligand binding assays in fluorescent (e.g. HTRF or DELFIA) or radioactive format Fluorescent (e.g. HTRF or DELFIA) epitope competition assay Cell-based functional assays including STAT6 Phosphorylation of human or cynomolgous PBMCs, proliferation of TF-1 cells, eotaxin release from human or cynomolgous fibroblast cell lines, VCAM-1 upregulation on human endothelial vein cells or proliferation of human T-cells.

Some of these assays methods are also described in the Examples.

Neutralising potency of a binding member as calculated in an assay using IL-4Rα from a first species (e.g. human) may be compared with neutralising potency of the binding member in the same assay using IL-4Rα from a second species (e.g. cynomolgus monkey), in order to assess the extent of cross-reactivity of the binding member for IL-4Rα of the two species. There are great advantages in having a binding member, e.g. an antibody or antibody fragment, which binds both the human target and the orthologous target from another species. A key advantage arises when the binding-member is being advanced as a therapeutic product and safety studies (e.g. toxicity) need to be conducted in another species. Potency or affinity to another species, which is for example less than 10-fold different than the human activity may be appropriate for such an evaluation.

There are various ways of determining the ratio of binding of the binding members of the present invention to the human and the "other species'" (e.g. cynomologus monkey) IL-4Rα. One method is the receptor-ligand binding assay, such as that used in Example 4.3.

According to a particular embodiment of the binding members of the present invention the ratio of binding of the binding member when as a scFv to hIL-4Rα and to cyIL-4Rα measured using the receptor-ligand binding assay is at least 6:1. As used here, "at least" 6:1, includes 8:1, 10:1 etc; rather than 2:1, 1:1.

Binding members of the invention bind human IL-4Rα and cynomolgus monkey IL-4Rα, and may have a less than 250-fold, e.g. less than 150-, 100-, 75-, 50-, 25-, 20-, 15-, 10-fold difference in potency for neutralising human and cynomolgus IL-4Rα as determined in the receptor-ligand binding assay, with the binding member being in scFv format, as in Example 4.3.

For example, the data herein indicate that Antibody nos: 2, 4-8, 12, 16, 19, 20, 22, 23, 24, 26, 28, 32, 33, 34, 37 and 37GL, for example, have a less than or equal to 25-fold difference in potency for neutralising human and cynomolgus IL-4Rα respectively, when in scFv format in the receptor-ligand binding assay described herein. Data are presented in Example 4.3 and Table 1. Thus, in some embodiments, neutralisation potency of binding members of the invention (when in scFv format) for human and cynomolgus IL-4Rα measured using the receptor-ligand binding assay is within 25-fold. Particular examples of antibodies described herein that exhibit less than or equal to 10-fold neutralisation potency for human and cynomolgus IL-4Rα include Antibody nos 2, 4, 5, 20 and 22. In one embodiment the neutralisation potency of binding members of the invention for human and cynomolgus IL-4Rα is within 210-fold; i.e binding to human IL-4Rα is no greater than 210-fold that against cynomologous IL-4Rα. In another embodiment, said neutralisation potency is between 5:1 and 210:1, such as between 5:1 and 100:1.

For functional cell-based assays potency is normally expressed as an $IC_{50}$ value, in nM unless otherwise stated. In functional assays, $IC_{50}$ is the molar concentration of a binding member that reduces a biological (or biochemical) response by 50% of its maximum. $IC_{50}$ may be calculated by plotting % of maximal biological response as a function of the log of the binding member concentration, and using a software program such as Prism (GraphPad) or Origin (Origin Labs) to fit a sigmoidal function to the data to generate $IC_{50}$ values.

For receptor-ligand binding assays, potency is normally expressed as Ki (the inhibition constant), the concentration of binding member that would occupy 50% of receptors if no labelled ligand were present. Whereas $IC_{50}$ may vary between experiments depending on ligand concentration, the Ki is an absolute value calculated from the Cheng Prusoff equation.

A binding member of the invention may have a neutralising potency or Ki of up to 5 nM in a human IL-4RαHTRF® assay as described herein. This assay can be used to determine Ki for binding members in scFv format. The Ki may for example be up to 5.0, 4.0, 3.0, 2.0, 1.0, 0.5, 0.2, 0.1, 0.05, or 0.02 nM. Examples of Ki data are presented in Example 4.3 (see Table 1), wherein a final concentration of 0.125 nM human IL-4Rα and 2 nM IL-4 is used in the HTRF® receptor-ligand binding assay and a detailed method is provided.

Additionally, binding kinetics and affinity (expressed as the equilibrium dissociation constant, KD) of IL-4Rα binding members for IL-4Rα may be determined, e.g. using surface plasmon resonance such as BIAcore®, or Kd may be estimated from $pA_2$ analysis.

Surface plasmon resonance is a well-established technique for determining affinity of a binding member for a target. It involves passing an analyte in fluid phase over a ligand attached to a support, and determining binding between analyte and ligand. Surface plasmon resonance may for example be performed whereby recombinant IL-4Rα is passed in fluid phase over a binding member attached to a support. Surface plasmon resonance data may be fitted to a bivalent analyte data model or a monovalent analyte data model. As shown in the Examples herein, a monovalent analyte data model was found to be particularly appropriate for determining affinity of binding members to IL-4Rα. An affinity constant Kd may be calculated from the ratio of rate constants kd1/ka1 as determined by surface plasmon resonance using a 1:1 Langmuir binding model.

Examples of estimated KD values for binding IL-4Rα calculated using surface plasmon resonance are presented in Example 4.7 (see Table 4). These data demonstrate good binding properties of Antibody 37GL for recombinantly produced human and cynomolgus IL-4Rα. Binding to IL-4Rα from HEK-EBNA cells demonstrates that the antibody binds native glycosylated human IL-4Rα. Because Antibody 37GL binds to the native glycosylated human IL-4Rα form allows one to predict that all of antibodies described herein (e.g. Antibodies 1 to 42) are able to bind native glycosylated human IL-4Rα, given that all these antibodies were derived from a single parent antibody (Antibody 1) and are thus believed to all bind the same or highly similar epitope of IL-4Rα.

Thus, according to particular embodiments, the binding members of the invention are capable of binding to glycosylated hIL-4Rα.

As illustrated in Example 4.7 and Table 4, a good cross-reactivity in binding human and cynomolgus IL-4Rα was determined by surface plasmon resonance for a representative panel of antibodies derived from Antibody 1.

Binding members of the invention may optionally be specific for IL-4Rα over other structurally related molecules (e.g. other interleukin receptors) and thus bind IL-4Rα selectively. For example, binding members of the invention may not cross-react with any of IL-13Rα1 or IL-13Rα2 and the common gamma chain (γc). This may be determined or demonstrated, for example, in a DELFIA® epitope competition assay as exemplified in Example 4.6.

A binding member of the invention may comprise an antibody molecule, e.g. a human antibody molecule. The binding member comprises an antibody VH and/or VL domain. VH domains of binding members are also provided as part of the invention. Within each of the VH and VL domains are complementarity determining regions, ("CDRs"), and framework regions, ("FRs"). A VH domain comprises a set of HCDRs, and a VL domain comprises a set of LCDRs. An antibody molecule may comprise an antibody VH domain comprising a VH CDR1, CDR2 and CDR3 and a framework. It may alternatively or also comprise an antibody VL domain comprising a VL CDR1, CDR2 and CDR3 and a framework. A VH or VL domain framework comprises four framework regions, FR1, FR2, FR3 and FR4, interspersed with CDRs in the following structure:

FR1-CDR1-FR2-CDR2-FR3-CDR3-FR4.

Examples of antibody VH and VL domains, FRs and CDRs according to the present invention are as listed in the appended sequence listing that forms part of the present disclosure. All VH and VL sequences, CDR sequences, sets of CDRs and sets of HCDRs and sets of LCDRs disclosed herein represent aspects and embodiments of the invention. As described herein, a "set of CDRs" comprises CDR1, CDR2 and CDR3. Thus, a set of HCDRs refers to HCDR1, HCDR2 and HCDR3, and a set of LCDRs refers to LCDR1, LCDR2 and LCDR3. Unless otherwise stated, a "full set of CDRs" includes HCDRs and LCDRs. Typically, binding members of the invention are monoclonal antibodies.

A further aspect of the invention is an antibody molecule comprising a VH domain that has at least 75, 80, 85, 90, 95, 98 or 99% amino acid sequence identity with a VH domain of any of Antibodies 1 to 42 shown in the appended sequence listing, and/or comprising a VL domain that has at least 75, 80, 85, 90, 95, 98 or 99% amino acid sequence identity with a VL domain of any of Antibodies 1 to 42 shown in the appended sequence listing. Accelerys' "MacVector™" program may be used to calculate % identity of two amino acid sequences.

A binding member of the invention may comprise an antigen-binding site within a non-antibody molecule, normally provided by one or more CDRs e.g. an HCDR3 and/or LCDR3, or a set of CDRs, in a non-antibody protein scaffold, as discussed further below.

As described in more detail in the Experimental Section, the inventors isolated a parent antibody molecule (Antibody 1) with a set of CDR sequences as shown in FIGS. 1 (VH domain) and 2 (VL domain). Through a process of optimisation they generated a panel of antibody clones, including those numbered 2 to 20, with CDR3 sequences derived from the parent CDR3 sequences and having substitutions at the positions indicated in FIG. 1 (VH domain) and FIG. 2 (VL domain). Thus for example, it can be seen from FIG. 1 (A to D), that Antibody 2 has the parent HCDR1, HCDR2, LCDR1 and LCDR2 sequences, and has the parent LCDR3 sequence in which Kabat residue 95 is replaced by Q, Kabat residue 95A, 95B and 96 are each replaced by P and Kabat residue 97 is replaced by L; and has parent HCDR3 sequence in which Kabat residue 101 is replaced by Y and Kabat residue 102 is replaced by N.

The parent antibody molecule, and Antibody molecules 2 to 20, as described herein refer respectively to antibody molecules with CDRs of the parent antibody molecule and to antibody molecules with CDRs of antibody molecules 2 to 20. Through a further process of optimisation the inventors generated a panel of antibody clones numbered 21-42, with additional substitutions throughout the VH and VL domains. Thus, for example, Antibody 21 has the same LCDR1, LCDR2, LCDR3, HCDR1, and HCDR3 as Antibody 20; it has the parent HCDR2 sequence of Antibody 20 but with Kabat residue 57 replaced by A; and it has Kabat residues 85 and 87 (in LFW3) replaced by V and F, respectively.

Described herein is a reference binding member comprising the Antibody 20 set of CDRs as shown in FIGS. 3 (VH) and 4 (VL), in which HCDR1 is SEQ ID NO: 193 (Kabat residues 31-35), HCDR2 is SEQ ID NO: 194 (Kabat residues 50-65), HCDR3 is SEQ ID NO: 195 (Kabat residues 95-102), LCDR1 is SEQ ID NO: 198 (Kabat residues 24-34), LCDR2 is SEQ ID NO: 199 (Kabat residues 50-56) and LCDR3 is SEQ ID NO: 200 (Kabat residues 89-97). Further binding members can be described with reference to the sequence in the reference binding member.

A binding member of the invention may comprise one or more CDRs (i.e. at least one, at least 2, at least 3, at least 4 at least 5 and at least 6) as described herein, e.g. a CDR3, and optionally also a CDR1 and CDR2 to form a set of CDRs. The CDR or set of CDRs may be a parent CDR or parent set of CDRs, or may be a CDR or set of CDRs of any of Antibodies 2 to 42, or may be a variant thereof as described herein.

For example, a binding member or a VL domain according to the invention may comprise the reference LCDR3 with one or more of Kabat residues 92-97 substituted for another amino acid. Exemplary substitutions include:
Kabat residue 92 replaced by Phe (F), Val (V) or Ala (A);
Kabat residue 93 replaced by Gly (G) or Ser (S);
Kabat residue 94 replaced by Thr (T)
Kabat residue 95 replaced by Leu (L), GLn (Q), Pro (P) or Ser (S);
Kabat residue 95a replaced by Ser (S), Prol (P), Ala (A), Thr (T), H is (H) or Gly (G);
Kabat residue 95b replaced by Ala (A), Pro (P), Ser (S), Tyr (Y), Met (M), Leu (L), Thr (T), Arg (R) or Asp (D);
Kabat residue 95c replaced by Asn (N), Gln (Q), H is (H), Tyr (Y), Thr (T), Ile (I), Lys (K), Arg (R) or Met (M);
Kabat residue 96 replaced by Tyr (Y) or Pro (P);
Kabat residue 97 replaced by Val (V), Leu (L) or Ile (I).

A binding member or a VH domain may comprise the reference HCDR3 with one or more of Kabat residues 97-102 substituted for another amino acid. Exemplary substitutions include:
Kabat residue 97 replaced by Trp (W) or Leu (L);
Kabat residue 98 replaced by Leu (L);
Kabat residue 99 replaced by Leu (L), Lys (K), Phe (F) or Trp (W);

Kabat residue 101 replaced by Asp (D), Asn (N) or Gln (Q); Kabat residue 102 replaced by Tyr (Y), Asn (N), Pro (P) or H is (H).

Binding members of the invention may comprise an HCDR1, HCDR2 and/or HCDR3 of any of Antibodies 1 to 42 and/or an LCDR1, LCDR2 and/or LCDR3 of any of Antibodies 1 to 42, e.g. a set of CDRs of any of Antibodies 1 to 42 shown in FIG. 1 or 2. A binding member may comprise a set of VH CDRs of one of these antibodies. Optionally it may also comprise a set of VL CDRs of one of these antibodies, and the VL CDRs may be from the same or a different antibody as the VH CDRs. A VH domain comprising a set of HCDRs of any of Antibodies 1 to 42, and/or a VL domain comprising a set of LCDRs of any of Antibodies 1 to 42, are also individual embodiments of the invention.

Typically, a VH domain is paired with a VL domain to provide an antibody antigen-binding site, although as discussed further below a VH or VL domain alone may be used to bind antigen. In one embodiment, the Antibody 1 VH domain is paired with the Antibody 1 VL domain, so that an antibody antigen-binding site is formed comprising both the Antibody 1 VH and VL domains. Analogous embodiments are provided for the other VH and VL domains disclosed herein. In other embodiments, the Antibody 1 VH is paired with a VL domain other than the antibody 1 VL. Light-chain promiscuity is well established in the art. Again, analogous embodiments are provided by the invention for the other VH and VL domains disclosed herein. Thus, the VH of the parent (Antibody 1) or of any of Antibodies 2 to 42 may be paired with the VL of the parent or of any of Antibodies 2 to 42.

One aspect of the invention is an antibody comprising a VH and VL domain wherein the VH domain comprises a sequence disclosed in FIG. 1 or 3.

Another aspect of the invention is an antibody comprising a VH and VL domain wherein the VL domain comprises a sequence disclosed in FIG. 2 or 4.

Another aspect of the invention is an isolated antibody molecule comprising a VH domain with the VH domain amino acid sequence shown in SEQ ID NO: 362, 442, 232, 422 or 432 and a VL domain with the VL domain amino acid sequence shown in SEQ ID NOs: 367, 237, 447, 437 or 427

A binding member may comprise a set of H and/or L CDRs of the parent antibody or any of Antibodies 2 to 42 with twelve or ten or nine or fewer, e.g. one, two, three, four or five, substitutions within the disclosed set of H and/or L CDRs. For example, a binding member of the invention may comprise the Antibody 16 or Antibody 20 set of H and/or L CDRs with 12 or fewer substitutions, e.g. seven or fewer substitutions, e.g. zero, one, two, three, four, five, or six substitutions. Substitutions may potentially be made at any residue within the set of CDRs, and may be within CDR1, CDR2 and/or CDR3.

Thus, according to one aspect of the invention there is provided an isolated binding member for human interleukin-4 receptor alpha (hIL-4Rα), comprising a set of CDRs: HCDR1, HCDR2, HCDR3, LCDR1, LCDR2 and LCDR3, wherein the set of CDRs has 12 or fewer amino acid alterations from a reference set of CDRs in which:
HCDR1 has amino acid sequence SEQ ID NO: 153;
HCDR2 has amino acid sequence SEQ ID NO: 154;
HCDR3 has amino acid sequence SEQ ID NO: 155;
LCDR1 has amino acid sequence SEQ ID NO: 158;
LCDR2 has amino acid sequence SEQ ID NO: 159; and
LCDR3 has amino acid sequence SEQ ID NO: 160.
The reference antibody in this instance is Antibody 16.

The isolated binding member may have 10 or fewer, 8 or fewer, 7 or fewer, e.g. 6, 5, 4, 3, 2, 1 or 0 amino acid alterations from the reference set of CDRs. Particular alterations are amino acid substitutions.

According to another aspect of the invention there is provided an isolated binding member for human interleukin-4 receptor alpha (hIL-4Rα), comprising a set of CDRs: HCDR1, HCDR2, HCDR3, LCDR1, LCDR2 and LCDR3, wherein the set of CDRs has 12 or fewer amino acid alterations from a reference set of CDRs in which:
HCDR1 has amino acid sequence SEQ ID NO: 193;
HCDR2 has amino acid sequence SEQ ID NO: 194;
HCDR3 has amino acid sequence SEQ ID NO: 195;
LCDR1 has amino acid sequence SEQ ID NO: 198;
LCDR2 has amino acid sequence SEQ ID NO: 199; and
LCDR3 has amino acid sequence SEQ ID NO: 200.
The reference antibody in this instance is Antibody 20.

The isolated binding member may have 10 or fewer, 8 or fewer, 7 or fewer e.g. 6, 5, 4, 3, 2, 1 or 0 amino acid alterations from the reference set of CDRs. Particular alterations are amino acid substitutions. In a particular embodiment, the isolated binding member has 4 or fewer amino acid substitutions from the reference set of CDRs identified above.

According to another aspect of the invention there is provided an isolated binding member for human interleukin-4 receptor alpha (hIL-4Rα), comprising a set of CDRs: HCDR1, HCDR2, HCDR3, LCDR1, LCDR2 and LCDR3, wherein the set of CDRs has 6 or fewer amino acid alterations from a reference set of CDRs in which:
HCDR1 has amino acid sequence SEQ ID NO: 363;
HCDR2 has amino acid sequence SEQ ID NO: 364;
HCDR3 has amino acid sequence SEQ ID NO: 365;
LCDR1 has amino acid sequence SEQ ID NO: 368;
LCDR2 has amino acid sequence SEQ ID NO: 369; and
LCDR3 has amino acid sequence SEQ ID NO: 370.
The reference antibody in this instance is Antibody 37.

Substitutions may be within CDR3, e.g. at the positions substituted in any of Antibodies 2 to 42, as shown in FIG. 1 or 3 (VH domain) and 2 or 4 (VL domain). Thus, the one or more substitutions may comprise one or more substitutions at the following residues:
Kabat residue 97, 98, 99, 101 or 102 in HCDR3; or
Kabat residue 92, 93, 94, 95, 95A, 95B, 95C, 96 or 97 in LCDR3.

Thus, a CDR3 may for example be a reference LCDR3 having one or more substitutions at Kabat residues 92, 93, 94, 95, 95A, 95B, 95C, 96 or 97.

Examples of substitutions in parent/reference CDRs are described elsewhere herein. As described, the substitutions may comprise one or more substitutions as shown in FIGS. 1 to 4.

A binding member of the invention may comprise the HCDR1, HCDR2 and/or HCDR3 of the reference Antibody 20, or with one or more of the following substitutions:
HCDR2 wherein Kabat residue 53 is Arg (R);
HCDR2 wherein Kabat residue 57 is Ala (A);
HCDR3 wherein Kabat residue 97 is Trp (W) or Leu (L);
Kabat residue 98 is Leu; Kabat residue 99 is Leu (L), Lys (K) or Trp (W); Kabat residue 101 is Asn (N) or Gln (Q); and/or Kabat residue 102 is Tyr (Y), Asn (N), Pro (P) or H is (H).

A binding member of the invention may comprise an LCDR1, LCDR2 and/or LCDR3 of the reference Antibody 20, or with one or more of the following substitutions:
LCDR1 wherein Kabat residue 27 is Gly (G);
Kabat residue 27A is Thr (T);
Kabat residue 27B is Ser (S);
Kabat residue 31 is Asn (N);

LCDR2 wherein Kabat residue 56 is Pro (P);
LCDR3 wherein Kabat residue 92 is Phe (F), Val (V) or Ala (A);
Kabat residue 93 is Gly (G) or Ser (S);
Kabat residue 94 is Thr (T);
Kabat residue 95 is Leu (L), Gln (Q), Pro (P) or Ser (S);
Kabat residue 95A is Ser (S), Pro (P), Ala (A), Thr (T), H is (H) or Gly (G);
Kabat residue 95B is Ala (A), Pro (P), Ser (S), Tyr (Y), Met (M), Leu (L), Thr (T), Asp (D) or Arg (R);
Kabat residue 95C is Asn (N), Gln (Q), H is (H), Tyr (Y), Ile (I), Lys (K), Arg (R), Thr (T) or Met (M);
Kabat residue 96 is Tyr (Y) or Pro (P);
and/or Kabat residue 97 is Val (V), Leu (L) or Ile (I).

In a particular embodiment, with reference to Antibody 20 sequence, Kabat residue 53 in HCDR2 is replaced by Arg (R); and/or Kabat residue 57 in HCDR2 is replaced by Ala (A); and/or Kabat residue 27 in LCDR1 is replaced by Gly (G); and/or Kabat residue 27B in LCDR1 is replaced by Ser (S); and/or Kabat residue 95 in LCDR3 is replaced by Pro (P).

According to a particular aspect of the invention there is provided an isolated binding member for human interleukin-4 receptor alpha (hIL-4Rα), wherein
the HCDR1 has amino acid sequence SEQ ID NO: 363;
the HCDR2 has amino acid sequence SEQ ID NO: 364;
the HCDR3 has amino acid sequence SEQ ID NO: 365;
the LCDR1 has amino acid sequence SEQ ID NO: 368;
the LCDR2 has amino acid sequence SEQ ID NO: 369; and
the LCDR3 has amino acid sequence SEQ ID NO: 370;

According to another particular aspect of the invention there is provided an isolated binding member for human interleukin-4 receptor alpha (hIL-4Rα), wherein
the HCDR1 has amino acid sequence SEQ ID NO: 233;
the HCDR2 has amino acid sequence SEQ ID NO: 234;
the HCDR3 has amino acid sequence SEQ ID NO: 235;
the LCDR1 has amino acid sequence SEQ ID NO: 238;
the LCDR2 has amino acid sequence SEQ ID NO: 239; and
the LCDR3 has amino acid sequence SEQ ID NO: 240;

In a binding member of the invention:
HCDR1 may be 5 amino acids long, consisting of Kabat residues 31-35;
HCDR2 may be 17 amino acids long, consisting of Kabat residues 50-65;
HCDR3 may be 9 amino acids long, consisting of Kabat residues 95-102;
LCDR1 may be 13 amino acids long, consisting of Kabat residues 24-34;
LCDR2 may be 7 amino acids long, consisting of Kabat residues 50-56; and/or, LCDR3 may be 9 amino acids long, consisting of Kabat residues 89-97.

Kabat numbering of a set of HCDRs and LCDRs, wherein HCDR1 is Kabat residues 31-35, HCDR2 is Kabat residues 50-65, HCDR3 is Kabat residues 95-102 is shown in FIGS. 1 and 3; LCDR1 is Kabat residues 24-34, LCDR2 is Kabat residues 50-56 and LCDR3 is Kabat residues 89-97, is shown in FIGS. 2 and 4.

According to another aspect of the invention there is provided an isolated binding member for human interleukin-4 receptor alpha (hIL-4Rα), comprising a set of CDRs: HCDR1, HCDR2, HCDR3, LCDR1, LCDR2 and LCDR3, wherein the set of CDRs has 6 or fewer amino acid alterations from the reference set of CDRs present in the clone deposited at NCIMB on 9 Dec. 2008 with accession number: NCIMB 41600.

According to another aspect of the invention there is provided an isolated binding member for human interleukin-4 receptor alpha (hIL-4Rα), comprising a VH sequence as found in the clone deposited at NCIMB on 9 Dec. 2008 with accession number: NCIMB 41600.

According to another aspect of the invention there is provided an isolated binding member for human interleukin-4 receptor alpha (hIL-4Rα), comprising a VL sequence as found in the clone deposited at NCIMB on 9 Dec. 2008 with accession number: NCIMB 41600.

According to another aspect of the invention there is provided an isolated binding member for human interleukin-4 receptor alpha (hIL-4Rα), comprising a VH and VL sequence as found in the clone deposited at NCIMB on 9 Dec. 2008 with accession number: NCIMB 41600.

According to another aspect of the invention there is provided an isolated antibody or fragment of an antibody, wherein the antibody or the fragment immunospecifically binds to human interleukin-4 receptor alpha and comprises:
(a) a VH CDR1 having an amino acid sequence identical to or comprising 1, 2, or 3 amino acid residue substitutions relative to the VH CDR1 present in the clone deposited at NCIMB on 9 Dec. 2008 with accession number: NCIMB 41600;
(b) a VH CDR2 having an amino acid sequence identical to or comprising 1, 2, or 3 amino acid residue substitutions relative to the VH CDR2 present in the clone deposited at NCIMB on 9 Dec. 2008 with accession number: NCIMB 41600;
(c) a VH CDR3 having an amino acid sequence identical to or comprising 1, 2, or 3 amino acid residue substitutions relative to the VH CDR3 present in the clone deposited at NCIMB on 9 Dec. 2008 with accession number: NCIMB 41600;
(d) a VL CDR1 having an amino acid sequence identical to or comprising 1, 2, or 3 amino acid residue substitutions relative to the VL CDR1 present in the clone deposited at NCIMB on 9 Dec. 2008 with accession number: NCIMB 41600;
(e) a VL CDR2 having an amino acid sequence identical to or comprising 1, 2, or 3 amino acid residue substitutions relative to the VL CDR2 present in the clone deposited at NCIMB on 9 Dec. 2008 with accession number: NCIMB 41600; and
(f) a VL CDR3 having an amino acid sequence identical to or comprising 1, 2, or 3 amino acid residue substitutions relative to the VL CDR3 present in the clone deposited at NCIMB on 9 Dec. 2008 with accession number: NCIMB 41600.

According to another aspect of the invention there is provided an isolated antibody or fragment of an antibody, wherein the antibody or the fragment immunospecifically binds to human interleukin-4 receptor alpha and comprises:
(a) a VH sequence having an amino acid sequence identical to or comprising 1, 2, 3, 4, 5, or 6 amino acid residue substitutions relative to the VH sequence present in the clone deposited at NCIMB on 9 Dec. 2008 with accession number: NCIMB 41600;
(b) a VL sequence having an amino acid sequence identical to or comprising 1, 2, 3, 4, 5, or 6 amino acid residue substitutions relative to the VL sequence present in the clone deposited at NCIMB on 9 Dec. 2008 with accession number: NCIMB 41600.

A binding member may comprise an antibody molecule having one or more CDRs, e.g. a set of CDRs, within an antibody framework. For example, one or more CDRs or a set of CDRs of an antibody may be grafted into a framework (e.g. human framework) to provide an antibody molecule. Framework regions may comprise human germline gene segment sequences. Thus, the framework may be germlined, whereby one or more residues within the framework are changed to match the residues at the equivalent position in the most similar human germline framework. The skilled person can select a germline segment that is closest in sequence to the framework sequence of the antibody before germlining and test the affinity or activity of the antibodies to confirm that germlining does not significantly reduce antigen binding or potency in assays described herein. Human germline gene segment sequences are known to those skilled in the art and can be accessed for example from the VBase compilation (see Tomlinson. Journal of Molecular Biology. 224. 487-499, 1997).

In one embodiment, a binding member of the invention is an isolated human antibody molecule having a VH domain comprising a set of HCDRs in a human germline framework, e.g. Vh1_DP-7_(1-46). Thus, the VH domain framework regions FR1, FR2 and/or FR3 may comprise framework regions of human germline gene segment Vh1_DP-7_(1-46). FR4 may comprise a framework region of human germline j segment JH1, JH4 or JH5 (these j segments have identical amino acid sequences) or it may comprise a framework region of human germline j segment JH3. The amino acid sequence of VH FR1 may be SEQ ID NO: 442 (residues 1-30). The amino acid sequence of VH FR2 may be SEQ ID NO: 442 (residues 36-49). The amino acid sequence of VH FR3 may be SEQ ID NO: 442 (residues 66-94). The amino acid sequence of VH FR4 may be SEQ ID NO: 442 (103-113). Normally the binding member also has a VL domain comprising a set of LCDRs, e.g. in a human germline framework, e.g. Vλ1_DPL5. Thus, the VL domain framework regions FR1, FR2 and/or FR3 may comprise framework regions of human germline gene segment Vλ1_DPL5. FR4 may comprise a framework region of human germline j segment JL2 or JL3 (these j segments have identical amino acid sequences). The amino acid sequence of VL FR1 may be SEQ ID NO: 447 (residues 1-23). The amino acid sequence of VL FR2 may be SEQ ID NO: 447 (residues 35-49). The amino acid sequence of VL FR3 may be SEQ ID NO: 447 (residues 57-88). The amino acid sequence of VL FR4 may be SEQ ID NO: 447 (residues 98-107). A germlined VH or VL domain may or may not be germlined at one or more Vernier residues, but is normally not.

An antibody molecule or VH domain of the invention may comprise the following set of heavy chain framework regions:
FR1 SEQ ID NO: 442 (residues 1-30);
FR2 SEQ ID NO: 442 (residues 36-49);
FR3 SEQ ID NO: 442 (residues 66-94);
FR4 SEQ ID NO: 442 (residues 103-113); or may comprise the said set of heavy chain framework regions with one, two, three, four, five, or six amino acid alterations, e.g. substitutions.

An antibody molecule or VL domain of the invention may comprise the following set of light chain framework regions:
FR1 SEQ ID NO: 447 (residues 1-23);
FR2 SEQ ID NO: 447 (residues 35-49);
FR3 SEQ ID NO: 447 (residues 57-88);
FR4 SEQ ID NO: 447 (residues 98-107); or may comprise the said set of heavy chain framework regions with one, two, three, four, five, or six amino acid alterations, e.g. substitutions.

An amino acid alteration may be a substitution, an insertion (addition) or a deletion.

The most common alteration is likely to be a substitution.

For example, an antibody molecule of the invention may comprise a set of heavy and light chain framework regions, wherein:
heavy chain FR1 is SEQ ID NO: 192(residues 1-30);
heavy chain FR2 is SEQ ID NO: 192 (residues 36-49);
heavy chain FR3 is SEQ ID NO: 192 (residues 66-94);
heavy chain FR4 is SEQ ID NO: 192 (residues 103-113);
light chain FR1 is SEQ ID NO: 197 (residues 1-23);
light chain FR2 is SEQ ID NO: 197 (residues 35-49);
light chain FR3 is SEQ ID NO: 197 (residues 57-88);
light chain FR4 is SEQ ID NO: 197 (residues 98-107); or may comprise the said set of heavy and light chain framework regions with seven or fewer, e.g. six or fewer, amino acid alterations, e.g. substitutions. For example there may be one or two amino acid substitutions in the said set of heavy and light chain framework regions.

As indicated in Example 4.2, Antibodies 21-42 are based on Antibody 20, but with certain additional alterations within the CDRs and framework regions. Like Antibody 20, Antibodies 21-42 bind hIL-4Rα and cyIL-4Rα. Such CDR and/or framework substitutions may therefore be considered as optional or additional substitutions generating binding members with potentially greater binding.

Thus, in addition to the substitutions within any of the 6 CDR regions of the VH and VL domains, the binding members may also comprise one or more amino acid substitutions at the following residues within the framework regions, using the standard numbering of Kabat:
11, 12 in HFW1;
37, 48 in HFW2;
68, 84, 85 in HFW3;
105, 108, 113 in HFW4;
1, 2, 3, 9 in LFW1;
38, 42 in LFW2; or
58, 65, 66, 70, 74, 85, 87 in LFW3.

Suitable framework substitutions are shown in FIGS. 1 to 4. And a binding member of the present invention may comprise one or more of the specific substitutions shown in FIGS. 1 to 4.

An antibody molecule or VH domain of the invention may comprise a VH FR1 wherein Kabat residue 11 is Val or Glu and/or Kabat residue 12 is Lys or Arg; An antibody molecule or VH domain of the invention may comprise a VH FR2 wherein Kabat residue 37 is Ala or Val and/or Kabat residue 48 is Met or Val; An antibody molecule or VH domain of the invention may comprise a VH FR3 wherein Kabat residue 68 is Ser, Ala or Thr and/or Kabat residue 84 is Ser or Pro and/or Kabat residue 85 is Glu or Gly; An antibody molecule or VH domain of the invention may comprise a VH FR4 wherein Kabat residue 105 is Lys or Asn and/or Kabat residue 108 is Gln, Arg or Leu and/or Kabat residue 113 is Ser or Gly.

An antibody molecule or VL domain of the invention may comprise a VL FR1 wherein Kabat residue 1 is Gln or Leu and/or Kabat residue 2 is Ser or Pro or Ala and/or Kabat residue 3 is Val or Ala and/or Kabat residue 9 is Ser or Leu; An antibody molecule or VL domain of the invention may comprise a VL FR2 wherein Kabat residue 38 is Gln or Arg and/or Kabat residue 42 is Thr or Ala; An antibody molecule or VL domain of the invention may comprise a VL FR3 wherein Kabat residue 58 is Ile or Val and/or Kabat residue 65 is Ser or Phe and/or Kabat residue 66 is Lys or Arg and/or Kabat residue 70 is Ser or Thr and/or Kabat residue 74 is Ala or Gly and/or Kabat residue 85 is Asp or Val and/or Kabat residue 87 is Tyr or Phe.

A non-germlined antibody has the same CDRs, but different frameworks, compared with a germlined antibody. Of the antibody sequences shown herein, VH and VL domains of Antibodies 24PGL and 37GL are germlined.

FIGS. 5, 6 and 7, depict the composite sequence identity that each of Antibodies 1-42 have with each other. The composite sequence being an artificial alignment of key CDR regions. Thus, for FIG. 5, the 6 CDR domains (LCDR1, LCDR2, LCDR3, HCDR1, HCDR2, HCDR3; 6xCDR) have been aligned such that the last codon of LCDR1 is adjacent to the first codon of LCDR2, the last codon of LCDR2 is adjacent the first codon of LCDR3 etc. In this manner a sequence that lacks the intervening framework regions is created. The composite sequence can be of all CDR regions, as for FIG. 5, or just the heavy or light chain CDR sequences (as for FIGS. 6 and 7 respectively). Sequence alignment of each Antibody composite sequence to each other Antibody composite sequence can then be generated and the identity score depicted in the charts of FIGS. 5, 6 and 7. As can be seen from FIG. 5, with respect to all 6 CDR regions, the lowest degree of sequence identity that any of Antibodies 1-42 has to another is 73% (this being Antibody 3 compared to Antibodies 23, 25, 37, 37GL and 41); if you exclude Antibody 3 the degree of sequence identity is 78%. The lowest degree of sequence identity comparing only the three Heavy chain CDR (3×HCDR) regions is 75% and 79% if you exclude Antibody 3. The lowest degree of sequence identity comparing only the three Light chain CDR (3×LCDR) regions is 65%; and, 75% if you exclude Antibody 3.

In a particular embodiment the isolated binding member has at least 73% amino acid sequence identity with the 6xCDR composite score of any of Antibodies 1-42.

According to a further aspect of the invention there is provided an isolated binding member for human interleukin-4 receptor alpha (hIL-4Rα), comprising a set of CDRs: HCDR1, HCDR2, HCDR3, LCDR1, LCDR2 and LCDR3, which binding member has at least 73% amino acid sequence identity with the composite sequence of HCDR1, HCDR2, HCDR3, LCDR1, LCDR2 and LCDR3 in line sequence without any intervening framework sequences, of any of Antibodies 1-42. In a particular embodiment the isolated binding member has at least 78% amino acid sequence identity with the composite score of any of Antibodies 1-42.

According to a further aspect of the invention there is provided an isolated binding member for human interleukin-4 receptor alpha (hIL-4Rα), comprising a set of CDRs: HCDR1, HCDR2, HCDR3, LCDR1, LCDR2 and LCDR3, which binding member has at least 75% amino acid sequence identity with the composite sequence of HCDR1, HCDR2 and HCDR3 of any of Antibodies 1-42.

According to a further aspect of the invention there is provided an isolated binding member for human interleukin-4 receptor alpha (hIL-4Rα), comprising a set of CDRs: HCDR1, HCDR2, HCDR3, LCDR1, LCDR2 and LCDR3, which binding member has at least 65% amino acid sequence identity with the composite sequence of LCDR1, LCDR2 and LCDR3 of any of Antibodies 1-42.

A binding member of the present invention may be one which competes for binding to IL-4Rα with any binding member which both binds IL-4Rα and comprises a binding member, VH and/or VL domain, CDR e.g. HCDR3, and/or set of CDRs disclosed herein. Competition between binding members may be assayed easily in vitro, for example using ELISA and/or by tagging a specific reporter molecule to one binding member which can be detected in the presence of one or more other untagged binding members, to enable identification of binding members which bind the same epitope or an overlapping epitope. Competition may be determined for example using ELISA in which IL-4Rα is immobilized to a plate and a first tagged binding member along with one or more other untagged binding members is added to the plate. Presence of an untagged binding member that competes with the tagged binding member is observed by a decrease in the signal emitted by the tagged binding member. Such methods are readily known to one of ordinary skill in the art, and are described in more detail herein. In one embodiment, competitive binding is assayed using an epitope competition assay as described herein. A binding member of the present invention may comprise a antibody antigen-binding site that competes with an antibody molecule, for example especially an antibody molecule comprising a VH and/or VL domain, CDR e.g. HCDR3 or set of CDRs of the parent antibody or any of Antibodies 2 to 42 for binding to IL-4Rα.

Aspects of the invention provide binding members that compete for binding to IL-4Rα with any binding member defined herein, e.g. compete with the parent antibody or any of Antibodies 2 to 42, e.g. in scFv or IgG1, IgG2 or IgG4 format. A binding member that competes for binding to IL-4Rα with any binding member defined herein may have any one or more of the structural and/or functional properties disclosed herein for binding members of the invention.

In further aspects, the invention provides an isolated nucleic acid which comprises a sequence encoding a binding member, such as a VH domain and/or VL domain according to the present invention, and methods of preparing a binding member, such as a VH domain and/or a VL domain of the invention, which comprise expressing said nucleic acid under conditions to bring about production of said binding member, such as a VH domain and/or VL domain and/or antibody, and recovering it.

Another aspect of the present invention provides nucleic acid, generally isolated, encoding a VH CDR or VL CDR sequence disclosed herein.

A further aspect provides a host cell containing or transformed with nucleic acid of the invention.

Further aspects of the present invention provide for compositions containing binding members of the invention, and their use in methods of inhibiting and/or neutralising IL-4Rα, including methods of treatment of the human or animal body by therapy.

Binding members according to the invention may be used in a method of treatment or diagnosis of the human or animal body, such as a method of treatment (which may include prophylactic treatment) of a disease or disorder in a human patient which comprises administering to said patient an effective amount of a binding member of the invention. Conditions treatable in accordance with the present invention include any in which IL-4Rα, IL-4 and/or IL-13 plays a role, as discussed in detail elsewhere herein.

These and other aspects of the invention are described in further detail below.

Terminology

It is convenient to point out here that "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

IL-4Rα

IL-4Rα, is interleukin-4 receptor alpha. References to IL-4Rα are normally to human IL-4Rα unless otherwise indicated. A sequence of wild-type mature human IL-4Rα is deposited under Accession number P24394 (Swiss-Prot), which shows the full-length IL-4Rα including the signal peptide.

Cynomolgus IL-4Rα was sequenced in house, the cDNA sequence of cynomolgus IL-4Rα is shown as SEQ ID NO: 455.

As described elsewhere herein, IL-4Rα may be recombinant, and/or may be either glycosylated or unglycosylated. IL-4Rα is expressed naturally in vivo in N-linked glycosylated form. Glycosylated IL-4Rα may also be expressed in recombinant systems, e.g. in HEK-EBNA cells. IL-4Rα may also be expressed in non-glycosylated form in E. coli cells.

Binding Member

This describes one member of a pair of molecules that bind one another. The members of a binding pair may be naturally derived or wholly or partially synthetically produced. One member of the pair of molecules has an area on its surface, or a cavity, which binds to and is therefore complementary to a particular spatial and polar organization of the other member of the pair of molecules. Examples of types of binding pairs are antigen-antibody, biotin-avidin, hormone-hormone receptor, receptor-ligand, enzyme-substrate. The present invention is concerned with antigen-antibody type reactions.

A binding member normally comprises a molecule having an antigen-binding site. For example, a binding member may be an antibody molecule or a non-antibody protein that comprises an antigen-binding site.

An antigen binding site may be provided by means of arrangement of CDRs on non-antibody protein scaffolds such as fibronectin or cytochrome B etc. (Haan & Maggos, Bio-Century, 12(5):A1-A6, 2004; Koide, Journal of Molecular Biology, 284:1141-1151, 1998; Nygren et al., Current Opinion in Structural Biology, 7:463-469, 1997), or by randomising or mutating amino acid residues of a loop within a protein scaffold to confer binding specificity for a desired target. Scaffolds for engineering novel binding sites in proteins have been reviewed in detail by Nygren et al. (supra). Protein scaffolds for antibody mimics are disclosed in WO/0034784, which is herein incorporated by reference in its entirety, in which the inventors describe proteins (antibody mimics) that include a fibronectin type III domain having at least one randomised loop. A suitable scaffold into which to graft one or more CDRs, e.g. a set of HCDRs or an HCDR and/or LCDR3, may be provided by any domain member of the immunoglobulin gene superfamily. The scaffold may be a human or non-human protein. An advantage of a non-antibody protein scaffold is that it may provide an antigen-binding site in a scaffold molecule that is smaller and/or easier to manufacture than at least some antibody molecules. Small size of a binding member may confer useful physiological properties such as an ability to enter cells, penetrate deep into tissues or reach targets within other structures, or to bind within protein cavities of the target antigen. Use of antigen binding sites in non-antibody protein scaffolds is reviewed in Wess, 2004. Typical are proteins having a stable backbone and one or more variable loops, in which the amino acid sequence of the loop or loops is specifically or randomly mutated to create an antigen-binding site that binds the target antigen. Such proteins include the IgG-binding domains of protein A from S. aureus, transferrin, tetranectin, fibronectin (e.g. 10th fibronectin type III domain) and lipocalins. Other approaches include synthetic "Microbodies" (Selecore GmbH), which are based on cyclotides—small proteins having intra-molecular disulphide bonds.

In addition to antibody sequences and/or an antigen-binding site, a binding member according to the present invention may comprise other amino acids, e.g. forming a peptide or polypeptide, such as a folded domain, or to impart to the molecule another functional characteristic in addition to ability to bind antigen. Binding members of the invention may carry a detectable label, or may be conjugated to a toxin or a targeting moiety or enzyme (e.g. via a peptidyl bond or linker). For example, a binding member may comprise a catalytic site (e.g. in an enzyme domain) as well as an antigen binding site, wherein the antigen binding site binds to the antigen and thus targets the catalytic site to the antigen. The catalytic site may inhibit biological function of the antigen, e.g. by cleavage.

Although, as noted, CDRs can be carried by non-antibody scaffolds, the structure for carrying a CDR, e.g. CDR3, or a set of CDRs of the invention will generally be an antibody heavy or light chain sequence or substantial portion thereof in which the CDR or set of CDRs is located at a location corresponding to the CDR or set of CDRs of naturally occurring VH and VL antibody variable domains encoded by rearranged immunoglobulin genes. The structures and locations of immunoglobulin variable domains may be determined by reference to Kabat (Sequences of Proteins of Immunological Interest, $4^{th}$ Edition. US Department of Health and Human Devices, 1987), and updates thereof, such as the $5^{th}$ Edition (Sequences of Proteins of Immunological Interest, 5th Edition. US Department of Health and Human Services, Public Service, NIH, Washington, 1991).

Unless indicated otherwise, the locations of particular residues, as well as CDR and framework regions, referred to herein uses the Kabat numbering system.

By CDR region or CDR, it is intended to indicate the hypervariable regions of the heavy and light chains of the immunoglobulin as defined by Kabat et al., (supra). An antibody typically contains 3 heavy chain CDRs and 3 light chain CDRs. The term CDR or CDRs is used here in order to indicate, according to the case, one of these regions or several, or even the whole, of these regions which contain the majority of the amino acid residues responsible for the binding by affinity of the antibody for the antigen or the epitope which it recognizes.

Among the six short CDR sequences, the third CDR of the heavy chain (HCDR3) has greater size variability (greater diversity essentially due to the mechanisms of arrangement of the genes which give rise to it). It can be as short as 2 amino acids although the longest size known is 26. Functionally, HCDR3 plays a role in part in the determination of the specificity of the antibody (Segal et al. PNAS, 71:4298-4302, 1974; Amit et al., Science, 233:747-753, 1986; Chothia et al. J. Mol. Biol., 196:901-917, 1987; Chothia et al. Nature, 342:877-883, 1989; et al. J. Immunol., 144:1965-1968, 1990; Sharon et al. PNAS, 87:4814-4817, 1990(a); Sharon et al. J. Immunol., 144:4863-4869, 1990; Kabat et al., et al., J. Immunol., 147:1709-1719, 1991b).

HCDR1 may be 5 amino acids long, consisting of Kabat residues 31-35.

HCDR2 may be 17 amino acids long, consisting of Kabat residues 50-65.

HCDR3 may be 7 amino acids long, consisting of Kabat residues 95-102.

LCDR1 may be 13 amino acids long, consisting of Kabat residues 24-34.

LCDR2 may be 7 amino acids long, consisting of Kabat residues 50-56.

LCDR3 may be 12 amino acids long, consisting of Kabat residues 89-97.

Antibody Molecule

This describes an immunoglobulin whether natural or partly or wholly synthetically produced. The term also covers any polypeptide or protein comprising an antibody antigen-binding site. It must be understood here that the invention does not relate to the antibodies in natural form, that is to say they are not in their natural environment but that they have been able to be isolated or obtained by purification from natural sources, or else obtained by genetic recombination, or by chemical synthesis, and that they can then contain unnatural amino acids as will be described later. Antibody fragments that comprise an antibody antigen-binding site include, but are not limited to molecules such as Fab, Fab', Fab'-SH, scFv, Fv, dAb, Fd; and diabodies.

Antibody molecules of the invention may be IgG, e.g. IgG1, IgG4, IgG2 or aglycosyl IgG2.

It is possible to take monoclonal and other antibodies and use techniques of recombinant DNA technology to produce other antibodies or chimeric molecules that bind the target antigen. Such techniques may involve introducing DNA encoding the immunoglobulin variable region, or the CDRs, of an antibody to the constant regions, or constant regions plus framework regions, of a different immunoglobulin. See, for instance, EP-A-184187, GB 2188638A or EP-A-239400, and a large body of subsequent literature. A hybridoma or other cell producing an antibody may be subject to genetic mutation or other changes, which may or may not alter the binding specificity of antibodies produced.

As antibodies can be modified in a number of ways, the term "antibody molecule" should be construed as covering any binding member or substance having an antibody antigen-binding site with the required specificity and/or binding to antigen. Thus, this term covers antibody fragments and derivatives, including any polypeptide comprising an antibody antigen-binding site, whether natural or wholly or partially synthetic. Chimeric molecules comprising an antibody antigen-binding site, or equivalent, fused to another polypeptide (e.g. derived from another species or belonging to another antibody class or subclass) are therefore included. Cloning and expression of chimeric antibodies are described in EP-A-0120694 and EP-A-0125023, and a large body of subsequent literature.

Further techniques available in the art of antibody engineering have made it possible to isolate human and humanised antibodies. For example, human hybridomas can be made as described by Kontermann & Dubel (Antibody Engineering, Springer-Verlag New York, LLC; 2001, ISBN: 3540413545). Phage display, another established technique for generating binding members has been described in detail in many publications such as WO92/01047 (discussed further below) and U.S. Pat. No. 5,969,108, U.S. Pat. No. 5,565,332, U.S. Pat. No. 5,733,743, U.S. Pat. No. 5,858,657, U.S. Pat. No. 5,871,907, U.S. Pat. No. 5,872,215, U.S. Pat. No. 5,885,793, U.S. Pat. No. 5,962,255, U.S. Pat. No. 6,140,471, U.S. Pat. No. 6,172,197, U.S. Pat. No. 6,225,447, U.S. Pat. No. 6,291,650, U.S. Pat. No. 6,492,160, U.S. Pat. No. 6,521,404 and Kontermann & Dubel (supra). Transgenic mice in which the mouse antibody genes are inactivated and functionally replaced with human antibody genes while leaving intact other components of the mouse immune system, can be used for isolating human antibodies (Mendez et al. Nature Genet, 15(2): 146-156, 1997).

Synthetic antibody molecules may be created by expression from genes generated by means of oligonucleotides synthesized and assembled within suitable expression vectors, for example as described by Knappik et al. (J. Mol. Biol. 296, 57-86, 2000) or Krebs et al. (Journal of Immunological Methods, 254:67-84, 2001).

It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward et al., Nature 341:544-546, 1989; McCafferty et al. Nature, 348:552-554, 1990; Holt et al. Trends in Biotechnology 21, 484-490, 2003), which consists of a VH or a VL domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al. Science, 242, 423-426, 1988; Huston PNAS USA, 85, 5879-5883, 1988); (viii) bispecific single chain Fv dimers (PCT/US92/09965) and (ix) "diabodies", multivalent or multispecific fragments constructed by gene fusion (WO94/13804; Holliger et al, PNAS USA 90:6444-6448, 1993a). Fv, scFv or diabody molecules may be stabilized by the incorporation of disulphide bridges linking the VH and VL domains (Reiter et al, Nature Biotech, 14:1239-1245, 1996). Minibodies comprising a scFv joined to a CH3 domain may also be made (Hu et al, Cancer Res., 56, 3055-3061, 1996). Other examples of binding fragments are Fab', which differs from Fab fragments by the addition of a few residues at the carboxyl terminus of the heavy chain CH1 domain, including one or more cysteines from the antibody hinge region, and Fab'-SH, which is a Fab' fragment in which the cysteine residue(s) of the constant domains bear a free thiol group.

Antibody fragments of the invention can be obtained starting from any of the antibody molecules described herein, e.g. antibody molecules comprising VH and/or VL domains or CDRs of any of Antibodies 1 to 42, by methods such as digestion by enzymes, such as pepsin or papain and/or by cleavage of the disulfide bridges by chemical reduction. In another manner, the antibody fragments comprised in the present invention can be obtained by techniques of genetic recombination likewise well known to the person skilled in the art or else by peptide synthesis by means of, for example, automatic peptide synthesizers such as those supplied by the company Applied Biosystems, etc., or by nucleic acid synthesis and expression.

Functional antibody fragments according to the present invention include any functional fragment whose half-life is increased by a chemical modification, especially by PEGylation, or by incorporation in a liposome.

A dAb (domain antibody) is a small monomeric antigen-binding fragment of an antibody, namely the variable region of an antibody heavy or light chain (Holt et al. Trends in Biotechnology 21, 484-490, 2003). VH dAbs occur naturally in camelids (e.g. camel, llama) and may be produced by immunizing a camelid with a target antigen, isolating antigen-specific B cells and directly cloning dAb genes from individual B cells. dAbs are also producible in cell culture. Their small size, good solubility and temperature stability makes them particularly physiologically useful and suitable for selection and affinity maturation. A binding member of the present invention may be a dAb comprising a VH or VL domain substantially as set out herein, or a VH or VL domain comprising a set of CDRs substantially as set out herein.

As used herein, the phrase "substantially as set out" refers to the characteristic(s) of the relevant CDRs of the VH or VL domain of binding members described herein will be either identical or highly similar to the specified regions of which the sequence is set out herein. As described herein, the phrase "highly similar" with respect to specified region(s) of one or more variable domains, it is contemplated that from 1 to about 12, e.g. from 1 to 8, including 1 to 7, 1 to 6, 1 to 5, 1 to 4, 1 to 3, or 1 or 2, amino acid substitutions may be made in the CDRs of the VH and/or VL domain.

Antibodies of the invention include bispecific antibodies. Bispecific or bifunctional antibodies form a second generation of monoclonal antibodies in which two different variable regions are combined in the same molecule (Holliger, P. & Winter, G. 1999 Cancer and metastasis rev. 18:411-419, 1999). Their use has been demonstrated both in the diagnostic field and in the therapy field from their capacity to recruit new effector functions or to target several molecules on the surface of tumor cells. Where bispecific antibodies are to be used, these may be conventional bispecific antibodies, which can be manufactured in a variety of ways (Holliger et al, PNAS USA 90:6444-6448, 1993), e.g. prepared chemically or from hybrid hybridomas, or may be any of the bispecific antibody fragments mentioned above. These antibodies can be obtained by chemical methods (Glennie et al., 1987 J. Immunol. 139, 2367-2375; Repp et al., J. Hemat. 377-382, 1995) or somatic methods (Staerz U. D. and Bevan M. J. PNAS 83, 1986; et al., Method Enzymol. 121:210-228, 1986) but likewise by genetic engineering techniques which allow the heterodimerization to be forced and thus facilitate the process of purification of the antibody sought (Merchand et al. Nature Biotech, 16:677-681, 1998). Examples of bispecific antibodies include those of the BiTE™ technology in which the binding domains of two antibodies with different specificity can be used and directly linked via short flexible peptides. This combines two antibodies on a short single polypeptide chain. Diabodies and scFv can be constructed without an Fc region, using only variable domains, potentially reducing the effects of anti-idiotypic reaction.

Bispecific antibodies can be constructed as entire IgG, as bispecific Fab'2, as Fab'PEG, as diabodies or else as bispecific scFv. Further, two bispecific antibodies can be linked using routine methods known in the art to form tetravalent antibodies.

Bispecific diabodies, as opposed to bispecific whole antibodies, may also be particularly useful because they can be readily constructed and expressed in E. coli. Diabodies (and many other polypeptides such as antibody fragments) of appropriate binding specificities can be readily selected using phage display (WO94/13804) from libraries. If one arm of the diabody is to be kept constant, for instance, with a specificity directed against IL-4Rα, then a library can be made where the other arm is varied and an antibody of appropriate specificity selected. Bispecific whole antibodies may be made by alternative engineering methods as described in Ridgeway et al, (Protein Eng., 9:616-621, 1996).

Various methods are available in the art for obtaining antibodies against IL-4Rα. The antibodies may be monoclonal antibodies, especially of human, murine, chimeric or humanized origin, which can be obtained according to the standard methods well known to the person skilled in the art.

In general, for the preparation of monoclonal antibodies or their functional fragments, especially of murine origin, it is possible to refer to techniques which are described in particular in the manual "Antibodies" (Harlow and Lane, Antibodies: A Laboratory Manual, Cold Spring Harbor Laboratory, Cold Spring Harbor N.Y., pp. 726, 1988) or to the technique of preparation from hybridomas described by Kohler and Milstein (Nature, 256:495-497, 1975).

Monoclonal antibodies can be obtained, for example, from an animal cell immunized against IL-4Rα, or one of their fragments containing the epitope recognized by said monoclonal antibodies. The IL-4Rα, or one of its fragments, can especially be produced according to the usual working methods, by genetic recombination starting with a nucleic acid sequence contained in the cDNA sequence coding for IL-4Rα or fragment thereof, by peptide synthesis starting from a sequence of amino acids comprised in the peptide sequence of the IL-4Rα and/or fragment thereof. The monoclonal antibodies can, for example, be purified on an affinity column on which IL-4Rα or one of its fragments containing the epitope recognized by said monoclonal antibodies, has previously been immobilized. More particularly, the monoclonal antibodies can be purified by chromatography on protein A and/or G, followed or not followed by ion-exchange chromatography aimed at eliminating the residual protein contaminants as well as the DNA and the LPS, in itself, followed or not followed by exclusion chromatography on Sepharose gel in order to eliminate the potential aggregates due to the presence of dimers or of other multimers. In one embodiment, the whole of these techniques can be used simultaneously or successively.

Antigen-Binding Site

This describes the part of a molecule that binds to and is complementary to all or part of the target antigen. In an antibody molecule it is referred to as the antibody antigen-binding site, and comprises the part of the antibody that binds to and is complementary to all or part of the target antigen. Where an antigen is large, an antibody may only bind to a particular part of the antigen, which part is termed an epitope. An antibody antigen-binding site may be provided by one or more antibody variable domains. An antibody antigen-binding site may comprise an antibody light chain variable region (VL) and an antibody heavy chain variable region (VH).

Isolated

This refers to the state in which binding members of the invention, or nucleic acid encoding such binding members, will generally be in accordance with the present invention. Thus, binding members, including VH and/or VL domains, and encoding nucleic acid molecules and vectors according to the present invention may be provided isolated and/or purified, e.g. from their natural environment, in substantially pure or homogeneous form, or, in the case of nucleic acid, free or substantially free of nucleic acid or genes of origin other than the sequence encoding a polypeptide with the required function. Isolated members and isolated nucleic acid will be free or substantially free of material with which they are naturally associated such as other polypeptides or nucleic acids with which they are found in their natural environment, or the environment in which they are prepared (e.g. cell culture) when such preparation is by recombinant DNA technology practised in vitro or in vivo. Members and nucleic acid may be formulated with diluents or adjuvants and still for practical purposes be isolated—for example the members will normally be mixed with gelatin or other carriers if used to coat microtitre plates for use in immunoassays, or will be mixed with pharmaceutically acceptable carriers or diluents when used in diagnosis or therapy. Binding members may be glycosylated, either naturally or by systems of heterologous eukaryotic cells (e.g. CHO or NS0 (ECACC 85110503)) cells, or they may be (for example if produced by expression in a prokaryotic cell) unglycosylated.

Heterogeneous preparations comprising anti-IL-4Rα antibody molecules also form part of the invention. For example, such preparations may be mixtures of antibodies with full-length heavy chains and heavy chains lacking the C-terminal lysine, with various degrees of glycosylation and/or with derivatized amino acids, such as cyclization of an N-terminal glutamic acid to form a pyroglutamic acid residue.

As noted above, a binding member in accordance with the present invention modulates and may neutralise a biological activity of IL-4Rα. As described herein, IL-4Rα-binding members of the present invention may be optimised for neutralizing potency. Generally, potency optimisation involves mutating the sequence of a selected binding member (normally the variable domain sequence of an antibody) to generate a library of binding members, which are then assayed for potency and the more potent binding members are selected. Thus selected "potency-optimised" binding members tend to have a higher potency than the binding member from which the library was generated. Nevertheless, high potency binding members may also be obtained without optimisation, for example a high potency binding member may be obtained directly from an initial screen e.g. a biochemical neutralization assay. A "potency optimized" binding member refers to a binding member with an optimized potency of binding or neutralization of a particular activity or downstream function of IL-4Rα. Assays and potencies are described in more detail elsewhere herein. The present invention provides both potency-optimized and non-optimized binding members, as well as methods for potency optimization from a selected binding member. The present invention thus allows the skilled person to generate binding members having high potency.

Although potency optimization may be used to generate higher potency binding members from a given binding member, it is also noted that high potency binding members may be obtained even without potency optimization.

In a further aspect, the present invention provides a method of obtaining one or more binding members able to bind the antigen, the method including bringing into contact a library of binding members according to the invention and said antigen, and selecting one or more binding members of the library able to bind said antigen.

The library may be displayed on particles or molecular complexes, e.g. replicable genetic packages such as yeast, bacterial or bacteriophage (e.g. T7) particles, viruses, cells or covalent, ribosomal or other in vitro display systems, each particle or molecular complex containing nucleic acid encoding the antibody VH variable domain displayed on it, and optionally also a displayed VL domain if present. Phage display is described in WO92/01047 and e.g. U.S. Pat. No. 5,969,108, U.S. Pat. No. 5,565,332, U.S. Pat. No. 5,733,743, U.S. Pat. No. 5,858,657, U.S. Pat. No. 5,871,907, U.S. Pat. No. 5,872,215, U.S. Pat. No. 5,885,793, U.S. Pat. No. 5,962,255, U.S. Pat. No. 6,140,471, U.S. Pat. No. 6,172,197, U.S. Pat. No. 6,225,447, U.S. Pat. No. 6,291,650, U.S. Pat. No. 6,492,160 and U.S. Pat. No. 6,521,404, each of which is herein incorporated by reference in their entirety.

Following selection of binding members able to bind the antigen and displayed on bacteriophage or other library particles or molecular complexes, nucleic acid may be taken from a bacteriophage or other particle or molecular complex displaying a said selected binding member. Such nucleic acid may be used in subsequent production of a binding member or an antibody VH or VL variable domain by expression from nucleic acid with the sequence of nucleic acid taken from a bacteriophage or other particle or molecular complex displaying a said selected binding member.

An antibody VH domain with the amino acid sequence of an antibody VH domain of a said selected binding member may be provided in isolated form, as may a binding member comprising such a VH domain.

Ability to bind IL-4Rα and/or ability to compete with e.g. a parent antibody molecule (e.g. Antibody 1) or an optimised antibody molecule, Antibodies 2 to 42 (e.g. in scFv format and/or IgG format, e.g. IgG 1, IgG2 or IgG4) for binding to IL-4Rα, may be further tested. Ability to neutralize IL-4Rα may be tested, as discussed further elsewhere herein.

A binding member according to the present invention may bind IL-4Rα with the affinity of one of Antibodies 1 to 42, e.g. in scFv or IgG 1 or IgG2 or IgG4 format, or with an affinity that is better.

A binding member according to the present invention may neutralize a biological activity of IL-4Rα with the potency of one of Antibodies 1 to 42 e.g. in scFv or IgG 1 or IgG2 or IgG4 format, or with a potency that is better.

Binding affinity and neutralization potency of different binding members can be compared under appropriate conditions.

Variants of antibody molecules disclosed herein may be produced and used in the present invention. Following the lead of computational chemistry in applying multivariate data analysis techniques to the structure/property-activity relationships (Wold et al Multivariate data analysis in chemistry. Chemometrics—Mathematics and Statistics in Chemistry (Ed.: B. Kowalski), D. Reidel Publishing Company, Dordrecht, Holland, 1984 (ISBN 90-277-1846-6)) quantitative activity-property relationships of antibodies can be derived using well-known mathematical techniques such as statistical regression, pattern recognition and classification (Norman et al. Applied Regression Analysis. Wiley-Interscience; 3$^{rd}$ edition (April 1998) ISBN: 0471170828; Kandel, Abraham & Backer, Computer-Assisted Reasoning in Cluster Analysis. Prentice Hall PTR, (May 11, 1995), ISBN: 0133418847; Principles of Multivariate Analysis: A User's Perspective (Oxford Statistical Science Series, No 22 (Paper)). Oxford University Press; (December 2000), ISBN: 0198507089; Witten & Frank Data Mining: Practical Machine Learning Tools and Techniques with Java Implementations. Morgan Kaufmann; (Oct. 11, 1999), ISBN: 1558605525; Denison DGT. (Editor), Holmes, C C. et al. Bayesian Methods for Nonlinear Classification and Regression (Wiley Series in Probability and Statistics). John Wiley & Sons; (July 2002), ISBN: 0471490369; Ghose, A K. & Viswanadhan, V N. Combinatorial Library Design and Evaluation Principles, Software, Tools, and Applications in Drug Discovery. ISBN: 0-8247-0487-8). The properties of antibodies can be derived from empirical and theoretical models (for example, analysis of likely contact residues or calculated physicochemical property) of antibody sequence, functional and three-dimensional structures and these properties can be considered singly and in combination.

An antibody antigen-binding site composed of a VH domain and a VL domain is typically formed by six loops of polypeptide: three from the light chain variable domain (VL) and three from the heavy chain variable domain (VH). Analysis of antibodies of known atomic structure has elucidated relationships between the sequence and three-dimensional structure of antibody combining sites (Chothia et al. Journal Molecular Biology 1992227, 799-817, 1992; Al-Lazikani et al. Journal Molecular Biology 273(4):927-948, 1997). These relationships imply that, except for the third region (loop) in VH domains, binding site loops have one of a small number of main-chain conformations: canonical structures. The canonical structure formed in a particular loop has been shown to be determined by its size and the presence of certain residues at key sites in both the loop and in framework regions (Chothia et al, Journal Molecular Biology 1992227, 799-817, 1992; Al-Lazikani supra).

This study of sequence-structure relationship can be used for prediction of those residues in an antibody of known sequence, but of an unknown three-dimensional structure, which are important in maintaining the three-dimensional structure of its CDR loops and hence maintain binding specificity. These predictions can be backed up by comparison of the predictions to the output from lead optimization experiments. In a structural approach, a model can be created of the antibody molecule (Chothia et al. Science, 223:755-758, 1986) using any freely available or commercial package such as WAM (Whitelegg & Rees, Prot. Eng., 12:815-824, 2000). A protein visualisation and analysis software package such as Insight II (Accelerys, Inc.) or Deep View (Guex & Peitsch, Electrophoresis (1997) 18, 2714-2723) may then be used to evaluate possible substitutions at each position in the CDR. This information may then be used to make substitutions likely to have a minimal or beneficial effect on activity.

The techniques required to make substitutions within amino acid sequences of CDRs, antibody VH or VL domains and binding members generally are available in the art. Variant sequences may be made, with substitutions that may or may not be predicted to have a minimal or beneficial effect on activity, and tested for ability to bind and/or neutralize IL-4Rα and/or for any other desired property.

Variable domain amino acid sequence variants of any of the VH and VL domains whose sequences are specifically disclosed herein may be employed in accordance with the present invention, as discussed. Particular variants may include one or more amino acid sequence alterations (addition, deletion, substitution and/or insertion of an amino acid residue), may be less than about 20 alterations, less than about 15 alterations, less than about 12 alterations, less than about 10 alterations, or less than about 6 alterations, maybe 5, 4, 3, 2 or 1. Alterations may be made in one or more framework regions and/or one or more CDRs. The alterations normally do not result in loss of function, so a binding member comprising a thus-altered amino acid sequence may retain an ability to bind and/or neutralize IL-4Rα. For example, it may retain the same quantitative binding and/or neutralizing ability as a binding member in which the alteration is not made, e.g. as measured in an assay described herein. The binding member comprising a thus-altered amino acid sequence may have an improved ability to bind and/or neutralize IL-4Rα. Indeed, Antibodies 21 to 42, generated from random mutagenesis of Antibody 20, exhibits substitutions relative to Antibody 20, mostly within the various framework regions and each of these still bind and/or neutralises IL-4Rα, indeed some show improved ability to bind and/or neutralize IL-4Rα.

Alteration may comprise replacing one or more amino acid residue with a non-naturally occurring or non-standard amino acid, modifying one or more amino acid residue into a non-naturally occurring or non-standard form, or inserting one or more non-naturally occurring or non-standard amino acid into the sequence. Example numbers and locations of alterations in sequences of the invention are described elsewhere herein. Naturally occurring amino acids include the 20 "standard" L-amino acids identified as G, A, V, L, I, M, P, F, W, S, T, N, Q, Y, C, K, R, H, D, E by their standard single-letter codes. Non-standard amino acids include any other residue that may be incorporated into a polypeptide backbone or result from modification of an existing amino acid residue. Non-standard amino acids may be naturally occurring or non-naturally occurring. Several naturally occurring non-standard amino acids are known in the art, such as 4-hydroxyproline, 5-hydroxylysine, 3-methylhistidine, N-acetylserine, etc. (Voet & Voet, Biochemistry, 2nd Edition, (Wiley) 1995). Those amino acid residues that are derivatised at their N-alpha position will only be located at the N-terminus of an amino-acid sequence. Normally in the present invention an amino acid is an L-amino acid, but in some embodiments it may be a D-amino acid. Alteration may therefore comprise modifying an L-amino acid into, or replacing it with, a D-amino acid. Methylated, acetylated and/or phosphorylated forms of amino acids are also known, and amino acids in the present invention may be subject to such modification.

Amino acid sequences in antibody domains and binding members of the invention may comprise non-natural or non-standard amino acids described above. In some embodiments non-standard amino acids (e.g. D-amino acids) may be incorporated into an amino acid sequence during synthesis, while in other embodiments the non-standard amino acids may be introduced by modification or replacement of the "original" standard amino acids after synthesis of the amino acid sequence.

Use of non-standard and/or non-naturally occurring amino acids increases structural and functional diversity, and can thus increase the potential for achieving desired IL-4Rα-binding and neutralizing properties in a binding member of the invention. Additionally, D-amino acids and analogues have been shown to have better pharmacokinetic profiles compared with standard L-amino acids, owing to in vivo degradation of polypeptides having L-amino acids after administration to an animal e.g. a human.

Novel VH or VL regions carrying CDR-derived sequences of the invention may be generated using random mutagenesis of one or more selected VH and/or VL genes to generate mutations within the entire variable domain. Such a technique is described by Gram et al. (Proc. Natl. Acad. Sci., USA, 89:3576-3580, 1992), who used error-prone PCR. In some embodiments one or two amino acid substitutions are made within an entire variable domain or set of CDRs. Another method that may be used is to direct mutagenesis to CDR regions of VH or VL genes. Such techniques are disclosed by Barbas et al. (Proc. Natl. Acad. Sci., 91:3809-3813, 1994) and Schier et al. (J. Mol. Biol. 263:551-567, 1996).

All the above-described techniques are known as such in the art and the skilled person will be able to use such techniques to provide binding members of the invention using routine methodology in the art.

A further aspect of the invention provides a method for obtaining an antibody antigen-binding site for IL-4Rα, the method comprising providing by way of addition, deletion, substitution or insertion of one or more amino acids in the amino acid sequence of a VH domain set out herein a VH domain which is an amino acid sequence variant of the VH domain, optionally combining the VH domain thus provided with one or more VL domains, and testing the VH domain or VH/VL combination or combinations to identify a binding member or an antibody antigen-binding site for IL-4Rα and optionally with one or more functional properties, e.g. ability to neutralize IL-4Rα activity. Said VL domain may have an amino acid sequence which is substantially as set out herein. An analogous method may be employed in which one or more sequence variants of a VL domain disclosed herein are combined with one or more VH domains.

As noted above, a CDR amino acid sequence substantially as set out herein may be carried as a CDR in a human antibody variable domain or a substantial portion thereof. The HCDR3 sequences substantially as set out herein represent embodiments of the present invention and for example each of these may be carried as a HCDR3 in a human heavy chain variable domain or a substantial portion thereof.

Variable domains employed in the invention may be obtained or derived from any germ-line or rearranged human variable domain, or may be a synthetic variable domain based on consensus or actual sequences of known human variable domains. A variable domain can be derived from a non-human antibody. A CDR sequence of the invention (e.g. CDR3) may be introduced into a repertoire of variable domains lacking a CDR (e.g. CDR3), using recombinant DNA technology. For example, Marks et al. (Bio/Technology, 10:779-783, 1992) describe methods of producing repertoires of antibody variable domains in which consensus primers directed at or adjacent to the 5' end of the variable domain area are used in conjunction with consensus primers to the third framework region of human VH genes to provide a repertoire of VH variable domains lacking a CDR3. Marks et al. further describe how this repertoire may be combined with a CDR3 of a particular antibody. Using analogous techniques, the CDR3-derived sequences of the present invention may be shuffled with repertoires of VH or VL domains lacking a CDR3, and the shuffled complete VH or VL domains combined with a cognate VL or VH domain to provide binding members of the invention. The repertoire may then be displayed in a suitable host system such as the phage display system of WO92/01047, which is herein incorporated by reference in its entirety, or any of a subsequent large body of literature, including Kay, Winter & McCafferty (Phage Display of Peptides and Proteins: A Laboratory Manual, San Diego: Academic Press, 1996), so that suitable binding members may be selected. A repertoire may consist of from anything from $10^4$ individual members upwards, for example at least $10^5$, at least $10^6$, at least $10^7$, at least $10^8$, at least $10^9$ or at least $10^{10}$ members. Other suitable host systems include, but are not limited to, yeast display, bacterial display, T7 display, viral display, cell display, ribosome display and covalent display.

Analogous shuffling or combinatorial techniques are also disclosed by Stemmer (Nature, 370:389-391, 1994), who describes the technique in relation to a β-lactamase gene but observes that the approach may be used for the generation of antibodies.

A method of preparing a binding member for IL-4Rα antigen is provided, which method comprises:

(a) providing a starting repertoire of nucleic acids encoding a VH domain which either include a CDR3 to be replaced or lack a CDR3 encoding region;

(b) combining said repertoire with a donor nucleic acid encoding an amino acid sequence substantially as set out herein for a VH CDR3 such that said donor nucleic acid is inserted into the CDR3 region in the repertoire, so as to provide a product repertoire of nucleic acids encoding a VH domain;

(c) expressing the nucleic acids of said product repertoire;

(d) selecting a binding member for IL-4Rα; and (e) recovering said binding member or nucleic acid encoding it.

Again, an analogous method may be employed in which a VL CDR3 of the invention is combined with a repertoire of nucleic acids encoding a VL domain that either include a CDR3 to be replaced or lack a CDR3 encoding region.

Similarly, other VH and VL domains, sets of CDRs and sets of HCDRs and/or sets of LCDRs disclosed herein may be employed.

Similarly, one or more, or all three CDRs may be grafted into a repertoire of VH or VL domains that are then screened for a binding member or binding members for IL-4Rα.

Alternatively, nucleic acid encoding the VH and/or VL domains of any of a binding member of the present invention, e.g. Antibodies 1-42, can be subjected to mutagenesis (e.g. targeted or random) to generate one or more mutant nucleic acids. Binding members encoded by these sequences can then be generated.

In one embodiment, one or more of Antibodies 1 to 42 HCDR1, HCDR2 and HCDR3, or an Antibody 1 to 42 set of HCDRs, may be employed, and/or one or more of Antibodies 1 to 42 LCDR1, LCDR2 and LCDR3 or an Antibody 1 to 42 set of LCDRs may be employed.

According to one aspect of the invention there is provided a method for producing a binding member that binds IL-4Rα, which method comprises:

providing starting nucleic acid encoding a VH domain or a VL domain, or a starting repertoire of nucleic acids each encoding a VH or VL domain, wherein the VH or VL domains either comprise a CDR1, CDR2 and/or CDR3 to be replaced or lack a CDR1, CDR2 and/or CDR3 encoding region;

combining said starting nucleic acid or starting repertoire with donor nucleic acid or donor nucleic acids encoding or produced by mutation of the amino acid sequence of an CDR1, CDR2, and/or CDR3 of any of Antibodies 1-42, such that said donor nucleic acid is or donor nucleic acids are inserted into the CDR1, CDR2 and/or CDR3 region in the starting nucleic acid or starting repertoire, so as to provide a product repertoire of nucleic acids encoding VH or VL domains;

expressing the nucleic acids of said product repertoire to produce product VH or VL domains;

optionally combining said product VH or VL domains with one or more companion VL or VH domains;

selecting a binding member for IL-4Rα, which binding member comprises a product VH or VL domain and optionally a companion VL or VH domain; and recovering said binding member or nucleic acid encoding it.

In particular embodiments the donor nucleic acid is produced by targeted or random mutagenesis of the VH or VL domains or any CDR region therein.

In another embodiment, the product VH or VL domain is attached to an antibody constant region.

In another embodiment the product VH or VL domain and a companion VL or VH domain respectively, is comprised in an IgG, scFV or Fab antibody molecule.

In another embodiment the recovered binding member or antibody molecule is tested for ability to neutralise IL-4Rα.

In another embodiment the antibody molecule is formulated into a composition comprising at least one additional component. Such component could, for example, be an inert pharmaceutical excipient or carrier.

In some embodiments, a substantial portion of an immunoglobulin variable domain will comprise at least the three CDR regions, together with their intervening framework regions. The portion may also include at least about 50% of either or both of the first and fourth framework regions, the 50% being the C-terminal 50% of the first framework region and the N-terminal 50% of the fourth framework region. Additional residues at the N-terminal or C-terminal end of the substantial part of the variable domain may be those not normally associated with naturally occurring variable domain regions. For example, construction of binding members of the present invention made by recombinant DNA techniques may result in the introduction of N- or C-terminal residues encoded by linkers introduced to facilitate cloning or other manipulation steps. Other manipulation steps include the introduction of linkers to join variable domains of the invention to further protein sequences including antibody constant regions, other variable domains (for example in the production of diabodies) or detectable/functional labels as discussed in more detail elsewhere herein.

Although in some aspects of the invention, binding members comprise a pair of VH and VL domains, single binding domains based on either VH or VL domain sequences form further aspects of the invention. It is known that single immunoglobulin domains, especially VH domains, are capable of binding target antigens in a specific manner. For example, see the discussion of dAbs above.

In the case of either of the single binding domains, these domains may be used to screen for complementary domains capable of forming a two-domain binding member able to bind IL-4Rα. This may be achieved by phage display screening methods using the so-called hierarchical dual combinatorial approach as disclosed in WO92/01047, herein incorporated by reference in its entirety, in which an individual colony containing either an H or L chain clone is used to infect a complete library of clones encoding the other chain (L or H) and the resulting two-chain binding member is selected in accordance with phage display techniques such as those described in that reference. This technique is also disclosed in Marks et al. (Bio/Technology, 10:779-783, 1992).

Binding members of the present invention may further comprise antibody constant regions or parts thereof, e.g. human antibody constant regions or parts thereof. For example, a VL domain may be attached at its C-terminal end to antibody light chain constant domains including human Cκ or Cλ chains, e.g. Cλ chains. Similarly, a binding member based on a VH domain may be attached at its C-terminal end to all or part (e.g. a CH1 domain) of an immunoglobulin heavy chain derived from any antibody isotype, e.g. IgG, IgA, IgD, IgY, IgE and IgM and any of the isotype sub-classes (e.g., IgG1, IgG2, IgG3, IgG4, IgA1 and IgA2; particularly IgG1 and IgG4). IgG1 is advantageous, due to its effector function and ease of manufacture. Any synthetic or other constant region variant that has these properties and stabilizes variable regions is also useful in embodiments of the present invention.

The term "isotype" refers to the classification of an antibody's heavy or light chain constant region. The constant domains of antibodies are not involved in binding to antigen, but exhibit various effector functions. Depending on the amino acid sequence of the heavy chain constant region, a given human antibody or immunoglobulin can be assigned to one of five major classes of immunoglobulins: IgA, IgD, IgE, IgG, and IgM. Several of these classes may be further divided into subclasses (isotypes), e.g., IgG1 (gamma 1), IgG2 (gamma 2), IgG3 (gamma 3), and IgG4 (gamma 4), and IgA1 and IgA2. The heavy chain constant regions that correspond to the different classes of immunoglobulins are called α, δ, ε, γ, and μ, respectively. The structures and three-dimensional configurations of different classes of immunoglobulins are well-known. Of the various human immunoglobulin classes, only human IgG1, IgG2, IgG3, IgG4, and IgM are known to activate complement. Human IgG1 and IgG3 are known to mediate ADCC in humans. Human light chain constant regions may be classified into two major classes, kappa and lambda.

Antibody Format

The present invention also includes binding members of the invention, and in particular the antibodies of the invention, that have modified IgG constant domains. Antibodies of the human IgG class, which have functional characteristics such a long half-life in serum and the ability to mediate various effector functions are used in certain embodiments of the invention (*Monoclonal Antibodies: Principles and Applications*, Wiley-Liss, Inc., Chapter 1 (1995)). The human IgG class antibody is further classified into the following 4 subclasses: IgG1, IgG2, IgG3 and IgG4. A large number of studies have so far been conducted for ADCC and CDC as effector functions of the IgG class antibody, and it has been reported that among antibodies of the human IgG class, the IgG1 subclass has the highest ADCC activity and CDC activity in humans (*Chemical Immunology*, 65, 88 (1997)).

"Antibody-dependent cell-mediated cytotoxicity" and "ADCC" refer to a cell-mediated reaction in which non-specific cytotoxic cells (e.g., Natural Killer (NK) cells, neutrophils, and macrophages) recognize bound antibody on a target cell and subsequently cause lysis of the target cell. In one embodiment, such cells are human cells. While not wishing to be limited to any particular mechanism of action, these cytotoxic cells that mediate ADCC generally express Fc receptors (FcRs). The primary cells for mediating ADCC, NK cells, express FcγRIII, whereas monocytes express FcγRI, FcγRII, FcγRIII and/or FcγRIV. FcR expression on hematopoietic cells is summarized in Ravetch and Kinet, Annu. Rev. Immunol., 9:457-92 (1991). To assess ADCC activity of a molecule, an in vitro ADCC assay, such as that described in U.S. Pat. Nos. 5,500,362 or 5,821,337 may be performed. Useful effector cells for such assays include peripheral blood mononuclear cells (PBMC) and Natural Killer (NK) cells. Alternatively, or additionally, ADCC activity of the molecules of interest may be assessed in vivo, e.g., in an animal model such as that disclosed in Clynes et al., Proc. Natl. Acad. Sci. (USA), 95:652-656 (1998).

Complement dependent cytotoxicity" or "CDC" refers to the ability of a molecule to initiate complement activation and lyse a target in the presence of complement. The complement activation pathway is initiated by the binding of the first component of the complement system (C1q) to a molecule (e.g., an antibody) complexed with a cognate antigen. To assess complement activation, a CDC assay, e.g., as described in Gazzano-Santaro et al., J. Immunol. Methods, 202:163 (1996), may be performed.

Expression of ADCC activity and CDC activity of the human IgG1 subclass antibodies generally involves binding of the Fc region of the antibody to a receptor for an antibody (hereinafter referred to as "FcγR") existing on the surface of effector cells such as killer cells, natural killer cells or activated macrophages. Various complement components can be bound. Regarding the binding, it has been suggested that several amino acid residues in the hinge region and the second domain of C region (hereinafter referred to as "Cγ2 domain") of the antibody are important (*Eur. J. Immunol.,* 23, 1098 (1993), *Immunology,* 86, 319 (1995), *Chemical Immunology,* 65, 88 (1997)) and that a sugar chain in the Cγ2 domain (*Chemical Immunology,* 65, 88 (1997)) is also important.

"Effector cells" are leukocytes that express one or more FcRs and perform effector functions. The cells express at least FcγRI, FCγRII, FcγRIII and/or FcγRIV and carry out ADCC effector function. Examples of human leukocytes which mediate ADCC include peripheral blood mononuclear cells (PBMC), natural killer (NK) cells, monocytes, cytotoxic T cells and neutrophils.

The terms "Fc receptor" or "FcR" are used to describe a receptor that binds to the Fc region of an antibody. In one embodiment, the FcR is a native sequence human FcR. Moreover, in certain embodiments, the FcR is one that binds an IgG antibody (a gamma receptor) and includes receptors of the FcγRI, FcγRII, FcγRIII, and FcγRIV subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (See, Daëron, Annu. Rev. Immunol., 15:203-234 (1997)). FcRs are reviewed in Ravetch and Kinet, Annu. Rev. Immunol., 9:457-92 (1991); Capel et al., Immunomethods, 4:25-34 (1994); and de Haas et al., J. Lab. Clin. Med., 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., Immunol., 117:587 (1976) and Kim et al., J. Immunol., 24:249 (1994)).

Anti-IL-4Rα antibodies can be modified with respect to effector function, e.g., so as to enhance ADCC and/or complement dependent cytotoxicity (CDC) of the antibody. This may be achieved by introducing one or more amino acid substitutions in the Fc region of an antibody. Cysteine residue(s) may also be introduced in the Fc region, allowing for interchain disulfide bond formation in this region. In this way a homodimeric antibody can be generated that may have improved internalization capability and/or increased complement-mediated cell killing and ADCC (Caron et al., *J. Exp. Med.*, 176:1191-1195 (1992) and Shopes, *J. Immunol*, 148: 2918-2922 (1992)). Heterobifunctional cross-linkers can also be used to generate homodimeric antibodies with enhanced anti-tumor activity (Wolff et al., *Cancer Research*, 53:2560-2565 (1993)). Antibodies can also be engineered to have two or more Fc regions resulting in enhanced complement lysis and ADCC capabilities (Stevenson et al., *Anti-Cancer Drug Design*, (3): 219-230 (1989)).

Other methods of engineering Fc regions of antibodies so as to alter effector functions are known in the art (e.g., U.S. Patent Publication No. 20040185045 and PCT Publication No. WO 2004/016750, both to Koenig et al., which describe altering the Fc region to enhance the binding affinity for FcγRIIB as compared with the binding affinity for FCγRIIA; see also PCT Publication Nos. WO 99/58572 to Armour et al., WO 99/51642 to Idusogie et al., and U.S. Pat. No. 6,395,272 to Deo et al.; the disclosures of which are incorporated herein in their entireties). Methods of modifying the Fc region to decrease binding affinity to FcγRIIB are also known in the art (e.g., U.S. Patent Publication No. 20010036459 and PCT Publication No. WO 01/79299, both to Ravetch et al., the disclosures of which are incorporated herein in their entireties). Modified antibodies having variant Fc regions with enhanced binding affinity for FcγRIIIA and/or FcγRIIA as compared with a wildtype Fc region have also been described (e.g., PCT Publication No. WO 2004/063351, to Stavenhagen et al.; the disclosure of which is incorporated herein in its entirety).

At least four different types of FcγR have been found, which are respectively called FcγRI (CD64), FcγRII (CD32), FcγRIII (CD16), and FcγRIV. In human, FcγRII and FcγRIII are further classified into FcγRIIa and FcγRIIb, and FcγRIIIa and FcγRIIIb, respectively. FcγR is a membrane protein belonging to the immunoglobulin superfamily, FcγRII, FcγRIII, and FcγRIV have an α chain having an extracellular region containing two immunoglobulin-like domains, FcγRI has an α chain having an extracellular region containing three immunoglobulin-like domains, as a constituting component, and the α chain is involved in the IgG binding activity. In addition, FcγRI and FcγRIII have a γ chain or ζ chain as a constituting component which has a signal transduction function in association with the α chain (*Annu. Rev. Immunol.*, 18, 709 (2000), *Annu. Rev. Immunol.*, 19, 275 (2001)). FcγRIV has been described by Bruhns et al., *Clin. Invest. Med.*, (Canada) 27:3 D (2004).

To assess ADCC activity of an anti-IL-4Rα antibody of interest, an in vitro ADCC assay can be used, such as that described in U.S. Pat. Nos. 5,500,362 or 5,821,337. The assay may also be performed using a commercially available kit, e.g. CytoTox 96 ® (Promega). Useful effector cells for such assays include, but are not limited to peripheral blood mononuclear cells (PBMC), Natural Killer (NK) cells, and NK cell lines. NK cell lines expressing a transgenic Fc receptor (e.g. CD16) and associated signaling polypeptide (e.g. FCεRI-γ) may also serve as effector cells (see, e.g. WO 2006/023148 A2 to Campbell). For example, the ability of any particular antibody to mediate lysis of the target cell by complement activation and/or ADCC can be assayed. The cells of interest are grown and labeled in vitro; the antibody is added to the cell culture in combination with immune cells which may be activated by the antigen antibody complexes; i.e., effector cells involved in the ADCC response. The antibody can also be tested for complement activation. In either case, cytolysis of the target cells is detected by the release of label from the lysed cells. The extent of target cell lysis may also be determined by detecting the release of cytoplasmic proteins (e.g. LDH) into the supernatant. In fact, antibodies can be screened using the patient's own serum as a source of complement and/or immune cells. The antibodies that are capable of mediating human ADCC in the in vitro test can then be used therapeutically in that particular patient. ADCC activity of the molecule of interest may also be assessed in vivo, e.g., in an animal model such as that disclosed in Clynes et al., *Proc. Natl. Acad. Sci.* (USA) 95:652-656 (1998). Moreover, techniques for modulating (i.e., increasing or decreasing) the level of ADCC, and optionally CDC activity, of an antibody are well-known in the art. See, e.g., U.S. Pat. No. 6,194,551. Antibodies of the present invention may be capable or may have been modified to have the ability of inducing ADCC and/or CDC. Assays to determine ADCC function can be practiced using human effector cells to assess human ADCC function. Such assays may also include those intended to screen for antibodies that induce, mediate, enhance, block cell death by necrotic and/or apoptotic mechanisms. Such methods including assays utilizing viable dyes, methods of detecting and analyzing caspases, and assays measuring DNA breaks can be used to assess the apoptotic activity of cells cultured in vitro with an anti-IL-4Rα antibody of interest.

For example, Annexin V or TdT-mediated dUTP nick-end labeling (TUNEL) assays can be carried out as described in Decker et al., *Blood* (USA) 103:2718-2725 (2004) to detect apoptotic activity. The TUNEL assay involves culturing the cell of interest with fluorescein-labeled dUTP for incorporation into DNA strand breaks. The cells are then processed for analysis by flow cytometry. The Annexin V assay detects the appearance of phosphatidylserine (PS) on the outside of the plasma membrane of apoptotic cells using a fluorescein-conjugated Annexin V that specifically recognizes the exposed PS molecules. Concurrently, a viable dye such as propidium iodide can be used to exclude late apoptotic cells. The cells are stained with the labeled Annexin V and are analyzed by flow cytometry.

Thus according to a further aspect of the invention there is provided binding members, in particular antibodies, which have been modified so as to change, i.e. increase, decrease or eliminate, the biological effector function of the binding members, for example antibodies with modified Fc regions. In some embodiments, the binding members or antibodies as disclosed herein can be modified to enhance their capability of fixing complement and participating in complement-dependent cytotoxicity (CDC). In other embodiments, the binding members or antibodies can be modified to enhance their capability of activating effector cells and participating in antibody-dependent cytotoxicity (ADCC). In yet other embodiments, the binding members or antibodies as disclosed herein can be modified both to enhance their capability of activating effector cells and participating in antibody-dependent cytotoxicity (ADCC) and to enhance their capability of fixing complement and participating in complement-dependent cytotoxicity (CDC).

In some embodiments, the binding members or antibodies as disclosed herein can be modified to reduce their capability of fixing complement and participating in complement-dependent cytotoxicity (CDC). In other embodiments, the binding members or antibodies can be modified to reduce their capability of activating effector cells and participating in antibody-dependent cytotoxicity (ADCC). In yet other embodiments, the binding members or antibodies as disclosed herein can be modified both to reduce their capability of activating effector cells and participating in antibody-dependent cytotoxicity (ADCC) and to reduce their capability of fixing complement and participating in complement-dependent cytotoxicity (CDC).

In one embodiment, a binding member with an Fc variant region has enhanced ADCC activity relative to a comparable molecule. In a specific embodiment, a binding member with an Fc variant region has ADCC activity that is at least 2 fold, or at least 3 fold, or at least 5 fold or at least 10 fold or at least 50 fold or at least 100 fold greater than that of a comparable molecule. In another specific embodiment, a binding member with an Fc variant region has enhanced binding to the Fc receptor FcγRIIIA and has enhanced ADCC activity relative to a comparable molecule. In other embodiments, the binding member with an Fc variant region has both enhanced ADCC activity and enhanced serum half-life relative to a comparable molecule.

In one embodiment, a binding member with an Fc variant region has reduced ADCC activity relative to a comparable molecule. In a specific embodiment, a binding member with an Fc variant region has ADCC activity that is at least 2 fold, or at least 3 fold, or at least 5 fold or at least 10 fold or at least 50 fold or at least 100 fold lower than that of a comparable molecule. In another specific embodiment, the binding member with an Fc variant region has reduced binding to the Fc receptor FcγRIIIA and has reduced ADCC activity relative to a comparable molecule. In other embodiments, the binding member with an Fc variant region has both reduced ADCC activity and enhanced serum half-life relative to a comparable molecule.

In one embodiment, the binding member with an Fc variant region has enhanced CDC activity relative to a comparable molecule. In a specific embodiment the binding member with an Fc variant region has CDC activity that is at least 2 fold, or at least 3 fold, or at least 5 fold or at least 10 fold or at least 50 fold or at least 100 fold greater than that of a comparable molecule. In other embodiments, the binding member with an Fc variant region has both enhanced CDC activity and enhanced serum half-life relative to a comparable molecule.

In one embodiment, the binding member with an Fc variant region has reduced binding to one or more Fc ligand relative to a comparable molecule. In another embodiment, the binding member with an Fc variant region has an affinity for an Fc ligand that is at least 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold lower than that of a comparable molecule. In a specific embodiment, the binding member with an Fc variant region has reduced binding to an Fc receptor. In another specific embodiment, the binding member with an Fc variant region has reduced binding to the Fc receptor FcγRIIIA. In a further specific embodiment, an binding member with an Fc variant region described herein has an affinity for the Fc receptor FcγRIIIA that is at least about 5 fold lower than that of a comparable molecule, wherein said Fc variant has an affinity for the Fc receptor FcγRIIB that is within about 2 fold of that of a comparable molecule. In still another specific embodiment, the binding member with an Fc variant region has reduced binding to the Fc receptor FcRn. In yet another specific embodiment, the binding member with an Fc variant region has reduced binding to C1q relative to a comparable molecule.

In one embodiment, the binding member with the Fc variant region has enhanced binding to one or more Fc ligand(s) relative to a comparable molecule. In another embodiment, the binding member with the Fc variant region has an affinity for an Fc ligand that is at least 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold greater than that of a comparable molecule. In a specific embodiment, the binding member with the Fc variant region has enhanced binding to an Fc receptor. In another specific embodiment, the binding member with the Fc variant region has enhanced binding to the Fc receptor FcγRIIIA. In a further specific embodiment, the binding member with the Fc variant region has enhanced biding to the Fc receptor FcγRIIB. In still another specific embodiment, the binding member with the Fc variant region has enhanced binding to the Fc receptor FcRn. In yet another specific embodiment, the binding member with the Fc variant region has enhanced binding to C1q relative to a comparable molecule.

In one embodiment, an anti-IL-4Rα antibody of the invention comprises a variant Fc domain wherein said variant Fc domain has enhanced binding affinity to Fc gamma receptor IIB relative to a comparable non-variant Fc domain. In a further embodiment, an anti-IL-4Rα antibody of the invention comprises a variant Fc domain wherein said variant Fc domain has an affinity for Fc gamma receptor IIB that is at least 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold greater than that of a comparable non-variant Fc domain.

In one embodiment, the present invention provides a binding member with an Fc variant region or formulations comprising these, wherein the Fc region comprises a non-native amino acid residue at one or more positions selected from the group consisting of 228, 234, 235, 236, 237, 238, 239, 240, 241, 243, 244, 245, 247, 251, 252, 254, 255, 256, 262, 263, 264, 265, 266, 267, 268, 269, 279, 280, 284, 292, 296, 297, 298, 299, 305, 313, 316, 325, 326, 327, 328, 329, 330, 331, 332, 333, 334, 339, 341, 343, 370, 373, 378, 392, 416, 419, 421, 440 and 443 as numbered by the EU index as set forth in Kabat. Optionally, the Fc region may comprise a non-native amino acid residue at additional and/or alternative positions known to one skilled in the art (see, e.g., U.S. Pat. Nos. 5,624,821; 6,277,375; 6,737,056; PCT Patent Publications WO 01/58957; WO 02/06919; WO 04/016750; WO 04/029207; WO 04/035752; WO 04/074455; WO 04/099249; WO 04/063351; WO 05/070963; WO 05/040217, WO 05/092925 and WO 06/020114).

By "non-native amino acid residue", we mean an amino acid residue that is not present at the recited position in the naturally occurring protein. Typically, this will mean that the or a native/natural amino acid residue has been substituted for one or more other residues, which may comprise one of the other 20 naturally-occurring (common) amino acids or a non-classical amino acids or a chemical amino acid analog. Non-classical amino acids include, but are not limited to, the D-isomers of the common amino acids, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general.

In a specific embodiment, the present invention provides a binding member with an variant Fc region or a formulation comprising such binding member with an variant Fc region, wherein the Fc region comprises at least one non-native amino acid residue selected from the group consisting of 234D, 234E, 234N, 234Q, 234T, 234H, 234Y, 234I, 234V, 234F, 235A, 235D, 235R, 235W, 235P, 235S, 235N, 235Q, 235T, 235H, 235Y, 235I, 235V, 235F, 236E, 239D, 239E, 239N, 239Q, 239F, 239T, 239H, 239Y, 240I, 240A, 240T, 240M, 241W, 241 L, 241Y, 241E, 241R. 243W, 243L 243Y, 243R, 243Q, 244H, 245A, 247L, 247V, 247G, 251F, 252Y, 254T, 255L, 256E, 256M, 262I, 262A, 262T, 262E, 263I, 263A, 263T, 263M, 264L, 264I, 264W, 264T, 264R, 264F, 264M, 264Y, 264E, 265G, 265N, 265Q, 265Y, 265F, 265V, 265I, 265L, 265H, 265T, 266I, 266A, 266T, 266M, 267Q, 267L, 268E, 269H, 269Y, 269F, 269R, 270E, 280A, 284M, 292P, 292L, 296E, 296Q, 296D, 296N, 296S, 296T, 296L, 296I, 296H, 269G, 297S, 297D, 297E, 298H, 298I, 298T, 298F, 299I, 299L, 299A, 299S, 299V, 299H, 299F, 299E, 305I, 313F, 316D, 325Q, 325L, 325I, 325D, 325E, 325A, 325T, 325V, 325H, 327G, 327W, 327N, 327L, 328S, 328M, 328D, 328E, 328N, 328Q, 328F, 328I, 328V, 328T, 328H, 328A, 329F, 329H, 329Q, 330K, 330G, 330T, 330C, 330L, 330Y, 330V, 330I, 330F, 330R, 330H, 331G, 331A, 331L, 331M, 331F, 331W, 331K, 331Q, 331E, 331S, 331V, 331I, 331C, 331Y, 331H, 331R, 331N, 331D, 331T, 332D, 332S, 332W, 332F, 332E, 332N, 332Q, 332T, 332H, 332Y, 332A, 339T, 370E, 370N, 378D, 392T, 396L, 416G, 419H, 421K, 440Y and 434W as numbered by the EU index as set forth in Kabat. Optionally, the Fc region may comprise additional and/or alternative non-native amino acid residues known to one skilled in the art (see, e.g., U.S. Pat. Nos. 5,624,821; 6,277,375; 6,737,056; PCT Patent Publications WO 01/58957; WO 02/06919; WO 04/016750; WO 04/029207; WO 04/035752 and WO 05/040217).

It will be understood that Fc region as used herein includes the polypeptides comprising the constant region of an antibody excluding the first constant region immunoglobulin domain. Thus Fc refers to the last two constant region immunoglobulin domains of IgA, IgD, and IgG, and the last three constant region immunoglobulin domains of IgE and IgM, and the flexible hinge N-terminal to these domains. For IgA and IgM Fc may include the J chain. For IgG, Fc comprises immunoglobulin domains Cgamma2 and Cgamma3 (Cγ2 and Cγ3) and the hinge between Cgamma1 (Cγ1) and Cgamma2 (Cγ2). Although the boundaries of the Fc region may vary, the human IgG heavy chain Fc region is usually defined to comprise residues C226 or P230 to its carboxyl-terminus, wherein the numbering is according to the EU index as in Kabat et al. (1991, NIH Publication 91-3242, National Technical Information Service, Springfield, Va.). The "EU index as set forth in Kabat" refers to the residue numbering of the human IgG1 EU antibody as described in Kabat et al. supra. Fc may refer to this region in isolation, or this region in the context of an antibody, antibody fragment, or Fc fusion protein. An variant Fc protein may be an antibody, Fc fusion, or any protein or protein domain that comprises an Fc region including, but not limited to, proteins comprising variant Fc regions, which are non naturally occurring variants of an Fc.

The present invention encompasses binding members with variant Fc regions, which have altered binding properties for an Fc ligand (e.g., an Fc receptor, C1q) relative to a comparable molecule (e.g., a protein having the same amino acid sequence except having a wild type Fc region). Examples of binding properties include but are not limited to, binding specificity, equilibrium dissociation constant ($K_D$), dissociation and association rates ($k_{off}$ and $k_{on}$ respectively), binding affinity and/or avidity. It is generally understood that a binding molecule (e.g., a variant Fc protein such as an antibody) with a low $K_D$ may be preferable to a binding molecule with a high $K_D$. However, in some instances the value of the $k_{on}$ or $k_{off}$ may be more relevant than the value of the $K_D$. One skilled in the art can determine which kinetic parameter is most important for a given antibody application.

The affinities and binding properties of an Fc domain for its ligand may be determined by a variety of in vitro assay methods (biochemical or immunological based assays) known in the art for determining Fc-FcγR interactions, i.e., specific binding of an Fc region to an FcγR including but not limited to, equilibrium methods (e.g., enzyme-linked immunoabsorbent assay (ELISA), or radioimmunoassay (RIA)), or kinetics (e.g., BIACORE® analysis), and other methods such as indirect binding assays, competitive inhibition assays, fluorescence resonance energy transfer (FRET), gel electrophoresis and chromatography (e.g., gel filtration). These and other methods may utilize a label on one or more of the components being examined and/or employ a variety of detection methods including but not limited to chromogenic, fluorescent, luminescent, or isotopic labels. A detailed description of binding affinities and kinetics can be found in Paul, W. E., ed., Fundamental Immunology, 4th Ed., Lippincott-Raven, Philadelphia (1999), which focuses on antibody-immunogen interactions. The serum half-life of proteins comprising Fc regions may be increased by increasing the binding affinity of the Fc region for FcRn. In one embodiment, the Fc variant protein has enhanced serum half-life relative to comparable molecule.

The term "antibody half-life" as used herein means a pharmacokinetic property of an antibody that is a measure of the mean survival time of antibody molecules following their administration. Antibody half-life can be expressed as the time required to eliminate 50 percent of a known quantity of immunoglobulin from the patient's body or a specific compartment thereof, for example, as measured in serum or plasma, i.e., circulating half-life, or in other tissues. Half-life may vary from one immunoglobulin or class of immunoglobulin to another. In general, an increase in antibody half-life results in an increase in mean residence time (MRT) in circulation for the antibody administered.

In certain embodiments, the half-life of an anti-IL-4Rα antibody or compositions and methods of the invention is at least about 4 to 7 days. In certain embodiments, the mean half-life of an anti-IL-4Rα antibody of compositions and methods of the invention is at least about 2 to 5 days, 3 to 6 days, 4 to 7 days, 5 to 8 days, 6 to 9 days, 7 to 10 days, 8 to 11 days, 8 to 12, 9 to 13, 10 to 14, 11 to 15, 12 to 16, 13 to 17, 14 to 18, 15 to 19, or 16 to 20 days. In other embodiments, the mean half-life of an anti-IL-4Rα antibody of compositions and methods of the invention is at least about 17 to 21 days, 18 to 22 days, 19 to 23 days, 20 to 24 days, 21 to 25, days, 22 to 26 days, 23 to 27 days, 24 to 28 days, 25 to 29 days, or 26 to 30 days. In still further embodiments the half-life of an anti-IL-4Rα antibody of compositions and methods of the invention can be up to about 50 days. In certain embodiments, the half-lives of antibodies of compositions and methods of the invention can be prolonged by methods known in the art. Such prolongation can in turn reduce the amount and/or frequency of dosing of the antibody compositions. Antibodies with improved in vivo half-lives and methods for preparing them are disclosed in U.S. Pat. No. 6,277,375, U.S. Pat. No. 7,083, 784; and International Publication Nos. WO 98/23289 and WO 97/3461.

The serum circulation of anti-IL-4Rα antibodies in vivo may also be prolonged by attaching inert polymer molecules such as high molecular weight polyethyleneglycol (PEG) to the antibodies with or without a multifunctional linker either through site-specific conjugation of the PEG to the N- or C-terminus of the antibodies or via epsilon-amino groups present on lysyl residues. Linear or branched polymer derivatization that results in minimal loss of biological activity will be used. The degree of conjugation can be closely monitored by SDS-PAGE and mass spectrometry to ensure proper conjugation of PEG molecules to the antibodies. Unreacted PEG can be separated from antibody-PEG conjugates by size-exclusion or by ion-exchange chromatography. PEG-derivatized antibodies can be tested for binding activity as well as for in vivo efficacy using methods known to those of skill in the art, for example, by immunoassays described herein.

Further, the antibodies of compositions and methods of the invention can be conjugated to albumin in order to make the antibody more stable in vivo or have a longer half-life in vivo. The techniques are well known in the art, see, e.g., International Publication Nos. WO 93/15199, WO 93/15200, and WO 01/77137; and European Patent No. EP 413, 622, all of which are incorporated herein by reference.

In certain embodiments, the half-life of a binding member or antibody as disclosed herein and of compositions of the invention is at least about 4 to 7 days. In certain embodiments, the mean half-life of a binding member or antibody as disclosed herein and of compositions of the invention is at least about 2 to 5 days, 3 to 6 days, 4 to 7 days, 5 to 8 days, 6 to 9 days, 7 to 10 days, 8 to 11 days, 8 to 12, 9 to 13, 10 to 14, 11 to 15, 12 to 16, 13 to 17, 14 to 18, 15 to 19, or 16 to 20 days. In other embodiments, the mean half-life of a binding member or antibody as disclosed herein and of compositions of the invention is at least about 17 to 21 days, 18 to 22 days, 19 to 23 days, 20 to 24 days, 21 to 25, days, 22 to 26 days, 23 to 27 days, 24 to 28 days, 25 to 29 days, or 26 to 30 days. In still further embodiments the half-life of a binding member or antibody as disclosed herein and of compositions of the invention can be up to about 50 days. In certain embodiments, the half-lives of antibodies and of compositions of the invention can be prolonged by methods known in the art. Such prolongation can in turn reduce the amount and/or frequency of dosing of the antibody compositions. Antibodies with improved in vivo half-lives and methods for preparing them are disclosed in U.S. Pat. No. 6,277,375; U.S. Pat. No. 7,083,784; and International Publication Nos. WO 1998/23289 and WO 1997/34361.

In another embodiment, the present invention provides a binding member, particularly an antibody with a variant Fc region, or a formulation comprising these, wherein the Fc region comprises at least one non-native modification at one or more positions selected from the group consisting of 239, 330 and 332, as numbered by the EU index as set forth in Kabat. In a specific embodiment, the present invention provides an Fc variant, wherein the Fc region comprises at least one non-native amino acid selected from the group consisting of 239D, 330L and 332E, as numbered by the EU index as set forth in Kabat. Optionally, the Fc region may further comprise additional non-native amino acid at one or more positions selected from the group consisting of 252, 254, and 256, as numbered by the EU index as set forth in Kabat. In a specific embodiment, the present invention provides an Fc variant, wherein the Fc region comprises at least one non-native amino acid selected from the group consisting of 239D, 330L and 332E, as numbered by the EU index as set forth in Kabat and at least one normative amino acid at one or more positions selected from the group consisting of 252Y, 254T and 256E, as numbered by the EU index as set forth in Kabat.

In another embodiment, the present invention provides a binding member, particularly an antibody with a variant Fc region, or a formulation comprising these, wherein the Fc region comprises at least one non-native amino acid at one or more positions selected from the group consisting of 234, 235 and 331, as numbered by the EU index as set forth in Kabat. In a specific embodiment, the present invention provides an Fc variant, wherein the Fc region comprises at least one non-native amino acid selected from the group consisting of 234F, 235F, 235Y, and 331, Sas numbered by the EU index as set forth in Kabat. In a further specific embodiment, an Fc variant of the invention comprises the 234F, 235F, and 331S amino acid residues, as numbered by the EU index as set forth in Kabat. In another specific embodiment, an Fc variant of the invention comprises the 234F, 235Y, and 331S amino acid residues, as numbered by the EU index as set forth in Kabat. Optionally, the Fc region may further comprise additional non-native amino acid residues at one or more positions selected from the group consisting of 252, 254, and 256, as numbered by the EU index as set forth in Kabat. In a specific embodiment, the present invention provides an Fc variant, wherein the Fc region comprises at least one non-native amino acid selected from the group consisting of 234F, 235F, 235Y, and 331S, as numbered by the EU index as set forth in Kabat; and at least one non-native amino acid at one or more positions selected from the group consisting of 252Y, 254T and 256E, as numbered by the EU index as set forth in Kabat.

In a particular embodiment, the invention provides a binding member of the present invention with a variant Fc region, wherein the variant comprises a tyrosine (Y) residue at position 252, a threonine (T) residue at position 254 and a glutamic acid (E) residue at position 256, as numbered by the EU index as set forth in Kabat.

The M252Y, S254T and T256E mutations, as numbered by the EU index as set forth in Kabat, hereinafter referred to as YTE mutations, have been reported to increase serum half-life of a particular IgG1 antibody molecule (Dall'Acqua et al. J. Biol. Chem. 281(33):23514-23524, 2006).

In a further embodiment, the invention provides a binding member of the present invention with a variant Fc region, wherein the variant comprises a tyrosine (Y) residue at position 252, a threonine (T) residue at position 254, a glutamic acid (E) residue at position 256 and a proline (P) residue at position 241, as numbered by the EU index as set forth in Kabat.

The serine228proline mutation (S228P), as numbered by the EU index as set forth in Kabat, hereinafter referred to as the P mutation, has been reported to increase the stability of a particular IgG4 molecule (Lu et al., J Pharmaceutical Sciences 97(2):960-969, 2008). Note: In Lu et al. it is referred to as position 241 because therein they use the Kabat numbering system, not the "EU index" as set forth in Kabat.

This P mutation may be combined with L235E to further knock out ADCC. This combination of mutations is hereinafter referred to as the double mutation (DM).

In a particular embodiment, the invention provides a binding member of the present invention with a variant Fc region, wherein the variant comprises a phenylalanine (F) residue at position 234, a phenylalanine (F) residue or a glutamic acid (E) residue at position 235 and a serine (S) residue at position 331, as numbered by the EU index as set forth in Kabat. Such a mutation combinations are hereinafter referred to as the triple mutant (TM).

According to a further embodiment, the invention provides an antibody of the present invention in IgG1 format with the YTE mutations in the Fc region.

According to a further embodiment, the invention provides an antibody of the present invention in IgG1 format with the TM mutations in the Fc region.

According to a further embodiment, the invention provides an antibody of the present invention in IgG1 format with the YTE mutations and the TM mutations in the Fc region.

According to embodiment, the invention provides an antibody of the present invention in IgG4 format with the YTE and P mutations in the Fc region.

According to embodiment, the invention provides an antibody of the present invention in IgG4 format with the YTE and DM mutations in the Fc region.

According to particular embodiments of the inventions there is provided an antibody of the present invention in a format selected from: IgG1 YTE, IgG1 TM, IgG1 TM+YTE, IgG4 P, IgG4 DM, IgG4 YTE, IgG4 P+YTE and IgG4 DM+YTE.

In terms of the nomenclature used, it will be appreciated that DM+YTE means that the constant domain Fc region possesses both the double mutations (S228P and L235E) and the YTE mutations (M252Y, S254T and T256E).

Methods for generating non naturally occurring Fc regions are known in the art. For example, amino acid substitutions and/or deletions can be generated by mutagenesis methods, including, but not limited to, site-directed mutagenesis (Kunkel, Proc. Natl. Acad. Sci. USA 82:488-492, 1985), PCR mutagenesis (Higuchi, in "PCR Protocols: A Guide to Methods and Applications", Academic Press, San Diego, pp. 177-183, 1990), and cassette mutagenesis (Wells et al., Gene 34:315-323, 1985). Preferably, site-directed mutagenesis is performed by the overlap-extension PCR method (Higuchi, in "PCR Technology: Principles and Applications for DNA Amplification", Stockton Press, New York, pp. 61-70, 1989). The technique of overlap-extension PCR (Higuchi, ibid.) can also be used to introduce any desired mutation(s) into a target sequence (the starting DNA). For example, the first round of PCR in the overlap-extension method involves amplifying the target sequence with an outside primer (primer 1) and an internal mutagenesis primer (primer 3), and separately with a second outside primer (primer 4) and an internal primer (primer 2), yielding two PCR segments (segments A and B). The internal mutagenesis primer (primer 3) is designed to contain mismatches to the target sequence specifying the desired mutation(s). In the second round of PCR, the products of the first round of PCR (segments A and B) are amplified by PCR using the two outside primers (primers 1 and 4). The resulting full-length PCR segment (segment C) is digested with restriction enzymes and the resulting restriction fragment is cloned into an appropriate vector. As the first step of mutagenesis, the starting DNA (e.g., encoding an Fc fusion protein, an antibody or simply an Fc region), is operably cloned into a mutagenesis vector. The primers are designed to reflect the desired amino acid substitution. Other methods useful for the generation of variant Fc regions are known in the art (see, e.g., U.S. Pat. Nos. 5,624,821; 5,885,573; 5,677, 425; 6,165,745; 6,277,375; 5,869,046; 6,121,022; 5,624,821; 5,648,260; 6,528,624; 6,194,551; 6,737,056; 6,821,505; 6,277,375; U.S. Patent Publication Nos. 2004/0002587 and PCT Publications WO 94/29351; WO 99/58572; WO 00/42072; WO 02/060919; WO 04/029207; WO 04/099249; WO 04/063351; WO 06/23403).

In some embodiments of the invention, the glycosylation patterns of the binding members provided herein are modified to enhance ADCC and CDC effector function. (See Shields R L et al., (JBC. 277:26733-26740, 2002; Shinkawa T et al., JBC. 278:3466-3473, 2003; and Okazaki A et al., J. Mol. Biol., 336:1239, 2004). In some embodiments, an Fc variant protein comprises one or more engineered glycoforms, i.e., a carbohydrate composition that is covalently attached to the molecule comprising an Fc region. Engineered glycoforms may be useful for a variety of purposes, including but not limited to enhancing or reducing effector function. Engineered glycoforms may be generated by any method known to one skilled in the art, for example by using engineered or variant expression strains, by co-expression with one or more enzymes, for example DI N-acetylglucosaminyltransferase III (GnTI11), by expressing a molecule comprising an Fc region in various organisms or cell lines from various organisms, or by modifying carbohydrate(s) after the molecule comprising Fc region has been expressed. Methods for generating engineered glycoforms are known in the art, and include but are not limited to those described in Umana et al, Nat. Biotechnol 17:176-180, 1999; Davies et al., Biotechnol Bioeng 74:288-294, 2007; Shields et al, J Biol Chem 277: 26733-26740, 2002; Shinkawa et al., J Biol Chem 278:3466-3473, 2003) U.S. Pat. No. 6,602,684; U.S. Ser. No. 10/277, 370; U.S. Ser. No. 10/113,929; PCT WO 00/61739A1; PCT WO 01/292246A1; PCT WO 02/311140A1; PCT WO 02/30954A1; Potillegent™ technology (Biowa, Inc. Princeton, N.J.); GlycoMAb™ glycosylation engineering technology (Glycart Biotechnology AG, Zurich, Switzerland). See, e.g., WO 00/061739; EA01229125; US 20030115614; Okazaki et al., JMB. 336:1239-49, 2004.

Binding members of the invention may be labelled with a detectable or functional label. A label can be any molecule that produces or can be induced to produce a signal, including but not limited to fluorescers, radiolabels, enzymes, chemiluminescers or photosensitizers. Thus, binding may be detected and/or measured by detecting fluorescence or luminescence, radioactivity, enzyme activity or light absorbance.

Suitable labels include, by way of illustration and not limitation, enzymes such as alkaline phosphatase, glucose-6-phosphate dehydrogenase ("G6PDH") and horseradish peroxidase; dyes; fluorescers, such as fluorescein, rhodamine compounds, phycoerythrin, phycocyanin, allophycocyanin, o-phthaldehyde, fluorescamine, fluorophores such as lanthanide cryptates and chelates (Perkin Elmer and C is Biointernational); chemiluminescers such as isoluminol; sensitizers; coenzymes; enzyme substrates; radiolabels including but not limited to $^{125}$I, $^{131}$I, $^{35}$S, $^{32}$P, $^{14}$C, $^{3}$H, $^{57}$Co, $^{99}$Tc and $^{75}$Se and other radiolabels mentioned herein; particles such as latex or carbon particles; metal sol; crystallite; liposomes; cells, etc., which may be further labelled with a dye, catalyst or other detectable group. Suitable enzymes and coenzymes are disclosed in U.S. Pat. No. 4,275,149 and U.S. Pat. No. 4,318,980, each of which are herein incorporated by reference in their entireties. Suitable fluorescers and chemiluminescers are also disclosed in U.S. Pat. No. 4,275,149, which is incorporated herein by reference in its entirety. Labels further include chemical moieties such as biotin that may be detected via binding to a specific cognate detectable moiety, e.g. labelled avidin or streptavidin. Detectable labels may be attached to antibodies of the invention using conventional chemistry known in the art.

There are numerous methods by which the label can produce a signal detectable by external means, for example, by visual examination, electromagnetic radiation, heat, and chemical reagents. The label can also be bound to another binding member that binds the antibody of the invention, or to a support.

The label can directly produce a signal, and therefore, additional components are not required to produce a signal. Numerous organic molecules, for example fluorescers, are able to absorb ultraviolet and visible light, where the light absorption transfers energy to these molecules and elevates them to an excited energy state. This absorbed energy is then dissipated by emission of light at a second wavelength. This second wavelength emission may also transfer energy to a labelled acceptor molecule, and the resultant energy dissipated from the acceptor molecule by emission of light for example fluorescence resonance energy transfer (FRET). Other labels that directly produce a signal include radioactive isotopes and dyes.

Alternately, the label may need other components to produce a signal, and the signal producing system would then include all the components required to produce a measurable signal, which may include substrates, coenzymes, enhancers, additional enzymes, substances that react with enzymic products, catalysts, activators, cofactors, inhibitors, scavengers, metal ions, and a specific binding substance required for binding of signal generating substances. A detailed discussion of suitable signal producing systems can be found in U.S. Pat. No. 5,185,243, which is herein incorporated herein by reference in its entirety.

The binding member, antibody, or one of its functional fragments, can be present in the form of an immunoconjugate so as to obtain a detectable and/or quantifiable signal. The immunoconjugates can be conjugated, for example, with enzymes such as peroxidase, alkaline phosphatase, alpha-D-galactosidase, glucose oxydase, glucose amylase, carbonic anhydrase, acetylcholinesterase, lysozyme, malate dehydrogenase or glucose 6-phosphate dehydrogenase or by a molecule such as biotin, digoxygenin or 5-bromodeoxyuridine. Fluorescent labels can be likewise conjugated to the immunoconjugates or to their functional fragments according to the invention and especially include fluorescein and its derivatives, fluorochrome, rhodamine and its derivatives, GFP (GFP for "Green Fluorescent Protein"), dansyl, umbelliferone, Lanthanide chelates or cryptates eg. Europium etc.

The immunoconjugates or their functional fragments can be prepared by methods known to the person skilled in the art. They can be coupled to the enzymes or to the fluorescent labels directly or by the intermediary of a spacer group or of a linking group such as a polyaldehyde, like glutaraldehyde, ethylenediaminetetraacetic acid (EDTA), diethylene-triaminepentaacetic acid (DPTA), or in the presence of coupling agents such as those mentioned above for the therapeutic conjugates. The conjugates containing labels of fluorescein type can be prepared by reaction with an isothiocyanate. Other immunoconjugates can likewise include chemoluminescent labels such as luminol and the dioxetanes, bio-luminescent labels such as luciferase and luciferin, or else radioactive labels such as iodine123, iodine125, iodine126, iodine131, iodine133, bromine77, technetium99m, indium111, indium 113m, gallium67, gallium 68, sulphur35, phosphorus32, carbonl4, tritium (hydrogen3), cobalt57, selenium75, ruthenium95, ruthenium97, ruthenium103, ruthenium105, mercury107, mercury203, rhenium99m, rhenium 101, rhenium105, scandium47, tellurium121 m, tellurium122m, tellurium125m, thulium165, thulium167, thulium168, fluorine8, yttrium 199. The methods known to the person skilled in the art existing for coupling the therapeutic radioisotopes to the antibodies either directly or via a chelating agent such as EDTA, DTPA mentioned above can be used for the radioelements which can be used in diagnosis. It is likewise possible to mention labelling with Na[I 125] by the chloramine T method (Hunter and Greenwood, Nature, 194:495, 1962) or else with technetium99m by the technique of Crockford et al., (U.S. Pat. No. 4,424,200, herein incorporated by reference in its entirety) or attached via DTPA as described by Hnatowich (U.S. Pat. No. 4,479,930, herein incorporated by reference in its entirety). Further immunoconjugates can include a toxin moiety such as for example a toxin moiety selected from a group of Pseudomonas exotoxin (PE or a cytotoxic fragment or mutant thereof), Diptheria toxin or a cytotoxic fragment or mutant thereof, a botulinum toxin A through F, ricin or a cytotoxic fragment thereof, abrin or a cytotoxic fragment thereof, saporin or a cytotoxic fragment thereof, pokeweed antiviral toxin or a cytotoxic fragment thereof and bryodin 1 or a cytotoxic fragment thereof.

The present invention provides a method comprising causing or allowing binding of a binding member as provided herein to IL-4Rα. As noted, such binding may take place in vivo, e.g. following administration of a binding member, or nucleic acid encoding a binding member, or it may take place in vitro, for example in ELISA, Western blotting, immunocytochemistry, immuno-precipitation, affinity chromatography, and biochemical or cell based assays such as are described herein. The invention also provides for measuring levels of antigen directly, by employing a binding member according to the invention for example in a biosensor system.

For instance, the present invention comprises a method of detecting and/or measuring binding to IL-4Rα, comprising, (i) exposing said binding member to IL-4Rα and (ii) detecting binding of said binding member to IL-4Rα, wherein binding is detected using any method or detectable label described herein. This, and any other binding detection method described herein, may be interpreted directly by the person performing the method, for instance, by visually observing a detectable label. Alternatively, this method, or any other binding detection method described herein, may produce a report in the form of an autoradiograph, a photograph, a computer printout, a flow cytometry report, a graph, a chart, a test tube or container or well containing the result, or any other visual or physical representation of a result of the method.

The amount of binding of binding member to IL-4Rα may be determined. Quantification may be related to the amount of the antigen in a test sample, which may be of diagnostic interest. Screening for IL-4Rα binding and/or the quantification thereof may be useful, for instance, in screening patients for diseases or disorders associated with IL-4Rα, such as are referred to elsewhere herein. In one embodiment, among others, a diagnostic method of the invention comprises (i) obtaining a tissue or fluid sample from a subject, (ii) exposing said tissue or fluid sample to one or more binding members of the present invention; and (iii) detecting bound IL-4Rα as compared to a control sample, wherein an increase in the amount of IL-4Rα binding as compared to the control may indicate an aberrant level of IL-4Rα expression or activity. Tissue or fluid samples to be tested include blood, serum, urine, biopsy material, tumours, or any tissue suspected of containing aberrant IL-4Rα levels. Subjects testing positive for aberrant IL-4Rα levels or activity may also benefit from the treatment methods disclosed later herein.

Those skilled in the art are able to choose a suitable mode of determining binding of the binding member to an antigen according to their preference and general knowledge, in light of the methods disclosed herein.

The reactivities of binding members in a sample may be determined by any appropriate means. Radioimmunoassay (RIA) is one possibility. Radioactive labelled antigen is mixed with unlabelled antigen (the test sample) and allowed to bind to the binding member. Bound antigen is physically separated from unbound antigen and the amount of radioactive antigen bound to the binding member determined. The more antigen there is in the test sample the less radioactive antigen will bind to the binding member. A competitive binding assay may also be used with non-radioactive antigen, using antigen or an analogue linked to a reporter molecule. The reporter molecule may be a fluorochrome, phosphor or laser dye with spectrally isolated absorption or emission characteristics. Suitable fluorochromes include fluorescein, rhodamine, phycoerythrin, Texas Red, and lanthanide chelates or cryptates. Suitable chromogenic dyes include diaminobenzidine.

Other reporters include macromolecular colloidal particles or particulate material such as latex beads that are coloured, magnetic or paramagnetic, and biologically or chemically active agents that can directly or indirectly cause detectable signals to be visually observed, electronically detected or otherwise recorded. These molecules may be enzymes, which catalyze reactions that develop, or change colours or cause changes in electrical properties, for example. They may be molecularly excitable, such that electronic transitions between energy states result in characteristic spectral absorptions or emissions. They may include chemical entities used in conjunction with biosensors. Biotin/avidin or biotin/streptavidin and alkaline phosphatase detection systems may be employed.

The signals generated by individual binding member-reporter conjugates may be used to derive quantifiable absolute or relative data of the relevant binding member binding in samples (normal and test).

A kit comprising a binding member according to any aspect or embodiment of the present invention is also provided as an aspect of the present invention. In the kit, the binding member may be labelled to allow its reactivity in a sample to be determined, e.g. as described further below. Further the binding member may or may not be attached to a solid support. Components of a kit are generally sterile and in sealed vials or other containers. Kits may be employed in diagnostic analysis or other methods for which binding members are useful. A kit may contain instructions for use of the components in a method, e.g. a method in accordance with the present invention. Ancillary materials to assist in or to enable performing such a method may be included within a kit of the invention. The ancillary materials include a second, different binding member, which binds to the first binding member and is conjugated to a detectable label (e.g., a fluorescent label, radioactive isotope or enzyme). Antibody-based kits may also comprise beads for conducting an immunoprecipitation. Each component of the kits is generally in its own suitable container. Thus, these kits generally comprise distinct containers suitable for each binding member. Further, the kits may comprise instructions for performing the assay and methods for interpreting and analyzing the data resulting from the performance of the assay.

The present invention also provides the use of a binding member as above for measuring antigen levels in a competition assay, that is to say a method of measuring the level of antigen in a sample by employing a binding member as provided by the present invention in a competition assay. This may be where the physical separation of bound from unbound antigen is not required. Linking a reporter molecule to the binding member so that a physical or optical change occurs on binding is one possibility. The reporter molecule may directly or indirectly generate detectable signals, which may be quantifiable. The linkage of reporter molecules may be directly or indirectly, covalently, e.g. via a peptide bond or non-covalently. Linkage via a peptide bond may be as a result of recombinant expression of a gene fusion encoding antibody and reporter molecule.

For example, the present invention includes a method of identifying an IL-4Rα binding compound, comprising (i) immobilizing IL-4Rα to a support, (ii) contacting said immobilized IL-4Rα simultaneously or in a step-wise manner with at least one tagged or labelled binding member according to the invention and one or more untagged or unlabelled test binding compounds, and (iii) identifying a new IL-4Rα binding compound by observing a decrease in the amount of bound tag from the tagged binding member.

An alternative method of identifying an IL-4Rα binding compound may comprise (i) immobilizing binding member to a support, (ii) contacting said immobilized binding member simultaneously or in a step-wise manner with tagged IL-4Rα and one or more untagged or unlabelled test binding members or binding compounds, (iii) identifying a new IL-4Rα binding compound by observing a decrease in the amount of bound tag from the tagged IL-4Rα.

Such methods can be performed in a high-throughput manner using a multiwell or array format. Such assays may also be performed in solution for example as an HTRF® assay as described in Example 4.3. See, for instance, U.S. Pat. No. 5,814,468, which is herein incorporated by reference in its entirety. As described above, detection of binding may be interpreted directly by the person performing the method, for instance, by visually observing a detectable label, or a decrease in the presence thereof. Alternatively, the binding methods of the invention may produce a report in the form of an autoradiograph, a photograph, a computer printout, a flow cytometry report, a graph, a chart, a test tube or container or well containing the result, or any other visual or physical representation of a result of the method.

Competition assays can also be used in epitope mapping. In one instance epitope mapping may be used to identify the epitope bound by an IL-4Rα binding member, which optionally may have optimized neutralizing and/or modulating characteristics. Such an epitope can be linear or conformational. A conformational epitope can comprise at least two different fragments of IL-4Rα, wherein said fragments are positioned in proximity to each other when IL-4Rα is folded in its tertiary or quaternary structure to form a conformational epitope which is recognized by an inhibitor of IL-4Rα, such as an IL-4Rα binding member. In testing for competition a peptide fragment of the antigen may be employed, especially a peptide including or consisting essentially of an epitope of interest. A peptide having the epitope sequence plus one or more amino acids at either end may be used. Binding members according to the present invention may be such that their binding for antigen is inhibited by a peptide with or including the sequence given.

The present invention further provides an isolated nucleic acid encoding a binding member of the present invention. Nucleic acid may include DNA and/or RNA. In one aspect, the present invention provides a nucleic acid that codes for a CDR or set of CDRs or VH domain or VL domain or antibody antigen-binding site or antibody molecule, e.g. scFv or IgG, e.g. IgG1, IgG2 or IgG4, of the invention as defined above.

The present invention also provides constructs in the form of plasmids, vectors, transcription or expression cassettes which comprise at least one polynucleotide as above.

The present invention also provides a recombinant host cell that comprises one or more constructs as above. A nucleic acid encoding any CDR or set of CDRs or VH domain or VL domain or antibody antigen-binding site or antibody molecule, e.g. scFv or IgG1, IgG2 or IgG4 as provided, itself forms an aspect of the present invention, as does a method of production of the encoded product, which method comprises expression from encoding nucleic acid. Expression may conveniently be achieved by culturing under appropriate conditions recombinant host cells containing the nucleic acid. Following production by expression a VH or VL domain, or binding member may be isolated and/or purified using any suitable technique, then used as appropriate.

Nucleic acid according to the present invention may comprise DNA or RNA and may be wholly or partially synthetic. Reference to a nucleotide sequence as set out herein encompasses a DNA molecule with the specified sequence, and encompasses a RNA molecule with the specified sequence in which U is substituted for T, unless context requires otherwise.

A yet further aspect provides a method of production of an antibody VH variable domain, the method including causing expression from encoding nucleic acid. Such a method may comprise culturing host cells under conditions for production of said antibody VH variable domain.

Analogous methods for production of VL variable domains and binding members comprising a VH and/or VL domain are provided as further aspects of the present invention.

A method of production may comprise a step of isolation and/or purification of the product. A method of production may comprise formulating the product into a composition including at least one additional component, such as a pharmaceutically acceptable excipient.

Systems for cloning and expression of a polypeptide in a variety of different host cells are well known. Suitable host cells include bacteria, mammalian cells, plant cells, filamentous fungi, yeast and baculovirus systems and transgenic plants and animals. The expression of antibodies and antibody fragments in prokaryotic cells is well established in the art. For a review, see for example Plückthun 1991. A common bacterial host is *E. coli*.

Expression in eukaryotic cells in culture is also available to those skilled in the art as an option for production of a binding member for example Chadd & Chamow (Current Opinion in Biotechnology 12:188-194, 2001), Andersen & Krummen (Current Opinion in Biotechnology 13:117, 2002) and Larrick & Thomas (Current Opinion in Biotechnology 12:411-418, 2001). Mammalian cell lines available in the art for expression of a heterologous polypeptide include Chinese hamster ovary (CHO) cells, HeLa cells, baby hamster kidney cells, NS0 mouse melanoma cells, YB2/0 rat myeloma cells, human embryonic kidney cells, human embryonic retina cells and many others.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids e.g. phagemid, or viral e.g. 'phage, as appropriate. For further details see, for example, Sambrook & Russell (Molecular Cloning: a Laboratory Manual: 3rd edition, 2001, Cold Spring Harbor Laboratory Press). Many known techniques and protocols for manipulation of nucleic acid, for example in preparation of nucleic acid constructs, mutagenesis, sequencing, introduction of DNA into cells and gene expression, and analysis of proteins, are described in detail in Ausubel et al. eds., Short Protocols in Molecular Biology: A Compendium of Methods from Current Protocols in Molecular Biology, John Wiley & Sons, 4$^{th}$ edition 1999.

A further aspect of the present invention provides a host cell containing nucleic acid as disclosed herein. Such a host cell may be in vitro and may be in culture. Such a host cell may be in vivo. In vivo presence of the host cell may allow intracellular expression of the binding members of the present invention as "intrabodies" or intracellular antibodies. Intrabodies may be used for gene therapy.

A still further aspect provides a method comprising introducing nucleic acid of the invention into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. Introducing nucleic acid in the host cell, in particular a eukaryotic cell may use a viral or a plasmid based system. The plasmid system may be maintained episomally or may incorporated into the host cell or into an artificial chromosome. Incorporation may be either by random or targeted integration of one or more copies at single or multiple loci. For bacterial cells, suitable techniques may include calcium chloride transformation, electroporation and transfection using bacteriophage.

The introduction may be followed by causing or allowing expression from the nucleic acid, e.g. by culturing host cells under conditions for expression of the gene. The purification of the expressed product may be achieved by methods known to one of skill in the art.

In one embodiment, the nucleic acid of the invention is integrated into the genome (e.g. chromosome) of the host cell. Integration may be promoted by inclusion of sequences that promote recombination with the genome, in accordance with standard techniques.

The present invention also provides a method that comprises using a construct as stated above in an expression system in order to express a binding member or polypeptide as above.

Binding members of the present invention may be used in methods of diagnosis or treatment in human or animal subjects, e.g. human. For instance, binding members may be used in diagnosis or treatment of IL-4Rα-associated diseases or disorders, examples of which are referred to elsewhere herein.

Particular conditions for which a binding member of the invention may be used in treatment or diagnosis include: asthma, COPD (including chronic bronchitis, small airway disease and emphysema), inflammatory bowel disease, fibrotic conditions (including systemic sclerosis, pulmonary fibrosis, parasite-induced liver fibrosis, and cystic fibrosis, allergy (including for example atopic dermatitis and food allergy), transplantation therapy to prevent transplant rejection, as well as suppression of delayed-type hypersensitivity or contact hypersensitivity reactions, as adjuvants to allergy immunotherapy and as vaccine adjuvants.

Thus, binding members of the invention are useful as therapeutic agents in the treatment of conditions involving IL-4, IL-13 or IL-4Rα expression and/or activity. One embodiment, among others, is a method of treatment comprising administering an effective amount of a binding member of the invention to a patient in need thereof, wherein functional consequences of IL-4Rα activation are decreased. Another embodiment, among others, is a method of treatment comprising (i) identifying a patient demonstrating IL-4, IL-13 or IL-4Rα expression or activity, for instance using the diagnostic methods described above, and (ii) administering an effective amount of a binding member of the invention to the patient, wherein the functional consequences of IL-4Rα activation are attenuated. An effective amount according to the invention is an amount that modulates (e.g. decreases) the functional consequences of IL-4Rα activation so as to modulate (e.g. decrease or lessen) the severity of at least one symptom of the particular disease or disorder being treated, but not necessarily cure the disease or disorder. Accordingly, one embodiment of the invention is a method of treating or reducing the severity of at least one symptom of any of the disorders referred to herein, comprising administering to a patient in need thereof an effective amount of one or more binding members of the present invention alone or in a combined therapeutic regimen with another appropriate medicament known in the art or described herein such that the severity of at least one symptom of any of the disorders is reduced. Another embodiment of the invention, among others, is a method of antagonizing at least one effect of IL-4Rα comprising contacting with or administering an effective amount of one or more binding members of the present invention such that said at least one effect of IL-4Rα is antagonized, e.g. the ability of IL-4Rα to form a complex (the precursor to active signalling) with IL-4.

Accordingly, further aspects of the invention provide methods of treatment comprising administration of a binding member as provided, or pharmaceutical compositions comprising such a binding member, and/or use of such a binding member in the manufacture of a medicament for administration, for example in a method of making a medicament or pharmaceutical composition comprising formulating the binding member with a pharmaceutically acceptable excipient. A pharmaceutically acceptable excipient may be a compound or a combination of compounds entering into a pharmaceutical composition not provoking secondary reactions and which allows, for example, facilitation of the administration of the active compound(s), an increase in its lifespan and/or in its efficacy in the body, an increase in its solubility in solution or else an improvement in its conservation. These pharmaceutically acceptable vehicles are well known and will be adapted by the person skilled in the art as a function of the nature and of the mode of administration of the active compound(s) chosen.

Binding members of the present invention will usually be administered in the form of a pharmaceutical composition, which may comprise at least one component in addition to the binding member. Thus pharmaceutical compositions according to the present invention, and for use in accordance with the present invention, may comprise, in addition to active ingredient, a pharmaceutically acceptable excipient, carrier, buffer, stabilizer or other materials well known to those skilled in the art. Such materials should be non-toxic and should not interfere with the efficacy of the active ingredient. The precise nature of the carrier or other material will depend on the route of administration, which may be oral, inhaled or by injection, e.g. intravenous. In on embodiment the composition is sterile.

Pharmaceutical compositions for oral administration such as for example nanobodies etc are also envisaged in the present invention. Such oral formulations may be in tablet, capsule, powder, liquid or semi-solid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives may be employed, as required, including buffers such as phosphate, citrate, histidine and other organic acids; antioxidants such as ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3'-pentanol; and m-cresol); low molecular weight polypeptides; proteins such as serum albumin, gelatin or immunoglobulins; hydrophilic polymers such as polyvinylpyrrolidone; amino acids such as glycine, glutamine, asparagines, histidine, arginine, or lysine; monosaccharides, disaccharides and other carbohydrates including glucose, mannose or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

Binding members of the present invention may be formulated in liquid, semi-solid or solid forms depending on the physicochemical properties of the molecule and the route of delivery. Formulations may include excipients, or combinations of excipients, for example: sugars, amino acids and surfactants. Liquid formulations may include a wide range of antibody concentrations and pH. Solid formulations may be produced by lyophilisation, spray drying, or drying by supercritical fluid technology, for example. Formulations of anti-IL-4Rα will depend upon the intended route of delivery: for example, formulations for pulmonary delivery may consist of particles with physical properties that ensure penetration into the deep lung upon inhalation; topical formulations may include viscosity modifying agents, which prolong the time that the drug is resident at the site of action. In certain embodiments, the binding member may be prepared with a carrier that will protect the binding member against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are known to those skilled in the art. See, e.g., Robinson, 1978.

Anti-IL-4Rα treatment with a binding member of the invention may be given orally (for example nanobodies) by injection (for example, subcutaneously, intra-articular, intravenously, intraperitoneal, intra-arterial or intramuscularly), by inhalation, by the intravesicular route (instillation into the urinary bladder), or topically (for example intraocular, intranasal, rectal, into wounds, on skin). The treatment may be administered by pulse infusion, particularly with declining doses of the binding member. The route of administration can be determined by the physicochemical characteristics of the treatment, by special considerations for the disease or by the requirement to optimize efficacy or to minimize side-effects. One particular route of administration is intravenous. Another route of administering pharmaceutical compositions of the present invention is subcutaneously. It is envisaged that anti-IL-4Rα treatment will not be restricted to use in hospitals or doctor's offices but rather may include homes and places of work. Therefore, subcutaneous injection using a needle-free device is advantageous.

A composition may be administered alone or in combination with other treatments, concurrently or sequentially or as a combined preparation with another therapeutic agent or agents, dependent upon the condition to be treated.

A binding member for IL-4Rα may be used as part of a combination therapy in conjunction with an additional medicinal component. Combination treatments may be used to provide significant synergistic effects, particularly the combination of an anti-IL-4Rα binding member with one or more other drugs. A binding member for IL-4Rα may be administered concurrently or sequentially or as a combined preparation with another therapeutic agent or agents, for the treatment of one or more of the conditions listed herein.

A binding member according to the present invention may be provided in combination or addition with one or more of the following agents:

a cytokine or agonist or antagonist of cytokine function (e.g. an agent which acts on cytokine signalling pathways, such as a modulator of the SOCS system), such as an alpha-, beta- and/or gamma-interferon; insulin-like growth factor type I (IGF-1), its receptors and associated binding proteins; interleukins (IL), e.g. one or more of IL-1 to -33, and/or an interleukin antagonist or inhibitor, such as anakinra; inhibitors of receptors of interleukin family members or inhibitors of specific subunits of such receptors, a tumour necrosis factor alpha (TNF-α) inhibitor, such as an anti-TNF monoclonal antibodies (for example infliximab, adalimumab and/or CDP-870) and/or a TNF receptor antagonist, e.g. an immunoglobulin molecule (such as etanercept) and/or a low-molecular-weight agent, such as pentoxyfylline;

a modulator of B cells, e.g. a monoclonal antibody targeting B-lymphocytes (such as CD20 (rituximab) or MRA-aIL16R) or T-lymphocytes (e.g. CTLA4-Ig or Abatacept);

a modulator that inhibits osteoclast activity, for example an antibody to RANKL;

a modulator of chemokine or chemokine receptor function, such as an antagonist of CCR1, CCR2, CCR2A, CCR2B, CCR3, CCR4, CCR5, CCR6, CCR7, CCR8, CCR9, CCR10 or CCR11 (for the C-C family); CXCR1, CXCR2, CXCR3, CXCR4, CXCR5, CXCR6 or CXCL13 (for the C-X-C family) or $CX_3CR1$ (for the $C-X_3-C$ family);

an inhibitor of matrix metalloproteases (MMPs), i.e. one or more of the stromelysins, the collagenases and the gelatinases as well as aggrecanase, especially collagenase-1 (MMP-1), collagenase-2 (MMP-8), collagenase-3 (MMP-13), stromelysin-1 (MMP-3), stromelysin-2 (MMP-10) and/or stromelysin-3 (MMP-11) and/or MMP-9 and/or MMP-12, e.g. an agent such as doxycycline;

a leukotriene biosynthesis inhibitor, 5-lipoxygenase (5-LO) inhibitor or 5-lipoxygenase activating protein (FLAP) antagonist, such as zileuton; ABT-761; fenleuton; tepoxalin; Abbott-79175; Abbott-85761; N-(5-substituted)-thiophene-2-alkylsulfonamides; 2,6-di-tert-butylphenolhydrazones; methoxytetrahydropyrans such as Zeneca ZD-2138; the compound SB-210661; a pyridinyl-substituted 2-cyanonaphthalene compound, such as L-739,010; a 2-cyanoquinoline compound, such as L-746,530; indole and/or a quinoline compound, such as MK-591, MK-886 and/or BAY x 1005;

a receptor antagonist for leukotrienes (LT) B4, LTC4, LTD4, and LTE4, selected from the group consisting of the phenothiazin-3-1s, such as L-651,392; amidino compounds, such as CGS-25019c; benzoxalamines, such as ontazolast; benzenecarboximidamides, such as BIIL 284/260; and compounds, such as zafirlukast, ablukast, montelukast, pranlukast, verlukast (MK-679), RG-12525, Ro-245913, iralukast (CGP 45715A) and BAY x 7195;

a phosphodiesterase (PDE) inhibitor, such as a methylxanthanine, e.g. theophylline and/or aminophylline; and/or a selective PDE isoenzyme inhibitor, e.g. a PDE4 inhibitor and/or inhibitor of the isoform PDE4D and/or an inhibitor of PDE5;

a histamine type 1 receptor antagonist, such as cetirizine, loratadine, desloratadine, fexofenadine, acrivastine, terfenadine, astemizole, azelastine, levocabastine, chlorpheniramine, promethazine, cyclizine, and/or mizolastine (generally applied orally, topically or parenterally);

a proton pump inhibitor (such as omeprazole) or gastroprotective histamine type 2 receptor antagonist;

an antagonist of the histamine type 4 receptor;

an alpha-1/alpha-2 adrenoceptor agonist vasoconstrictor sympathomimetic agent, such as propylhexedrine, phenylephrine, phenylpropanolamine, ephedrine, pseudoephedrine, naphazoline hydrochloride, oxymetazoline hydrochloride, tetrahydrozoline hydrochloride, xylometazoline hydrochloride, tramazoline hydrochloride and ethylnorepinephrine hydrochloride;

an anticholinergic agent, e.g. a muscarinic receptor (e.g. M1, M2, M3, M4 or M5) antagonist, such as atropine, hyoscine, glycopyrrrolate, ipratropium bromide, tiotropium bromide, oxitropium bromide, pirenzepine and telenzepine;

a beta-adrenoceptor agonist (including beta receptor subtypes 1-4), such as isoprenaline, salbutamol, formoterol, salmeterol, terbutaline, orciprenaline, bitolterol mesylate and/or pirbuterol, e.g. a chiral enantiomer thereof;

a chromone, e.g. sodium cromoglycate and/or nedocromil sodium;

a glucocorticoid, such as flunisolide, triamcinolone acetonide, beclomethasone dipropionate, budesonide, fluticasone propionate, ciclesonide, and/or mometasone furoate;

an agent that modulate nuclear hormone receptors, such as a PPAR;

an immunoglobulin (Ig) or Ig preparation or an antagonist or antibody modulating Ig function, such as anti-IgE (e.g. omalizumab);

other systemic or topically-applied anti-inflammatory agent, e.g. thalidomide or a derivative thereof, a retinoid, dithranol and/or calcipotriol;

combinations of aminosalicylates and sulfapyridine, such as sulfasalazine, mesalazine, balsalazide, and olsalazine; and immunomodulatory agents, such as the thiopurines; and corticosteroids, such as budesonide;

an antibacterial agent, e.g. a penicillin derivative, a tetracycline, a macrolide, a beta-lactam, a fluoroquinolone, metronidazole and/or an inhaled aminoglycoside; and/or an antiviral agent, e.g. acyclovir, famciclovir, valaciclovir, ganciclovir, cidofovir; amantadine, rimantadine; ribavirin; zanamavir and/or oseltamavir; a protease inhibitor, such as indinavir, nelfinavir, ritonavir and/or saquinavir; a nucleoside reverse transcriptase inhibitor, such as didanosine, lamivudine, stavudine, zalcitabine, zidovudine; a non-nucleoside reverse transcriptase inhibitor, such as nevirapine, efavirenz;

a cardiovascular agent, such as a calcium channel blocker, beta-adrenoceptor blocker, angiotensin-converting enzyme (ACE) inhibitor, angiotensin-2 receptor antagonist; lipid lowering agent, such as a statin and/or fibrate; a modulator of blood cell morphology, such as pentoxyfylline; a thrombolytic and/or an anticoagulant, e.g. a platelet aggregation inhibitor;

a CNS agent, such as an antidepressant (such as sertraline), anti-Parkinsonian drug (such as deprenyl, L-dopa, ropinirole, pramipexole; MAOB inhibitor, such as selegine and rasagiline; comP inhibitor, such as tasmar; A-2 inhibitor, dopamine reuptake inhibitor, NMDA antagonist, nicotine agonist, dopamine agonist and/or inhibitor of neuronal nitric oxide synthase) and an anti-Alzheimer's drug, such as donepezil, rivastigmine, tacrine, COX-2 inhibitor, propentofylline or metrifonate;

an agent for the treatment of acute and chronic pain, e.g. a centrally or peripherally-acting analgesic, such as an opioid analogue or derivative, carbamazepine, phenyloin, sodium valproate, amitryptiline or other antidepressant agent, paracetamol, or non-steroidal anti-inflammatory agent;

a parenterally or topically-applied (including inhaled) local anaesthetic agent, such as lignocaine or an analogue thereof, an anti-osteoporosis agent, e.g. a hormonal agent, such as raloxifene, or a biphosphonate, such as alendronate;

(i) a tryptase inhibitor; (ii) a platelet activating factor (PAF) antagonist; (iii) an interleukin converting enzyme (ICE) inhibitor; (iv) an IMPDH inhibitor; (v) an adhesion molecule inhibitors including VLA-4 antagonist; (vi) a cathepsin; (vii) a kinase inhibitor, e.g. an inhibitor of tyrosine kinases (such as Btk, Itk, Jak3 MAP examples of inhibitors might include Gefitinib, Imatinib mesylate), a serine/threonine kinase (e.g. an inhibitor of MAP kinase, such as p38, JNK, protein kinases A, B and C and IKK), or a kinase involved in cell cycle regulation (e.g. a cylin dependent kinase); (viii) a glucose-6 phosphate dehydrogenase inhibitor; (ix) a kinin-B.sub1.- and/or B.sub2.-receptor antagonist; (x) an anti-gout agent, e.g. colchicine; (xi) a xanthine oxidase inhibitor, e.g. allopurinol; (xii) a uricosuric agent, e.g. probenecid, sulfinpyrazone, and/or benzbromarone; (xiii) a growth hormone secretagogue; (xiv) transforming growth factor (TGFβ); (xv) platelet-derived growth factor (PDGF); (xvi) fibroblast growth factor, e.g. basic fibroblast growth factor (bFGF); (xvii) granulocyte macrophage colony stimulating factor (GM-CSF); (xviii) capsaicin cream; (xix) a tachykinin NK.sub 1. and/or NK.sub3. receptor antagonist, such as NKP-608C, SB-233412 (talnetant) and/or D-4418; (xx) an elastase inhibitor, e.g. UT-77 and/or ZD-0892; (xxi) a TNF-alpha converting enzyme inhibitor (TACE); (xxii) induced nitric oxide synthase (iNOS) inhibitor or (xxiii) a chemoattractant receptor-homologous molecule expressed on TH2 cells (such as a CRTH2 antagonist); (xxiv) an inhibitor of a P38 (xxv) agent modulating the function of Toll-like receptors (TLR) and (xxvi) an agent modulating the activity of purinergic receptors, such as P2x7; (xxvii) an inhibitor of transcription factor activation, such as NFkB, API, and/or STATS.

An inhibitor may be specific or may be a mixed inhibitor, e.g. an inhibitor targeting more than one of the molecules (e.g. receptors) or molecular classes mentioned above.

The binding member could also be used in association with a chemotherapeutic agent or another tyrosine kinase inhibitor in co-administration or in the form of an immunoconjugate. Fragments of said antibody could also be use in bispecific antibodies obtained by recombinant mechanisms or biochemical coupling and then associating the specificity of the above described antibody with the specificity of other antibodies able to recognize other molecules involved in the activity for which IL-4Rα is associated.

For treatment of an inflammatory disease, e.g. rheumatoid arthritis, osteoarthritis, asthma, allergic rhinitis, chronic obstructive pulmonary disease (COPD), or psoriasis, a binding member of the invention may be combined with one or more agents, such as non-steroidal anti-inflammatory agents (hereinafter NSAIDs) including non-selective cyclo-oxygenase (COX)-1/COX-2 inhibitors whether applied topically or systemically, such as piroxicam, diclofenac, propionic acids, such as naproxen, flurbiprofen, fenoprofen, ketoprofen and ibuprofen, fenamates, such as mefenamic acid, indomethacin, sulindac, azapropazone, pyrazolones, such as phenylbutazone, salicylates, such as aspirin); selective COX-2 inhibitors (such as meloxicam, celecoxib, rofecoxib, valdecoxib, lumarocoxib, parecoxib and etoricoxib); cyclo-oxygenase inhibiting nitric oxide donors (CINODs); glucocorticosteroids (whether administered by topical, oral, intra-muscular, intra-venous or intra-articular routes); methotrexate, leflunomide; hydroxychloroquine, d-penicillamine, auranofin or other parenteral or oral gold preparations; analgesics; diacerein; intra-articular therapies, such as hyaluronic acid derivatives; and nutritional supplements, such as glucosamine.

A binding member of the invention can also be used in combination with an existing therapeutic agent for the treatment of cancer. Suitable agents to be used in combination include:

(i) antiproliferative/antineoplastic drugs and combinations thereof, as used in medical oncology, such as Gleevec (imatinib mesylate), alkylating agents (for example cis-platin, carboplatin, cyclophosphamide, nitrogen mustard, melphalan, chlorambucil, busulphan and nitrosoureas); antimetabolites (for example antifolates, such as fluoropyrimidines like 5-fluorouracil and tegafur, raltitrexed, methotrexate, cytosine arabinoside, hydroxyurea, gemcitabine and paclitaxel); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecins);

(ii) cytostatic agents, such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase, such as finasteride;

(iii) Agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab and the anti-erbb1 antibody cetuximab [C225]), farnesyl transferase inhibitors, tyrosine kinase inhibitors and serine/threonine kinase inhibitors, for example inhibitors of the epidermal growth factor family (for example EGFR family tyrosine kinase inhibitors, such as N-(3-chloro-4-fluorophenyl)-7-methoxy-6-(3-morpholinopropoxy)quinazolin-4-amine (gefitinib, AZD1839), N-(3-ethynylphenyl)-6,7-bis (2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI 1033)), for example inhibitors of the platelet-derived growth factor family and for example inhibitors of the hepatocyte growth factor family;

(v) antiangiogenic agents, such as those which inhibit the effects of vascular endothelial growth factor (for example the anti-vascular endothelial cell growth factor antibody bevacizumab, compounds, such as those disclosed in International Patent Applications WO 97/22596, WO 97/30035, WO 97/32856 and WO 98/13354, each of which is incorporated herein in its entirety) and compounds that work by other mechanisms (for example linomide, inhibitors of integrin αvβ3 function and angiostatin);

(vi) vascular damaging agents, such as combretastatin A4 and compounds disclosed in International Patent Applications WO 99/02166, WO 00/40529, WO 00/41669, WO 01/92224, WO 02/04434 and WO 02/08213 (each of which is incorporated herein in its entirety);

(vii) antisense therapies, for example those which are directed to the targets listed above, such as ISIS 2503, an anti-ras antisense;

(viii) gene therapy approaches, including for example approaches to replace aberrant genes, such as aberrant p53 or aberrant BRCA1 or BRCA2, GDEPT (gene directed enzyme pro-drug therapy) approaches, such as those using cytosine deaminase, thymidine kinase or a bacterial nitroreductase enzyme and approaches to increase patient tolerance to chemotherapy or radiotherapy, such as multi-drug resistance gene therapy; and (ix) immunotherapeutic approaches, including for example ex vivo and in vivo approaches to increase the immunogenicity of patient tumour cells, such as transfection with cytokines, such as interleukin 2, interleukin 4 or granulocyte macrophage colony stimulating factor, approaches to decrease T-cell anergy, approaches using transfected immune cells, such as cytokine-transfected dendritic cells, approaches using cytokine-transfected tumour cell lines and approaches using anti-idiotypic antibodies.

A binding member of the invention and one or more of the above additional medicinal components may be used in the manufacture of a medicament. The medicament may be for separate or combined administration to an individual, and accordingly may comprise the binding member and the additional component as a combined preparation or as separate preparations. Separate preparations may be used to facilitate separate and sequential or simultaneous administration, and allow administration of the components by different routes e.g. oral and parenteral administration.

In accordance with the present invention, compositions provided may be administered to mammals. Administration may be in a "therapeutically effective amount", this being sufficient to show benefit to a patient. Such benefit may be at least amelioration of at least one symptom. The actual amount administered, and rate and time-course of administration, will depend on the nature and severity of what is being treated, the particular mammal being treated, the clinical condition of the individual patient, the cause of the disorder, the site of delivery of the composition, the type of binding member, the method of administration, the scheduling of administration and other factors known to medical practitioners. Prescription of treatment, e.g. decisions on dosage etc, is within the responsibility of general practitioners and other medical doctors, and may depend on the severity of the symptoms and/or progression of a disease being treated. Appropriate doses of antibody are well known in the art (Ledermann et al. Int. J. Cancer 47:659-664, 1991; Bagshawe et al. Antibody, Immunoconjugates and Radiopharmaceuticals 4:915-922, 1991). Specific dosages indicated herein, or in the Physician's Desk Reference (2003) as appropriate for the type of medicament being administered, may be used. A therapeutically effective amount or suitable dose of a binding member of the invention can be determined by comparing its in vitro activity and in vivo activity in an animal model. Methods for extrapolation of effective dosages in mice and other test animals to humans are known. The precise dose will depend upon a number of factors, including whether the antibody is for diagnosis, prevention or for treatment, the size and location of the area to be treated, the precise nature of the antibody (e.g. whole antibody, fragment or diabody), and the nature of any detectable label or other molecule attached to the antibody. A typical antibody dose will be in the range 100 µg to 1 g for systemic applications, and 1 µg to 1 mg for topical applications. An initial higher loading dose, followed by one or more lower doses, may be administered. Typically, the antibody will be a whole antibody, e.g. the IgG1 isotype. This is a dose for a single treatment of an adult patient, which may be proportionally adjusted for children and infants, and also adjusted for other antibody formats in proportion to molecular weight. Treatments may be repeated at daily, twice-weekly, weekly or monthly intervals, at the discretion of the physician. Treatments may be every two to four weeks for subcutaneous administration and every four to eight weeks for intravenous administration. In some embodiments of the present invention, treatment is periodic, and the period between administrations is about two weeks or more, e.g. about three weeks or more, about four weeks or more, or about once a month. In other embodiments of the invention, treatment may be given before, and/or after surgery, and may be administered or applied directly at the anatomical site of surgical treatment.

The invention will be further described by following non-limiting Examples and Figures in which:

FIG. 1 shows alignment of the VH domains of Antibodies 2-42 against Antibody 1 (split into sheets A, B, C, and D).

FIG. 2 shows alignment of the VL domains of Antibodies 2-42 against Antibody 1 (split into sheets A, B, C, and D).

FIG. 3 shows alignment of VH domains of Antibodies 1-19 and 21-42 against Antibody 20 (split into sheets A, B, C, and D).

FIG. 4 shows alignment of VL domains of Antibodies 1-19 and 21-42 against Antibody 20 (split into sheets A, B, C, and D).

FIG. 5 is sequence identity tables for 6xCDRs (split into A, B, and C).

FIG. 6 is sequence identity tables for 3xVH CDRs (split into A, B, and C).

FIG. 7 is sequence identity tables for 3xVL CDRs (split into A, B, and C).

EXAMPLES

Example 1

1.1 Cloning of Human IL-4Rα Extracellular Domain

A cDNA encoding the sequence of human IL-4Rα extracellular domain (amino acid residues 1-229 Swiss-Prot Accession number P24394) was amplified from HUVEC cDNA library via PCR using primers based on the human IL-4Rα cDNA sequence (RefSeq NM_000418). The resulting cDNA was sub-cloned following the manufacture's instructions into pDONR201 (Invitrogen).

The cDNA fragments coding the IL-4Rα extracellular domains were then transferred to mammalian expression vector pDEST12.2 (Invitrogen) using LR Gateway® reaction (Invitrogen). The pDEST12.2 vector had been modified to contain the human IgG1 Fc coding region, polyhistidine (His6) tag in-frame with the inserted gene of interest, and also by insertion of the oriP origin of replication from the pCEP4 vector (Invitrogen) allowing episomal plasmid replication upon transfection into cell lines expressing the EBNA-1 gene product (such as HEK293-EBNA cells).

The public database accession number for human IL-4Rα mRNA is NM-000418; the key region of interest with this database sequence is 243-929. The predicted amino acid sequence for the resultant human IL-4Rα/Fc is shown in SEQ ID NO: 454.

1.1.1 Expression and Purification

HEK-EBNA cells were transfected using PEI. Protein was purified from conditioned media using Protein G chromatography followed by Size Exclusion chromatography.

1.2 Cloning of Recombinant Cynomolgus Monkey IL-4Rα and Human IL-4Rα 175V Mutant The cynomolgus monkey IL-4Rα subunit was amplified from cynomolgous monkey thymus and lymph node (BioCat GmbH) via the polymerase chain reaction (PCR) using the following oligonucleotides as primers:

```
                                         (SEQ ID NO: 451)
5' ggggacaagt ttgtacaaaa aagcaggctt ctttaacttt
aagaaggaga tataaccatg gggtggcttt gctctgggct
cctgttgcct gtgagc-3'

(SEQ ID NO: 452)
5'-ggggaccact ttgtacaaga aagctgggtc ctgctcgaag
ggctccctgt aggagttgta cca-3'
```

The resulting cDNA was sub-cloned following the manufacturer's instructions into pDONR201 (Invitrogen). The sequence of the cynomolgus monkey IL-4Rα extracellular domain is shown in SEQ ID NO: 455.

1.3 Cloning Human IL-4Rα 175V Variant

The polymorphism of the human IL-4Rα, 175V was generated using the pDONR201 vector containing the coding sequence for the human IL-4Rα (amino acid residues 1-229 NP_000409). The isoleucine at amino acid position 75 was mutated to valine using the QuikChange Multi site-directed mutagenesis kit (Stratagene) using the following oligonucleotide as mutation primer: 5'-gaagcccacacgtgtgccctgagaacaacgga-3' (SEQ ID NO: 453)

1.4 Generation of Recombinant Baculovirus for Cynomolgus and 175V Variant IL-4Rα/Fc Cynomolgus monkey IL-4Rα and human IL-4Rα 175V variant, were then inserted into a Gateway adapted pFastBac vector (in-house) containing a human IgG1 Fc coding region. Nucleotide and protein sequences for cynomolgus IL4Rα/Fc are shown in SEQ ID NO: 456 and SEQ ID NO: 457, respectively. Nucleotide and protein sequences for 175V IL4Rα/Fc are shown in SEQ ID NO: 458 and SEQ ID NO: 459, respectively. Generation of recombinant Bacmid was done by transformation of DH10Bac *E. coli* (Invitrogen) and plated on LB agar with selection medium. Sf9 cells were transfected with recombinant bacmids, and high titre recombinant baculovirus were produced.

1.5 Expression and Purification of Human 175V and Cynomolgus Fc Tagged IL-4Rα Protein Variants Proteins were expressed in Sf21 cells (400 ml) infected with virus MOI 1 at cell density of $3 \times 10^6$ cells/ml in SF-900 II SFM media (Invitrogen). Media containing the secreted IL-4Rα-Fc fusion proteins were harvested after 72 and 96 hours, respectively. The growth medium from the Sf21 cells (400 ml) was adjusted to pH 8.0. Protein was purified using Protein G chromatography followed by Size Exclusion chromatography.

Example 2

Lead Isolation 2.1 Selections

Naïve human single chain Fv (scFv) phage display libraries cloned in to a phagemid vector based on the filamentous phage M13 were used for selections (Vaughan et al. Nature Biotechnology 14(3):309-314, 1996; Hutchings, C. *Generation of Naïve Human Antibody Libraries*, in Antibody Engineering, R. Kontermann and S. Dubel, Editors. 2001, Springer Laboratory Manuals, Berlin. p. 93). Anti-IL-4Rα specific scFv antibodies were isolated from the phage display libraries using a series of selection cycles on recombinant human IL-4Rα Fc (R & D Systems) essentially as previously described by Vaughan et al (Vaughan, T J. et al. Nature Biotechnology 14(3):309-14, 1996) and Hawkins et al. Journal of Molecular Biology 226:889-896, 1992). In brief, for panning selections, human IL-4Rα Fc in PBS (Dulbecco's PBS, pH7.4) was adsorbed onto wells of an Immobilizer™ microtitre plate (Nunc) overnight at 4° C. Wells were washed with PBS then blocked for 1 h with PBS-Marvel (3% w/v). Purified phage in PBS-Marvel (3% w/v), containing a 10 fold excess of irrelevant Fc tagged protein, were added to the wells and allowed to bind coated antigen for 1 h. Unbound phage was removed by a series of wash cycles using PBS-Tween (0.1% v/v) and PBS. Bound phage particles were eluted, infected into *E. coli* TG1 bacteria and rescued for the next round of selection (Vaughan et al. Nature Biotechnology 14(3):309-314, 1996).

2.2 Inhibition of IL4 Binding to IL-4 Receptor by Unpurified scFv

Unpurified scFv from periplasmic preparations were screened in two homogeneous time-resolved fluorescence (HTRF®) receptor-ligand binding assays, run in parallel to measure inhibitory activity against both human and cynomolgus IL4Rα. In the human assay, unpurified scFv samples competed with human biotinylated IL4 (Peprotec with in-house biotinylation) for binding to human IL4Rα-Fc receptor (R and D Systems, 604-4R). In the cynomolgus assay, unpurified scFv samples competed with cynomolgus biotinylated IL4 (in-house *E. coli* expressed with biotinylation in-house) for binding to cynomolgus IL4Rα-Fc-HIS6 (in-house HEK expressed). The detailed assay methods are provided in the Materials and Methods section (2.4).

ScFv which showed an inhibitory effect as unpurified periplasmic extracts, on the binding of IL4 to IL4Rα in both human and cynomolgus receptor-ligand assays, were subjected to DNA sequencing (see: Osbourn et al. Immunotechnology. 2:181-196, 1996). ScFvs with unique sequences were expressed in bacteria and purified by affinity chromatography (as described by Bannister et al. Biotechnology and bioengineering, 94. 931-937, 2006).

2.3 Inhibition of IL-4 Binding to IL-4 Receptor by Purified scFv

Potency of scFv samples was determined by competing a dilution series of the purified scFv preparation against IL4 for binding to IL4Rα. Both human and cynomolgus receptor-ligand assays were performed in parallel as described in the Materials and Methods section 2.4 Purified scFv preparations of Antibody 1 inhibited binding of human IL4 to the IL4Rα with a $K_i$ value of 12 nM (95% Cl 8.7, 16.6). Inhibition of cynomolgus IL4 binding to IL4Rα by Antibody 1 was incomplete with 10% inhibition of assay signal observed. It was therefore not possible to calculate accurate $K_i$ potency data from the results obtained.

2.4 Materials and Methods

Receptor-Ligand HTRF® Assay for Inhibition of IL4 Binding to IL4Rα

High-Throughput Screening

Selection outputs were screened in screened in two homogeneous time-resolved fluorescence (HTRF®) receptor-ligand binding assays, run in parallel to measure inhibitory activity against both human and cynomolgus IL4Rα.

For both assays selection outputs were screened as undiluted or diluted, unpurified bacterial periplasmic extracts containing scFv, prepared in; 50 mM MOPS buffer pH7.4, 0.5 mM EDTA and 0.5 M sucrose. All dilutions were performed in phosphate buffered saline (PBS) containing 0.4 M potassium fluoride and 0.1% BSA (assay buffer).

Europium cryptate labelled goat-anti-human Fc antibody, at 3.2 nM (CIS Bio International 61HFCKLB) was pre-mixed with human IL4Rα/Fc (R and D Systems 604-4R) at 0.5 nM (Premix "A"). XL665-conjugated streptavidin at 10 nM (CIS Bio International 611 SAXLB) was pre-mixed with human biotinylated IL4 (Peprotec with in-house biotinylation) at 4 nM (Pre-Mix "B").

In parallel, for the cynomolgus assay, europium cryptate labelled goat-anti-human Fc antibody, at 3.2 nM (CIS Bio International 61HFCKLB) was pre-mixed with cynomolgus IL4RαFc (Isolation/Sf21 expressed) or cynomolgus IL4Rα/Fc HIS6 (Optimisation/HEK-expressed) at 0.5 nM (Premix "A"). XL665-conjugated streptavidin at 10 nM (CIS Bio International 611SAXLB) was pre-mixed with cynomolgus biotinylated IL4 (in-house E. coli expressed with biotinylation in-house) at 3 nM (Pre-Mix "B").

For each assay, 5 µl of Premix "A" was added to a 384 well low volume assay plate (Costar 3676). 5 µl of unpurified scFv sample was then added. This was followed by the addition of 10 µl of Premix "B".

Non-specific binding was defined using monoclonal mouse IgG2a clone 25463 (R and D Systems) at 10 nM final or cynomolgus IL4 at 50 nM final (in-house E. coli expressed) for the human and cynomolgus IL4Rα receptor-ligand binding assays respectively.

Assay plates were incubated for 4 h at room temperature, prior to reading time resolved fluorescence at 620 nm and 665 nm emission wavelengths using an EnVision plate reader (Perkin Elmer).

Data was analysed by calculating % Delta F values for each sample. Delta F was determined according to equation 1.

$$\% \text{ Delta } F = \frac{(\text{sample 665 nm/620 nm ratio value}) - \left(\begin{array}{c}\text{non-specific control} \\ \text{665 nm/620 nm ratio value}\end{array}\right)}{\left(\begin{array}{c}\text{non-specific control} \\ \text{665 nm/620 nm ratio value}\end{array}\right)} \times 100 \qquad \text{Equation 1}$$

% Delta F values were subsequently used to calculate % specific binding as described in equation 2.

$$\% \text{ specific binding} = \frac{\% \text{ Delta } F \text{ of sample}}{\% \text{ Delta } F \text{ of total binding control}} \times 100 \qquad \text{Equation 2}$$

$K_i$ Determination

A dilution series of purified scFv concentrations was prepared to determine the scFv potency $K_i$ values in both human and cynomolgus assays. 5 µl of Premix "A" was added to a 384 well low volume assay plate (Costar 3676). 5 µl of scFv dilution sample was then added. This was followed by the addition of 10 µl of Premix "B".

Non-specific binding was defined using monoclonal mouse IgG2a clone 25463 (R and D Systems) at 10 nM final or cynomolgus IL4 at 50 nM final (in-house E. coli expressed) for the human and cynomolgus IL4Rα receptor-ligand binding assays respectively.

Assay plates were incubated for 4 h at room temperature, prior to reading time resolved fluorescence at 620 nm and 665 nm emission wavelengths using an EnVision plate reader (Perkin Elmer).

Data was analysed by calculating % Delta F values for each sample. Delta F was determined according to equation 1.

$$\% \text{ Delta } F = \frac{(\text{sample 665 nm/620 nm ratio value}) - \left(\begin{array}{c}\text{non-specific control} \\ \text{665 nm/620 nm ratio value}\end{array}\right)}{\left(\begin{array}{c}\text{non-specific control} \\ \text{665 nm/620 nm ratio value}\end{array}\right)} \times 100 \qquad \text{Equation 1}$$

% Delta F values were subsequently used to calculate % specific binding as described in equation 2.

$$\% \text{ specific binding} = \frac{\% \text{ Delta } F \text{ of sample}}{\% \text{ Delta } F \text{ of total binding control}} \times 100 \qquad \text{Equation 2}$$

$IC_{50}$ values were determined using GraphPad Prism software by curve fitting using a four-parameter logistic equation (Equation 3).

$$Y = \text{Bottom} + (\text{Top} - \text{Bottom})/(1 + 10\hat{\,}((\text{Log EC50} - X)^* \text{HillSlope})) \qquad \text{Equation 3}$$

X is the logarithm of concentration. Y is specific binding Y starts at Bottom and goes to Top with a sigmoid shape.

$IC_{50}$ values were converted to $K_i$ using the Cheng-Prusoff equation as described in equation 4:

$$K_i = IC_{50}/(1 + [L]/K_d) \qquad \text{Equation 4}$$

Example 3

Reformatting of scFv to IgG2

3.1

Clones were converted from scFv to IgG format by subcloning the $V_H$ and $V_L$ domains into vectors expressing whole antibody heavy and light chains respectively. The $V_H$ domain was cloned into a vector (pEU9.2) containing the human heavy chain constant domains and regulatory elements to express whole IgG heavy chain in mammalian cells. Similarly, the $V_L$ domain was cloned into a vector (pEU4.4) for the expression of the human lambda light chain constant domains, with regulatory elements to express whole IgG light chain in mammalian cells. Vectors for the expression of heavy chains and light chains were originally described in Peric et al., (Gene 187:9-18, 1997). These vectors have been engineered simply by introducing an OriP element. To obtain IgGs, the heavy and light chain IgG expressing vectors were transfected into EBNA-HEK293 mammalian cells (Invitrogen R620-07-). IgGs were expressed and secreted into the medium. Harvests were pooled and filtered prior to purification. The IgG was purified using Protein A chromatography. Culture supernatants are loaded on a column of appropriate size of Ceramic Protein A (BioSepra) and washed with 50 mM Tris-HCl pH 8.0, 250 mM NaCl. Bound IgG was eluted from the column using 0.1 M Sodium Citrate (pH 3.0) and neutralised by the addition of Tris-HCl (pH 9.0). The eluted material was buffer exchanged into PBS using Nap10 columns (Amersham, #17-0854-2) and the concentration of IgG was determined spectrophotometrically using an extinction coefficient based on the amino acid sequence of the IgG (Mach et al., Anal Biochem. 200 (1):20-26, 1992). The purified IgG were analysed for aggregation or degradation using SEC-HPLC and by SDS-PAGE.

3.2 Inhibition of IL-13 and IL-4 Induced Proliferation of TF-1 Cells by IgG

The neutralisation potency of purified IgG preparations against human IL-13 and IL-4 bioactivity was assessed using TF-1 cell proliferation assay. TF-1 is a human premyeloid cell line established from a patient with erythroleukemia (Kitamura et al. J. Cell Physiol. 140(2):323-34, 1989). The TF-1 cell line is factor dependent for survival and proliferation. TF-1 cells were shown to respond to both human IL-13 and IL-4 (Peprotech, E. coli derived). Inhibition of IL-4 and IL-13 dependent proliferation was determined by measuring the reduction in incorporation of tritiated thymidine into the newly synthesized DNA of dividing cells. A detailed description of the protocol is provided in materials and Methods section 3.2.1.

Re-formatted IgG preparations of Antibody 1 inhibited the IL-13 and IL-4 induced proliferation of the TF-1 cells in a concentration dependent manner. The $IC_{50}$ geomean for Antibody 1 against IL-13 and IL-4 was calculated as being 18 nM and 38 nM respectively.

3.2.1 Materials and Methods—Inhibition of IL-4 and IL-13 Induced Proliferation of TF-1 Cells by Purified IgG TF-1 cells (R&D Systems) were maintained according to supplied protocols. Assay media comprised RPMI-1640 with GLUTAMAX I (Invitrogen) containing 5% foetal bovine serum (JRH), 1% sodium pyruvate (Sigma), Penicillin/streptomycin (1-2%). Prior to each assay, TF-1 cells were pelleted by centrifugation at 300×g for 5 mins, the media removed by aspiration and the cells re-suspended in assay media. This process was repeated twice with cells re-suspended at a final concentration of $2 \times 10^5$ cells/ml in assay media. The cells were plated out using 100 μl/well in a 96 well assay plate. Test solutions of IgG (in duplicate) were titrated to the desired concentration range in assay media. An irrelevant antibody not directed at IL-4Rα was used as negative control. The assay was set up in a competition format, with 50 uL of each recombinant bacterially derived human IL-4 or IL-13 (Peprotech) and appropriate test antibody titrations added sequentially to 100 uL of cells. A final assay volume of 200 uL/well and a concentration of 18 pM (IL-4) or 400 pM (IL-13) was used in the assay. The concentration of IL-4 and IL-13 was selected as the dose that at gave approximately 50% of maximal proliferative response. Plates were incubated for 72 hours at 37° C. and 5% $CO_2$. 20 μl of tritiated thymidine (5 μCi/ml) was added to each assay point and the plates were returned to the incubator for further 4 to 5 hours. Cells were harvested on glass fibre filter plates (Perkin Elmer) using a cell harvester. Thymidine incorporation was determined using Packard TopCount microplate liquid scintillation counter. Data was then analysed using Graphpad Prism software.

Example 4

Antibody Optimisation 4.1 Optimisation of Parent Clone by Targeted Mutagenesis

There are advantages and benefits in the discovery and development of an antibody to human IL4Rα that also exhibits cross-reactivity to the orthologous protein from another species, for example cynomolgus monkey. Such an antibody would facilitate the characterization of such antibodies with respect to pharmacology and safety in vivo. Potency and affinity to another species, which is for example less than 10-fold different than the human activity may be appropriate for such and evaluation.

To achieve the required species cross-reactivity, the parent antibody (Antibody 1) was optimised for improved affinity to both human and cynomolgus IL4Rα. This was achieved using a targeted mutagenesis approach with affinity-based phage display selections. For the targeted mutagenesis approach, large scFv-phage libraries derived from the Antibody 1 were created by oligonucleotide-directed mutagenesis of the variable heavy ($V_H$) and light ($V_L$) chain complementarity determining regions 3 (CDR3) using standard molecular biology techniques as described by Clackson and Lowman (2004) A Practical Approach, 2004. Oxford University Press.

The libraries were subjected to affinity-based phage display selections in order to select variants with higher affinity for human and cynomolgus forms of IL-4Rα. The selections were performed essentially as described previously (Thompson. Journal of Molecular Biology. 256:77-88, 1996). In brief, the scFv phage particles were incubated with either recombinant biotinylated human or cynomolgus IL-4Rα in solution (bio-huIL-4Rα FLAG HIS or bio-cyno-IL-4RαFc HIS, both in house HEK-EBNA derived). The species of antigen used was alternated at each round of selection. ScFv-phage bound to antigen were then captured on streptavidin-coated paramagnetic beads (Dynabeads® M280) following the manufacturer's recommendations. The selected scFv-phage particles were then rescued as described previously (Osbourn, J K. et al. Immunotechnology, 2(3):181-96, 1996), and the selection process was repeated in the presence of decreasing concentrations of either bio-huIL-4Rα or bio-cyno-IL-4Rα, alternating the species between rounds of selection (500 nM to 250 pM over 6 rounds).

Upon completion of 6 rounds of selection, the VH and VL randomised libraries were recombined to form a single library in which clones contained randomly paired individually randomised VH and VL sequences. Selections were then continued as previously described in the presence of decreasing concentrations of either bio-huIL-4Rα or bio-cyno-IL-4Rα (2.5 nM to 0.5 pM over a further 5 rounds), alternating the species of antigen where appropriate.

4.2 Optimisation of the Antibody by Random Mutagenesis

One of the antibodies (Antibody 20) was further optimised using a random mutagenesis approach to identify key residues within the antibody sequence that may improve binding to human and cynomolgus IL4Rα. Large scFv-phage libraries were generated by the introduction of random mutations throughout the variable regions of the Antibody 20 scFv sequence. This was achieved by two rounds of mutagenesis using a Diversify™ PCR random mutagenesis kit (BD biosciences), following the manufacturers instructions to incorporate on average, 8.1 mutations per kilobase in the nucleic acid sequence per round of mutagenesis. The protocol for the strategy is in accordance with International Patent Application Publication Number WO2006/072801 (Cambridge Antibody Technology). The libraries were subjected to affinity-based phage display selections to select for variants with higher affinity for human and cynomolgus forms of IL-4Rα.

The selections were performed essentially as described previously (Thompson, Journal of Molecular Biology. 256: 77-88, 1996). In brief, the scFv phage particles were incubated with recombinant biotinylated human or cynomologous IL-4Rα in solution (bio-huIL-4Rα FLAG HIS or bio-cyno-IL-4Rα Fc HIS, both in house HEK-EBNA derived). The species of antigen was alternated between human and cynomolgus in order to improve affinity for the particular species of IL-4Rα accordingly. ScFv-phage bound to antigen were then captured on streptavidin-coated paramagnetic beads (Dynabeads® M280) following the manufacturer's recommendations. The selected scFv-phage particles were then rescued as described previously (Osbourn et al. Immunotechnology, 2(3):181-96, 1996), and the selection process was repeated in the presence of decreasing concentrations of either bio-huIL-4Rα or bio-cyno-IL-4Rα (20 nM to 1 pM over 4 rounds).

4.3 Identification of Improved Clones from Random Mutagenesis Using a Receptor-Ligand Binding Assay ScFv from the targeted and random mutagenesis selections were expressed in the bacterial periplasm and screened in two homogeneous time-resolved fluorescence (HTRF®) receptor-ligand binding assays, run in parallel to measure inhibitory activity against both human and cynomolgus IL4Rα. The detailed assay method is provided in the Materials and Methods section. 2.4. ScFv that showed a significant inhibitory effect in both assays, were subjected to DNA sequencing and scFv with unique sequences were prepared as purified preparations.

Purified scFv antibody potencies were determined by competing a dilution series of the purified scFv preparation against IL4 for binding to IL4Rα. Both human and cynomolgus receptor-ligand assays were performed in parallel as described in the Materials and Methods section 2.4.

Example potency data for scFv for each sample is provided in Table 1.

| | Ki (nM) Geomean with 95% confidence limit in parentheses | |
|---|---|---|
| scFv | Human IL4R | Cyno IL4R |
| Antibody 1 | 12.0 (8.7, 16.6) | Incomplete |
| Antibody 2 | 0.6 (0.5, 0.7) | 4.3 (2.1, 8.9) |
| Antibody 3 | 0.5 | 48.0 |
| Antibody 4 | 0.8 (0.4, 1.8) | 6.8 (3.4, 13.6) |
| Antibody 5 | 0.6 (0.1, 2.8) | 3.8 (1.8, 8.2) |
| Antibody 6 | 0.3 | 3.5 |
| Antibody 7 | 1.1 | 16.5 |
| Antibody 8 | 0.4 | 9.4 |
| Antibody 9 | 0.1 (0.1, 0.3) | 12.9 (9.0, 19) |
| Antibody 10 | 0.5 | 19.6 |
| Antibody 11 | 0.7 | 26.1 |
| Antibody 12 | 0.3 | 7.2 |
| Antibody 13 | 0.3 | 22.2 |
| Antibody 14 | 0.6 (0.4, 0.9) | 27.7 |
| Antibody 15 | 1.0 (0.8, 1.2) | 32.3 |
| Antibody 16 | 0.4 (0.2, 1.0) | 8.7 |
| Antibody 17 | 0.9 | 43.5 |
| Antibody 18 | 0.7 | 56.5 |
| Antibody 19 | 0.8 (0.4, 1.6) | 18.5 |
| Antibody 20 | 0.7 (0.6, 0.8) | 4.2 (3.4, 5.3) |
| Antibody 21 | 31 pM (13, 76) | 1.0 (0.5, 1.9) |
| Antibody 22 | 0.3 | 2.6 |
| Antibody 23 | 0.2 | 4.8 |
| Antibody 24 | 49 pM (25, 94) | 0.8 (0.5, 1.0) |
| Antibody 24PGL | 65 pM | 0.7 |
| Antibody 25 | 39 pM (20, 79) | 1.3 (0.7, 2.7) |
| Antibody 26 | 0.1 | 1.2 |
| Antibody 27 | 63 pM | 2.8 |
| Antibody 28 | 94 pM | 1.8 |
| Antibody 29 | 61 pM | 2.4 |

-continued

| | Ki (nM) Geomean with 95% confidence limit in parentheses | |
|---|---|---|
| scFv | Human IL4R | Cyno IL4R |
| Antibody 30 | 69 pM | 3.6 |
| Antibody 31 | 44 pM (26, 76) | 2.2 (1.4, 3.4) |
| Antibody 32 | 75 pM | 1.3 |
| Antibody 33 | 92 pM | 1.4 |
| Antibody 34 | 56 pM | 1.2 |
| Antibody 35 | 71 pM | 2.6 |
| Antibody 36 | 0.1 | 5.3 |
| Antibody 37 | 40 pM (30, 51) | 0.8 (0.7, 1.0) |
| Antibody 37 GL | 61 pM (40, 92) | 0.7 (0.5, 1.1) |
| Antibody 38 | 66 pM | 2.7 |
| Antibody 39 | 27 pM | 1.6 |
| Antibody 40 | 31 pM | 6.5 |
| Antibody 41 | 53 pM | 2.7 |
| Antibody 42 | 27 pM (16, 49) | 2.5 (1.4, 4.5) |

4.4 Inhibition of IL-13 and IL-4 Induced Proliferation of TF1 Cells by Optimised Clones Purified scFv antibody potencies were also determined in the TF1 proliferation assay.

The most potent clones in the TF-1 proliferation assay were converted to IgG as described previously, and were re-tested in the TF-1 proliferation assay. Example potency data for IgG for each sample is provided in Table 2.

TABLE 2

Example potencies of improved clones when tested in the TF-1 cell proliferation assay

| | $IC_{50}$ (pM) | |
|---|---|---|
| Clone (non-germlined) | IL-4 | IL-13 |
| Antibody 2 | 41.7 (33.2, 52.3) | 171 (68.0, 429) |
| Antibody 4 | 20.9 (13.5, 32.3) | 58.1 |
| Antibody 7 | 12.3 | 42.7 |
| Antibody 8 | 7.9 | 22.4 |
| Antibody 9 | 8.88 (5.94, 13.3) | 20.4 (13.9, 29.9) |
| Antibody 10 | 10.1 | 25.4 |
| Antibody 11 | 18.8 | 32.7 |
| Antibody 12 | 18.2 | 40.7 |
| Antibody 14 | 3.8 | 27.2 |
| Antibody 15 | 2.8 | 17.8 |
| Antibody 16 | 6.2 | 19.5 |
| Antibody 19 | 7.6 | 22.4 |
| Antibody 20 | 31.1 (19.9, 48.6) | 66.1 (34.2, 128) |
| Antibody 13 | 15.7 (7.47, 33.1) | 24.6 |
| Antibody 21 | 19.7 | 34.7 |
| Antibody 24 | 12.6 (9.5, 16.7) | 30.2 (14.5, 62.8) |
| Antibody 25 | 9.8 | 23.2 |
| Antibody 31 | 20.2 | 44.2 |
| Antibody 37 | 10.4 (7.5, 14.5) | 22.1 (11.7, 41.8) |
| Antibody 42 | 20.2 | 42.7 |
| 12B5* | 42.7 (25.9, 70.4) | 79.1 (34.7, 180) |

*12B5 = Benchmark antibody was made according to the teaching in WO 01/92340.

4.5. Germlining

The amino acid sequences of the $V_H$ and $V_L$ domains of the optimised anti-IL-4Rα antibodies were aligned to the known human germline sequences in the VBASE database (MRC Centre For Protein Engineering) and the closest germline was identified by sequence similarity. For the $V_H$ domains of the optimised antibody lineage this was Vh1_DP-7_(1-46). For the VL domains it was Vλ1_DPL5.

Without considering the Vernier residues (Foote & Winter, J Mol. Biol. Mar 20:224(2):487-99, 1992), which were left unchanged, there were 3 changes in the frameworks of the $V_H$ domains and 2 changes in the $V_L$ domains of Antibody 37, all of which were reverted to the closest germline sequence to identically match human antibodies. Antibody 24 had one change in the $V_H$ domains and 2 changes in the $V_L$ domains away from the closest human germline match. Changes at Kabat number 37 in the $V_H$ domain and Kabat number 73 in the $V_L$ domain were reverted to that of the closest human germline match. The amino acid change at position 87 in the $V_L$ domain was left unchanged, to retain potency (Antibody 24PGL). Germlining of these amino acid residues was carried out using standard site directed mutagenesis techniques with the appropriate mutagenic primers.

The Antibody 37GL scFv sequence was cloned into a cloning vector, transformed into *E. coli* Top10 cells (F-mcrA Δ(mrr-hsdRMS-mcrBC) Φ80lacZΔM15 ΔlacX74 recA1 araD139 Δ(araleu) 7697 galU galK rpsL (StrR) endA1 nupG) and deposited under the Budapest Treaty at NCIMB (Aberdeen, Scotland) on 9 Dec. 2008. The Applicant's clone reference is "Antibody 37 GL" and the NCIMB accession number is NCIMB 41600.

Germlined IgG were then re-evaluated in the IL-4 and IL-13 induced TF-1 proliferation assay to confirm there had not been a reduction in potency. Example potencies for germlined (GL) antibodies are provided in Table 3.

TABLE 3

Example potency data for germlined optimised clones when evaluated in the IL-4 and IL-13 induced TF-1 cell proliferation assay

| | $IC_{50}$ (pM) | |
|---|---|---|
| Clone (germlined) | IL-4 | IL-13 |
| Antibody 24 (PGL) | 15.3 (6.63, 35.1) | 55.0 (29.3, 103.1) |
| Antibody 37 (PGL) | 14.9 (7.8, 28.6) | 41.7 (18.6, 93.4) |
| Antibody 37 (FGL) | 11.4 (9.8, 13.3) | 21.1 (12.4, 35.9) |

Data are expressed as Geometric mean and 95% confidence intervals 4.6 Selectivity and Species Cross Reactivity of Optimised Antibodies in DELFIA® Epitope Competition Assays The species cross reactivity and selectivity of antibodies to IL-4Rα and structurally related molecules; IL13Rα1 Fc, IL13Rα2 Fc and the common gamma chain (IL-2Rγ), was established using DELFIA® epitope competition assays. The assay determines relative cross reactivity by measuring inhibition of biotinylated IL-4Rα HIS FLAG (in house HEK-EBNA derived), binding each immobilised anti-IL-4Rα antibody.

Titrations of purified, IL13Rα1 Fc, IL13Rα2 Fc and the common gamma chain (IL-2Rγ) (all R & D Systems) were tested in each assay to establish the specificity profile for each structurally related protein, as measured by $IC_{50}$ values in the assay.

Titrations of IL-4Rα species including cynomolgus IL-4Rα HIS Fc (in house HEK-EBNA derived), human IL-4Rα 175V Fc (AstraZeneca), human IL-4Rα Fc and murine IL-4Rα (both R & D Systems) were tested in each assay to establish the species cross-reactivity of the antibodies. Unbiotinylated human IL-4Rα HIS FLAG was used as a positive control. Human and cynomolgus IL-4Rα HIS Fc, along with Human IL-4Rα 175V Fc, produced overlapping inhibition curves with equivocal $IC_{50}$ values. No inhibition was observed for murine IL-4Rα or any of the related human proteins tested. The results demonstrate that Antibody 37GL is cross reactive to cynomolgus Il-4Rα and human IL-4Rα 175V but does not bind to murine IL-4Rα or any of the most related human proteins to human IL-4Rα. Details of the protocol are provided in the Materials and Methods section 4.6.1.

4.6.1 Materials and Methods—DELFIA® Epitope Competition Assays

Purified IgG were adsorbed onto 96-well Maxisorp microtitre plates (Nunc) in PBS at a concentration which gave a significant signal when biotinylated human IL-4Rα HIS FLAG was added at approximately its estimated KD for that particular IgG. Excess IgG was washed away with PBS-Tween (0.1% v/v) and the wells were blocked with PBS-Marvel (3% w/v) for 1 h. A dilution series of each of the following competitors was prepared in PBS, starting at a concentration of approximately 400-fold the KD value of the interaction between biotinylated human IL-4Rα and the respective IgG; human IL-4Rα Fc (R & D Systems, 604-4R-050), human IL-4Rα 175V Fc (AstraZeneca), cynomolgus IL-4Rα HIS Fc (In house), murine IL4Rα Fc (R & D Systems 530-MR-100), Human common gamma chain (sIL-2Rγ) (R & D Systems 384-RG-050-CF), human IL-13Rα1 Fc (R & D Systems, 146-IR-100), human IL-13Rα2 Fc (R & D Systems, 614-IR-100). Unbiotinylated human IL-4Rα HIS FLAG was used as a positive control. To this series, an equal volume of biotinylated recombinant human IL-4Rα at a concentration of approximately 2-fold the KD was added (resulting in a series starting at a ratio of competitor antigen:biotinylated human IL-Rα of approximately 200:1). These mixtures were then transferred onto the blocked IgG and allowed to equilibrate for 1.5 h. Unbound antigen was removed by washing with PBS-Tween (0.1% v/v), while the remaining biotinylated human IL-4Rα was detected by streptavidin-Europium3+ conjugate (DELFIA® detection, PerkinElmer). Time-resolved fluorescence was measured at 620 nm on an EnVision plate reader (PerkinElmer). Fluorescence data was converted to % specific binding (100% was determined from control wells containing biotinylated human IL-4Rα but no competitor, 0% was from wells containing biotinylated human IL-4Rα and a 1000-fold excess of unbiotinylated human IL-4Rα). Resultant data were analysed using Prism curve fitting software (Graphpad) to determine $IC_{50}$ values.

4.7 Calculation of Affinity Data for Optimised Clones Using BIAcore

The binding affinity of purified IgG samples of representative panel of antibodies to human and cynomolgus IL-4Rα was determined by surface plasmon resonance using a BIAcore 2000 biosensor (BIAcore AB) essentially as described by Karlsson et al. (J. Immunol. Methods, 145(1-2):229-240, 1991). In brief, Protein G' (Sigma Aldrich, P4689) was covalently coupled to the surface of a CM5 sensor chip using standard amine coupling reagents according to manufacturer's instructions (BIAcore). This Protein G' surface was used to capture a constant amount of purified anti-IL4Rα antibodies or isotype control via the Fc domain. Human or cynomolgus IL-4Rα HIS FLAG prepared in HBS-EP buffer (BIAcore AB), at a range of concentrations, between 100 nM and 0.2 nM, were passed over the sensor chip surface. The surface was regenerated using 10 mM Glycine, pH 1.75 between each injection of antibody. The resulting sensorgrams were evaluated using BIA evaluation 4.1 software and fitted to 1:1 Langmuir binding model, to provide the relative binding data. The experiments were performed over the course of at least three separate days to calculate an average monovalent affinity. From the data fits obtained, the affinity of Antibody 37GL to human and cynomolgus IL-4Rα was determined to be approx 504 pM and 4.4 nM respectively, as reported in Table 4.

TABLE 4

Example Kinetic Analysis of a representative panel of antibodies for binding to human and cyno IL4Rα

| | Human IL4Rα HIS FLAG | | | Cyno IL4Rα HIS FLAG | | |
|---|---|---|---|---|---|---|
| | Ka ($M^{-1}s^{-1}$) | Kd ($s^{-1}$) | KD (nM) | Ka ($M^{-1}s^{-1}$) | Kd ($s^{-1}$) | KD (nM) |
| Antibody 2 | $6.51 \times 10^5$ | $2.94 \times 10^{-3}$ | 4.51 | $9.67 \times 10^4$ | $4.59 \times 10^{-3}$ | 47.5 |
| Antibody 9 | $5.43 \times 10^5$ | $2.29 \times 10^{-4}$ | 0.422 | $1.31 \times 10^5$ | $1.63 \times 10^{-2}$ | 124 |
| Antibody 20 | $6.98 \times 10^5$ | $8.73 \times 10^{-4}$ | 1.25 | $1.63 \times 10^5$ | $4.52 \times 10^{-3}$ | 27.7 |
| Antibody 37 | $6.40 \times 10^5$ | $1.62 \times 10^{-4}$ | 0.255 (0.313, 0.250, 0.203) | $2.43 \times 10^5$ | $6.88 \times 10^{-4}$ | 2.97 (2.59, 2.36, 3.96) |
| Antibody 37GL | $6.88 \times 10^5$ | $3.46 \times 10^{-4}$ | 0.504 (0.533, 0.531, 0.459) | $2.44 \times 10^5$ | $1.08 \times 10^{-3}$ | 4.41 (4.67, 4.34, 4.41) |

Example 5

Epitope Mapping of IL-4Rα:Antibody Interaction Using Chimeric Human/Mouse IL4Ra Extracellular Domains 5.1 Generation of Whole Domain Swap Chimetic IL-4Rα Molecules.

The binding members of the invention bind strongly to human IL-4Rα but extremely poorly, almost indiscernibly, to mouse IL-4Rα. Using this property, chimeric IL-4Rα molecules were generated for epitope mapping. Whole domain-swap chimeras were created by replacing domain 1 (D1) (M1-E119) or domain 2 (D2) (H120-F229) of human IL-4Rα ectodomain with corresponding mouse IL-4Rα sequence. Loop swap chimeras were generated by replacing loop regions known to interact with IL4 (Hage et al, *Cell* 97:271-281, 1999) from human IL-4Rα with corresponding regions from mouse IL-4Rα. An HTRF (homogeneous time resolved fluorescence) competition assay was used to determine chimeras binding to antibody. In the assay antibody labelled with $Eu^{3+}$ cryptate interacted with Human IL-4Rα labelled with biotin. The interaction was detected by a FRET (Fluorescence Resonance Energy Transfer) signal between $Eu^{3+}$ cryptate and XL665 labelled streptavidin (Mathis et al., *Clin Chem* 41: 1391-1397, 1995).

5.1.1 Materials and Methods—Cloning, Expression and Purification of Chimeras cDNA molecules encoding chimeras of human IL-4Rα extracellular domain (amino acid residues 1-229 NP_000409) and mouse IL-4Rα extracellular domain (amino acid residues 1-230 NP_001008700) were synthesised by primer extension PCR cloning and cloned into pDONR221 (Invitrogen Cat. No. 12536-017). The cDNA fragments coding for the IL-4Rα extracellular domain chimeras were then transferred to mammalian expression vector pDEST12.2 (Invitrogen) using LR Gateway Clonase II enzyme according to the manufacturer's instructions (Invitrogen Cat. No. 12538-120). The pDEST12.2 vector had been modified to contain a FLAG 10xhis tag (DYKDDDDKAAHHHHHHHHHH; e.g. see SEQ ID NO: 460, positions 252-261) in-frame with the inserted gene of interest, and also by insertion of the oriP origin of replication from the pCEP4 vector (Invitrogen cat. no. V044-50) allowing episomal plasmid replication upon transfection into cell lines expressing the EBNA-1 gene product (such as HEK293-EBNA cells). Expressed protein in HEK293-EBNA supernatant was purified using Ni-NTA affinity chromatography (Histrap HP column (GE Healthcare Cat. No. 17-5248-02)) followed by Size Exclusion chromatography (Superdex 200 column (GE Healthcare Cat. No. 17-1069-01)).

The sequence of human IL-4Rα extracellular domain (positions 1-229; and same in NP_000409), vector encoded sequence (positions 230-241), FLAG tag (positions 242-249) and 10xhis tag (positions 252-261) is disclosed in SEQ ID NO: 460. The sequence of murine IL-4Rα extracellular domain (positions 1-230; and same in NP_001008700), vector encoded sequence (positions 233-242), FLAG tag (positions 243-250) and 10xhis tag (positions 253-262) is disclosed in SEQ ID NO: 461.

5.1.2 Binding of Antibody to IL-4Rα Chimeras

Antibody was cryptate labelled with $Eu^{3+}$ Cryptate labelling kit according to the manufacturer's instructions (CisBio International Cat No. 62EUSPEA) and IL-4Rα/Fc (R&D systems Cat. No. 604-4R-050) was Biotin labelled with EZ Link NHS-Biotin according to the manufacturer's instructions (Perbio Cat No. 20217). Assay conditions were 0.4 nM Cryptate labelled antibody, 0.25 nM biotin labelled IL-4Rα/Fc, 2.5 nM streptavidin XL665 (CisBio International Cat. No. 611SAXLB) in 1×DPBS, 0.1% BSA, 0.4M potassium fluoride in a total volume of 20 μl in a 384 well microtitre plate (Greiner). To the assay a dilution series (from 1000 nM to 0.017 nM) of test proteins was added and the assay incubated overnight at 4° C. FRET signal was detected using a PerkinElmer EnVision plate reader using a 320 nm excitation filter and 620 nm and 665 nm emission filters. Results were calculated from the 665/620 ratio as a percentage of specific binding (signal with no competitor antigen). Results were analysed with Prism (GraphPad Software) using the sigmoidal dose response model.

5.2 Results

Antibody binding of chimeric molecules was tested in an HTRF (Homogeneous Time Resolved Fluorescence) competition assay. Molecules which bound antibody at the same paratope as human IL-4Rα inhibited the binding interaction, leading to a reduction in signal. From inhibition curves $IC_{50}$ values for human IL-4Rα, mouse IL-4Rα and chimeric molecules were calculated (Table 5). If a molecule did not fully inhibit binding the percentage inhibition seen at the highest concentration was calculated. Chimeras that gave similar $IC_{50}$ values to native human IL-4Rα still contained the epitope. Chimeras, which did not fully inhibit IL-4Rα binding to antibody, or showed an increased $IC_{50}$ value, did not contain the full epitope. These data enabled the localisation of the antibody epitope.

TABLE 5

IC$_{50}$ (in nM) of chimeric IL-4Rα molecules competing against human IL-4Rα binding to antibody. Chimeras composed of amino acid sequence from human (NP_000409) and mouse (NP_001008700) IL-4Rα were tested for the ability to compete with human IL-4Rα in binding antibody.

| Chimera | Sequence from NP_000409 | Sequence from NP_001008700 | $IC_{50}$ (nM) in competition assay |
|---|---|---|---|
| HuIL-4Rα | M1-F229 | | 0.673 |
| MoIL-4Rα | | M1-L230 | 45% inhibition* |
| HuD1MoD2IL-4Rα | M1-E119 | N121-L230 | 3.4 |
| MoD1HuD2IL-4Rα | H120-F229 | M1-G120 | 34% inhibition* |
| MoLoop1HuIL-4Rα | M1-Y38; S42-F229 | I39-T41 | 1.9 |
| MoLoop2HuIL-4Rα | M1-L64; T73-F229 | M65-L73 | 23 |
| MoLoop3HuIL-4Rα | M1-L88; Y99-F229 | E90-R99 | 58% inhibition* |
| MoLoop4HuIL-4Rα | M1-W143; N151-F229 | N145-N151 | 0.663 |
| MoLoop5HuIL-4Rα | M1-W204; T211-F229 | S206-G211 | 1.4 |
| AllMoLoopsHuIL-4Rα | M1-Y38; S42-L88; Y99-W143; N151-W204; T211-F229 | I39-T41; M65-173; E90-R99; N145-N151; S206-G211 | 41% inhibition* |

$IC_{50}$ values were calculated where a complete competition curve was obtained.

*Where the chimera failed to completely inhibit human IL-4Rα binding to antibody the percentage inhibition seen at the highest concentration of chimera (1000 nM) is shown.

The binding of chimeric human/mouse IL-4Rα chimeras has enabled the localisation of the human IL-4Rα epitope bound by antibody. Whole domain swap chimeras localised the epitope to D1 of human IL-4Rα (residues M1-E119) as a human D1-mouse D2 chimera was able to compete with human IL-4Rα whereas a mouse D1-human D2 chimera failed to completely inhibit Human IL-4Rα binding (Table 5). The epitope is almost entirely composed of loop regions since the AllMoLoops chimera and MoIL-4Rα show very similar percentage inhibition (Table 5).

Human IL-4Rα contains five loop regions, which are in close proximity to IL4 in a crystal structure (Hage et al., Cell 97:271-281, 1999). Loop swap chimeras enabled the localisation of the human IL-4Rα epitope to a major component in loop 3 (residues L89-N98) and a minor component in loop 2 (residues V65-H72). Chimeras without human loop 3 failed to inhibit human IL-4Rα binding to antibody and chimeras without loop 2 gave a 100 fold higher $IC_{50}$ than human IL-4Rα (Table 5). Consistent with the domain swap data both loop2 and loop3 are located in D1 (Hage et al., *Cell* 97:271-281, 1999).

From these data the antibody epitope was located to a discontinuous epitope of 18 amino acids in two loop regions of human IL-4Rα; V65-H72 and L89-N98.

5.3 Further Localisation of the IL-4Rα Epitope of Antibody Using Mutants of MoLoop2Hu IL-4Rα and MoLoop3HuIL-4Rα

To localise important residues of the antibody epitope of human IL-4Rα mutants of MoLoop2HuIL-4Rα and MoLoop3HuIL-4Rα were generated and tested for activity in an HTRF competition assay.

MoLoop2HuIL-4Rα (Table 5) was mutated to convert mouse residues back to human. When epitope-important residues were mutated, the $IC_{50}$ values were lower than that of MoLoop2HuIL-4Rα (Table 6). Three mutants (constructs EM18, EM22 and EM23) gave similar $IC_{50}$ values to MoLoop2HuIL-4Rα (Table 6). In addition when mouse residues N72 and L73 are placed to human IL-4Rα the resultant chimeric molecule is able to strongly inhibit the human IL-4Rα/antibody interaction (Table 6). These data suggest that human IL-4Rα residues V65, A71 and H72 are not important parts of the antibody epitope. The remaining three mouse residues of loop 2 (F67, E68, F69) correspond to two human residues (L67, L68). In MoLoop2HuIL-4Rα mutants where any of the two mouse phenylalanine residues is replaced with a human lysine residue the $IC_{50}$ is reduced (Table 6). When mouse E68 is removed from MoLoop2HuIL-4Rα the $IC_{50}$ is also reduced suggesting that acidic glutamic acid residue of mouse loop2 is blocking part of the antibody epitope. In addition when all three mouse residues (F67, E68, F69) are placed into human IL-4Rα the chimera only weakly inhibits human IL-4Rα/antibody interaction (Table 6). These data show human residues L67 and L68 are part of the antibody binding epitope of human IL-4Rα.

TABLE 6

$IC_{50}$ (in nM) of chimeric IL-4Rα molecules competing against human IL-4Rα binding to antibody. Chimeras composed of amino acids M1-L64 and T73-F229 from human IL-4Rα (NP_000409) with different loop2 regions were tested for the ability to compete with human IL-4Rα in binding antibody. Conserved residues between human and mouse are shown in lowercase, human residues different from mouse residues are shown in uppercase bold italics and mouse residues different from human residues are shown in uppercase plain text. $IC_{50}$ values were calculated where a complete competition curve was obtained.

| Construct name | Loop2 sequence | $IC_{50}$ (nM) in competition assay |
|---|---|---|
| Human IL-4Rα | *V*f***L-L***se***AH*** | 0.673 |
| MoLoop2HuIL-4Rα | MfFEFseNL | 25 |
| EM18 | *V*fFEFseNL | 20 |
| EM19 | Mf***L***EFseNL | 4.5 |
| EM20 | MfF-FseNL | 3.8 |
| EM21 | MfFE***L***seNL | 5.7 |
| EM22 | MfFEFse***A***L | 19 |
| EM23 | MfFEFseN***H*** | 56 |
| EM24 | *V*fFEFse***AH*** | 13 |
| EM25 | *V*f***L-L***seNL | 0.448 |

For loop 3 mutants in human IL-4Rα were constructed where individual residues were changed to mouse residues (Table 7). A lower IC$_{50}$ than human IL-4Rα is seen when epitope-important residues are mutated.

Two mutants had drastically reduced ability to block the human IL-4Rα/antibody interaction showing that they are part of the epitope. When human IL-4Rα D92 is mutated to R (in mutant EM03) the mutant protein is unable to block the IL-4Rα/antibody interaction at 1000 nM. When human IL-4Rα V93 is mutated to P (in mutant EM04) the IC$_{50}$ value is 20 fold higher than human IL-4Rα (Table 7). In comparison the human IL-4Rα mutants L89E, D91N, S95Q, A96V and N98R (chimeras EM01, EM02, EM05, EM06 and EM07) all gave similar IC$_{50}$ values to human IL-4Rα (Table 3). These data suggest that the antibody epitope includes human IL-4Rα D92 and V93 and that D92 is the most important residue in the human IL-4Rα/antibody interaction.

TABLE 7

IC$_{50}$ (in nM) of chimeric IL-4Rα molecules competing against human IL-4Rα binding to antibody. Chimeras composed of amino acids M1-L88 and Y99-F229 from human IL-4Rα (NP_000409) with different loop3 regions were tested for the ability to compete with human IL-4Rα in binding antibody. Conserved residues between human and mouse are shown in lowercase, human residues different from mouse residues are shown in uppercase bold italics and mouse residues different from human residues are shown in uppercase plain text.

| Construct name | Loop3 sequence | IC$_{50}$ (nM) in competition assay |
| --- | --- | --- |
| Human IL-4Rα | Lm*DDV*v*SA*d*N* | 0.673 |
| MoLoop3HuIL-4Rα | EmNRPvQSdR | 45% inhibition* |
| EM01 | Em*DDV*v*SA*d*N* | 0.71 |
| EM02 | LmN*DV*v*SA*d*N* | 2.25 |
| EM03 | Lm*D*R*V*v*SA*d*N* | 29% inhibition* |
| EM04 | Lm*DD*P v*SA*d*N* | 15 |
| EM05 | Lm*DDV*v*S*Q*A*d*N* | 1.65 |
| EM06 | Lm*DDV*v*S*S d*N* | 3.25 |
| EM07 | Lm*DDV*v*SA*dR | 1.41 |

IC$_{50}$ values were calculated where a complete competition curve was obtained.
*Where the chimera failed to completely inhibit human IL-4Rα binding to antibody the percentage inhibition seen at the highest concentration of chimera (1000 nM) is shown.

Domain swapping and mutagenesis has localised the antibody epitope to loops 2 (residues 65 to 72) and 3 (residues 89-98) of human IL-4Rα. The epitope can be further localised to amino acid residues L67 and L68 of loop 2 and D92 and V93 of loop3 (see SEQ ID NO: 454 for location of residues 67, 68, 92 and 93).

The antibodies of the invention are also cross-reactive with cynomologus monkey IL-4Rα. Of interest is the fact that the epitope residues D92 and V93 are also present in cynomologus monkey IL-4Rα.

All publications, patents and patent applications mentioned in this specification are herein incorporated by reference in to the specification to the same extent as if each individual publication, patent or patent application was specifically and individually indicated to be incorporated herein by reference.

Sequences

Sequences of binding members of the invention are shown in the appended sequence listing, in which SEQ ID Nos correspond as follows:

| Sequence | Description |
| --- | --- |
| 1 | Antibody 1 VH DNA |
| 2 | Antibody 1 VH PRT |
| 3 | Antibody 1 CDR1 PRT |
| 4 | Antibody 1 CDR2 PRT |
| 5 | Antibody 1 CDR3 PRT |
| 6 | Antibody 1 VL DNA |
| 7 | Antibody 1 VL PRT |
| 8 | Antibody 1 CDR1 PRT |
| 9 | Antibody 1 CDR2 PRT |
| 10 | Antibody 1 CDR3 PRT |
| 11 | Antibody 2 VH DNA |
| 12 | Antibody 2 VH PRT |
| 13 | Antibody 2 CDR1 PRT |
| 14 | Antibody 2 CDR2 PRT |
| 15 | Antibody 2 CDR3 PRT |
| 16 | Antibody 2 VL DNA |
| 17 | Antibody 2 VL PRT |
| 18 | Antibody 2 CDR1 PRT |
| 19 | Antibody 2 CDR2 PRT |
| 20 | Antibody 2 CDR3 PRT |
| 21 | Antibody 3 VH DNA |
| 22 | Antibody 3 VH PRT |
| 23 | Antibody 3 CDR1 PRT |
| 24 | Antibody 3 CDR2 PRT |
| 25 | Antibody 3 CDR3 PRT |
| 26 | Antibody 3 VL DNA |
| 27 | Antibody 3 VL PRT |
| 28 | Antibody 3 CDR1 PRT |
| 29 | Antibody 3 DR2 PRT |
| 30 | Antibody 3 CDR3 PRT |
| 31 | Antibody 4 VH DNA |
| 32 | Antibody 4 VH PRT |
| 33 | Antibody 4 CDR1 PRT |
| 34 | Antibody 4 CDR2 PRT |
| 35 | Antibody 4 CDR3 PRT |
| 36 | Antibody 4 VL DNA |
| 37 | Antibody 4 VL PRT |
| 38 | Antibody 4 CDR1 PRT |
| 39 | Antibody 4 CDR2 PRT |
| 40 | Antibody 4 CDR3 PRT |
| 41 | Antibody 5 VH DNA |
| 42 | Antibody 5 VH PRT |
| 43 | Antibody 5 CDR1 PRT |
| 44 | Antibody 5 CDR2 PRT |
| 45 | Antibody 5 CDR3 PRT |
| 46 | Antibody 5 VL DNA |
| 47 | Antibody 5 VL PRT |
| 48 | Antibody 5 CDR1 PRT |
| 49 | Antibody 5 CDR2 PRT |
| 50 | Antibody 5 CDR3 PRT |
| 51 | Antibody 6 VH DNA |
| 52 | Antibody 6 VH PRT |
| 53 | Antibody 6 CDR1 PRT |
| 54 | Antibody 6 CDR2 PRT |
| 55 | Antibody 6 CDR3 PRT |
| 56 | Antibody 6 VL DNA |
| 57 | Antibody 6 VL PRT |
| 58 | Antibody 6 CDR1 PRT |
| 59 | Antibody 6 CDR2 PRT |
| 60 | Antibody 6 CDR3 PRT |
| 61 | Antibody 7 VH DNA |
| 62 | Antibody 7 VH PRT |
| 63 | Antibody 7 CDR1 PRT |
| 64 | Antibody 7 CDR2 PRT |
| 65 | Antibody 7 CDR3 PRT |
| 66 | Antibody 7 VL DNA |
| 67 | Antibody 7 VL PRT |
| 68 | Antibody 7 CDR1 PRT |
| 69 | Antibody 7 CDR2 PRT |
| 70 | Antibody 7 CDR3 PRT |
| 71 | Antibody 8 VH DNA |
| 72 | Antibody 8 VH PRT |
| 73 | Antibody 8 CDR1 PRT |
| 74 | Antibody 8 CDR2 PRT |
| 75 | Antibody 8 CDR3 PRT |
| 76 | Antibody 8 VL DNA |
| 77 | Antibody 8 VL PRT |
| 78 | Antibody 8 CDR1 PRT |
| 79 | Antibody 8 CDR2 PRT |
| 80 | Antibody 8 CDR3 PRT |
| 81 | Antibody 9 VH DNA |

-continued

| Sequence | Description |
|---|---|
| 82 | Antibody 9 VH PRT |
| 83 | Antibody 9 CDR1 PRT |
| 84 | Antibody 9 CDR2 PRT |
| 85 | Antibody 9 CDR3 PRT |
| 86 | Antibody 9 VL DNA |
| 87 | Antibody 9 VL PRT |
| 88 | Antibody 9 CDR1 PRT |
| 89 | Antibody 9 CDR2 PRT |
| 90 | Antibody 9 CDR3 PRT |
| 91 | Antibody 10 VH DNA |
| 92 | Antibody 10 VH PRT |
| 93 | Antibody 10 CDR1 PRT |
| 94 | Antibody 10 CDR2 PRT |
| 95 | Antibody 10 CDR3 PRT |
| 96 | Antibody 10 VL DNA |
| 97 | Antibody 10 VL PRT |
| 98 | Antibody 10 CDR1 PRT |
| 99 | Antibody 10 CDR2 PRT |
| 100 | Antibody 10 CDR3 PRT |
| 101 | Antibody 11 VH DNA |
| 102 | Antibody 11 VH PRT |
| 103 | Antibody 11 CDR1 PRT |
| 104 | Antibody 11 CDR2 PRT |
| 105 | Antibody 11 CDR3 PRT |
| 106 | Antibody 11 VL DNA |
| 107 | Antibody 11 VL PRT |
| 108 | Antibody 11 CDR1 PRT |
| 109 | Antibody 11 CDR2 PRT |
| 110 | Antibody 11 CDR3 PRT |
| 111 | Antibody 12 VH DNA |
| 112 | Antibody 12 VH PRT |
| 113 | Antibody 12 CDR1 PRT |
| 114 | Antibody 12 CDR2 PRT |
| 115 | Antibody 12 CDR3 PRT |
| 116 | Antibody 12 VL DNA |
| 117 | Antibody 12 VL PRT |
| 118 | Antibody 12 CDR1 PRT |
| 119 | Antibody 12 CDR2 PRT |
| 120 | Antibody 12 CDR3 PRT |
| 121 | Antibody 13 VH DNA |
| 122 | Antibody 13 VH PRT |
| 123 | Antibody 13 CDR1 PRT |
| 124 | Antibody 13 CDR2 PRT |
| 125 | Antibody 13 CDR3 PRT |
| 126 | Antibody 13 VL DNA |
| 127 | Antibody 13 VL PRT |
| 128 | Antibody 13 CDR1 PRT |
| 129 | Antibody 13 CDR2 PRT |
| 130 | Antibody 13 CDR3 PRT |
| 131 | Antibody 14 VH DNA |
| 132 | Antibody 14 VH PRT |
| 133 | Antibody 14 CDR1 PRT |
| 134 | Antibody 14 CDR2 PRT |
| 135 | Antibody 14 CDR3 PRT |
| 136 | Antibody 14 VL DNA |
| 137 | Antibody 14 VL PRT |
| 138 | Antibody 14 CDR1 PRT |
| 139 | Antibody 14 CDR2 PRT |
| 140 | Antibody 14 CDR3 PRT |
| 141 | Antibody 15 VH DNA |
| 142 | Antibody 15 VH PRT |
| 143 | Antibody 15 CDR1 PRT |
| 144 | Antibody 15 CDR2 PRT |
| 145 | Antibody 15 CDR3 PRT |
| 146 | Antibody 15 VL DNA |
| 147 | Antibody 15 VL PRT |
| 148 | Antibody 15 CDR1 PRT |
| 149 | Antibody 15 CDR2 PRT |
| 150 | Antibody 15 CDR3 PRT |
| 151 | Antibody 16 VH DNA |
| 152 | Antibody 16 VH PRT |
| 153 | Antibody 16 CDR1 PRT |
| 154 | Antibody 16 CDR2 PRT |
| 155 | Antibody 16 CDR3 PRT |
| 156 | Antibody 16 VL DNA |
| 157 | Antibody 16 VL PRT |
| 158 | Antibody 16 CDR1 PRT |
| 159 | Antibody 16 CDR2 PRT |

-continued

| Sequence | Description |
|---|---|
| 160 | Antibody 16 CDR3 PRT |
| 161 | Antibody 17 VH DNA |
| 162 | Antibody 17 VH PRT |
| 163 | Antibody 17 CDR1 PRT |
| 164 | Antibody 17 CDR2 PRT |
| 165 | Antibody 17 CDR3 PRT |
| 166 | Antibody 17 VL DNA |
| 167 | Antibody 17 VL PRT |
| 168 | Antibody 17 CDR1 PRT |
| 169 | Antibody 17 CDR2 PRT |
| 170 | Antibody 17 CDR3 PRT |
| 171 | Antibody 18 VH DNA |
| 172 | Antibody 18 VH PRT |
| 173 | Antibody 18 CDR1 PRT |
| 174 | Antibody 18 CDR2 PRT |
| 175 | Antibody 18 CDR3 PRT |
| 176 | Antibody 18 VL DNA |
| 177 | Antibody 18 VL PRT |
| 178 | Antibody 18 CDR1 PRT |
| 179 | Antibody 18 CDR2 PRT |
| 180 | Antibody 18 CDR3 PRT |
| 181 | Antibody 19 VH DNA |
| 182 | Antibody 19 VH PRT |
| 183 | Antibody 19 CDR1 PRT |
| 184 | Antibody 19 CDR2 PRT |
| 185 | Antibody 19 CDR3 PRT |
| 186 | Antibody 19 VL DNA |
| 187 | Antibody 19 VL PRT |
| 188 | Antibody 19 CDR1 PRT |
| 189 | Antibody 19 CDR2 PRT |
| 190 | Antibody 19 CDR3 PRT |
| 191 | Antibody 20 VH DNA |
| 192 | Antibody 20 VH PRT |
| 193 | Antibody 20 CDR1 PRT |
| 194 | Antibody 20 CDR2 PRT |
| 195 | Antibody 20 CDR3 PRT |
| 196 | Antibody 20 VL DNA |
| 197 | Antibody 20 VL PRT |
| 198 | Antibody 20 CDR1 PRT |
| 199 | Antibody 20 CDR2 PRT |
| 200 | Antibody 20 CDR3 PRT |
| 201 | Antibody 21 VH DNA |
| 202 | Antibody 21 VH PRT |
| 203 | Antibody 21 CDR1 PRT |
| 204 | Antibody 21 CDR2 PRT |
| 205 | Antibody 21 CDR3 PRT |
| 206 | Antibody 21 VL DNA |
| 207 | Antibody 21 VL PRT |
| 208 | Antibody 21 CDR1 PRT |
| 209 | Antibody 21 CDR2 PRT |
| 210 | Antibody 21 CDR3 PRT |
| 211 | Antibody 22 VH DNA |
| 212 | Antibody 22 VH PRT |
| 213 | Antibody 22 CDR1 PRT |
| 214 | Antibody 22 CDR2 PRT |
| 215 | Antibody 22 CDR3 PRT |
| 216 | Antibody 22 VL DNA |
| 217 | Antibody 22 VL PRT |
| 218 | Antibody 22 CDR1 PRT |
| 219 | Antibody 22 CDR2 PRT |
| 220 | Antibody 22 CDR3 PRT |
| 221 | Antibody 23 VH DNA |
| 222 | Antibody 23 VH PRT |
| 223 | Antibody 23 CDR1 PRT |
| 224 | Antibody 23 CDR2 PRT |
| 225 | Antibody 23 CDR3 PRT |
| 226 | Antibody 23 VL DNA |
| 227 | Antibody 23 VL PRT |
| 228 | Antibody 23 CDR1 PRT |
| 229 | Antibody 23 CDR2 PRT |
| 230 | Antibody 23 CDR3 PRT |
| 231 | Antibody 24 VH DNA |
| 232 | Antibody 24 VH PRT |
| 233 | Antibody 24 CDR1 PRT |
| 234 | Antibody 24 CDR2 PRT |
| 235 | Antibody 24 CDR3 PRT |
| 236 | Antibody 24 VL DNA |
| 237 | Antibody 24 VL PRT |

| Sequence | Description |
|---|---|
| 238 | Antibody 24 CDR1 PRT |
| 239 | Antibody 24 CDR2 PRT |
| 240 | Antibody 24 CDR3 PRT |
| 241 | Antibody 25 VH DNA |
| 242 | Antibody 25 VH PRT |
| 243 | Antibody 25 CDR1 PRT |
| 244 | Antibody 25 CDR2 PRT |
| 245 | Antibody 25 CDR3 PRT |
| 246 | Antibody 25 VL DNA |
| 247 | Antibody 25 VL PRT |
| 248 | Antibody 25 CDR1 PRT |
| 249 | Antibody 25 CDR2 PRT |
| 250 | Antibody 25 CDR3 PRT |
| 251 | Antibody 26 VH DNA |
| 252 | Antibody 26 VH PRT |
| 253 | Antibody 26 CDR1 PRT |
| 254 | Antibody 26 CDR2 PRT |
| 255 | Antibody 26 CDR3 PRT |
| 256 | Antibody 26 VL DNA |
| 257 | Antibody 26 VL PRT |
| 258 | Antibody 26 CDR1 PRT |
| 259 | Antibody 26 CDR2 PRT |
| 260 | Antibody 26 CDR3 PRT |
| 261 | Antibody 27 VH DNA |
| 262 | Antibody 27 VH PRT |
| 263 | Antibody 27 CDR1 PRT |
| 264 | Antibody 27 CDR2 PRT |
| 265 | Antibody 27 CDR3 PRT |
| 266 | Antibody 27 VL DNA |
| 267 | Antibody 27 VL PRT |
| 268 | Antibody 27 CDR1 PRT |
| 269 | Antibody 27 CDR2 PRT |
| 270 | Antibody 27 CDR3 PRT |
| 271 | Antibody 28 VH DNA |
| 272 | Antibody 28 VH PRT |
| 273 | Antibody 28 CDR1 PRT |
| 274 | Antibody 28 CDR2 PRT |
| 275 | Antibody 28 CDR3 PRT |
| 276 | Antibody 28 VL DNA |
| 277 | Antibody 28 VL PRT |
| 278 | Antibody 28 CDR1 PRT |
| 279 | Antibody 28 CDR2 PRT |
| 280 | Antibody 28 CDR3 PRT |
| 281 | Antibody 29 VH DNA |
| 282 | Antibody 29 VH PRT |
| 283 | Antibody 29 CDR1 PRT |
| 284 | Antibody 29 CDR2 PRT |
| 285 | Antibody 29 CDR3 PRT |
| 286 | Antibody 29 VL DNA |
| 287 | Antibody 29 VL PRT |
| 288 | Antibody 29 CDR1 PRT |
| 289 | Antibody 29 CDR2 PRT |
| 290 | Antibody 29 CDR3 PRT |
| 291 | Antibody 30 VH DNA |
| 292 | Antibody 30 VH PRT |
| 293 | Antibody 30 CDR1 PRT |
| 294 | Antibody 30 CDR2 PRT |
| 295 | Antibody 30 CDR3 PRT |
| 296 | Antibody 30 VL DNA |
| 297 | Antibody 30 VL PRT |
| 298 | Antibody 30 CDR1 PRT |
| 299 | Antibody 30 CDR2 PRT |
| 300 | Antibody 30 CDR3 PRT |
| 301 | Antibody 31 VH DNA |
| 302 | Antibody 31 VH PRT |
| 303 | Antibody 31 CDR1 PRT |
| 304 | Antibody 31 CDR2 PRT |
| 305 | Antibody 31 CDR3 PRT |
| 306 | Antibody 31 VL DNA |
| 307 | Antibody 31 VL PRT |
| 308 | Antibody 31 CDR1 PRT |
| 309 | Antibody 31 CDR2 PRT |
| 310 | Antibody 31 CDR3 PRT |
| 311 | Antibody 32 VH DNA |
| 312 | Antibody 32 VH PRT |
| 313 | Antibody 32 CDR1 PRT |
| 314 | Antibody 32 CDR2 PRT |
| 315 | Antibody 32 CDR3 PRT |
| 316 | Antibody 32 VL DNA |
| 317 | Antibody 32 VL PRT |
| 318 | Antibody 32 CDR1 PRT |
| 319 | Antibody 32 CDR2 PRT |
| 320 | Antibody 32 CDR3 PRT |
| 321 | Antibody 33 VH DNA |
| 322 | Antibody 33 VH PRT |
| 323 | Antibody 33 CDR1 PRT |
| 324 | Antibody 33 CDR2 PRT |
| 325 | Antibody 33 CDR3 PRT |
| 326 | Antibody 33 VL DNA |
| 327 | Antibody 33 VL PRT |
| 328 | Antibody 33 CDR1 PRT |
| 329 | Antibody 33 CDR2 PRT |
| 330 | Antibody 33 CDR3 PRT |
| 331 | Antibody 34 VH DNA |
| 332 | Antibody 34 VH PRT |
| 333 | Antibody 34 CDR1 PRT |
| 334 | Antibody 34 CDR2 PRT |
| 335 | Antibody 34 CDR3 PRT |
| 336 | Antibody 34 VL DNA |
| 337 | Antibody 34 VL PRT |
| 338 | Antibody 34 CDR1 PRT |
| 339 | Antibody 34 CDR2 PRT |
| 340 | Antibody 34 CDR3 PRT |
| 341 | Antibody 35 VH DNA |
| 342 | Antibody 35 VH PRT |
| 343 | Antibody 35 CDR1 PRT |
| 344 | Antibody 35 CDR2 PRT |
| 345 | Antibody 35 CDR3 PRT |
| 346 | Antibody 35 VL DNA |
| 347 | Antibody 35 VL PRT |
| 348 | Antibody 35 CDR1 PRT |
| 349 | Antibody 35 CDR2 PRT |
| 350 | Antibody 35 CDR3 PRT |
| 351 | Antibody 36 VH DNA |
| 352 | Antibody 36 VH PRT |
| 353 | Antibody 36 CDR1 PRT |
| 354 | Antibody 36 CDR2 PRT |
| 355 | Antibody 36 CDR3 PRT |
| 356 | Antibody 36 VL DNA |
| 357 | Antibody 36 VL PRT |
| 358 | Antibody 36 CDR1 PRT |
| 359 | Antibody 36 CDR2 PRT |
| 360 | Antibody 36 CDR3 PRT |
| 361 | Antibody 37 VH DNA |
| 362 | Antibody 37 VH PRT |
| 363 | Antibody 37 CDR1 PRT |
| 364 | Antibody 37 CDR2 PRT |
| 365 | Antibody 37 CDR3 PRT |
| 366 | Antibody 37 VL DNA |
| 367 | Antibody 37 VL PRT |
| 368 | Antibody 37 CDR1 PRT |
| 369 | Antibody 37 CDR2 PRT |
| 370 | Antibody 37 CDR3 PRT |
| 371 | Antibody 38 VH DNA |
| 372 | Antibody 38 VH PRT |
| 373 | Antibody 38 CDR1 PRT |
| 374 | Antibody 38 CDR2 PRT |
| 375 | Antibody 38 CDR3 PRT |
| 376 | Antibody 38 VL DNA |
| 377 | Antibody 38 VL PRT |
| 378 | Antibody 38 CDR1 PRT |
| 379 | Antibody 38 CDR2 PRT |
| 380 | Antibody 38 CDR3 PRT |
| 381 | Antibody 39 VH DNA |
| 382 | Antibody 39 VH PRT |
| 383 | Antibody 39 CDR1 PRT |
| 384 | Antibody 39 CDR2 PRT |
| 385 | Antibody 39 CDR3 PRT |
| 386 | Antibody 39 VL DNA |
| 387 | Antibody 39 VL PRT |
| 388 | Antibody 39 CDR1 PRT |
| 389 | Antibody 39 CDR2 PRT |
| 390 | Antibody 39 CDR3 PRT |
| 391 | Antibody 40 VH DNA |
| 392 | Antibody 40 VH PRT |
| 393 | Antibody 40 CDR1 PRT |

| Sequence | Description |
|---|---|
| 394 | Antibody 40 CDR2 PRT |
| 395 | Antibody 40 CDR3 PRT |
| 396 | Antibody 40 VL DNA |
| 397 | Antibody 40 VL PRT |
| 398 | Antibody 40 CDR1 PRT |
| 399 | Antibody 40 CDR2 PRT |
| 400 | Antibody 40 CDR3 PRT |
| 401 | Antibody 41 VH DNA |
| 402 | Antibody 41 VH PRT |
| 403 | Antibody 41 CDR1 PRT |
| 404 | Antibody 41 CDR2 PRT |
| 405 | Antibody 41 CDR3 PRT |
| 406 | Antibody 41 VL DNA |
| 407 | Antibody 41 VL PRT |
| 408 | Antibody 41 CDR1 PRT |
| 409 | Antibody 41 CDR2 PRT |
| 410 | Antibody 41 CDR3 PRT |
| 411 | Antibody 42 VH DNA |
| 412 | Antibody 42 VH PRT |
| 413 | Antibody 42 CDR1 PRT |
| 414 | Antibody 42 CDR2 PRT |
| 415 | Antibody 42 CDR3 PRT |
| 416 | Antibody 42 VL DNA |
| 417 | Antibody 42 VL PRT |
| 418 | Antibody 42 CDR1 PRT |
| 419 | Antibody 42 CDR2 PRT |
| 420 | Antibody 42 CDR3 PRT |
| 421 | Antibody 24 PGLVH DNA |
| 422 | Antibody 24 PGLVH PRT |
| 423 | Antibody 24 PGLCDR1 PRT |
| 424 | Antibody 24 PGLCDR2 PRT |
| 425 | Antibody 24 PGLCDR3 PRT |
| 426 | Antibody 24 PGLVL DNA |
| 427 | Antibody 24 PGLVL PRT |
| 428 | Antibody 24 PGLCDR1 PRT |
| 429 | Antibody 24 PGLCDR2 PRT |
| 430 | Antibody 24 PGLCDR3 PRT |
| 431 | Antibody 24 GLVH DNA |
| 432 | Antibody 24 GLVH PRT |
| 433 | Antibody 24 GLCDR1 PRT |
| 434 | Antibody 24 GLCDR2 PRT |
| 435 | Antibody 24 GLCDR3 PRT |
| 436 | Antibody 24 GLVL DNA |
| 437 | Antibody 24 GLVL PRT |
| 438 | Antibody 24 GLCDR1 PRT |
| 439 | Antibody 24 GLCDR2 PRT |
| 440 | Antibody 24 GLCDR3 PRT |
| 441 | Antibody 37 GLVH DNA |
| 442 | Antibody 37 GLVH PRT |
| 443 | Antibody 37 GLCDR1 PRT |
| 444 | Antibody 37 GLCDR2 PRT |
| 445 | Antibody 37 GLCDR3 PRT |
| 446 | Antibody 37 GLVL DNA |
| 447 | Antibody 37 GLVL PRT |
| 448 | Antibody 37 GLCDR1 PRT |
| 449 | Antibody 37 GLCDR2 PRT |
| 450 | Antibody 37 GLCDR3 PRT |
| 451 | Cyno IL4R primer 1 |
| 452 | Cyno IL4R primer 2 |
| 453 | I75V oligonucleotide mutation primer |
| 454 | Human IL-4Rα/Fc protein |
| 455 | Cynomolgus monkey IL-4Rα cDNA nucleotide |
| 456 | Cynomolgus monkey IL-4Rα/Fc cDNA nucleotide |
| 457 | Cynomolgus monkey IL-4Rα/Fc cDNA protein |
| 458 | Human I75V IL4-Rα/Fc cDNA nucleotide sequence |
| 459 | Human I75V IL4-Rα/Fc protein |
| 460 | Human IL4-Rα/FLAG/HIS tag amino acid sequence |
| 461 | Murine IL4-Rα/FLAG/HIS tag amino acid sequence |

The invention claimed is:

1. An isolated antibody or fragment thereof that specifically binds human interleukin-4 receptor alpha (hIL-4Rα), comprising a set of CDRs: HCDR1, HCDR2, HCDR3, LCDR1, LCDR2 and LCDR3, wherein the set of CDRs has 10 or fewer amino acid substitutions from a reference set of CDRs in which:
   HCDR1 has amino acid sequence SEQ ID NO: 193;
   HCDR2 has amino acid sequence SEQ ID NO: 194;
   HCDR3 has amino acid sequence SEQ ID NO: 195;
   LCDR1 has amino acid sequence SEQ ID NO: 198;
   LCDR2 has amino acid sequence SEQ ID NO: 199; and
   LCDR3 has amino acid sequence SEQ ID NO: 200.

2. The antibody or fragment thereof according to claim 1, wherein the amino acid substitutions comprise one or more substitutions as shown in FIGS. 3 and 4.

3. The antibody or fragment thereof according to claim 1, wherein the amino acid substitutions comprise an amino acid substitution at one or more of the following residues within the CDRs, using the standard numbering of Kabat:
   53, 57, in HCDR2;
   97, 98, 99, 101, 102 in HCDR3;
   27, 27A, 27B, 31 in LCDR1;
   56 in LCDR2; or
   92, 93, 94, 95, 95A 95B, 95C, 96, 97 in LCDR3.

4. The antibody or fragment thereof according to claim 1, which in addition comprises one or more amino acid substitutions at the following residues within the framework regions, using the standard numbering of Kabat:
   11, 12 in HFW1;
   37, 48 in HFW2;
   68, 84, 85 in HFW3;
   105, 108, 113 in HFW4;
   1, 2, 3, 9 in LFW1;
   38, 42 in LFW2; or
   58, 65, 66, 70, 74, 85, 87 in LFW3.

5. The antibody or fragment thereof according to claim 4, wherein the amino acid substitutions in the framework regions comprise one or more substitutions as shown in FIGS. 3 and 4.

6. An isolated antibody or fragment thereof that specifically binds human interleukin-4 receptor alpha (hIL-4Rα), wherein:
   (i) the HCDR1 has amino acid sequence SEQ ID NO: 363;
   the HCDR2 has amino acid sequence SEQ ID NO: 364;
   the HCDR3 has amino acid sequence SEQ ID NO: 365;
   the LCDR1 has amino acid sequence SEQ ID NO: 368;
   the LCDR2 has amino acid sequence SEQ ID NO: 369; and
   the LCDR3 has amino acid sequence SEQ ID NO: 370; or
   (ii) the HCDR1 has amino acid sequence SEQ ID NO: 233;
   the HCDR2 has amino acid sequence SEQ ID NO: 234;
   the HCDR3 has amino acid sequence SEQ ID NO: 235;
   the LCDR1 has amino acid sequence SEQ ID NO: 238;

the LCDR2 has amino acid sequence SEQ ID NO: 239; and the LCDR3 has amino acid sequence SEQ ID NO: 240.

7. The antibody or fragment thereof according to claims 1 or 6, wherein the antibody or fragment thereof comprises an antibody VH domain and an antibody VL domain, wherein the VH domain comprises HCDR1, HCDR2, HCDR3 and a first framework and the VL domain comprises LCDR1, LCDR2, LCDR3 and a second framework.

8. The antibody or fragment thereof according to claim 7, wherein the antibody molecule is an scFv.

9. The antibody or fragment thereof according to claim 7, wherein the antibody molecule comprises an antibody constant region.

10. The antibody or fragment thereof according to claim 7, wherein the antibody molecule is an IgG1, IgG2 or IgG4 molecule.

11. A composition comprising an isolated antibody or fragment thereof according to claims 1 or 6, and a pharmaceutically acceptable excipient.

12. An isolated nucleic acid molecule comprising a nucleotide sequence encoding the antibody or fragment thereof according to claims 1 or 6.

13. A host cell in vitro transformed with the nucleic acid according to claim 12.

14. An isolated antibody or fragment thereof for human interleukin-4 receptor alpha (hIL-4Rα), having at least 73% amino acid sequence identity with the 6xCDR composite score of any of Antibodies 1-42.

15. An isolated antibody or fragment thereof that specifically binds human interleukin-4 receptor alpha (hIL-4Rα), comprising a VH domain wherein:
 (i) the VH domain has amino acid sequence SEQ ID NO: 192;
 (ii) the VH domain has amino acid sequence SEQ ID NO: 362; or
 (iii) the VH domain has amino acid sequence SEQ ID NO: 232;
 and, wherein the VH domain comprises one or more amino acid substitutions at the following residues within the framework regions, using the standard numbering of Kabat:
 11, 12 in HFW1;
 37, 48 in HFW2;
 68, 84, 85 in HFW3; or
 105, 108, 113 in HFW4.

16. The antibody or fragment thereof according to claim 15, wherein the amino acid substitutions in the framework regions comprise one or more substitutions as shown in FIGS. 3 and 4.

17. The antibody or fragment thereof according to claim 15, wherein the antibody molecule is an scFv.

18. The antibody or fragment thereof according to claim 15, wherein the antibody molecule comprises an antibody constant region.

19. The antibody or fragment thereof according to claim 15, wherein the antibody molecule is an IgG1, IgG2 or IgG4 molecule.

20. A composition comprising an isolated antibody or fragment thereof according to claim 15, and a pharmaceutically acceptable excipient.

21. An isolated nucleic acid molecule comprising a nucleotide sequence encoding the antibody or fragment thereof according to claim 15.

22. A host cell in vitro transformed with the nucleic acid according to claim 21.

23. An isolated antibody or fragment thereof that specifically binds human interleukin-4 receptor alpha (hIL-4Rα), comprising a VL domain wherein:
 (i) the VL domain has amino acid sequence SEQ ID NO: 197;
 (ii) the VL domain has amino acid sequence SEQ ID NO: 367; or
 (iii) the VL domain has amino acid sequence SEQ ID NO: 237;
 and, wherein the VL domain comprises one or more amino acid substitutions at the following residues within the framework regions, using the standard numbering of Kabat:
 1, 2, 3, 9 in LFW1;
 38, 42 in LFW2; or
 58, 65, 66, 70, 74, 85, 87 in LFW3.

24. The antibody or fragment thereof according to claim 23, wherein the amino acid substitutions in the framework regions comprise one or more substitutions as shown in FIGS. 3 and 4.

25. The antibody or fragment thereof according to claim 23, wherein the amino acid substitutions in the framework regions comprise one or more substitutions as shown in FIGS. 3 and 4.

26. The antibody or fragment thereof according to claim 23, wherein the antibody molecule is an scFv.

27. The antibody or fragment thereof according to claim 23, wherein the antibody molecule comprises an antibody constant region.

28. The antibody or fragment thereof according to claim 23, wherein the antibody molecule is an IgG1, IgG2 or IgG4 molecule.

29. A composition comprising an isolated antibody or fragment thereof according to claim 23, and a pharmaceutically acceptable excipient.

30. An isolated nucleic acid molecule comprising a nucleotide sequence encoding the antibody or fragment thereof according to claim 23.

31. A host cell in vitro transformed with the nucleic acid according to claim 30.

32. An isolated antibody or fragment thereof that specifically binds human interleukin-4 receptor alpha (hIL-4Rα), comprising a VH and a VL domain wherein:
 (i) the VH domain has amino acid sequence SEQ ID NO: 192 and the VL domain has amino acid sequence SEQ ID NO: 197;
 (ii) the VH domain has amino acid sequence SEQ ID NO: 362 and the VL domain has amino acid sequence SEQ ID NO: 367; or
 (iii) the VH domain has amino acid sequence SEQ ID NO: 232 and the VL domain has amino acid sequence SEQ ID NO: 237;
 and, wherein the VH domain and VL domain comprise one or more amino acid substitutions at the following residues within the framework regions, using the standard numbering of Kabat:
 11, 12 in HFW1;
 37, 48 in HFW2;
 68, 84, 85 in HFW3;
 105, 108, 113 in HFW4;
 1, 2, 3, 9 in LFW1;
 38, 42 in LFW2; or
 58, 65, 66, 70, 74, 85, 87 in LFW3.

33. The antibody or fragment thereof according to claim 32, wherein the amino acid substitutions in the framework regions comprise one or more substitutions as shown in FIGS. 3 and 4.

34. The antibody or fragment thereof according to claim 32, wherein the antibody molecule is an scFv.

35. The antibody or fragment thereof according to claim 32, wherein the antibody molecule comprises an antibody constant region.

36. The antibody or fragment thereof according to claim 32, wherein the antibody molecule is an IgG1, IgG2 or IgG4 molecule.

37. A composition comprising an isolated antibody or fragment thereof according to claim 32, and a pharmaceutically acceptable excipient.

38. An isolated nucleic acid molecule comprising a nucleotide sequence encoding the antibody or fragment thereof according to claim 32.

39. A host cell in vitro transformed with the nucleic acid according to claim 38.

* * * * *

SEQUENCE LISTING

<160> NUMBER OF SEQ ID NOS: 461

<210> SEQ ID NO 1
<211> LENGTH: 348
<212> TYPE: DNA
<213> ORGANISM: Homo sapiens
<220> FEATURE:
<223> OTHER INFORMATION: Antibody 1

<400> SEQUENCE: 1

```
caggtccagc tggtgcagtc tggggctgag gtgaagaagc ctggggcctc agtgaaggtt      60
tcctgcaagg catctggata cgccttcacc agctactata tgcactgggc gcgacaggcc     120
cctggacaag gcttgagtg gatgggaata atcaaccccta gtggtggtag cacaagctac     180
gcacagaagt tccagggcag agtcaccatg accagggaca cgtccacgag cacagtctac     240
atggagctga gcagcctgag atctgaggac acggccgtgt attactgtgc gagaggaaaa     300
tggtggcttg actactgggg caaaggcacc ctggtcaccg tctcgagt                  348
```

<210> SEQ ID NO 2
<211> LENGTH: 116
<212> TYPE: PRT
<213> ORGANISM: Homo sapiens
<220> FEATURE:
<223> OTHER INFORMATION: Antibody 1

<400> SEQUENCE: 2

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Ser Tyr
            20                  25                  30

Tyr Met His Trp Ala Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Lys Trp Trp Leu Asp Tyr Trp Gly Lys Gly Thr Leu Val
            100                 105                 110

Thr Val Ser Ser
        115

<210> SEQ ID NO 3
<211> LENGTH: 5
<212> TYPE: PRT
<213> ORGANISM: Homo sapiens
<220> FEATURE:
<223> OTHER INFORMATION: Antibody 1

<400> SEQUENCE: 3

Ser Tyr Tyr Met His
1               5

<210> SEQ ID NO 4
<211> LENGTH: 17
<212> TYPE: PRT
<213> ORGANISM: Homo sapiens
<220> FEATURE:
<223> OTHER INFORMATION: Antibody 1

<400> SEQUENCE: 4

Ile Ile Asn Pro Ser Gly Gly Ser Thr Ser Tyr Ala Gln Lys Phe Gln
1               5                   10                  15

Gly

<210> SEQ ID NO 5
<211> LENGTH: 7
<212> TYPE: PRT
<213> ORGANISM: Homo sapiens
<220> FEATURE:
<223> OTHER INFORMATION: Antibody 1

<400> SEQUENCE: 5

Gly Lys Trp Trp Leu Asp Tyr
1               5

<210> SEQ ID NO 6
<211> LENGTH: 333
<212> TYPE: DNA
<213> ORGANISM: Homo sapiens
<220> FEATURE:
<223> OTHER INFORMATION: Antibody 1

<400> SEQUENCE: 6
cagtctgtgt tgacgcagcc gccctcagtg tctgcggccc caggacagaa ggtcaccatc        60
tcctgctctg gaggcagctc caacattggg aatagttatg tatcctggta ccagcaactc       120

```
ccaggaacag ccccaaaact cctcatttac gacaataata agcgaccctc agggattcct    180
gaccgattct ctggctccaa gtctggcacg tcagccaccc tggccatcac cggactccag    240
actggggacg aggccgatta ttactgcgga acatgggata ccagcctgag tgccaattat    300
gtcttcggaa ctgggaccaa gctgaccgtc cta                                  333
```

<210> SEQ ID NO 7
<211> LENGTH: 111
<212> TYPE: PRT
<213> ORGANISM: Homo sapiens
<220> FEATURE:
<223> OTHER INFORMATION: Antibody 1

<400> SEQUENCE: 7

Gln Ser Val Leu Thr Gln Pro Pro Ser Val Ala Ala Pro Gly Gln
              5                   10                  15
Lys Val Thr Ile Ser Cys Ser Gly Gly Ser Ser Asn Ile Gly Asn Ser
         20                  25                  30
Tyr Val Ser Trp Tyr Gln Gln Leu Pro Gly Thr Ala Pro Lys Leu Leu
     35                  40                  45
Ile Tyr Asp Asn Asn Lys Arg Pro Ser Gly Ile Pro Asp Arg Phe Ser
 50                  55                  60
Gly Ser Lys Ser Gly Thr Ser Ala Thr Leu Ala Ile Thr Gly Leu Gln
65                  70                  75                  80
Thr Gly Asp Glu Ala Asp Tyr Tyr Cys Gly Thr Trp Asp Thr Ser Leu
                 85                  90                  95
Ser Ala Asn Tyr Val Phe Gly Thr Gly Thr Lys Leu Thr Val Leu
            100                 105                 110

<210> SEQ ID NO 8
<211> LENGTH: 13
<212> TYPE: PRT
<213> ORGANISM: Homo sapiens
<220> FEATURE:
<223> OTHER INFORMATION: Antibody 1

<400> SEQUENCE: 8

Ser Gly Gly Ser Ser Asn Ile Gly Asn Ser Tyr Val Ser
              5                   10

<210> SEQ ID NO 9
<211> LENGTH: 7
<212> TYPE: PRT
<213> ORGANISM: Homo sapiens
<220> FEATURE:
<223> OTHER INFORMATION: Antibody 1

<400> SEQUENCE: 9

Asp Asn Asn Lys Arg Pro Ser
              5

<210> SEQ ID NO 10
<211> LENGTH: 12
<212> TYPE: PRT
<213> ORGANISM: Homo sapiens
<220> FEATURE:
<223> OTHER INFORMATION: Antibody 1

<400> SEQUENCE: 10

Gly Thr Trp Asp Thr Ser Leu Ser Ala Asn Tyr Val
              5                   10

<210> SEQ ID NO 11
<211> LENGTH: 348
<212> TYPE: DNA
<213> ORGANISM: Homo sapiens
<220> FEATURE:
<223> OTHER INFORMATION: Antibody 2

<400> SEQUENCE: 11

```
caggtccagc tggtgcagtc tggggctgag gtgaagaagc ctggggcctc agtgaaggtt      60
tcctgcaagg catctggata cgccttcacc agctactata tgcactgggc gcgacaggcc     120
cctggacaag gcttgagtg gatgggaata atcaaccctag tggtggtag cacaagctac      180
gcacagaagt tccagggcag agtcaccatg accaggaca cgtccacgag cacagtctac      240
atggagctga gcagcctgag atctgaggac acggccgtgt attactgtgc gagaggaaaa     300
tggtggctgt acaactgggg caaaggcacc ctggtcaccg tctcgagt                  348
```

<210> SEQ ID NO 12
<211> LENGTH: 116
<212> TYPE: PRT
<213> ORGANISM: Homo sapiens
<220> FEATURE:
<223> OTHER INFORMATION: Antibody 2

<400> SEQUENCE: 12

Gln Val Gln Leu Val Gln Ser Gly Ala Glu Val Lys Lys Pro Gly Ala
            5                   10                  15

Ser Val Lys Val Ser Cys Lys Ala Ser Gly Tyr Ala Phe Thr Ser Tyr
        20                  25                  30

Tyr Met His Trp Ala Arg Gln Ala Pro Gly Gln Gly Leu Glu Trp Met
    35                  40                  45

Gly Ile Ile Asn Pro Ser Gly Gly Ser Thr Ser Tyr Ala Gln Lys Phe
50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Lys Trp Trp Leu Tyr Asn Trp Gly Lys Gly Thr Leu Val
            100                 105                 110

Thr Val Ser Ser
        115

<210> SEQ ID NO 13
<211> LENGTH: 5
<212> TYPE: PRT
<213> ORGANISM: Homo sapiens
<220> FEATURE:
<223> OTHER INFORMATION: Antibody 2

<400> SEQUENCE: 13

Ser Tyr Tyr Met His
                5

<210> SEQ ID NO 14
<211> LENGTH: 17
<212> TYPE: PRT
<213> ORGANISM: Homo sapiens
<220> FEATURE:
<223> OTHER INFORMATION: Antibody 2

<400> SEQUENCE: 14

Ile Ile Asn Pro Ser Gly Gly Ser Thr Ser Tyr Ala Gln Lys Phe Gln
            5                   10                  15

Gly

<210> SEQ ID NO 15
<211> LENGTH: 7
<212> TYPE: PRT
<213> ORGANISM: Homo sapiens
<220> FEATURE:
<223> OTHER INFORMATION: Antibody 2

<400> SEQUENCE: 15

Gly Lys Trp Trp Leu Tyr Asn
                5

<210> SEQ ID NO 16
<211> LENGTH: 333
<212> TYPE: DNA
<213> ORGANISM: Homo sapiens
<220> FEATURE:
<223> OTHER INFORMATION: Antibody 2

<400> SEQUENCE: 16
cagtctgtgt tgacgcagcc gccctcagtg tctgcggccc caggacagaa ggtcaccatc      60
tcctgctctg gaggcagctc caacattggg aatagttatg tatcctggta ccagcaactc     120
ccaggaacag cccccaaact cctcatttac gacaataata gcgaccctca gggattcct      180 gaccgattct ctggctccaa gtctggcacg tcagccaccc tggccatcac cggactccag     240
actggggacg aggccgatta ttactgcgga acatgggata ccagccagcc cccgaacccc     300
ctcttcggaa ctgggaccaa gctgaccgtc cta                                  333

<210> SEQ ID NO 17
<211> LENGTH: 111
<212> TYPE: PRT
<213> ORGANISM: Homo sapiens
<220> FEATURE:
<223> OTHER INFORMATION: Antibody 2

<400> SEQUENCE: 17

Gln Ser Val Leu Thr Gln Pro Pro Ser Val Ser Ala Ala Pro Gly Gln
                5                  10                  15

Lys Val Thr Ile Ser Cys Ser Gly Gly Ser Ser Asn Ile Gly Asn Ser
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Ala Ile Thr Gly Leu Gln
65                  70                  75                  80

Thr Gly Asp Glu Ala Asp Tyr Tyr Cys Gly Thr Trp Asp Thr Ser Gln
                85                  90                  95

Pro Pro Asn Pro Leu Phe Gly Thr Gly Thr Lys Leu Thr Val Leu
            100                 105                 110

<210> SEQ ID NO 18
<211> LENGTH: 13
<212> TYPE: PRT
<213> ORGANISM: Homo sapiens
<220> FEATURE:
<223> OTHER INFORMATION: Antibody 2

<400> SEQUENCE: 18

Ser Gly Gly Ser Ser Asn Ile Gly Asn Ser Tyr Val Ser

<210> SEQ ID NO 19
<211> LENGTH: 7
<212> TYPE: PRT
<213> ORGANISM: Homo sapiens
<220> FEATURE:
<223> OTHER INFORMATION: Antibody 2

<400> SEQUENCE: 19

Asp Asn Asn Lys Arg Pro Ser
                5

<210> SEQ ID NO 20
<211> LENGTH: 12
<212> TYPE: PRT
<213> ORGANISM: Homo sapiens
<220> FEATURE:
<223> OTHER INFORMATION: Antibody 2

<400> SEQUENCE: 20

Gly Thr Trp Asp Thr Ser Gln Pro Pro Asn Pro Leu
                5                   10

<210> SEQ ID NO 21
<211> LENGTH: 348
<212> TYPE: DNA
<213> ORGANISM: Homo sapiens
<220> FEATURE:
<223> OTHER INFORMATION: Antibody 3

<400> SEQUENCE: 21
caggtccagc tggtgcagtc tggggctgag gtgaagaagc ctggggcctc agtgaaggtt      60
tcctgcaagg catctggata cgccttcacc agctactata tgcactgggc gcgacaggcc     120
cctggacaag gcttgagtg gatgggaata atcaaccctagtggtgg tag cacaagctac     180 gcacagaagt tccagggcag agtcaccatg accaggaca cgtccacgag cacagtctac     240
atggagctga gcagcctgag atctgaggac acggccgtgt attactgtgc gagaggaaag     300
ttgttgaaga acccctgggg caaaggcacc ctggtcaccg tctcgagt                  348

<210> SEQ ID NO 22
<211> LENGTH: 116
<212> TYPE: PRT
<213> ORGANISM: Homo sapiens
<220> FEATURE:
<223> OTHER INFORMATION: Antibody 3

<400> SEQUENCE: 22

Gln Val Gln Leu Val Gln Ser Gly Ala Glu Val Lys Lys Pro Gly Ala
                5                   10                  15

Ser Val Lys Val Ser Cys Lys Ala Ser Gly Tyr Ala Phe Thr Ser Tyr
            20                  25                  30

Tyr Met His Trp Ala Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Lys Leu Leu Lys Asn Pro Trp Gly Lys Gly Thr Leu Val
            100                 105                 110

Thr Val Ser Ser
        115

<210> SEQ ID NO 23
<211> LENGTH: 5
<212> TYPE: PRT
<213> ORGANISM: Homo sapiens
<220> FEATURE:
<223> OTHER INFORMATION: Antibody 3

<400> SEQUENCE: 23

Ser Tyr Tyr Met His
                5

<210> SEQ ID NO 24
<211> LENGTH: 17
<212> TYPE: PRT
<213> ORGANISM: Homo sapiens
<220> FEATURE:
<223> OTHER INFORMATION: Antibody 3

<400> SEQUENCE: 24

Ile Ile Asn Pro Ser Gly Gly Ser Thr Ser Tyr Ala Gln Lys Phe Gln
                5                  10                  15

Gly

<210> SEQ ID NO 25
<211> LENGTH: 7
<212> TYPE: PRT
<213> ORGANISM: Homo sapiens
<220> FEATURE:
<223> OTHER INFORMATION: Antibody 3

<400> SEQUENCE: 25

Gly Lys Leu Leu Lys Asn Pro
                5

<210> SEQ ID NO 26
<211> LENGTH: 333
<212> TYPE: DNA
<213> ORGANISM: Homo sapiens
<220> FEATURE:
<223> OTHER INFORMATION: Antibody 3

<400> SEQUENCE: 26
cagtctgtgt tgacgcagcc gccctcagtg tctgcggccc caggacagaa ggtcaccatc      60
tcctgctctg gaggcagctc caacattggg aatagttatg tatcctggta ccagcaactc     120
ccaggaacag cccccaaact cctcatttac gacaataata agcgaccctc agggattcct     180
gaccgattct ctggctccaa gtctggcacg tcagccaccc tggccatcac cggactccag     240
actggggacg aggccgatta ttactgcgga acatggttcg caccccccgc gagcaattat     300
gtcttcggaa ctgggaccaa gctgaccgtc cta                                  333

<210> SEQ ID NO 27
<211> LENGTH: 111
<212> TYPE: PRT
<213> ORGANISM: Homo sapiens
<220> FEATURE:
<223> OTHER INFORMATION: Antibody 3

<400> SEQUENCE: 27

Gln Ser Val Leu Thr Gln Pro Pro Ser Val Ser Ala Ala Pro Gly Gln
                5                  10                  15

```
Lys Val Thr Ile Ser Cys Ser Gly Gly Ser Ser Asn Ile Gly Asn Ser
                20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
 50                  55                  60

Gly Ser Lys Ser Gly Thr Ser Ala Thr Leu Ala Ile Thr Gly Leu Gln
 65                  70                  75                  80

Thr Gly Asp Glu Ala Asp Tyr Tyr Cys Gly Thr Trp Phe Gly Thr Pro
                 85                  90                  95

Ala Ser Asn Tyr Val Phe Gly Thr Gly Thr Lys Leu Thr Val Leu
            100                 105                 110

<210> SEQ ID NO 28
<211> LENGTH: 13
<212> TYPE: PRT
<213> ORGANISM: Homo sapiens
<220> FEATURE:
<223> OTHER INFORMATION: Antibody 3

<400> SEQUENCE: 28

Ser Gly Gly Ser Ser Asn Ile Gly Asn Ser Tyr Val Ser
                  5                  10

<210> SEQ ID NO 29
<211> LENGTH: 7
<212> TYPE: PRT
<213> ORGANISM: Homo sapiens
<220> FEATURE:
<223> OTHER INFORMATION: Antibody 3

<400> SEQUENCE: 29

Asp Asn Asn Lys Arg Pro Ser
                  5

<210> SEQ ID NO 30
<211> LENGTH: 12
<212> TYPE: PRT
<213> ORGANISM: Homo sapiens
<220> FEATURE:
<223> OTHER INFORMATION: Antibody 3

<400> SEQUENCE: 30

Gly Thr Trp Phe Gly Thr Pro Ala Ser Asn Tyr Val
                  5                  10

<210> SEQ ID NO 31
<211> LENGTH: 348
<212> TYPE: DNA
<213> ORGANISM: Homo sapiens
<220> FEATURE:
<223> OTHER INFORMATION: Antibody 4

<400> SEQUENCE: 31
caggtccagc tggtgcagtc tggggctgag gtgaagaagc ctggggcctc agtgaaggtt      60
tcctgcaagg catctggata cgccttcacc agctactata tgcactgggc gcgacaggcc    120
cctggacaag gcttgagtg gatgggaata atcaaccta gtggtggtag cacaagctac     180
gcacagaagt tccagggcag agtcaccatg accagggaca cgtccacgag cacagtctac    240
atggagctga gcagcctgag atctgaggac acggccgtgt attactgtgc gagaggaaaa    300
tggtggctgt acaactgggg caaaggcacc ctggtcaccg tctcgagt                 348
```

```
<210> SEQ ID NO 32
<211> LENGTH: 116
<212> TYPE: PRT
<213> ORGANISM: Homo sapiens
<220> FEATURE:
<223> OTHER INFORMATION: Antibody 4

<400> SEQUENCE: 32

Gln Val Gln Leu Val Gln Ser Gly Ala Glu Val Lys Lys Pro Gly Ala
                  5                  10                  15
Ser Val Lys Val Ser Cys Lys Ala Ser Gly Tyr Ala Phe Thr Ser Tyr
             20                  25                  30
Tyr Met His Trp Ala Arg Gln Ala Pro Gly Gln Gly Leu Glu Trp Met
         35                  40                  45
Gly Ile Ile Asn Pro Ser Gly Gly Ser Thr Ser Tyr Ala Gln Lys Phe
     50                  55                  60
Gln Gly Arg Val Thr Met Thr Arg Asp Thr Ser Thr Ser Thr Val Tyr
 65                  70                  75                  80
Met Glu Leu Ser Ser Leu Arg Ser Glu Asp Thr Ala Val Tyr Tyr Cys
                 85                  90                  95
Ala Arg Gly Lys Trp Trp Leu Tyr Asn Trp Gly Lys Gly Thr Leu Val
            100                 105                 110
Thr Val Ser Ser
        115

<210> SEQ ID NO 33
<211> LENGTH: 5
<212> TYPE: PRT
<213> ORGANISM: Homo sapiens
<220> FEATURE:
<223> OTHER INFORMATION: Antibody 4

<400> SEQUENCE: 33

Ser Tyr Tyr Met His
              5

<210> SEQ ID NO 34
<211> LENGTH: 17
<212> TYPE: PRT
<213> ORGANISM: Homo sapiens
<220> FEATURE:
<223> OTHER INFORMATION: Antibody 4

<400> SEQUENCE: 34

Ile Ile Asn Pro Ser Gly Gly Ser Thr Ser Tyr Ala Gln Lys Phe Gln
                  5                  10                  15
Gly

<210> SEQ ID NO 35
<211> LENGTH: 7
<212> TYPE: PRT
<213> ORGANISM: Homo sapiens
<220> FEATURE:
<223> OTHER INFORMATION: Antibody 4

<400> SEQUENCE: 35

Gly Lys Trp Trp Leu Tyr Asn
                  5

<210> SEQ ID NO 36
<211> LENGTH: 333
<212> TYPE: DNA
<213> ORGANISM: Homo sapiens
<220> FEATURE:
```

<223> OTHER INFORMATION: Antibody 4

<400> SEQUENCE: 36

```
cagtctgtgt tgacgcagcc gccctcagtg tctgcggccc caggacagaa ggtcaccatc    60
tcctgctctg gaggcagctc caacattggg aatagttatg tatcctggta ccagcaactc   120
ccaggaacag cccccaaact cctcatttac gacaataata gcgaccctca gggattcct    180
gaccgattct ctggctccaa gtctggcacg tcagccaccc tggccatcac cggactccag   240
actggggacg aggccgatta ttactgcgga acatgggata ccagcagccc cccccagccg   300
atcttcggaa ctgggaccaa gctgaccgtc cta                                333
```

<210> SEQ ID NO 37
<211> LENGTH: 111
<212> TYPE: PRT
<213> ORGANISM: Homo sapiens
<220> FEATURE:
<223> OTHER INFORMATION: Antibody 4

<400> SEQUENCE: 37

Gln Ser Val Leu Thr Gln Pro Pro Ser Val Ser Ala Ala Pro Gly Gln
            5                   10                  15
Lys Val Thr Ile Ser Cys Ser Gly Gly Ser Ser Asn Ile Gly Asn Ser
        20                  25                  30
Tyr Val Ser Trp Tyr Gln Gln Leu Pro Gly Thr Ala Pro Lys Leu Leu
    35                  40                  45
Ile Tyr Asp Asn Asn Lys Arg Pro Ser Gly Ile Pro Asp Arg Phe Ser
50                  55                  60
Gly Ser Lys Ser Gly Thr Ser Ala Thr Leu Ala Ile Thr Gly Leu Gln
65                  70                  75                  80
Thr Gly Asp Glu Ala Asp Tyr Tyr Cys Gly Thr Trp Asp Thr Ser Ser
                85                  90                  95
Pro Pro Gln Pro Ile Phe Gly Thr Gly Thr Lys Leu Thr Val Leu
            100                 105                 110

<210> SEQ ID NO 38
<211> LENGTH: 13
<212> TYPE: PRT
<213> ORGANISM: Homo sapiens
<220> FEATURE:
<223> OTHER INFORMATION: Antibody 4

<400> SEQUENCE: 38

Ser Gly Gly Ser Ser Asn Ile Gly Asn Ser Tyr Val Ser
            5                   10

<210> SEQ ID NO 39
<211> LENGTH: 7
<212> TYPE: PRT
<213> ORGANISM: Homo sapiens
<220> FEATURE:
<223> OTHER INFORMATION: Antibody 4

<400> SEQUENCE: 39

Asp Asn Asn Lys Arg Pro Ser
            5

<210> SEQ ID NO 40
<211> LENGTH: 12
<212> TYPE: PRT
<213> ORGANISM: Homo sapiens
<220> FEATURE:
<223> OTHER INFORMATION: Antibody 4

<400> SEQUENCE: 40

Gly Thr Trp Asp Thr Ser Ser Pro Pro Gln Pro Ile
                5                   10

<210> SEQ ID NO 41
<211> LENGTH: 348
<212> TYPE: DNA
<213> ORGANISM: Homo sapiens
<220> FEATURE:
<223> OTHER INFORMATION: Antibody 5

<400> SEQUENCE: 41
caggtccagc tggtgcagtc tggggctgag gtgaagaagc ctggggcctc agtgaaggtt     60
tcctgcaagg catctggata cgccttcacc agctactata tgcactgggc gcgacaggcc    120
cctggacaag ggcttgagtg gatgggaata atcaaccctag tggtggtag cacaagctac    180 gcacagaagt tccagggcag agtcaccatg accagggaca cgtccacgag cacagtctac    240
atggagctga gcagcctgag atctgaggac acggccgtgt attactgtgc gagaggaaaa    300
tggtggttgt acgactgggg caaaggcacc ctggtcaccg tctcgagt               348

<210> SEQ ID NO 42
<211> LENGTH: 116
<212> TYPE: PRT
<213> ORGANISM: Homo sapiens
<220> FEATURE:
<223> OTHER INFORMATION: Antibody 5

<400> SEQUENCE: 42

Gln Val Gln Leu Val Gln Ser Gly Ala Glu Val Lys Lys Pro Gly Ala
                5                   10                  15

Ser Val Lys Val Ser Cys Lys Ala Ser Gly Tyr Ala Phe Thr Ser Tyr
            20                  25                  30

Tyr Met His Trp Ala Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Lys Trp Trp Leu Tyr Asp Trp Gly Lys Gly Thr Leu Val
            100                 105                 110

Thr Val Ser Ser
        115

<210> SEQ ID NO 43
<211> LENGTH: 5
<212> TYPE: PRT
<213> ORGANISM: Homo sapiens
<220> FEATURE:
<223> OTHER INFORMATION: Antibody 5

<400> SEQUENCE: 43

Ser Tyr Tyr Met His
                5

<210> SEQ ID NO 44
<211> LENGTH: 17
<212> TYPE: PRT
<213> ORGANISM: Homo sapiens
<220> FEATURE:
<223> OTHER INFORMATION: Antibody 5

<400> SEQUENCE: 44

Ile Ile Asn Pro Ser Gly Gly Ser Thr Ser Tyr Ala Gln Lys Phe Gln
                5                   10                  15
Gly

<210> SEQ ID NO 45
<211> LENGTH: 7
<212> TYPE: PRT
<213> ORGANISM: Homo sapiens
<220> FEATURE:
<223> OTHER INFORMATION: Antibody 5

<400> SEQUENCE: 45

Gly Lys Trp Trp Leu Tyr Asp
                5

<210> SEQ ID NO 46
<211> LENGTH: 333
<212> TYPE: DNA
<213> ORGANISM: Homo sapiens
<220> FEATURE:
<223> OTHER INFORMATION: Antibody 5

<400> SEQUENCE: 46
cagtctgtgt tgacgcagcc gccctcagtg tctgcggccc caggacagaa ggtcaccatc      60
tcctgctctg gaggcagctc aacattggg aatagttatg tatcctggta ccagcaactc     120
ccaggaacag cccccaaact cctcatttac gacaataata gcgaccctc agggattcct     180 gaccgattct ctggctccaa gtctggcacg tcagccaccc tggccatcac cggactccag     240
actggggacg aggccgatta ttactgcgga acatgggata ccagcagccc ccccagccg     300 atcttcggaa ctgggaccaa gctgaccgtc cta                                 333

<210> SEQ ID NO 47
<211> LENGTH: 111
<212> TYPE: PRT
<213> ORGANISM: Homo sapiens
<220> FEATURE:
<223> OTHER INFORMATION: Antibody 5

<400> SEQUENCE: 47

Gln Ser Val Leu Thr Gln Pro Pro Ser Val Ser Ala Ala Pro Gly Gln
                5                   10                  15
Lys Val Thr Ile Ser Cys Ser Gly Gly Ser Ser Asn Ile Gly Asn Ser
            20                  25                  30
Tyr Val Ser Trp Tyr Gln Gln Leu Pro Gly Thr Ala Pro Lys Leu Leu
        35                  40                  45
Ile Tyr Asp Asn Asn Lys Arg Pro Ser Gly Ile Pro Asp Arg Phe Ser
    50                  55                  60
Gly Ser Lys Ser Gly Thr Ser Ala Thr Leu Ala Ile Thr Gly Leu Gln
65                  70                  75                  80
Thr Gly Asp Glu Ala Asp Tyr Tyr Cys Gly Thr Trp Asp Thr Ser Ser
                85                  90                  95
Pro Pro Gln Pro Ile Phe Gly Thr Gly Thr Lys Leu Thr Val Leu
                100                 105                 110

<210> SEQ ID NO 48
<211> LENGTH: 13
<212> TYPE: PRT

<213> ORGANISM: Homo sapiens
<220> FEATURE:
<223> OTHER INFORMATION: Antibody 5

<400> SEQUENCE: 48

Ser Gly Gly Ser Ser Asn Ile Gly Asn Ser Tyr Val Ser
            5                   10

<210> SEQ ID NO 49
<211> LENGTH: 7
<212> TYPE: PRT
<213> ORGANISM: Homo sapiens
<220> FEATURE:
<223> OTHER INFORMATION: Antibody 5

<400> SEQUENCE: 49

Asp Asn Asn Lys Arg Pro Ser
            5

<210> SEQ ID NO 50
<211> LENGTH: 12
<212> TYPE: PRT
<213> ORGANISM: Homo sapiens
<220> FEATURE:
<223> OTHER INFORMATION: Antibody 5

<400> SEQUENCE: 50

Gly Thr Trp Asp Thr Ser Ser Pro Pro Gln Pro Ile
            5                   10

<210> SEQ ID NO 51
<211> LENGTH: 348
<212> TYPE: DNA
<213> ORGANISM: Homo sapiens
<220> FEATURE:
<223> OTHER INFORMATION: Antibody 6

<400> SEQUENCE: 51
caggtccagc tggtgcagtc tggggctgag gtgaagaagc ctggggcctc agtgaaggtt      60
tcctgcaagg catctggata cgccttcacc agctactata tgcactgggc gcgacaggcc     120
cctggacaag ggcttgagtg gatgggaata atcaaccta gtggtggtag cacaagctac     180
gcacagaagt tccagggcag agtcaccatg accagggaca cgtccacgag cacagtctac     240
atggagctga gcagcctgag atctgaggac acggccgtgt attactgtgc gagaggaaag     300
tactggatgt acgactgggg caaaggcacc ctggtcaccg tctcgagt                  348

<210> SEQ ID NO 52
<211> LENGTH: 116
<212> TYPE: PRT
<213> ORGANISM: Homo sapiens
<220> FEATURE:
<223> OTHER INFORMATION: Antibody 6

<400> SEQUENCE: 52

Gln Val Gln Leu Val Gln Ser Gly Ala Glu Val Lys Lys Pro Gly Ala
            5                   10                  15

Ser Val Lys Val Ser Cys Lys Ala Ser Gly Tyr Ala Phe Thr Ser Tyr
        20                  25                  30

Tyr Met His Trp Ala Arg Gln Ala Pro Gly Gln Gly Leu Glu Trp Met
    35                  40                  45

Gly Ile Ile Asn Pro Ser Gly Gly Ser Thr Ser Tyr Ala Gln Lys Phe
50                  55                  60

Gln Gly Arg Val Thr Met Thr Arg Asp Thr Ser Thr Ser Thr Val Tyr

```
                65                  70                  75                  80
Met Glu Leu Ser Ser Leu Arg Ser Glu Asp Thr Ala Val Tyr Tyr Cys
                    85                  90                  95
Ala Arg Gly Lys Tyr Trp Met Tyr Asp Trp Gly Lys Gly Thr Leu Val
            100                 105                 110
Thr Val Ser Ser
        115

<210> SEQ ID NO 53
<211> LENGTH: 5
<212> TYPE: PRT
<213> ORGANISM: Homo sapiens
<220> FEATURE:
<223> OTHER INFORMATION: Antibody 6

<400> SEQUENCE: 53

Ser Tyr Tyr Met His
              5

<210> SEQ ID NO 54
<211> LENGTH: 17
<212> TYPE: PRT
<213> ORGANISM: Homo sapiens
<220> FEATURE:
<223> OTHER INFORMATION: Antibody 6

<400> SEQUENCE: 54

Ile Ile Asn Pro Ser Gly Gly Ser Thr Ser Tyr Ala Gln Lys Phe Gln
                  5                  10                  15
Gly

<210> SEQ ID NO 55
<211> LENGTH: 7
<212> TYPE: PRT
<213> ORGANISM: Homo sapiens
<220> FEATURE:
<223> OTHER INFORMATION: Antibody 6

<400> SEQUENCE: 55

Gly Lys Tyr Trp Met Tyr Asp
                  5

<210> SEQ ID NO 56
<211> LENGTH: 333
<212> TYPE: DNA
<213> ORGANISM: Homo sapiens
<220> FEATURE:
<223> OTHER INFORMATION: Antibody 6

<400> SEQUENCE: 56
cagtctgtgt tgacgcagcc gccctcagtg tctgcggccc caggacagaa ggtcaccatc      60
tcctgctctg gaggcagctc caacattggg aatagttatg tatcctgta ccagcaactc     120 ccaggaacag cccccaaact cctcatttac gacaataata agcgaccctc agggattcct     180
gaccgattct ctggctccaa gtctggcacg tcagccaccc tggccatcac cggactccag     240
actggggacg aggccgatta ttactgcgga acatgggata ccagcacgac ctaccacccc     300
atcttcggaa ctgggaccaa gctgaccgtc cta                                  333

<210> SEQ ID NO 57
<211> LENGTH: 111
<212> TYPE: PRT
<213> ORGANISM: Homo sapiens
<220> FEATURE:
```

<223> OTHER INFORMATION: Antibody 6

<400> SEQUENCE: 57

Gln Ser Val Leu Thr Gln Pro Pro Ser Val Ser Ala Ala Pro Gly Gln
                 5                  10                  15
Lys Val Thr Ile Ser Cys Ser Gly Gly Ser Ser Asn Ile Gly Asn Ser
             20                  25                  30
Tyr Val Ser Trp Tyr Gln Gln Leu Pro Gly Thr Ala Pro Lys Leu Leu
         35                  40                  45
Ile Tyr Asp Asn Asn Lys Arg Pro Ser Gly Ile Pro Asp Arg Phe Ser
     50                  55                  60
Gly Ser Lys Ser Gly Thr Ser Ala Thr Leu Ala Ile Thr Gly Leu Gln
 65                  70                  75                  80
Thr Gly Asp Glu Ala Asp Tyr Tyr Cys Gly Thr Trp Asp Thr Ser Thr
                 85                  90                  95
Thr Tyr His Pro Ile Phe Gly Thr Gly Thr Lys Leu Thr Val Leu
            100                 105                 110

<210> SEQ ID NO 58
<211> LENGTH: 13
<212> TYPE: PRT
<213> ORGANISM: Homo sapiens
<220> FEATURE:
<223> OTHER INFORMATION: Antibody 6

<400> SEQUENCE: 58

Ser Gly Gly Ser Ser Asn Ile Gly Asn Ser Tyr Val Ser
                 5                  10

<210> SEQ ID NO 59
<211> LENGTH: 7
<212> TYPE: PRT
<213> ORGANISM: Homo sapiens
<220> FEATURE:
<223> OTHER INFORMATION: Antibody 6

<400> SEQUENCE: 59

Asp Asn Asn Lys Arg Pro Ser
                 5

<210> SEQ ID NO 60
<211> LENGTH: 12
<212> TYPE: PRT
<213> ORGANISM: Homo sapiens
<220> FEATURE:
<223> OTHER INFORMATION: Antibody 6

<400> SEQUENCE: 60

Gly Thr Trp Asp Thr Ser Thr Thr Tyr His Pro Ile
                 5                  10

<210> SEQ ID NO 61
<211> LENGTH: 348
<212> TYPE: DNA
<213> ORGANISM: Homo sapiens
<220> FEATURE:
<223> OTHER INFORMATION: Antibody 7

<400> SEQUENCE: 61
caggtccagc tggtgcagtc tggggctgag gtgaagaagc ctggggcctc agtgaaggtt     60
tcctgcaagg catctggata cgccttcacc agctactata tgcactgggc gcgacaggcc    120
cctggacaag ggcttgagtg gatgggaata atcaaccctc tgtggtggtag cacaagctac    180

```
gcacagaagt tccagggcag agtcaccatg accagggaca cgtccacgag cacagtctac    240
atggagctga gcagcctgag atctgaggac acggccgtgt attactgtgc gagaggaaaa    300
tggtggtggc agtactgggg caaaggcacc ctggtcaccg tctcgagt                 348
```

<210> SEQ ID NO 62
<211> LENGTH: 116
<212> TYPE: PRT
<213> ORGANISM: Homo sapiens
<220> FEATURE:
<223> OTHER INFORMATION: Antibody 7

<400> SEQUENCE: 62

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Ser Tyr
            20                  25                  30

Tyr Met His Trp Ala Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Lys Trp Trp Trp Gln Tyr Trp Gly Lys Gly Thr Leu Val
            100                 105                 110

Thr Val Ser Ser
        115

<210> SEQ ID NO 63
<211> LENGTH: 5
<212> TYPE: PRT
<213> ORGANISM: Homo sapiens
<220> FEATURE:
<223> OTHER INFORMATION: Antibody 7

<400> SEQUENCE: 63

Ser Tyr Tyr Met His
1               5

<210> SEQ ID NO 64
<211> LENGTH: 17
<212> TYPE: PRT
<213> ORGANISM: Homo sapiens
<220> FEATURE:
<223> OTHER INFORMATION: Antibody 7

<400> SEQUENCE: 64

Ile Ile Asn Pro Ser Gly Gly Ser Thr Ser Tyr Ala Gln Lys Phe Gln
1               5                   10                  15

Gly

<210> SEQ ID NO 65
<211> LENGTH: 7
<212> TYPE: PRT
<213> ORGANISM: Homo sapiens
<220> FEATURE:
<223> OTHER INFORMATION: Antibody 7

<400> SEQUENCE: 65

Gly Lys Trp Trp Trp Gln Tyr
1               5

<210> SEQ ID NO 66
<211> LENGTH: 333
<212> TYPE: DNA
<213> ORGANISM: Homo sapiens
<220> FEATURE:
<223> OTHER INFORMATION: Antibody 7

<400> SEQUENCE: 66

```
cagtctgtgt tgacgcagcc gccctcagtg tctgcggccc caggacagaa ggtcaccatc    60
tcctgctctg gaggcagctc caacattggg aatagttatg tatcctggta ccagcaactc   120
ccaggaacag cccccaaact cctcatttac gacaataata gcgaccctc agggattcct    180 gaccgattct ctggctccaa gtctggcacg tcagccaccc tggccatcac cggactccag   240
actggggacg aggccgatta ttactgcgga acatgggata ccagcagccc cccccagccg   300
atcttcggaa ctgggaccaa gctgaccgtc cta                                333
```

<210> SEQ ID NO 67
<211> LENGTH: 111
<212> TYPE: PRT
<213> ORGANISM: Homo sapiens
<220> FEATURE:
<223> OTHER INFORMATION: Antibody 7

<400> SEQUENCE: 67

```
Gln Ser Val Leu Thr Gln Pro Pro Ser Val Ser Ala Ala Pro Gly Gln
                 5                  10                  15

Lys Val Thr Ile Ser Cys Ser Gly Gly Ser Ser Asn Ile Gly Asn Ser
             20                  25                  30

Tyr Val Ser Trp Tyr Gln Gln Leu Pro Gly Thr Ala Pro Lys Leu Leu
         35                  40                  45

Ile Tyr Asp Asn Asn Lys Arg Pro Ser Gly Ile Pro Asp Arg Phe Ser
     50                  55                  60

Gly Ser Lys Ser Gly Thr Ser Ala Thr Leu Ala Ile Thr Gly Leu Gln
 65                  70                  75                  80

Thr Gly Asp Glu Ala Asp Tyr Tyr Cys Gly Thr Trp Asp Thr Ser Ser
                 85                  90                  95

Pro Pro Gln Pro Ile Phe Gly Thr Gly Thr Lys Leu Thr Val Leu
            100                 105                 110
```

<210> SEQ ID NO 68
<211> LENGTH: 13
<212> TYPE: PRT
<213> ORGANISM: Homo sapiens
<220> FEATURE:
<223> OTHER INFORMATION: Antibody 7

<400> SEQUENCE: 68

```
Ser Gly Gly Ser Ser Asn Ile Gly Asn Ser Tyr Val Ser
                 5                  10
```

<210> SEQ ID NO 69
<211> LENGTH: 7
<212> TYPE: PRT
<213> ORGANISM: Homo sapiens
<220> FEATURE:
<223> OTHER INFORMATION: Antibody 7

<400> SEQUENCE: 69

```
Asp Asn Asn Lys Arg Pro Ser
                 5
```

-continued

<210> SEQ ID NO 70
<211> LENGTH: 12
<212> TYPE: PRT
<213> ORGANISM: Homo sapiens
<220> FEATURE:
<223> OTHER INFORMATION: Antibody 7

<400> SEQUENCE: 70

Gly Thr Trp Asp Thr Ser Ser Pro Pro Gln Pro Ile
                  5                  10

<210> SEQ ID NO 71
<211> LENGTH: 348
<212> TYPE: DNA
<213> ORGANISM: Homo sapiens
<220> FEATURE:
<223> OTHER INFORMATION: Antibody 8

<400> SEQUENCE: 71
caggtccagc tggtgcagtc tggggctgag gtgaagaagc ctggggcctc agtgaaggtt      60
tcctgcaagg catctggata cgccttcacc agctactata tgcactgggc gcgacaggcc     120
cctggacaag ggcttgagtg gatgggaata atcaaccctagtggtggtag cacaagctac      180 gcacagaagt tccagggcag agtcaccatg accagggaca cgtccacgag cacagtctac     240
atggagctga gcagcctgag atctgaggac acggccgtgt attactgtgc gagaggaaaa     300
tggtggtggc agtactgggg caaaggcacc ctggtcaccg tctcgagt                  348

<210> SEQ ID NO 72
<211> LENGTH: 116
<212> TYPE: PRT
<213> ORGANISM: Homo sapiens
<220> FEATURE:
<223> OTHER INFORMATION: Antibody 8

<400> SEQUENCE: 72

Gln Val Gln Leu Val Gln Ser Gly Ala Glu Val Lys Lys Pro Gly Ala
                  5                  10                  15

Ser Val Lys Val Ser Cys Lys Ala Ser Gly Tyr Ala Phe Thr Ser Tyr
              20                  25                  30

Tyr Met His Trp Ala Arg Gln Ala Pro Gly Gln Gly Leu Glu Trp Met
          35                  40                  45

Gly Ile Ile Asn Pro Ser Gly Gly Ser Thr Ser Tyr Ala Gln Lys Phe
      50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                  85                  90                  95

Ala Arg Gly Lys Trp Trp Trp Gln Tyr Trp Gly Lys Gly Thr Leu Val
                 100                 105                 110

Thr Val Ser Ser
        115

<210> SEQ ID NO 73
<211> LENGTH: 5
<212> TYPE: PRT
<213> ORGANISM: Homo sapiens
<220> FEATURE:
<223> OTHER INFORMATION: Antibody 8

<400> SEQUENCE: 73

Ser Tyr Tyr Met His

<210> SEQ ID NO 74
<211> LENGTH: 17
<212> TYPE: PRT
<213> ORGANISM: Homo sapiens
<220> FEATURE:
<223> OTHER INFORMATION: Antibody 8

<400> SEQUENCE: 74

Ile Ile Asn Pro Ser Gly Gly Ser Thr Ser Tyr Ala Gln Lys Phe Gln
                5                   10                  15
Gly

<210> SEQ ID NO 75
<211> LENGTH: 7
<212> TYPE: PRT
<213> ORGANISM: Homo sapiens
<220> FEATURE:
<223> OTHER INFORMATION: Antibody 8

<400> SEQUENCE: 75

Gly Lys Trp Trp Trp Gln Tyr
                5

<210> SEQ ID NO 76
<211> LENGTH: 333
<212> TYPE: DNA
<213> ORGANISM: Homo sapiens
<220> FEATURE:
<223> OTHER INFORMATION: Antibody 8

<400> SEQUENCE: 76
cagtctgtgt tgacgcagcc gccctcagtg tctgcggccc caggacagaa ggtcaccatc      60
tcctgctctg gaggcagctc caacattggg aatagttatg tatcctggta ccagcaactc     120
ccaggaacag cccccaaact cctcatttac gacaataata gcgaccctc agggattcct     180 gaccgattct ctggctccaa gtctggcacg tcagccaccc tggccatcac cggactccag     240
actggggacg aggccgatta ttactgcgga acatgggata ccagcacgac ctaccacccc     300
atcttcggaa ctgggaccaa gctgaccgtc cta                                  333

<210> SEQ ID NO 77
<211> LENGTH: 111
<212> TYPE: PRT
<213> ORGANISM: Homo sapiens
<220> FEATURE:
<223> OTHER INFORMATION: Antibody 8

<400> SEQUENCE: 77

Gln Ser Val Leu Thr Gln Pro Pro Ser Val Ser Ala Ala Pro Gly Gln
                5                   10                  15
Lys Val Thr Ile Ser Cys Ser Gly Gly Ser Ser Asn Ile Gly Asn Ser
            20                  25                  30
Tyr Val Ser Trp Tyr Gln Gln Leu Pro Gly Thr Ala Pro Lys Leu Leu
        35                  40                  45
Ile Tyr Asp Asn Asn Lys Arg Pro Ser Gly Ile Pro Asp Arg Phe Ser
    50                  55                  60
Gly Ser Lys Ser Gly Thr Ser Ala Thr Leu Ala Ile Thr Gly Leu Gln
65                  70                  75                  80
Thr Gly Asp Glu Ala Asp Tyr Tyr Cys Gly Thr Trp Asp Thr Ser Thr
                85                  90                  95

Thr Tyr His Pro Ile Phe Gly Thr Gly Thr Lys Leu Thr Val Leu
            100                 105                 110

<210> SEQ ID NO 78
<211> LENGTH: 13
<212> TYPE: PRT
<213> ORGANISM: Homo sapiens
<220> FEATURE:
<223> OTHER INFORMATION: Antibody 8

<400> SEQUENCE: 78

Ser Gly Gly Ser Ser Asn Ile Gly Asn Ser Tyr Val Ser
                 5                  10

<210> SEQ ID NO 79
<211> LENGTH: 7
<212> TYPE: PRT
<213> ORGANISM: Homo sapiens
<220> FEATURE:
<223> OTHER INFORMATION: Antibody 8

<400> SEQUENCE: 79

Asp Asn Asn Lys Arg Pro Ser
                 5

<210> SEQ ID NO 80
<211> LENGTH: 12
<212> TYPE: PRT
<213> ORGANISM: Homo sapiens
<220> FEATURE:
<223> OTHER INFORMATION: Antibody 8

<400> SEQUENCE: 80

Gly Thr Trp Asp Thr Ser Thr Thr Tyr His Pro Ile
                 5                  10

<210> SEQ ID NO 81
<211> LENGTH: 348
<212> TYPE: DNA
<213> ORGANISM: Homo sapiens
<220> FEATURE:
<223> OTHER INFORMATION: Antibody 9

<400> SEQUENCE: 81
caggtccagc tggtgcagtc tggggctgag gtgaagaagc ctggggcctc agtgaaggtt      60
tcctgcaagg catctggata cgccttcacc agctactata tgcactgggc gcgacaggcc     120
cctggacaag gcttgagtg gatgggaata atcaaccctag tggtggtag cacaagctac     180 gcacagaagt tccagggcag agtcaccatg accagggaca cgtccacgag cacagtctac     240
atggagctga gcagcctgag atctgaggac acggccgtgt attactgtgc gagaggaaaa     300
tggtggctgt acaactgggg caaaggcacc ctggtcaccg tctcgagt                  348

<210> SEQ ID NO 82
<211> LENGTH: 116
<212> TYPE: PRT
<213> ORGANISM: Homo sapiens
<220> FEATURE:
<223> OTHER INFORMATION: Antibody 9

<400> SEQUENCE: 82

Gln Val Gln Leu Val Gln Ser Gly Ala Glu Val Lys Lys Pro Gly Ala
                 5                  10                  15

Ser Val Lys Val Ser Cys Lys Ala Ser Gly Tyr Ala Phe Thr Ser Tyr
            20                  25                  30

```
Tyr Met His Trp Ala Arg Gln Ala Pro Gly Gln Gly Leu Glu Trp Met
        35                  40                  45
Gly Ile Ile Asn Pro Ser Gly Gly Ser Thr Ser Tyr Ala Gln Lys Phe
 50                  55                  60
Gln Gly Arg Val Thr Met Thr Arg Asp Thr Ser Thr Ser Thr Val Tyr
65                  70                  75                  80
Met Glu Leu Ser Ser Leu Arg Ser Glu Asp Thr Ala Val Tyr Tyr Cys
                85                  90                  95
Ala Arg Gly Lys Trp Trp Leu Tyr Asn Trp Gly Lys Gly Thr Leu Val
            100                 105                 110
Thr Val Ser Ser
        115
```

<210> SEQ ID NO 83
<211> LENGTH: 5
<212> TYPE: PRT
<213> ORGANISM: Homo sapiens
<220> FEATURE:
<223> OTHER INFORMATION: Antibody 9

<400> SEQUENCE: 83

```
Ser Tyr Tyr Met His
                5
```

<210> SEQ ID NO 84
<211> LENGTH: 17
<212> TYPE: PRT
<213> ORGANISM: Homo sapiens
<220> FEATURE:
<223> OTHER INFORMATION: Antibody 9

<400> SEQUENCE: 84

```
Ile Ile Asn Pro Ser Gly Gly Ser Thr Ser Tyr Ala Gln Lys Phe Gln
                 5                  10                  15
Gly
```

<210> SEQ ID NO 85
<211> LENGTH: 7
<212> TYPE: PRT
<213> ORGANISM: Homo sapiens
<220> FEATURE:
<223> OTHER INFORMATION: Antibody 9

<400> SEQUENCE: 85

```
Gly Lys Trp Trp Leu Tyr Asn
                5
```

<210> SEQ ID NO 86
<211> LENGTH: 333
<212> TYPE: DNA
<213> ORGANISM: Homo sapiens
<220> FEATURE:
<223> OTHER INFORMATION: Antibody 9

<400> SEQUENCE: 86

```
cagtctgtgt tgacgcagcc gccctcagtg tctgcggccc caggacagaa ggtcaccatc      60
tcctgctctg gaggcagctc aacattggg aatagttatg tatcctggta ccagcaactc     120
ccaggaacag ccccccaaact cctcatttac gacaataata agcgaccctc agggattcct    180
gaccgattct ctggctccaa gtctggcacg tcagccaccc tggccatcac cggactccag     240
actggggacg aggccgatta ttactgcgga acatgggata ccagcacgac gatgtacccg     300
ttgttcggaa ctgggaccaa gctgaccgtc cta                                   333
```

```
<210> SEQ ID NO 87
<211> LENGTH: 111
<212> TYPE: PRT
<213> ORGANISM: Homo sapiens
<220> FEATURE:
<223> OTHER INFORMATION: Antibody 9

<400> SEQUENCE: 87

Gln Ser Val Leu Thr Gln Pro Pro Ser Val Ser Ala Ala Pro Gly Gln
                 5                  10                  15
Lys Val Thr Ile Ser Cys Ser Gly Gly Ser Ser Asn Ile Gly Asn Ser
             20                  25                  30
Tyr Val Ser Trp Tyr Gln Gln Leu Pro Gly Thr Ala Pro Lys Leu Leu
         35                  40                  45
Ile Tyr Asp Asn Asn Lys Arg Pro Ser Gly Ile Pro Asp Arg Phe Ser
     50                  55                  60
Gly Ser Lys Ser Gly Thr Ser Ala Thr Leu Ala Ile Thr Gly Leu Gln
 65                  70                  75                  80
Thr Gly Asp Glu Ala Asp Tyr Tyr Cys Gly Thr Trp Asp Thr Ser Thr
                 85                  90                  95
Thr Met Tyr Pro Leu Phe Gly Thr Gly Thr Lys Leu Thr Val Leu
            100                 105                 110

<210> SEQ ID NO 88
<211> LENGTH: 13
<212> TYPE: PRT
<213> ORGANISM: Homo sapiens
<220> FEATURE:
<223> OTHER INFORMATION: Antibody 9

<400> SEQUENCE: 88

Ser Gly Gly Ser Ser Asn Ile Gly Asn Ser Tyr Val Ser
                 5                  10

<210> SEQ ID NO 89
<211> LENGTH: 7
<212> TYPE: PRT
<213> ORGANISM: Homo sapiens
<220> FEATURE:
<223> OTHER INFORMATION: Antibody 9

<400> SEQUENCE: 89

Asp Asn Asn Lys Arg Pro Ser
                 5

<210> SEQ ID NO 90
<211> LENGTH: 12
<212> TYPE: PRT
<213> ORGANISM: Homo sapiens
<220> FEATURE:
<223> OTHER INFORMATION: Antibody 9

<400> SEQUENCE: 90

Gly Thr Trp Asp Thr Ser Thr Thr Met Tyr Pro Leu
                 5                  10

<210> SEQ ID NO 91
<211> LENGTH: 348
<212> TYPE: DNA
<213> ORGANISM: Homo sapiens
<220> FEATURE:
<223> OTHER INFORMATION: Antibody 10

<400> SEQUENCE: 91
```

```
caggtccagc tggtgcagtc tggggctgag gtgaagaagc ctggggcctc agtgaaggtt      60
tcctgcaagg catctggata cgccttcacc agctactata tgcactgggc gcgacaggcc     120
cctggacaag gcttgagtg gatgggaata atcaaccta gtggtggtag cacaagctac       180
gcacagaagt tccagggcag agtcaccatg accagggaca cgtccacgag cacagtctac     240
atggagctga gcagcctgag atctgaggac acggccgtgt attactgtgc gagaggaaaa     300
tggtggctct acgactgggg caaaggcacc ctggtcaccg tctcgagt                  348
```

<210> SEQ ID NO 92
<211> LENGTH: 116
<212> TYPE: PRT
<213> ORGANISM: Homo sapiens
<220> FEATURE:
<223> OTHER INFORMATION: Antibody 10

<400> SEQUENCE: 92

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Ser Tyr
            20                  25                  30

Tyr Met His Trp Ala Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Lys Trp Trp Leu Tyr Asp Trp Gly Lys Gly Thr Leu Val
            100                 105                 110

Thr Val Ser Ser
        115

<210> SEQ ID NO 93
<211> LENGTH: 5
<212> TYPE: PRT
<213> ORGANISM: Homo sapiens
<220> FEATURE:
<223> OTHER INFORMATION: Antibody 10

<400> SEQUENCE: 93

Ser Tyr Tyr Met His
1               5

<210> SEQ ID NO 94
<211> LENGTH: 17
<212> TYPE: PRT
<213> ORGANISM: Homo sapiens
<220> FEATURE:
<223> OTHER INFORMATION: Antibody 10

<400> SEQUENCE: 94

Ile Ile Asn Pro Ser Gly Gly Ser Thr Ser Tyr Ala Gln Lys Phe Gln
1               5                   10                  15

Gly

<210> SEQ ID NO 95
<211> LENGTH: 7
<212> TYPE: PRT
<213> ORGANISM: Homo sapiens

```
<220> FEATURE:
<223> OTHER INFORMATION: Antibody 10

<400> SEQUENCE: 95

Gly Lys Trp Trp Leu Tyr Asp
                5

<210> SEQ ID NO 96
<211> LENGTH: 333
<212> TYPE: DNA
<213> ORGANISM: Homo sapiens
<220> FEATURE:
<223> OTHER INFORMATION: Antibody 10

<400> SEQUENCE: 96
cagtctgtgt tgacgcagcc gccctcagtg tctgcggccc caggacagaa ggtcaccatc      60
tcctgctctg gaggcagctc caacattggg aatagttatg tatcctggta ccagcaactc     120
ccaggaacag cccccaaact cctcatttac gacaataata agcgaccctc agggattcct     180
gaccgattct ctggctccaa gtctggcacg tcagccaccc tggccatcac cggactccag     240
actggggacg aggccgatta ttactgcgga acatgggata ccagcaccgt cctcaccccc     300
atcttcggaa ctgggaccaa gctgaccgtc cta                                  333

<210> SEQ ID NO 97
<211> LENGTH: 111
<212> TYPE: PRT
<213> ORGANISM: Homo sapiens
<220> FEATURE:
<223> OTHER INFORMATION: Antibody 10

<400> SEQUENCE: 97

Gln Ser Val Leu Thr Gln Pro Pro Ser Val Ser Ala Ala Pro Gly Gln
                5                  10                  15

Lys Val Thr Ile Ser Cys Ser Gly Gly Ser Ser Asn Ile Gly Asn Ser
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Ala Ile Thr Gly Leu Gln
65                  70                  75                  80

Thr Gly Asp Glu Ala Asp Tyr Tyr Cys Gly Thr Trp Asp Thr Ser Thr
                85                  90                  95

Val Leu Thr Pro Ile Phe Gly Thr Gly Thr Lys Leu Thr Val Leu
            100                 105                 110

<210> SEQ ID NO 98
<211> LENGTH: 13
<212> TYPE: PRT
<213> ORGANISM: Homo sapiens
<220> FEATURE:
<223> OTHER INFORMATION: Antibody 10

<400> SEQUENCE: 98

Ser Gly Gly Ser Ser Asn Ile Gly Asn Ser Tyr Val Ser
                5                  10

<210> SEQ ID NO 99
<211> LENGTH: 7
<212> TYPE: PRT
<213> ORGANISM: Homo sapiens
<220> FEATURE:
```

```
<223> OTHER INFORMATION: Antibody 10

<400> SEQUENCE: 99

Asp Asn Asn Lys Arg Pro Ser
                5

<210> SEQ ID NO 100
<211> LENGTH: 12
<212> TYPE: PRT
<213> ORGANISM: Homo sapiens
<220> FEATURE:
<223> OTHER INFORMATION: Antibody 10

<400> SEQUENCE: 100

Gly Thr Trp Asp Thr Ser Thr Val Leu Thr Pro Ile
                5                   10

<210> SEQ ID NO 101
<211> LENGTH: 348
<212> TYPE: DNA
<213> ORGANISM: Homo sapiens
<220> FEATURE:
<223> OTHER INFORMATION: Antibody 11

<400> SEQUENCE: 101
caggtccagc tggtgcagtc tggggctgag gtgaagaagc ctggggcctc agtgaaggtt      60
tcctgcaagg catctggata cgccttcacc agctactata tgcactgggc gcgacaggcc     120
cctggacaag gcttgagtg gatgggaata atcaaccta gtggtggtag cacaagctac      180
gcacagaagt tccagggcag agtcaccatg accagggaca cgtccacgag cacagtctac     240
atggagctga gcagcctgag atctgaggac acggccgtgt attactgtgc gagaggaaaa     300
tggtggttct acgactgggg caaaggcacc ctggtcaccg tctcgagt                 348

<210> SEQ ID NO 102
<211> LENGTH: 116
<212> TYPE: PRT
<213> ORGANISM: Homo sapiens
<220> FEATURE:
<223> OTHER INFORMATION: Antibody 11

<400> SEQUENCE: 102

Gln Val Gln Leu Val Gln Ser Gly Ala Glu Val Lys Lys Pro Gly Ala
                5                   10                  15

Ser Val Lys Val Ser Cys Lys Ala Ser Gly Tyr Ala Phe Thr Ser Tyr
            20                  25                  30

Tyr Met His Trp Ala Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Lys Trp Trp Phe Tyr Asp Trp Gly Lys Gly Thr Leu Val
            100                 105                 110

Thr Val Ser Ser
        115

<210> SEQ ID NO 103
<211> LENGTH: 5
<212> TYPE: PRT
```

```
<213> ORGANISM: Homo sapiens
<220> FEATURE:
<223> OTHER INFORMATION: Antibody 11

<400> SEQUENCE: 103

Ser Tyr Tyr Met His
              5

<210> SEQ ID NO 104
<211> LENGTH: 17
<212> TYPE: PRT
<213> ORGANISM: Homo sapiens
<220> FEATURE:
<223> OTHER INFORMATION: Antibody 11

<400> SEQUENCE: 104

Ile Ile Asn Pro Ser Gly Gly Ser Thr Ser Tyr Ala Gln Lys Phe Gln
                 5                  10                  15

Gly

<210> SEQ ID NO 105
<211> LENGTH: 7
<212> TYPE: PRT
<213> ORGANISM: Homo sapiens
<220> FEATURE:
<223> OTHER INFORMATION: Antibody 11

<400> SEQUENCE: 105

Gly Lys Trp Trp Phe Tyr Asp
                 5

<210> SEQ ID NO 106
<211> LENGTH: 333
<212> TYPE: DNA
<213> ORGANISM: Homo sapiens
<220> FEATURE:
<223> OTHER INFORMATION: Antibody 11

<400> SEQUENCE: 106
cagtctgtgt tgacgcagcc gccctcagtg tctgcggccc caggacagaa ggtcaccatc      60
tcctgctctg gaggcagctc caacattggg aatagttatg tatcctggta ccagcaactc     120
ccaggaacag cccccaaact cctcatttac gacaataata agcgaccctc agggattcct     180
gaccgattct ctggctccaa gtctggcacg tcagccaccc tggccatcac cggactccag     240
actggggacg aggccgatta ttactgcgga acatgggata ccagcccag catgatcccg      300 ctcttcggaa ctgggaccaa gctgaccgtc cta                                  333

<210> SEQ ID NO 107
<211> LENGTH: 111
<212> TYPE: PRT
<213> ORGANISM: Homo sapiens
<220> FEATURE:
<223> OTHER INFORMATION: Antibody 11

<400> SEQUENCE: 107

Gln Ser Val Leu Thr Gln Pro Pro Ser Val Ala Ala Pro Gly Gln
                 5                  10                  15

Lys Val Thr Ile Ser Cys Ser Gly Gly Ser Ser Asn Ile Gly Asn Ser
                20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Arg Phe Ser
        50                  55                  60
```

```
Gly Ser Lys Ser Gly Thr Ser Ala Thr Leu Ala Ile Thr Gly Leu Gln
 65                  70                  75                  80

Thr Gly Asp Glu Ala Asp Tyr Tyr Cys Gly Thr Trp Asp Thr Ser Pro
                 85                  90                  95

Ser Met Ile Pro Leu Phe Gly Thr Gly Thr Lys Leu Thr Val Leu
            100                 105                 110

<210> SEQ ID NO 108
<211> LENGTH: 13
<212> TYPE: PRT
<213> ORGANISM: Homo sapiens
<220> FEATURE:
<223> OTHER INFORMATION: Antibody 11

<400> SEQUENCE: 108

Ser Gly Gly Ser Ser Asn Ile Gly Asn Ser Tyr Val Ser
                 5                  10

<210> SEQ ID NO 109
<211> LENGTH: 7
<212> TYPE: PRT
<213> ORGANISM: Homo sapiens
<220> FEATURE:
<223> OTHER INFORMATION: Antibody 11

<400> SEQUENCE: 109

Asp Asn Asn Lys Arg Pro Ser
                 5

<210> SEQ ID NO 110
<211> LENGTH: 12
<212> TYPE: PRT
<213> ORGANISM: Homo sapiens
<220> FEATURE:
<223> OTHER INFORMATION: Antibody 11

<400> SEQUENCE: 110

Gly Thr Trp Asp Thr Ser Pro Ser Met Ile Pro Leu
                 5                  10

<210> SEQ ID NO 111
<211> LENGTH: 348
<212> TYPE: DNA
<213> ORGANISM: Homo sapiens
<220> FEATURE:
<223> OTHER INFORMATION: Antibody 12

<400> SEQUENCE: 111
caggtccagc tggtgcagtc tggggctgag gtgaagaagc ctggggcctc agtgaaggtt      60
tcctgcaagg catctggata cgccttcacc agctactata tgcactgggc gcgacaggcc     120
cctggacaag ggcttgagtg gatgggaata atcaacccta gtggtggtag cacaagctac     180
gcacagaagt tccagggcag agtcaccatg accaggaca cgtccacgag cacagtctac      240
atggagctga gcagcctgag atctgaggac acggccgtgt attactgtgc gagaggaaaa     300
tggtggttct acgactgggg caaaggcacc ctggtcaccg tctcgagt                  348

<210> SEQ ID NO 112
<211> LENGTH: 116
<212> TYPE: PRT
<213> ORGANISM: Homo sapiens
<220> FEATURE:
<223> OTHER INFORMATION: Antibody 12

<400> SEQUENCE: 112
```

Gln Val Gln Leu Val Gln Ser Gly Ala Glu Val Lys Lys Pro Gly Ala
                5                   10                  15

Ser Val Lys Val Ser Cys Lys Ala Ser Gly Tyr Ala Phe Thr Ser Tyr
            20                  25                  30

Tyr Met His Trp Ala Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Lys Trp Trp Phe Tyr Asp Trp Gly Lys Gly Thr Leu Val
            100                 105                 110

Thr Val Ser Ser
        115

<210> SEQ ID NO 113
<211> LENGTH: 5
<212> TYPE: PRT
<213> ORGANISM: Homo sapiens
<220> FEATURE:
<223> OTHER INFORMATION: Antibody 12

<400> SEQUENCE: 113

Ser Tyr Tyr Met His
                5

<210> SEQ ID NO 114
<211> LENGTH: 17
<212> TYPE: PRT
<213> ORGANISM: Homo sapiens
<220> FEATURE:
<223> OTHER INFORMATION: Antibody 12

<400> SEQUENCE: 114

Ile Ile Asn Pro Ser Gly Gly Ser Thr Ser Tyr Ala Gln Lys Phe Gln
                5                   10                  15

Gly

<210> SEQ ID NO 115
<211> LENGTH: 7
<212> TYPE: PRT
<213> ORGANISM: Homo sapiens
<220> FEATURE:
<223> OTHER INFORMATION: Antibody 12

<400> SEQUENCE: 115

Gly Lys Trp Trp Phe Tyr Asp
                5

<210> SEQ ID NO 116
<211> LENGTH: 333
<212> TYPE: DNA
<213> ORGANISM: Homo sapiens
<220> FEATURE:
<223> OTHER INFORMATION: Antibody 12

<400> SEQUENCE: 116
cagtctgtgt tgacgcagcc gccctcagtg tctgcggccc caggacagaa ggtcaccatc     60
tcctgctctg gaggcagctc caacattggg aatagttatg tatcctggta ccagcaactc    120

```
ccaggaacag ccccaaaact cctcatttac gacaataata agcgaccctc agggattcct    180
gaccgattct ctggctccaa gtctggcacg tcagccaccc tggccatcac cggactccag    240
actggggacg aggccgatta ttactgcgga acatgggata ccagcacgac gatgtacccg    300
ttgttcggaa ctgggaccaa gctgaccgtc cta                                  333
```

<210> SEQ ID NO 117
<211> LENGTH: 111
<212> TYPE: PRT
<213> ORGANISM: Homo sapiens
<220> FEATURE:
<223> OTHER INFORMATION: Antibody 12

<400> SEQUENCE: 117

Gln Ser Val Leu Thr Gln Pro Pro Ser Val Ser Ala Ala Pro Gly Gln
1               5                   10                  15

Lys Val Thr Ile Ser Cys Ser Gly Gly Ser Ser Asn Ile Gly Asn Ser
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Ala Ile Thr Gly Leu Gln
65                  70                  75                  80

Thr Gly Asp Glu Ala Asp Tyr Tyr Cys Gly Thr Trp Asp Thr Ser Thr
                85                  90                  95

Thr Met Tyr Pro Leu Phe Gly Thr Gly Thr Lys Leu Thr Val Leu
            100                 105                 110

<210> SEQ ID NO 118
<211> LENGTH: 13
<212> TYPE: PRT
<213> ORGANISM: Homo sapiens
<220> FEATURE:
<223> OTHER INFORMATION: Antibody 12

<400> SEQUENCE: 118

Ser Gly Gly Ser Ser Asn Ile Gly Asn Ser Tyr Val Ser
1               5                   10

<210> SEQ ID NO 119
<211> LENGTH: 7
<212> TYPE: PRT
<213> ORGANISM: Homo sapiens
<220> FEATURE:
<223> OTHER INFORMATION: Antibody 12

<400> SEQUENCE: 119

Asp Asn Asn Lys Arg Pro Ser
1               5

<210> SEQ ID NO 120
<211> LENGTH: 12
<212> TYPE: PRT
<213> ORGANISM: Homo sapiens
<220> FEATURE:
<223> OTHER INFORMATION: Antibody 12

<400> SEQUENCE: 120

Gly Thr Trp Asp Thr Ser Thr Thr Met Tyr Pro Leu
1               5                   10

<210> SEQ ID NO 121

```
<211> LENGTH: 348
<212> TYPE: DNA
<213> ORGANISM: Homo sapiens
<220> FEATURE:
<223> OTHER INFORMATION: Antibody 13

<400> SEQUENCE: 121
caggtccagc tggtgcagtc tggggctgag gtgaagaagc ctggggcctc agtgaaggtt      60
tcctgcaagg catctggata cgccttcacc agctactata tgcactgggc gcgacaggcc     120
cctggacaag gcttgagtg gatgggaata atcaaccta gtggtggtag cacaagctac       180
gcacagaagt tccagggcag agtcaccatg accaggaca cgtccacgag cacagtctac      240
atggagctga gcagcctgag atctgaggac acggccgtgt attactgtgc gagaggaaag     300
tggtggctct acgactgggg caaaggcacc ctggtcaccg tctcgagt                  348

<210> SEQ ID NO 122
<211> LENGTH: 116
<212> TYPE: PRT
<213> ORGANISM: Homo sapiens
<220> FEATURE:
<223> OTHER INFORMATION: Antibody 13

<400> SEQUENCE: 122

Gln Val Gln Leu Val Gln Ser Gly Ala Glu Val Lys Lys Pro Gly Ala
                 5                  10                  15

Ser Val Lys Val Ser Cys Lys Ala Ser Gly Tyr Ala Phe Thr Ser Tyr
             20                  25                  30

Tyr Met His Trp Ala Arg Gln Ala Pro Gly Gln Gly Leu Glu Trp Met
         35                  40                  45

Gly Ile Ile Asn Pro Ser Gly Gly Ser Thr Ser Tyr Ala Gln Lys Phe
     50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Gly Lys Trp Trp Leu Tyr Asp Trp Gly Lys Gly Thr Leu Val
            100                 105                 110

Thr Val Ser Ser
        115

<210> SEQ ID NO 123
<211> LENGTH: 5
<212> TYPE: PRT
<213> ORGANISM: Homo sapiens
<220> FEATURE:
<223> OTHER INFORMATION: Antibody 13

<400> SEQUENCE: 123

Ser Tyr Tyr Met His
                 5

<210> SEQ ID NO 124
<211> LENGTH: 17
<212> TYPE: PRT
<213> ORGANISM: Homo sapiens
<220> FEATURE:
<223> OTHER INFORMATION: Antibody 13

<400> SEQUENCE: 124

Ile Ile Asn Pro Ser Gly Gly Ser Thr Ser Tyr Ala Gln Lys Phe Gln
                 5                  10                  15
```

Gly

<210> SEQ ID NO 125
<211> LENGTH: 7
<212> TYPE: PRT
<213> ORGANISM: Homo sapiens
<220> FEATURE:
<223> OTHER INFORMATION: Antibody 13

<400> SEQUENCE: 125

Gly Lys Trp Trp Leu Tyr Asp
            5

<210> SEQ ID NO 126
<211> LENGTH: 333
<212> TYPE: DNA
<213> ORGANISM: Homo sapiens
<220> FEATURE:
<223> OTHER INFORMATION: Antibody 13

<400> SEQUENCE: 126
cagtctgtgt tgacgcagcc gccctcagtg tctgcggccc caggacagaa ggtcaccatc      60
tcctgctctg gaggcagctc caacattggg aatagttatg tatcctggta ccagcaactc     120
ccaggaacag cccccaaact cctcatttac gacaataata gcgaccctc aggattcct      180 gaccgattct ctggctccaa gtctggcacg tcagccaccc tggccatcac cggactccag     240
actggggacg aggccgatta ttactgcgga acatgggata ccagcacgac cttgcagccg     300
ctgttcggaa ctgggaccaa gctgaccgtc cta                                  333

<210> SEQ ID NO 127
<211> LENGTH: 111
<212> TYPE: PRT
<213> ORGANISM: Homo sapiens
<220> FEATURE:
<223> OTHER INFORMATION: Antibody 13

<400> SEQUENCE: 127

Gln Ser Val Leu Thr Gln Pro Pro Ser Val Ser Ala Ala Pro Gly Gln
             5                  10                  15

Lys Val Thr Ile Ser Cys Ser Gly Gly Ser Ser Asn Ile Gly Asn Ser
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Ala Ile Thr Gly Leu Gln
65                  70                  75                  80

Thr Gly Asp Glu Ala Asp Tyr Tyr Cys Gly Thr Trp Asp Thr Ser Thr
                85                  90                  95

Thr Leu Gln Pro Leu Phe Gly Thr Gly Thr Lys Leu Thr Val Leu
            100                 105                 110

<210> SEQ ID NO 128
<211> LENGTH: 13
<212> TYPE: PRT
<213> ORGANISM: Homo sapiens
<220> FEATURE:
<223> OTHER INFORMATION: Antibody 13

<400> SEQUENCE: 128

Ser Gly Gly Ser Ser Asn Ile Gly Asn Ser Tyr Val Ser
             5                  10

<210> SEQ ID NO 129
<211> LENGTH: 7
<212> TYPE: PRT
<213> ORGANISM: Homo sapiens
<220> FEATURE:
<223> OTHER INFORMATION: Antibody 13

<400> SEQUENCE: 129

Asp Asn Asn Lys Arg Pro Ser
              5

<210> SEQ ID NO 130
<211> LENGTH: 12
<212> TYPE: PRT
<213> ORGANISM: Homo sapiens
<220> FEATURE:
<223> OTHER INFORMATION: Antibody 13

<400> SEQUENCE: 130

Gly Thr Trp Asp Thr Ser Thr Thr Leu Gln Pro Leu
              5                   10

<210> SEQ ID NO 131
<211> LENGTH: 348
<212> TYPE: DNA
<213> ORGANISM: Homo sapiens
<220> FEATURE:
<223> OTHER INFORMATION: Antibody 14

<400> SEQUENCE: 131
caggtccagc tggtgcagtc tggggctgag gtgaagaagc ctggggcctc agtgaaggtt      60
tcctgcaagg catctggata cgccttcacc agctactata tgcactgggc gcgacaggcc     120
cctggacaag ggcttgagtg gatgggaata atcaaccctag tggtggtag cacaagctac     180 gcacagaagt tccagggcag agtcaccatg accaggaca cgtccacgag cacagtctac     240
atggagctga gcagcctgag atctgaggac acggccgtgt attactgtgc gagaggaaaa     300
tggtggctgt acaactgggg caaaggcacc ctggtcaccg tctcgagt                  348

<210> SEQ ID NO 132
<211> LENGTH: 116
<212> TYPE: PRT
<213> ORGANISM: Homo sapiens
<220> FEATURE:
<223> OTHER INFORMATION: Antibody 14

<400> SEQUENCE: 132

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Ala Phe Thr Ser Tyr
             20                  25                  30

Tyr Met His Trp Ala Arg Gln Ala Pro Gly Gln Gly Leu Glu Trp Met
         35                  40                  45

Gly Ile Ile Asn Pro Ser Gly Gly Ser Thr Ser Tyr Ala Gln Lys Phe
     50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Gly Lys Trp Trp Leu Tyr Asn Trp Gly Lys Gly Thr Leu Val
            100                 105                 110

Thr Val Ser Ser
    115

<210> SEQ ID NO 133
<211> LENGTH: 5
<212> TYPE: PRT
<213> ORGANISM: Homo sapiens
<220> FEATURE:
<223> OTHER INFORMATION: Antibody 14

<400> SEQUENCE: 133

Ser Tyr Tyr Met His
              5

<210> SEQ ID NO 134
<211> LENGTH: 17
<212> TYPE: PRT
<213> ORGANISM: Homo sapiens
<220> FEATURE:
<223> OTHER INFORMATION: Antibody 14

<400> SEQUENCE: 134

Ile Ile Asn Pro Ser Gly Gly Ser Thr Ser Tyr Ala Gln Lys Phe Gln
                5                   10                  15

Gly

<210> SEQ ID NO 135
<211> LENGTH: 7
<212> TYPE: PRT
<213> ORGANISM: Homo sapiens
<220> FEATURE:
<223> OTHER INFORMATION: Antibody 14

<400> SEQUENCE: 135

Gly Lys Trp Trp Leu Tyr Asn
              5

<210> SEQ ID NO 136
<211> LENGTH: 333
<212> TYPE: DNA
<213> ORGANISM: Homo sapiens
<220> FEATURE:
<223> OTHER INFORMATION: Antibody 14

<400> SEQUENCE: 136
cagtctgtgt tgacgcagcc gccctcagtg tctgcggccc caggacagaa ggtcaccatc      60
tcctgctctg gaggcagctc aacattgggg aatagttatg tatcctggta ccagcaactc     120
ccaggaacag ccccaaaact cctcatttac gacaataata gcgaccctc aggattcct      180 gaccgattct ctggctccaa gtctggcacg tcagccaccc tggccatcac cggactccag     240
actggggacg aggccgatta ttactgcgga acatgggata ccagccccc gaccaagccc      300 ttgttcggaa ctgggaccaa gctgaccgtc cta                                   333

<210> SEQ ID NO 137
<211> LENGTH: 111
<212> TYPE: PRT
<213> ORGANISM: Homo sapiens
<220> FEATURE:
<223> OTHER INFORMATION: Antibody 14

<400> SEQUENCE: 137

Gln Ser Val Leu Thr Gln Pro Pro Ser Val Ser Ala Ala Pro Gly Gln
                5                   10                  15

Lys Val Thr Ile Ser Cys Ser Gly Gly Ser Ser Asn Ile Gly Asn Ser

```
                 20                  25                  30
Tyr Val Ser Trp Tyr Gln Gln Leu Pro Gly Thr Ala Pro Lys Leu Leu
             35                  40                  45
Ile Tyr Asp Asn Asn Lys Arg Pro Ser Gly Ile Pro Asp Arg Phe Ser
         50                  55                  60
Gly Ser Lys Ser Gly Thr Ser Ala Thr Leu Ala Ile Thr Gly Leu Gln
65                  70                  75                  80
Thr Gly Asp Glu Ala Asp Tyr Tyr Cys Gly Thr Trp Asp Thr Ser Pro
                 85                  90                  95
Pro Thr Lys Pro Leu Phe Gly Thr Gly Thr Lys Leu Thr Val Leu
             100                 105                 110

<210> SEQ ID NO 138
<211> LENGTH: 13
<212> TYPE: PRT
<213> ORGANISM: Homo sapiens
<220> FEATURE:
<223> OTHER INFORMATION: Antibody 14

<400> SEQUENCE: 138

Ser Gly Gly Ser Ser Asn Ile Gly Asn Ser Tyr Val Ser
              5                  10

<210> SEQ ID NO 139
<211> LENGTH: 7
<212> TYPE: PRT
<213> ORGANISM: Homo sapiens
<220> FEATURE:
<223> OTHER INFORMATION: Antibody 14

<400> SEQUENCE: 139

Asp Asn Asn Lys Arg Pro Ser
              5

<210> SEQ ID NO 140
<211> LENGTH: 12
<212> TYPE: PRT
<213> ORGANISM: Homo sapiens
<220> FEATURE:
<223> OTHER INFORMATION: Antibody 14

<400> SEQUENCE: 140

Gly Thr Trp Asp Thr Ser Pro Pro Thr Lys Pro Leu
              5                  10

<210> SEQ ID NO 141
<211> LENGTH: 348
<212> TYPE: DNA
<213> ORGANISM: Homo sapiens
<220> FEATURE:
<223> OTHER INFORMATION: Antibody 15

<400> SEQUENCE: 141
caggtccagc tggtgcagtc tggggctgag gtgaagaagc ctggggcctc agtgaaggtt        60
tcctgcaagg catctggata cgccttcacc agctactata tgcactgggc gcgacaggcc       120
cctggacaag ggcttgagtg gatgggaata atcaaccctaa gtggtggtag cacaagctac      180
gcacagaagt tccagggcag agtcaccatg accagggaca cgtccacgag cacagtctac      240
atggagctga gcagcctgag atctgaggac acggccgtgt attactgtgc gagaggaaaa      300
tggtggctgt acaactgggg caaaggcacc ctggtcaccg tctcgagt                   348

<210> SEQ ID NO 142
```

```
<211> LENGTH: 116
<212> TYPE: PRT
<213> ORGANISM: Homo sapiens
<220> FEATURE:
<223> OTHER INFORMATION: Antibody 15

<400> SEQUENCE: 142

Gln Val Gln Leu Val Gln Ser Gly Ala Glu Val Lys Pro Gly Ala
 1               5                  10                  15
Ser Val Lys Val Ser Cys Lys Ala Ser Gly Tyr Ala Phe Thr Ser Tyr
            20                  25                  30
Tyr Met His Trp Ala Arg Gln Ala Pro Gly Gln Gly Leu Glu Trp Met
        35                  40                  45
Gly Ile Ile Asn Pro Ser Gly Gly Ser Thr Ser Tyr Ala Gln Lys Phe
    50                  55                  60
Gln Gly Arg Val Thr Met Thr Arg Asp Thr Ser Thr Ser Thr Val Tyr
65                  70                  75                  80
Met Glu Leu Ser Ser Leu Arg Ser Glu Asp Thr Ala Val Tyr Tyr Cys
                85                  90                  95
Ala Arg Gly Lys Trp Trp Leu Tyr Asn Trp Gly Lys Gly Thr Leu Val
            100                 105                 110
Thr Val Ser Ser
        115

<210> SEQ ID NO 143
<211> LENGTH: 5
<212> TYPE: PRT
<213> ORGANISM: Homo sapiens
<220> FEATURE:
<223> OTHER INFORMATION: Antibody 15

<400> SEQUENCE: 143

Ser Tyr Tyr Met His
 1               5

<210> SEQ ID NO 144
<211> LENGTH: 17
<212> TYPE: PRT
<213> ORGANISM: Homo sapiens
<220> FEATURE:
<223> OTHER INFORMATION: Antibody 15

<400> SEQUENCE: 144

Ile Ile Asn Pro Ser Gly Gly Ser Thr Ser Tyr Ala Gln Lys Phe Gln
 1               5                  10                  15
Gly

<210> SEQ ID NO 145
<211> LENGTH: 7
<212> TYPE: PRT
<213> ORGANISM: Homo sapiens
<220> FEATURE:
<223> OTHER INFORMATION: Antibody 15

<400> SEQUENCE: 145

Gly Lys Trp Trp Leu Tyr Asn
 1               5

<210> SEQ ID NO 146
<211> LENGTH: 333
<212> TYPE: DNA
<213> ORGANISM: Homo sapiens
<220> FEATURE:
<223> OTHER INFORMATION: Antibody 15
```

<400> SEQUENCE: 146

```
cagtctgtgt tgacgcagcc gccctcagtg tctgcggccc caggacagaa ggtcaccatc    60
tcctgctctg gaggcagctc caacattggg aatagttatg tatcctggta ccagcaactc   120
ccaggaacag cccccaaact cctcatttac gacaataata gcgaccctc agggattcct    180 gaccgattct ctggctccaa gtctggcacg tcagccaccc tggccatcac cggactccag   240
actggggacg aggccgatta ttactgcgga acatgggata ccagcaccca ccggcatccc   300
ctcttcggaa ctgggaccaa gctgaccgtc cta                                333
```

<210> SEQ ID NO 147
<211> LENGTH: 111
<212> TYPE: PRT
<213> ORGANISM: Homo sapiens
<220> FEATURE:
<223> OTHER INFORMATION: Antibody 15

<400> SEQUENCE: 147

```
Gln Ser Val Leu Thr Gln Pro Pro Ser Val Ser Ala Ala Pro Gly Gln
                 5                  10                  15

Lys Val Thr Ile Ser Cys Ser Gly Gly Ser Ser Asn Ile Gly Asn Ser
             20                  25                  30

Tyr Val Ser Trp Tyr Gln Gln Leu Pro Gly Thr Ala Pro Lys Leu Leu
         35                  40                  45

Ile Tyr Asp Asn Asn Lys Arg Pro Ser Gly Ile Pro Asp Arg Phe Ser
     50                  55                  60

Gly Ser Lys Ser Gly Thr Ser Ala Thr Leu Ala Ile Thr Gly Leu Gln
 65                  70                  75                  80

Thr Gly Asp Glu Ala Asp Tyr Tyr Cys Gly Thr Trp Asp Thr Ser Thr
                 85                  90                  95

His Arg His Pro Leu Phe Gly Thr Gly Thr Lys Leu Thr Val Leu
            100                 105                 110
```

<210> SEQ ID NO 148
<211> LENGTH: 13
<212> TYPE: PRT
<213> ORGANISM: Homo sapiens
<220> FEATURE:
<223> OTHER INFORMATION: Antibody 15

<400> SEQUENCE: 148

```
Ser Gly Gly Ser Ser Asn Ile Gly Asn Ser Tyr Val Ser
                 5                  10
```

<210> SEQ ID NO 149
<211> LENGTH: 7
<212> TYPE: PRT
<213> ORGANISM: Homo sapiens
<220> FEATURE:
<223> OTHER INFORMATION: Antibody 15

<400> SEQUENCE: 149

```
Asp Asn Asn Lys Arg Pro Ser
                 5
```

<210> SEQ ID NO 150
<211> LENGTH: 12
<212> TYPE: PRT
<213> ORGANISM: Homo sapiens
<220> FEATURE:
<223> OTHER INFORMATION: Antibody 15

-continued

```
<400> SEQUENCE: 150

Gly Thr Trp Asp Thr Ser Thr His Arg His Pro Leu
                 5                   10

<210> SEQ ID NO 151
<211> LENGTH: 348
<212> TYPE: DNA
<213> ORGANISM: Homo sapiens
<220> FEATURE:
<223> OTHER INFORMATION: Antibody 16

<400> SEQUENCE: 151
caggtccagc tggtgcagtc tggggctgag gtgaagaagc ctggggcctc agtgaaggtt      60
tcctgcaagg catctggata cgccttcacc agctactata tgcactgggc gcgacaggcc     120
cctggacaag ggcttgagtg gatgggaata atcaacccta gtggtggtag cacaagctac     180
gcacagaagt tccagggcag agtcaccatg accaggaca cgtccacgag cacagtctac      240
atggagctga gcagcctgag atctgaggac acggccgtgt attactgtgc gagaggaaaa     300
tggtggctgt acaactgggg caaaggcacc ctggtcaccg tctcgagt                  348

<210> SEQ ID NO 152
<211> LENGTH: 116
<212> TYPE: PRT
<213> ORGANISM: Homo sapiens
<220> FEATURE:
<223> OTHER INFORMATION: Antibody 16

<400> SEQUENCE: 152

Gln Val Gln Leu Val Gln Ser Gly Ala Glu Val Lys Lys Pro Gly Ala
                 5                  10                  15

Ser Val Lys Val Ser Cys Lys Ala Ser Gly Tyr Ala Phe Thr Ser Tyr
            20                  25                  30

Tyr Met His Trp Ala Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Lys Trp Trp Leu Tyr Asn Trp Gly Lys Gly Thr Leu Val
            100                 105                 110

Thr Val Ser Ser
        115

<210> SEQ ID NO 153
<211> LENGTH: 5
<212> TYPE: PRT
<213> ORGANISM: Homo sapiens
<220> FEATURE:
<223> OTHER INFORMATION: Antibody 16

<400> SEQUENCE: 153

Ser Tyr Tyr Met His
                 5

<210> SEQ ID NO 154
<211> LENGTH: 17
<212> TYPE: PRT
<213> ORGANISM: Homo sapiens
<220> FEATURE:
```

<223> OTHER INFORMATION: Antibody 16

<400> SEQUENCE: 154

Ile Ile Asn Pro Ser Gly Gly Ser Thr Ser Tyr Ala Gln Lys Phe Gln
                 5                  10                  15

Gly

<210> SEQ ID NO 155
<211> LENGTH: 7
<212> TYPE: PRT
<213> ORGANISM: Homo sapiens
<220> FEATURE:
<223> OTHER INFORMATION: Antibody 16

<400> SEQUENCE: 155

Gly Lys Trp Trp Leu Tyr Asn
                 5

<210> SEQ ID NO 156
<211> LENGTH: 333
<212> TYPE: DNA
<213> ORGANISM: Homo sapiens
<220> FEATURE:
<223> OTHER INFORMATION: Antibody 16

<400> SEQUENCE: 156
cagtctgtgt tgacgcagcc gccctcagtg tctgcggccc caggacagaa ggtcaccatc      60
tcctgctctg gaggcagctc aacattggg aatagttatg tatcctggta ccagcaactc     120
ccaggaacag ccccaaaact cctcatttac gacaataata agcgaccctc agggattcct     180
gaccgattct ctggctccaa gtctggcacg tcagccaccc tggccatcac cggactccag     240
actggggacg aggccgatta ttactgcgga acatgggata ccagcacgac ctaccacccc     300
atcttcggaa ctgggaccaa gctgaccgtc cta                                  333

<210> SEQ ID NO 157
<211> LENGTH: 111
<212> TYPE: PRT
<213> ORGANISM: Homo sapiens
<220> FEATURE:
<223> OTHER INFORMATION: Antibody 16

<400> SEQUENCE: 157

Gln Ser Val Leu Thr Gln Pro Pro Ser Val Ala Ala Pro Gly Gln
                 5                  10                  15

Lys Val Thr Ile Ser Cys Ser Gly Gly Ser Ser Asn Ile Gly Asn Ser
                20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
        50                  55                  60

Gly Ser Lys Ser Gly Thr Ser Ala Thr Leu Ala Ile Thr Gly Leu Gln
65                  70                  75                  80

Thr Gly Asp Glu Ala Asp Tyr Tyr Cys Gly Thr Trp Asp Thr Ser Thr
                85                  90                  95

Thr Tyr His Pro Ile Phe Gly Thr Gly Thr Lys Leu Thr Val Leu
                100                 105                 110

<210> SEQ ID NO 158
<211> LENGTH: 13
<212> TYPE: PRT
<213> ORGANISM: Homo sapiens
<220> FEATURE:
<223> OTHER INFORMATION: Antibody 16

<400> SEQUENCE: 158

Ser Gly Gly Ser Ser Asn Ile Gly Asn Ser Tyr Val Ser
                5                   10

<210> SEQ ID NO 159
<211> LENGTH: 7
<212> TYPE: PRT
<213> ORGANISM: Homo sapiens
<220> FEATURE:
<223> OTHER INFORMATION: Antibody 16

<400> SEQUENCE: 159

Asp Asn Asn Lys Arg Pro Ser
                5

<210> SEQ ID NO 160
<211> LENGTH: 12
<212> TYPE: PRT
<213> ORGANISM: Homo sapiens
<220> FEATURE:
<223> OTHER INFORMATION: Antibody 16

<400> SEQUENCE: 160

Gly Thr Trp Asp Thr Ser Thr Thr Tyr His Pro Ile
                5                   10

<210> SEQ ID NO 161
<211> LENGTH: 348
<212> TYPE: DNA
<213> ORGANISM: Homo sapiens
<220> FEATURE:
<223> OTHER INFORMATION: Antibody 17

<400> SEQUENCE: 161
caggtccagc tggtgcagtc tggggctgag gtgaagaagc ctggggcctc agtgaaggtt      60
tcctgcaagg catctggata cgccttcacc agctactata tgcactgggc gcgacaggcc     120
cctggacaag ggcttgagtg gatgggaata atcaacccta gtggtggtag cacaagctac     180
gcacagaagt tccagggcag agtcaccatg accagggaca cgtccacgag cacagtctac     240
atggagctga gcagcctgag atctgaggac acggccgtgt attactgtgc gagaggaaaa     300
tggtggtggc agcactgggg caaaggcacc ctggtcaccg tctcgagt                  348

<210> SEQ ID NO 162
<211> LENGTH: 116
<212> TYPE: PRT
<213> ORGANISM: Homo sapiens
<220> FEATURE:
<223> OTHER INFORMATION: Antibody 17

<400> SEQUENCE: 162

Gln Val Gln Leu Val Gln Ser Gly Ala Glu Val Lys Lys Pro Gly Ala
                5                   10                  15

Ser Val Lys Val Ser Cys Lys Ala Ser Gly Tyr Ala Phe Thr Ser Tyr
            20                  25                  30

Tyr Met His Trp Ala Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

```
Met Glu Leu Ser Ser Leu Arg Ser Glu Asp Thr Ala Val Tyr Tyr Cys
                 85                  90                  95
Ala Arg Gly Lys Trp Trp Trp Gln His Trp Gly Lys Gly Thr Leu Val
            100                 105                 110
Thr Val Ser Ser
        115

<210> SEQ ID NO 163
<211> LENGTH: 5
<212> TYPE: PRT
<213> ORGANISM: Homo sapiens
<220> FEATURE:
<223> OTHER INFORMATION: Antibody 17

<400> SEQUENCE: 163

Ser Tyr Tyr Met His
                5

<210> SEQ ID NO 164
<211> LENGTH: 17
<212> TYPE: PRT
<213> ORGANISM: Homo sapiens
<220> FEATURE:
<223> OTHER INFORMATION: Antibody 17

<400> SEQUENCE: 164

Ile Ile Asn Pro Ser Gly Gly Ser Thr Ser Tyr Ala Gln Lys Phe Gln
                 5                  10                  15
Gly

<210> SEQ ID NO 165
<211> LENGTH: 7
<212> TYPE: PRT
<213> ORGANISM: Homo sapiens
<220> FEATURE:
<223> OTHER INFORMATION: Antibody 17

<400> SEQUENCE: 165

Gly Lys Trp Trp Trp Gln His
                5

<210> SEQ ID NO 166
<211> LENGTH: 333
<212> TYPE: DNA
<213> ORGANISM: Homo sapiens
<220> FEATURE:
<223> OTHER INFORMATION: Antibody 17

<400> SEQUENCE: 166
cagtctgtgt tgacgcagcc gccctcagtg tctgcggccc caggacagaa ggtcaccatc      60
tcctgctctg gaggcagctc caacattggg aatagttatg tatcctggta ccagcaactc     120
ccaggaacag cccccaaact cctcatttac gacaataata gcgaccctc agggattcct      180 gaccgattct ctggctccaa gtctggcacg tcagccaccc tggccatcac cggactccag     240
actggggacg aggccgatta ttactgcgga acatgggata ccagcccggt ggacaggccg     300
atcttcggaa ctgggaccaa gctgaccgtc cta                                  333

<210> SEQ ID NO 167
<211> LENGTH: 111
<212> TYPE: PRT
<213> ORGANISM: Homo sapiens
<220> FEATURE:
<223> OTHER INFORMATION: Antibody 17
```

<400> SEQUENCE: 167

Gln Ser Val Leu Thr Gln Pro Pro Ser Val Ser Ala Ala Pro Gly Gln
1               5                   10                  15
Lys Val Thr Ile Ser Cys Ser Gly Gly Ser Ser Asn Ile Gly Asn Ser
            20                  25                  30
Tyr Val Ser Trp Tyr Gln Gln Leu Pro Gly Thr Ala Pro Lys Leu Leu
        35                  40                  45
Ile Tyr Asp Asn Asn Lys Arg Pro Ser Gly Ile Pro Asp Arg Phe Ser
    50                  55                  60
Gly Ser Lys Ser Gly Thr Ser Ala Thr Leu Ala Ile Thr Gly Leu Gln
65                  70                  75                  80
Thr Gly Asp Glu Ala Asp Tyr Tyr Cys Gly Thr Trp Asp Thr Ser Pro
                85                  90                  95
Val Asp Arg Pro Ile Phe Gly Thr Gly Thr Lys Leu Thr Val Leu
            100                 105                 110

<210> SEQ ID NO 168
<211> LENGTH: 13
<212> TYPE: PRT
<213> ORGANISM: Homo sapiens
<220> FEATURE:
<223> OTHER INFORMATION: Antibody 17

<400> SEQUENCE: 168

Ser Gly Gly Ser Ser Asn Ile Gly Asn Ser Tyr Val Ser
1               5                   10

<210> SEQ ID NO 169
<211> LENGTH: 7
<212> TYPE: PRT
<213> ORGANISM: Homo sapiens
<220> FEATURE:
<223> OTHER INFORMATION: Antibody 17

<400> SEQUENCE: 169

Asp Asn Asn Lys Arg Pro Ser
1               5

<210> SEQ ID NO 170
<211> LENGTH: 12
<212> TYPE: PRT
<213> ORGANISM: Homo sapiens
<220> FEATURE:
<223> OTHER INFORMATION: Antibody 17

<400> SEQUENCE: 170

Gly Thr Trp Asp Thr Ser Pro Val Asp Arg Pro Ile
1               5                   10

<210> SEQ ID NO 171
<211> LENGTH: 348
<212> TYPE: DNA
<213> ORGANISM: Homo sapiens
<220> FEATURE:
<223> OTHER INFORMATION: Antibody 18

<400> SEQUENCE: 171
caggtccagc tggtgcagtc tggggctgag gtgaagaagc ctggggcctc agtgaaggtt      60
tcctgcaagg catctggata cgccttcacc agctactata tgcactgggc gcgacaggcc    120
cctggacaag ggcttgagtg gatgggaata atcaaccctg tggtggtag cacaagctac    180 gcacagaagt tccagggcag agtcaccatg accagggaca cgtccacgag cacagtctac    240

```
atggagctga gcagcctgag atctgaggac acggccgtgt attactgtgc gagaggaaaa    300
tggtggtggc agcactgggg caaaggcacc ctggtcaccg tctcgagt                 348
```

<210> SEQ ID NO 172
<211> LENGTH: 116
<212> TYPE: PRT
<213> ORGANISM: Homo sapiens
<220> FEATURE:
<223> OTHER INFORMATION: Antibody 18

<400> SEQUENCE: 172

Gln Val Gln Leu Val Gln Ser Gly Ala Glu Val Lys Lys Pro Gly Ala
                5                   10                  15

Ser Val Lys Val Ser Cys Lys Ala Ser Gly Tyr Ala Phe Thr Ser Tyr
            20                  25                  30

Tyr Met His Trp Ala Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Lys Trp Trp Trp Gln His Trp Gly Lys Gly Thr Leu Val
            100                 105                 110

Thr Val Ser Ser
        115

<210> SEQ ID NO 173
<211> LENGTH: 5
<212> TYPE: PRT
<213> ORGANISM: Homo sapiens
<220> FEATURE:
<223> OTHER INFORMATION: Antibody 18

<400> SEQUENCE: 173

Ser Tyr Tyr Met His
                5

<210> SEQ ID NO 174
<211> LENGTH: 17
<212> TYPE: PRT
<213> ORGANISM: Homo sapiens
<220> FEATURE:
<223> OTHER INFORMATION: Antibody 18

<400> SEQUENCE: 174

Ile Ile Asn Pro Ser Gly Gly Ser Thr Ser Tyr Ala Gln Lys Phe Gln
                5                   10                  15

Gly

<210> SEQ ID NO 175
<211> LENGTH: 7
<212> TYPE: PRT
<213> ORGANISM: Homo sapiens
<220> FEATURE:
<223> OTHER INFORMATION: Antibody 18

<400> SEQUENCE: 175

Gly Lys Trp Trp Trp Gln His
                5

<210> SEQ ID NO 176
<211> LENGTH: 333
<212> TYPE: DNA
<213> ORGANISM: Homo sapiens
<220> FEATURE:
<223> OTHER INFORMATION: Antibody 18

<400> SEQUENCE: 176

```
cagtctgtgt tgacgcagcc gccctcagtg tctgcggccc caggacagaa ggtcaccatc      60
tcctgctctg gaggcagctc caacattggg aatagttatg tatcctggta ccagcaactc     120
ccaggaacag cccccaaact cctcatttac gacaataata agcgaccctc agggattcct     180
gaccgattct ctggctccaa gtctggcacg tcagccaccc tggccatcac cggactccag     240
actgggacg aggccgatta ttactgcgga acatgggata ccagcaccac cccgatgccc      300
gtcttcggaa ctgggaccaa gctgaccgtc cta                                   333
```

<210> SEQ ID NO 177
<211> LENGTH: 111
<212> TYPE: PRT
<213> ORGANISM: Homo sapiens
<220> FEATURE:
<223> OTHER INFORMATION: Antibody 18

<400> SEQUENCE: 177

Gln Ser Val Leu Thr Gln Pro Pro Ser Val Ser Ala Ala Pro Gly Gln
1               5                   10                  15
Lys Val Thr Ile Ser Cys Ser Gly Gly Ser Ser Asn Ile Gly Asn Ser
            20                  25                  30
Tyr Val Ser Trp Tyr Gln Gln Leu Pro Gly Thr Ala Pro Lys Leu Leu
        35                  40                  45
Ile Tyr Asp Asn Asn Lys Arg Pro Ser Gly Ile Pro Asp Arg Phe Ser
    50                  55                  60
Gly Ser Lys Ser Gly Thr Ser Ala Thr Leu Ala Ile Thr Gly Leu Gln
65                  70                  75                  80
Thr Gly Asp Glu Ala Asp Tyr Tyr Cys Gly Thr Trp Asp Thr Ser Thr
                85                  90                  95
Thr Pro Met Pro Val Phe Gly Thr Gly Thr Lys Leu Thr Val Leu
            100                 105                 110

<210> SEQ ID NO 178
<211> LENGTH: 13
<212> TYPE: PRT
<213> ORGANISM: Homo sapiens
<220> FEATURE:
<223> OTHER INFORMATION: Antibody 18

<400> SEQUENCE: 178

Ser Gly Gly Ser Ser Asn Ile Gly Asn Ser Tyr Val Ser
1               5                   10

<210> SEQ ID NO 179
<211> LENGTH: 7
<212> TYPE: PRT
<213> ORGANISM: Homo sapiens
<220> FEATURE:
<223> OTHER INFORMATION: Antibody 18

<400> SEQUENCE: 179

Asp Asn Asn Lys Arg Pro Ser
1               5

<210> SEQ ID NO 180
<211> LENGTH: 12
<212> TYPE: PRT
<213> ORGANISM: Homo sapiens
<220> FEATURE:
<223> OTHER INFORMATION: Antibody 18

<400> SEQUENCE: 180

Gly Thr Trp Asp Thr Ser Thr Thr Pro Met Pro Val
                 5                   10

<210> SEQ ID NO 181
<211> LENGTH: 348
<212> TYPE: DNA
<213> ORGANISM: Homo sapiens
<220> FEATURE:
<223> OTHER INFORMATION: Antibody 19

<400> SEQUENCE: 181
caggtccagc tggtgcagtc tggggctgag gtgaagaagc ctggggcctc agtgaaggtt      60
tcctgcaagg catctggata cgccttcacc agctactata tgcactgggc gcgacaggcc     120
cctggacaag gcttgagtg gatgggaata atcaaccta gtggtggtag cacaagctac       180
gcacagaagt tccagggcag agtcaccatg accagggaca cgtccacgag cacagtctac     240
atggagctga gcagcctgag atctgaggac acggccgtgt attactgtgc gagaggaaaa     300
tggtggtggc agcactgggg caaaggcacc ctggtcaccg tctcgagt                  348

<210> SEQ ID NO 182
<211> LENGTH: 116
<212> TYPE: PRT
<213> ORGANISM: Homo sapiens
<220> FEATURE:
<223> OTHER INFORMATION: Antibody 19

<400> SEQUENCE: 182

Gln Val Gln Leu Val Gln Ser Gly Ala Glu Val Lys Lys Pro Gly Ala
                 5                   10                  15

Ser Val Lys Val Ser Cys Lys Ala Ser Gly Tyr Ala Phe Thr Ser Tyr
             20                  25                  30

Tyr Met His Trp Ala Arg Gln Ala Pro Gly Gln Gly Leu Glu Trp Met
         35                  40                  45

Gly Ile Ile Asn Pro Ser Gly Gly Ser Thr Ser Tyr Ala Gln Lys Phe
     50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Gly Lys Trp Trp Trp Gln His Trp Gly Lys Gly Thr Leu Val
            100                 105                 110

Thr Val Ser Ser
        115

<210> SEQ ID NO 183
<211> LENGTH: 5
<212> TYPE: PRT
<213> ORGANISM: Homo sapiens
<220> FEATURE:
<223> OTHER INFORMATION: Antibody 19

<400> SEQUENCE: 183

Ser Tyr Tyr Met His
                 5

<210> SEQ ID NO 184
<211> LENGTH: 17
<212> TYPE: PRT
<213> ORGANISM: Homo sapiens
<220> FEATURE:
<223> OTHER INFORMATION: Antibody 19

<400> SEQUENCE: 184

Ile Ile Asn Pro Ser Gly Gly Ser Thr Ser Tyr Ala Gln Lys Phe Gln
                5                   10                  15

Gly

<210> SEQ ID NO 185
<211> LENGTH: 7
<212> TYPE: PRT
<213> ORGANISM: Homo sapiens
<220> FEATURE:
<223> OTHER INFORMATION: Antibody 19

<400> SEQUENCE: 185

Gly Lys Trp Trp Trp Gln His
                5

<210> SEQ ID NO 186
<211> LENGTH: 333
<212> TYPE: DNA
<213> ORGANISM: Homo sapiens
<220> FEATURE:
<223> OTHER INFORMATION: Antibody 19

<400> SEQUENCE: 186
cagtctgtgt tgacgcagcc gccctcagtg tctgcggccc caggacagaa ggtcaccatc      60
tcctgctctg gaggcagctc caacattggg aatagttatg tatcctggta ccagcaactc     120
ccaggaacag ccccccaaact cctcatttac gacaataata agcgaccctc agggattcct     180
gaccgattct ctggctccaa gtctggcacg tcagccaccc tggccatcac cggactccag     240
actggggacg aggccgatta ttactgcgga acatgggata ccagcacgac ctaccacccc     300
atcttcggaa ctgggaccaa gctgaccgtc cta                                   333

<210> SEQ ID NO 187
<211> LENGTH: 111
<212> TYPE: PRT
<213> ORGANISM: Homo sapiens
<220> FEATURE:
<223> OTHER INFORMATION: Antibody 19

<400> SEQUENCE: 187

Gln Ser Val Leu Thr Gln Pro Pro Ser Val Ser Ala Ala Pro Gly Gln
                5                   10                  15

Lys Val Thr Ile Ser Cys Ser Gly Gly Ser Ser Asn Ile Gly Asn Ser
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Ala Ile Thr Gly Leu Gln
65                  70                  75                  80

Thr Gly Asp Glu Ala Asp Tyr Tyr Cys Gly Thr Trp Asp Thr Ser Thr
                85                  90                  95

Thr Tyr His Pro Ile Phe Gly Thr Gly Thr Lys Leu Thr Val Leu

<210> SEQ ID NO 188
<211> LENGTH: 13
<212> TYPE: PRT
<213> ORGANISM: Homo sapiens
<220> FEATURE:
<223> OTHER INFORMATION: Antibody 19

<400> SEQUENCE: 188

Ser Gly Gly Ser Ser Asn Ile Gly Asn Ser Tyr Val Ser
                 5                  10

<210> SEQ ID NO 189
<211> LENGTH: 7
<212> TYPE: PRT
<213> ORGANISM: Homo sapiens
<220> FEATURE:
<223> OTHER INFORMATION: Antibody 19

<400> SEQUENCE: 189

Asp Asn Asn Lys Arg Pro Ser
                 5

<210> SEQ ID NO 190
<211> LENGTH: 12
<212> TYPE: PRT
<213> ORGANISM: Homo sapiens
<220> FEATURE:
<223> OTHER INFORMATION: Antibody 19

<400> SEQUENCE: 190

Gly Thr Trp Asp Thr Ser Thr Thr Tyr His Pro Ile
                 5                  10

<210> SEQ ID NO 191
<211> LENGTH: 348
<212> TYPE: DNA
<213> ORGANISM: Homo sapiens
<220> FEATURE:
<223> OTHER INFORMATION: Antibody 20

<400> SEQUENCE: 191
caggtccagc tggtgcagtc tggggctgag gtgaagaagc ctggggcctc agtgaaggtt      60
tcctgcaagg catctggata cgccttcacc agctactata tgcactgggc gcgacaggcc     120
cctggacaag gcttgagtg gatgggaata tcaaccctag tggtggtag cacaagctac       180 gcacagaagt tccagggcag agtcaccatg accagggaca cgtccacgag cacagtctac     240
atggagctga gcagcctgag atctgaggac acggccgtgt attactgtgc gagaggaaag     300
tactggatgt acgactgggg caaaggcacc ctggtcaccg tctcgagt                  348

<210> SEQ ID NO 192
<211> LENGTH: 116
<212> TYPE: PRT
<213> ORGANISM: Homo sapiens
<220> FEATURE:
<223> OTHER INFORMATION: Antibody 20

<400> SEQUENCE: 192

Gln Val Gln Leu Val Gln Ser Gly Ala Glu Val Lys Lys Pro Gly Ala
                 5                  10                  15

Ser Val Lys Val Ser Cys Lys Ala Ser Gly Tyr Ala Phe Thr Ser Tyr
            20                  25                  30

Tyr Met His Trp Ala Arg Gln Ala Pro Gly Gln Gly Leu Glu Trp Met

```
            35                  40                  45
Gly Ile Ile Asn Pro Ser Gly Gly Ser Thr Ser Tyr Ala Gln Lys Phe
        50                  55                  60
Gln Gly Arg Val Thr Met Thr Arg Asp Thr Ser Thr Ser Thr Val Tyr
 65                  70                  75                  80
Met Glu Leu Ser Ser Leu Arg Ser Glu Asp Thr Ala Val Tyr Tyr Cys
                 85                  90                  95
Ala Arg Gly Lys Tyr Trp Met Tyr Asp Trp Gly Lys Gly Thr Leu Val
            100                 105                 110
Thr Val Ser Ser
        115

<210> SEQ ID NO 193
<211> LENGTH: 5
<212> TYPE: PRT
<213> ORGANISM: Homo sapiens
<220> FEATURE:
<223> OTHER INFORMATION: Antibody 20

<400> SEQUENCE: 193

Ser Tyr Tyr Met His
              5

<210> SEQ ID NO 194
<211> LENGTH: 17
<212> TYPE: PRT
<213> ORGANISM: Homo sapiens
<220> FEATURE:
<223> OTHER INFORMATION: Antibody 20

<400> SEQUENCE: 194

Ile Ile Asn Pro Ser Gly Gly Ser Thr Ser Tyr Ala Gln Lys Phe Gln
                  5                  10                  15
Gly

<210> SEQ ID NO 195
<211> LENGTH: 7
<212> TYPE: PRT
<213> ORGANISM: Homo sapiens
<220> FEATURE:
<223> OTHER INFORMATION: Antibody 20

<400> SEQUENCE: 195

Gly Lys Tyr Trp Met Tyr Asp
                  5

<210> SEQ ID NO 196
<211> LENGTH: 333
<212> TYPE: DNA
<213> ORGANISM: Homo sapiens
<220> FEATURE:
<223> OTHER INFORMATION: Antibody 20

<400> SEQUENCE: 196
cagtctgtgt tgacgcagcc gccctcagtg tctgcggccc caggacagaa ggtcaccatc    60
tcctgctctg gaggcagctc caacattggg aatagttatg tatcctggta ccagcaactc   120
ccaggaacag cccccaaact cctcatttac gacaataata gcgaccctca gggattcct    180 gaccgattct ctggctccaa gtctggcacg tcagccaccc tggccatcac cggactccag   240
actggggacg aggccgatta ttactgcgga acatgggata ccagcacggt gtgggagtgg   300
ccgttcggaa ctgggaccaa gctgaccgtc cta                                 333
```

```
<210> SEQ ID NO 197
<211> LENGTH: 111
<212> TYPE: PRT
<213> ORGANISM: Homo sapiens
<220> FEATURE:
<223> OTHER INFORMATION: Antibody 20

<400> SEQUENCE: 197

Gln Ser Val Leu Thr Gln Pro Pro Ser Val Ser Ala Ala Pro Gly Gln
                 5                  10                  15

Lys Val Thr Ile Ser Cys Ser Gly Gly Ser Ser Asn Ile Gly Asn Ser
             20                  25                  30

Tyr Val Ser Trp Tyr Gln Gln Leu Pro Gly Thr Ala Pro Lys Leu Leu
         35                  40                  45

Ile Tyr Asp Asn Asn Lys Arg Pro Ser Gly Ile Pro Asp Arg Phe Ser
     50                  55                  60

Gly Ser Lys Ser Gly Thr Ser Ala Thr Leu Ala Ile Thr Gly Leu Gln
 65                  70                  75                  80

Thr Gly Asp Glu Ala Asp Tyr Tyr Cys Gly Thr Trp Asp Thr Ser Thr
                 85                  90                  95

Val Trp Glu Trp Pro Phe Gly Thr Gly Thr Lys Leu Thr Val Leu
            100                 105                 110

<210> SEQ ID NO 198
<211> LENGTH: 13
<212> TYPE: PRT
<213> ORGANISM: Homo sapiens
<220> FEATURE:
<223> OTHER INFORMATION: Antibody 20

<400> SEQUENCE: 198

Ser Gly Gly Ser Ser Asn Ile Gly Asn Ser Tyr Val Ser
                 5                  10

<210> SEQ ID NO 199
<211> LENGTH: 7
<212> TYPE: PRT
<213> ORGANISM: Homo sapiens
<220> FEATURE:
<223> OTHER INFORMATION: Antibody 20

<400> SEQUENCE: 199

Asp Asn Asn Lys Arg Pro Ser
                 5

<210> SEQ ID NO 200
<211> LENGTH: 12
<212> TYPE: PRT
<213> ORGANISM: Homo sapiens
<220> FEATURE:
<223> OTHER INFORMATION: Antibody 20

<400> SEQUENCE: 200

Gly Thr Trp Asp Thr Ser Thr Val Trp Glu Trp Pro
                 5                  10

<210> SEQ ID NO 201
<211> LENGTH: 348
<212> TYPE: DNA
<213> ORGANISM: Homo sapiens
<220> FEATURE:
<223> OTHER INFORMATION: Antibody 21

<400> SEQUENCE: 201
```

```
caggtccagc tggtgcagtc tggggctgag gtgaagaagc ctggggcctc agtgaaggtt      60
tcctgcaagg catctggata cgccttcacc agctactata tgcactgggc gcgacaggcc     120
cctggacaag gcttgagtg gatgggata tcaaccccta gtggtggtag cgcaagctac      180
gcgcagaagt tccagggcag agtcaccatg accaggaca cgtccacgag cacagtctac      240
atggagctga gcagcctgag atctgaggac acggccgtgt attactgtgc gagaggaaag     300
tactggatgt acgactgggg caaaggcacc ctggtcaccg tctcgagt                  348
```

<210> SEQ ID NO 202
<211> LENGTH: 116
<212> TYPE: PRT
<213> ORGANISM: Homo sapiens
<220> FEATURE:
<223> OTHER INFORMATION: Antibody 21

<400> SEQUENCE: 202

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Ala Phe Thr Ser Tyr
            20                  25                  30

Tyr Met His Trp Ala Arg Gln Ala Pro Gly Gln Gly Leu Glu Trp Met
        35                  40                  45

Gly Ile Ile Asn Pro Ser Gly Gly Ser Ala Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Lys Tyr Trp Met Tyr Asp Trp Gly Lys Gly Thr Leu Val
            100                 105                 110

Thr Val Ser Ser
        115
```

<210> SEQ ID NO 203
<211> LENGTH: 5
<212> TYPE: PRT
<213> ORGANISM: Homo sapiens
<220> FEATURE:
<223> OTHER INFORMATION: Antibody 21

<400> SEQUENCE: 203

```
Ser Tyr Tyr Met His
 1               5
```

<210> SEQ ID NO 204
<211> LENGTH: 17
<212> TYPE: PRT
<213> ORGANISM: Homo sapiens
<220> FEATURE:
<223> OTHER INFORMATION: Antibody 21

<400> SEQUENCE: 204

```
Ile Ile Asn Pro Ser Gly Gly Ser Ala Ser Tyr Ala Gln Lys Phe Gln
 1               5                  10                  15

Gly
```

<210> SEQ ID NO 205
<211> LENGTH: 7
<212> TYPE: PRT
<213> ORGANISM: Homo sapiens
<220> FEATURE:

<223> OTHER INFORMATION: Antibody 21

<400> SEQUENCE: 205

Gly Lys Tyr Trp Met Tyr Asp
                5

<210> SEQ ID NO 206
<211> LENGTH: 333
<212> TYPE: DNA
<213> ORGANISM: Homo sapiens
<220> FEATURE:
<223> OTHER INFORMATION: Antibody 21

<400> SEQUENCE: 206

```
cagtctgtgt tgacgcagcc gccctcggtg tctgcggccc caggacagaa ggtcaccatc      60
tcctgctctg gaggcagctc aacattggga atagttatg tatcctggta ccagcaactc     120
ccaggaacag cccccaaact cctcatttac gacaataata agcgaccctc agggattcct    180
gaccgattct ctggctccaa gtctggcacg tcagccaccc tggccatcac cggactccag    240
actggggacg aggccgttta tttctgcgga acatgggata ccagcacggt gtgggagtgg    300
ccgttcggaa ctgggaccaa gctgaccgtc cta                                 333
```

<210> SEQ ID NO 207
<211> LENGTH: 111
<212> TYPE: PRT
<213> ORGANISM: Homo sapiens
<220> FEATURE:
<223> OTHER INFORMATION: Antibody 21

<400> SEQUENCE: 207

Gln Ser Val Leu Thr Gln Pro Pro Ser Val Ala Ala Pro Gly Gln
                5                  10                  15

Lys Val Thr Ile Ser Cys Ser Gly Gly Ser Ser Asn Ile Gly Asn Ser
             20                  25                  30

Tyr Val Ser Trp Tyr Gln Gln Leu Pro Gly Thr Ala Pro Lys Leu Leu
         35                  40                  45

Ile Tyr Asp Asn Asn Lys Arg Pro Ser Gly Ile Pro Asp Arg Phe Ser
 50                  55                  60

Gly Ser Lys Ser Gly Thr Ser Ala Thr Leu Ala Ile Thr Gly Leu Gln
65                  70                  75                  80

Thr Gly Asp Glu Ala Val Tyr Phe Cys Gly Thr Trp Asp Thr Ser Thr
                 85                  90                  95

Val Trp Glu Trp Pro Phe Gly Thr Gly Thr Lys Leu Thr Val Leu
            100                 105                 110

<210> SEQ ID NO 208
<211> LENGTH: 13
<212> TYPE: PRT
<213> ORGANISM: Homo sapiens
<220> FEATURE:
<223> OTHER INFORMATION: Antibody 21

<400> SEQUENCE: 208

Ser Gly Gly Ser Ser Asn Ile Gly Asn Ser Tyr Val Ser
                5                  10

<210> SEQ ID NO 209
<211> LENGTH: 7
<212> TYPE: PRT
<213> ORGANISM: Homo sapiens
<220> FEATURE:
<223> OTHER INFORMATION: Antibody 21

```
<400> SEQUENCE: 209

Asp Asn Asn Lys Arg Pro Ser
                5

<210> SEQ ID NO 210
<211> LENGTH: 12
<212> TYPE: PRT
<213> ORGANISM: Homo sapiens
<220> FEATURE:
<223> OTHER INFORMATION: Antibody 21

<400> SEQUENCE: 210

Gly Thr Trp Asp Thr Ser Thr Val Trp Glu Trp Pro
                5                  10

<210> SEQ ID NO 211
<211> LENGTH: 348
<212> TYPE: DNA
<213> ORGANISM: Homo sapiens
<220> FEATURE:
<223> OTHER INFORMATION: Antibody 22

<400> SEQUENCE: 211
caggtccagc tggtgcagtc tggggctgag gtgaagaagc ccggggcctc agtgaaggtt    60
tcctgcaagg catctggata cgccttcacc agctactata tgcactgggc gcgacaggcc   120
cctggacaag gcttgagtg gatgggaata atcaaccctag tggtggtag cacaagctac   180 gcacagaagt tccagggcag agtcaccatg accaggaca cgtccacgag cacagtctac   240
atggagctga gcagcctgag atctgaggac acggccgtgt attactgtgc gagaggaaag   300
tactggatgt acgactgggg caaaggcacc ctggtcaccg tctcgagt                348

<210> SEQ ID NO 212
<211> LENGTH: 116
<212> TYPE: PRT
<213> ORGANISM: Homo sapiens
<220> FEATURE:
<223> OTHER INFORMATION: Antibody 22

<400> SEQUENCE: 212

Gln Val Gln Leu Val Gln Ser Gly Ala Glu Val Lys Lys Pro Gly Ala
                5                  10                  15

Ser Val Lys Val Ser Cys Lys Ala Ser Gly Tyr Ala Phe Thr Ser Tyr
            20                  25                  30

Tyr Met His Trp Ala Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Lys Tyr Trp Met Tyr Asp Trp Gly Lys Gly Thr Leu Val
            100                 105                 110

Thr Val Ser Ser
        115

<210> SEQ ID NO 213
<211> LENGTH: 5
<212> TYPE: PRT
<213> ORGANISM: Homo sapiens
```

```
<220> FEATURE:
<223> OTHER INFORMATION: Antibody 22

<400> SEQUENCE: 213

Ser Tyr Tyr Met His
              5

<210> SEQ ID NO 214
<211> LENGTH: 17
<212> TYPE: PRT
<213> ORGANISM: Homo sapiens
<220> FEATURE:
<223> OTHER INFORMATION: Antibody 22

<400> SEQUENCE: 214

Ile Ile Asn Pro Ser Gly Gly Ser Thr Ser Tyr Ala Gln Lys Phe Gln
                5                   10                  15

Gly

<210> SEQ ID NO 215
<211> LENGTH: 7
<212> TYPE: PRT
<213> ORGANISM: Homo sapiens
<220> FEATURE:
<223> OTHER INFORMATION: Antibody 22

<400> SEQUENCE: 215

Gly Lys Tyr Trp Met Tyr Asp
                5

<210> SEQ ID NO 216
<211> LENGTH: 333
<212> TYPE: DNA
<213> ORGANISM: Homo sapiens
<220> FEATURE:
<223> OTHER INFORMATION: Antibody 22

<400> SEQUENCE: 216
cagcccgtgt tgacgcagcc gccctcagtg tctgcggccc caggacagaa ggtcaccatc      60
tcctgctctg gaggcagctc caacattggg aatagttatg tatcctggta ccagcaactc     120
ccaggaacag cccccaaact cctcatttac gacaataata gcgaccctc agggattcct      180 gaccgattct ctggctccaa gtctggcacg tcagccaccc tggccatcac cggactccag     240
actggggacg aggccgatta tttctgcgga acatgggata ccagcacggt gtgggagtgg     300
ccgttcggaa ctgggaccaa gctgaccgtc cta                                   333

<210> SEQ ID NO 217
<211> LENGTH: 111
<212> TYPE: PRT
<213> ORGANISM: Homo sapiens
<220> FEATURE:
<223> OTHER INFORMATION: Antibody 22

<400> SEQUENCE: 217

Gln Pro Val Leu Thr Gln Pro Pro Ser Val Ser Ala Ala Pro Gly Gln
                5                   10                  15

Lys Val Thr Ile Ser Cys Ser Gly Gly Ser Ser Asn Ile Gly Asn Ser
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60
```

Gly Ser Lys Ser Gly Thr Ser Ala Thr Leu Ala Ile Thr Gly Leu Gln
65                  70                  75                  80

Thr Gly Asp Glu Ala Asp Tyr Phe Cys Gly Thr Trp Asp Ser Thr
                85                  90                  95

Val Trp Glu Trp Pro Phe Gly Thr Gly Thr Lys Leu Thr Val Leu
            100                 105                 110

<210> SEQ ID NO 218
<211> LENGTH: 13
<212> TYPE: PRT
<213> ORGANISM: Homo sapiens
<220> FEATURE:
<223> OTHER INFORMATION: Antibody 22

<400> SEQUENCE: 218

Ser Gly Gly Ser Ser Asn Ile Gly Asn Ser Tyr Val Ser
                5                   10

<210> SEQ ID NO 219
<211> LENGTH: 7
<212> TYPE: PRT
<213> ORGANISM: Homo sapiens
<220> FEATURE:
<223> OTHER INFORMATION: Antibody 22

<400> SEQUENCE: 219

Asp Asn Asn Lys Arg Pro Ser
                5

<210> SEQ ID NO 220
<211> LENGTH: 12
<212> TYPE: PRT
<213> ORGANISM: Homo sapiens
<220> FEATURE:
<223> OTHER INFORMATION: Antibody 22

<400> SEQUENCE: 220

Gly Thr Trp Asp Thr Ser Thr Val Trp Glu Trp Pro
                5                   10

<210> SEQ ID NO 221
<211> LENGTH: 348
<212> TYPE: DNA
<213> ORGANISM: Homo sapiens
<220> FEATURE:
<223> OTHER INFORMATION: Antibody 23

<400> SEQUENCE: 221
caggtccagc tggtgcagtc tggggctgag gtgaggaagc ctggggcctc agtgaaggtt      60
tcctgcaagg catctggata cgccttcacc agctactata tgcactgggc gcgacaggcc     120
cccgggcaag ggcttgagtg gatgggaata atcaacccta gtggtggtag cacaagctac     180
gcgcagaagt tccagggcag agtcaccatg accagggaca cgtccacgag cacagtctac     240
atggagctga gcagcctgag atctgaggac acggccgtgt attactgtgc gagaggaaag     300
tactggatgt acgactgggg caaaggcacc ctggtcaccg tctcgagt                  348

<210> SEQ ID NO 222
<211> LENGTH: 116
<212> TYPE: PRT
<213> ORGANISM: Homo sapiens
<220> FEATURE:
<223> OTHER INFORMATION: Antibody 23

<400> SEQUENCE: 222

```
Gln Val Gln Leu Val Gln Ser Gly Ala Glu Val Arg Lys Pro Gly Ala
                  5                  10                  15
Ser Val Lys Val Ser Cys Lys Ala Ser Gly Tyr Ala Phe Thr Ser Tyr
             20                  25                  30
Tyr Met His Trp Ala Arg Gln Ala Pro Gly Gln Gly Leu Glu Trp Met
         35                  40                  45
Gly Ile Ile Asn Pro Ser Gly Gly Ser Thr Ser Tyr Ala Gln Lys Phe
 50                  55                  60
Gln Gly Arg Val Thr Met Thr Arg Asp Thr Ser Thr Ser Thr Val Tyr
 65                  70                  75                  80
Met Glu Leu Ser Ser Leu Arg Ser Glu Asp Thr Ala Val Tyr Tyr Cys
             85                  90                  95
Ala Arg Gly Lys Tyr Trp Met Tyr Asp Trp Gly Lys Gly Thr Leu Val
            100                 105                 110
Thr Val Ser Ser
        115

<210> SEQ ID NO 223
<211> LENGTH: 5
<212> TYPE: PRT
<213> ORGANISM: Homo sapiens
<220> FEATURE:
<223> OTHER INFORMATION: Antibody 23

<400> SEQUENCE: 223

Ser Tyr Tyr Met His
              5

<210> SEQ ID NO 224
<211> LENGTH: 17
<212> TYPE: PRT
<213> ORGANISM: Homo sapiens
<220> FEATURE:
<223> OTHER INFORMATION: Antibody 23

<400> SEQUENCE: 224

Ile Ile Asn Pro Ser Gly Gly Ser Thr Ser Tyr Ala Gln Lys Phe Gln
                  5                  10                  15
Gly

<210> SEQ ID NO 225
<211> LENGTH: 7
<212> TYPE: PRT
<213> ORGANISM: Homo sapiens
<220> FEATURE:
<223> OTHER INFORMATION: Antibody 23

<400> SEQUENCE: 225

Gly Lys Tyr Trp Met Tyr Asp
              5

<210> SEQ ID NO 226
<211> LENGTH: 333
<212> TYPE: DNA
<213> ORGANISM: Homo sapiens
<220> FEATURE:
<223> OTHER INFORMATION: Antibody 23

<400> SEQUENCE: 226
cagtctgtgt tgacgcagcc gccctcagtg tctgcggccc caggacagaa ggtcaccatc    60
tcctgctctg gaggcagctc caacattggg aataattatg tatcctggta ccagcaactc   120
ccaggaacag cccccaaact cctcatttac gacaataata gcgaccccc aggattcct    180
```

```
gaccgattct ctggctccaa gtctggcacg tcagccaccc tggccatcac cggactccag    240
actggggacg aggccgatta ttactgcgga acatgggata ccagcacggt gtgggagtgg    300
ccgttcggaa ctgggaccaa gctgaccgtc cta                                 333
```

```
<210> SEQ ID NO 227
<211> LENGTH: 111
<212> TYPE: PRT
<213> ORGANISM: Homo sapiens
<220> FEATURE:
<223> OTHER INFORMATION: Antibody 23

<400> SEQUENCE: 227
```

Gln Ser Val Leu Thr Gln Pro Pro Ser Val Ser Ala Ala Pro Gly Gln
  1               5                  10                  15

Lys Val Thr Ile Ser Cys Ser Gly Gly Ser Ser Asn Ile Gly Asn Asn
             20                  25                  30

Tyr Val Ser Trp Tyr Gln Gln Leu Pro Gly Thr Ala Pro Lys Leu Leu
         35                  40                  45

Ile Tyr Asp Asn Asn Lys Arg Pro Pro Gly Ile Pro Asp Arg Phe Ser
     50                  55                  60

Gly Ser Lys Ser Gly Thr Ser Ala Thr Leu Ala Ile Thr Gly Leu Gln
 65                  70                  75                  80

Thr Gly Asp Glu Ala Asp Tyr Tyr Cys Gly Thr Trp Asp Thr Ser Thr
                 85                  90                  95

Val Trp Glu Trp Pro Phe Gly Thr Gly Thr Lys Leu Thr Val Leu
            100                 105                 110

```
<210> SEQ ID NO 228
<211> LENGTH: 13
<212> TYPE: PRT
<213> ORGANISM: Homo sapiens
<220> FEATURE:
<223> OTHER INFORMATION: Antibody 23

<400> SEQUENCE: 228
```

Ser Gly Gly Ser Ser Asn Ile Gly Asn Asn Tyr Val Ser
  1               5                  10

```
<210> SEQ ID NO 229
<211> LENGTH: 7
<212> TYPE: PRT
<213> ORGANISM: Homo sapiens
<220> FEATURE:
<223> OTHER INFORMATION: Antibody 23

<400> SEQUENCE: 229
```

Asp Asn Asn Lys Arg Pro Pro
  1               5

```
<210> SEQ ID NO 230
<211> LENGTH: 12
<212> TYPE: PRT
<213> ORGANISM: Homo sapiens
<220> FEATURE:
<223> OTHER INFORMATION: Antibody 23

<400> SEQUENCE: 230
```

Gly Thr Trp Asp Thr Ser Thr Val Trp Glu Trp Pro
  1               5                  10

```
<210> SEQ ID NO 231
<211> LENGTH: 348
```

```
<212> TYPE: DNA
<213> ORGANISM: Homo sapiens
<220> FEATURE:
<223> OTHER INFORMATION: Antibody 24

<400> SEQUENCE: 231
caggtccagc tggtgcagtc tggggctgag gtgaagaagc ctggggcctc agtgaaggtt      60
tcctgcaagg catctggata cgccttcacc agctactata tgcactgggc gcgacaggcc     120
cctggacaag ggcttgagtg gatgggaata atcaaccctg aggtggtag cacaagctac      180 gcacagaagt tccagggcag agtcaccatg accaggaca cgtccacgag cacagtctac      240
atggagctga gcagcctgag atctgaggac acggccgtgt attactgtgc gagaggaaag     300
tactggatgt acgactgggg caaaggcacc ctggtcaccg tctcgagt                  348

<210> SEQ ID NO 232
<211> LENGTH: 116
<212> TYPE: PRT
<213> ORGANISM: Homo sapiens
<220> FEATURE:
<223> OTHER INFORMATION: Antibody 24

<400> SEQUENCE: 232

Gln Val Gln Leu Val Gln Ser Gly Ala Glu Val Lys Lys Pro Gly Ala
                 5                  10                  15

Ser Val Lys Val Ser Cys Lys Ala Ser Gly Tyr Ala Phe Thr Ser Tyr
            20                  25                  30

Tyr Met His Trp Ala Arg Gln Ala Pro Gly Gln Gly Leu Glu Trp Met
        35                  40                  45

Gly Ile Ile Asn Pro Arg Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Lys Tyr Trp Met Tyr Asp Trp Gly Lys Gly Thr Leu Val
            100                 105                 110

Thr Val Ser Ser
        115

<210> SEQ ID NO 233
<211> LENGTH: 5
<212> TYPE: PRT
<213> ORGANISM: Homo sapiens
<220> FEATURE:
<223> OTHER INFORMATION: Antibody 24

<400> SEQUENCE: 233

Ser Tyr Tyr Met His
                5

<210> SEQ ID NO 234
<211> LENGTH: 17
<212> TYPE: PRT
<213> ORGANISM: Homo sapiens
<220> FEATURE:
<223> OTHER INFORMATION: Antibody 24

<400> SEQUENCE: 234

Ile Ile Asn Pro Arg Gly Gly Ser Thr Ser Tyr Ala Gln Lys Phe Gln
                 5                  10                  15

Gly
```

<210> SEQ ID NO 235
<211> LENGTH: 7
<212> TYPE: PRT
<213> ORGANISM: Homo sapiens
<220> FEATURE:
<223> OTHER INFORMATION: Antibody 24

<400> SEQUENCE: 235

Gly Lys Tyr Trp Met Tyr Asp
            5

<210> SEQ ID NO 236
<211> LENGTH: 333
<212> TYPE: DNA
<213> ORGANISM: Homo sapiens
<220> FEATURE:
<223> OTHER INFORMATION: Antibody 24

<400> SEQUENCE: 236
cagtctgtgt tgacgcagcc gccctcagtg tctgcggccc caggacagaa ggtcaccatc      60
tcctgctctg gaggcagctc caacattggg aatagttatg tatcctggta ccagcaactc     120
ccaggaacag ccccccaaact cctcatttac gacaataata agcgaccctc agggattcct    180
gaccgattct ctggctccaa gtctggcacg tcagccaccc tggccatcac cggactccag     240
actggggacg aggccgatta tttctgcgga acatgggata ccagcacggt gtgggagtgg    300
ccgttcggaa ctgggaccaa gctgaccgtc cta                                  333

<210> SEQ ID NO 237
<211> LENGTH: 111
<212> TYPE: PRT
<213> ORGANISM: Homo sapiens
<220> FEATURE:
<223> OTHER INFORMATION: Antibody 24

<400> SEQUENCE: 237

Gln Ser Val Leu Thr Gln Pro Pro Ser Val Ser Ala Ala Pro Gly Gln
              5                   10                  15

Lys Val Thr Ile Ser Cys Ser Gly Gly Ser Ser Asn Ile Gly Asn Ser
         20                  25                  30

Tyr Val Ser Trp Tyr Gln Gln Leu Pro Gly Thr Ala Pro Lys Leu Leu
         35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Ala Ile Thr Gly Leu Gln
65                  70                  75                  80

Thr Gly Asp Glu Ala Asp Tyr Phe Cys Gly Thr Trp Asp Thr Ser Thr
                85                  90                  95

Val Trp Glu Trp Pro Phe Gly Thr Gly Thr Lys Leu Thr Val Leu
            100                 105                 110

<210> SEQ ID NO 238
<211> LENGTH: 13
<212> TYPE: PRT
<213> ORGANISM: Homo sapiens
<220> FEATURE:
<223> OTHER INFORMATION: Antibody 24

<400> SEQUENCE: 238

Ser Gly Gly Ser Ser Asn Ile Gly Asn Ser Tyr Val Ser
            5                   10

<210> SEQ ID NO 239
<211> LENGTH: 7
<212> TYPE: PRT
<213> ORGANISM: Homo sapiens
<220> FEATURE:
<223> OTHER INFORMATION: Antibody 24

<400> SEQUENCE: 239

Asp Asn Asn Lys Arg Pro Ser
                5

<210> SEQ ID NO 240
<211> LENGTH: 12
<212> TYPE: PRT
<213> ORGANISM: Homo sapiens
<220> FEATURE:
<223> OTHER INFORMATION: Antibody 24

<400> SEQUENCE: 240

Gly Thr Trp Asp Thr Ser Thr Val Trp Glu Trp Pro
                5                   10

<210> SEQ ID NO 241
<211> LENGTH: 348
<212> TYPE: DNA
<213> ORGANISM: Homo sapiens
<220> FEATURE:
<223> OTHER INFORMATION: Antibody 25

<400> SEQUENCE: 241
caggtccagc tggtgcagtc tggggctgag gtgaagaagc ctggggcctc agtgaaggtt      60
tcctgcaagg catctggata cgccttcacc agctactata tgcactgggc gcgacaggcc     120
cctggacaag ggcttgagtg gatgggaata atcaacccta gaggtggtag cgcaagctac     180
gcacagaagt tccagggcag agtctccatg accagggaca cgtccacgag cacagtctac     240
atggagctga gcagcctgag gtctgaggac acggccgtgt attactgtgc gagaggaaag     300
tactggatgt acgactgggg caaaggcacc ctggtcaccg tctcgagt                  348

<210> SEQ ID NO 242
<211> LENGTH: 116
<212> TYPE: PRT
<213> ORGANISM: Homo sapiens
<220> FEATURE:
<223> OTHER INFORMATION: Antibody 25

<400> SEQUENCE: 242

Gln Val Gln Leu Val Gln Ser Gly Ala Glu Val Lys Lys Pro Gly Ala
                5                   10                  15

Ser Val Lys Val Ser Cys Lys Ala Ser Gly Tyr Ala Phe Thr Ser Tyr
                20                  25                  30

Tyr Met His Trp Ala Arg Gln Ala Pro Gly Gln Gly Leu Glu Trp Met
                35                  40                  45

Gly Ile Ile Asn Pro Arg Gly Gly Ser Ala Ser Tyr Ala Gln Lys Phe
                50                  55                  60

Gln Gly Arg Val Ser Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Lys Tyr Trp Met Tyr Asp Trp Gly Lys Gly Thr Leu Val
                100                 105                 110

Thr Val Ser Ser

<210> SEQ ID NO 243
<211> LENGTH: 5
<212> TYPE: PRT
<213> ORGANISM: Homo sapiens
<220> FEATURE:
<223> OTHER INFORMATION: Antibody 25

<400> SEQUENCE: 243

Ser Tyr Tyr Met His
                5

<210> SEQ ID NO 244
<211> LENGTH: 17
<212> TYPE: PRT
<213> ORGANISM: Homo sapiens
<220> FEATURE:
<223> OTHER INFORMATION: Antibody 25

<400> SEQUENCE: 244

Ile Ile Asn Pro Arg Gly Gly Ser Ala Ser Tyr Ala Gln Lys Phe Gln
                5                   10                  15
Gly

<210> SEQ ID NO 245
<211> LENGTH: 7
<212> TYPE: PRT
<213> ORGANISM: Homo sapiens
<220> FEATURE:
<223> OTHER INFORMATION: Antibody 25

<400> SEQUENCE: 245

Gly Lys Tyr Trp Met Tyr Asp
                5

<210> SEQ ID NO 246
<211> LENGTH: 333
<212> TYPE: DNA
<213> ORGANISM: Homo sapiens
<220> FEATURE:
<223> OTHER INFORMATION: Antibody 25

<400> SEQUENCE: 246
cagtctgtgt tgacgcagcc gccctcagtg tctgcggccc cgggacagaa ggtcaccatc      60
tcctgctctg gaggcagctc caacattggg aatagttatg tatcctggta ccagcaactc     120
ccaggaacag cccccaaact cctcatttac gacaataata agcgaccctc agggattcct     180
gaccgattct ctggctccaa gtctggcacg acagccaccc tggccatcac cggactccag     240
actggggacg aggccgatta ttactgcgga acatgggtta ccagcacggt gtgggagtgg     300
ccgttcggaa ctgggaccaa gctgaccgtc cta                                  333

<210> SEQ ID NO 247
<211> LENGTH: 111
<212> TYPE: PRT
<213> ORGANISM: Homo sapiens
<220> FEATURE:
<223> OTHER INFORMATION: Antibody 25

<400> SEQUENCE: 247

Gln Ser Val Leu Thr Gln Pro Pro Ser Val Ser Ala Ala Pro Gly Gln
                5                   10                  15
Lys Val Thr Ile Ser Cys Ser Gly Gly Ser Ser Asn Ile Gly Asn Ser
            20                  25                  30

```
Tyr Val Ser Trp Tyr Gln Gln Leu Pro Gly Thr Ala Pro Lys Leu Leu
         35                  40                  45

Ile Tyr Asp Asn Asn Lys Arg Pro Ser Gly Ile Pro Asp Arg Phe Ser
 50                  55                  60

Gly Ser Lys Ser Gly Thr Thr Ala Thr Leu Ala Ile Thr Gly Leu Gln
 65                  70                  75                  80

Thr Gly Asp Glu Ala Asp Tyr Tyr Cys Gly Thr Trp Val Thr Ser Thr
                 85                  90                  95

Val Trp Glu Trp Pro Phe Gly Thr Gly Thr Lys Leu Thr Val Leu
            100                 105                 110

<210> SEQ ID NO 248
<211> LENGTH: 13
<212> TYPE: PRT
<213> ORGANISM: Homo sapiens
<220> FEATURE:
<223> OTHER INFORMATION: Antibody 25

<400> SEQUENCE: 248

Ser Gly Gly Ser Ser Asn Ile Gly Asn Ser Tyr Val Ser
                 5                  10

<210> SEQ ID NO 249
<211> LENGTH: 7
<212> TYPE: PRT
<213> ORGANISM: Homo sapiens
<220> FEATURE:
<223> OTHER INFORMATION: Antibody 25

<400> SEQUENCE: 249

Asp Asn Asn Lys Arg Pro Ser
                 5

<210> SEQ ID NO 250
<211> LENGTH: 12
<212> TYPE: PRT
<213> ORGANISM: Homo sapiens
<220> FEATURE:
<223> OTHER INFORMATION: Antibody 25

<400> SEQUENCE: 250

Gly Thr Trp Val Thr Ser Thr Val Trp Glu Trp Pro
                 5                  10

<210> SEQ ID NO 251
<211> LENGTH: 348
<212> TYPE: DNA
<213> ORGANISM: Homo sapiens
<220> FEATURE:
<223> OTHER INFORMATION: Antibody 26

<400> SEQUENCE: 251
caggtccagc tggtgcagtc tggggctgag gtgaagaagc ctggggcctc agtgaaggtt      60
tcctgcaagg catctggata cgccttcacc agctactata tgcactgggc gcgacaggcc     120
cctggacaag ggcttgagtg gatgggaata atcaaccctg tggtggtag cacaagctac      180 gcacagaagt tccagggcag agtcaccatg accagggaca cgtccacgag cacagtctac     240
atggagctga gcagcctgag atctgaggac acggccgtgt attactgtgc gagaggaaag     300
tactggatgt acgactgggg caaaggcacc ctggtcaccg tctcgagt                  348

<210> SEQ ID NO 252
<211> LENGTH: 116
```

```
<212> TYPE: PRT
<213> ORGANISM: Homo sapiens
<220> FEATURE:
<223> OTHER INFORMATION: Antibody 26

<400> SEQUENCE: 252

Gln Val Gln Leu Val Gln Ser Gly Ala Glu Val Lys Lys Pro Gly Ala
                 5                  10                  15
Ser Val Lys Val Ser Cys Lys Ala Ser Gly Tyr Ala Phe Thr Ser Tyr
             20                  25                  30
Tyr Met His Trp Ala Arg Gln Ala Pro Gly Gln Gly Leu Glu Trp Met
         35                  40                  45
Gly Ile Ile Asn Pro Ser Gly Gly Ser Thr Ser Tyr Ala Gln Lys Phe
     50                  55                  60
Gln Gly Arg Val Thr Met Thr Arg Asp Thr Ser Thr Ser Thr Val Tyr
 65                  70                  75                  80
Met Glu Leu Ser Ser Leu Arg Ser Glu Asp Thr Ala Val Tyr Tyr Cys
                 85                  90                  95
Ala Arg Gly Lys Tyr Trp Met Tyr Asp Trp Gly Lys Gly Thr Leu Val
            100                 105                 110
Thr Val Ser Ser
        115

<210> SEQ ID NO 253
<211> LENGTH: 5
<212> TYPE: PRT
<213> ORGANISM: Homo sapiens
<220> FEATURE:
<223> OTHER INFORMATION: Antibody 26

<400> SEQUENCE: 253

Ser Tyr Tyr Met His
                 5

<210> SEQ ID NO 254
<211> LENGTH: 17
<212> TYPE: PRT
<213> ORGANISM: Homo sapiens
<220> FEATURE:
<223> OTHER INFORMATION: Antibody 26

<400> SEQUENCE: 254

Ile Ile Asn Pro Ser Gly Gly Ser Thr Ser Tyr Ala Gln Lys Phe Gln
                 5                  10                  15
Gly

<210> SEQ ID NO 255
<211> LENGTH: 7
<212> TYPE: PRT
<213> ORGANISM: Homo sapiens
<220> FEATURE:
<223> OTHER INFORMATION: Antibody 26

<400> SEQUENCE: 255

Gly Lys Tyr Trp Met Tyr Asp
                 5

<210> SEQ ID NO 256
<211> LENGTH: 333
<212> TYPE: DNA
<213> ORGANISM: Homo sapiens
<220> FEATURE:
<223> OTHER INFORMATION: Antibody 26
```

-continued

<400> SEQUENCE: 256

```
cagtctgtgt tgacgcagcc gccctcagtg tctgcggccc caggacagaa ggtcaccatc    60
tcctgctctg gaggcagctc caacattggg aatagttatg tatcctggta ccagcaactc   120
ccaggaacag ccccaaaact cctcatttac gacaataata agcgaccctc agggattcct   180
gaccgattct ctggctccaa gtctggcacg tcagccaccc tggccatcac cggactccag   240
actggggacg aggccgatta tttctgcgga acatgggata ccagcaccgt gtgggagtgg   300
ccgttcggaa ctgggaccaa gctgaccgtc cta                                333
```

<210> SEQ ID NO 257
<211> LENGTH: 111
<212> TYPE: PRT
<213> ORGANISM: Homo sapiens
<220> FEATURE:
<223> OTHER INFORMATION: Antibody 26

<400> SEQUENCE: 257

Gln Ser Val Leu Thr Gln Pro Pro Ser Val Ser Ala Ala Pro Gly Gln
                5                  10                  15
Lys Val Thr Ile Ser Cys Ser Gly Gly Ser Ser Asn Ile Gly Asn Ser
            20                  25                  30
Tyr Val Ser Trp Tyr Gln Gln Leu Pro Gly Thr Ala Pro Lys Leu Leu
        35                  40                  45
Ile Tyr Asp Asn Asn Lys Arg Pro Ser Gly Ile Pro Asp Arg Phe Ser
    50                  55                  60
Gly Ser Lys Ser Gly Thr Ser Ala Thr Leu Ala Ile Thr Gly Leu Gln
65                  70                  75                  80
Thr Gly Asp Glu Ala Asp Tyr Phe Cys Gly Thr Trp Asp Thr Ser Thr
                85                  90                  95
Val Trp Glu Trp Pro Phe Gly Thr Gly Thr Lys Leu Thr Val Leu
            100                 105                 110

<210> SEQ ID NO 258
<211> LENGTH: 13
<212> TYPE: PRT
<213> ORGANISM: Homo sapiens
<220> FEATURE:
<223> OTHER INFORMATION: Antibody 26

<400> SEQUENCE: 258

Ser Gly Gly Ser Ser Asn Ile Gly Asn Ser Tyr Val Ser
                5                  10

<210> SEQ ID NO 259
<211> LENGTH: 7
<212> TYPE: PRT
<213> ORGANISM: Homo sapiens
<220> FEATURE:
<223> OTHER INFORMATION: Antibody 26

<400> SEQUENCE: 259

Asp Asn Asn Lys Arg Pro Ser
                5

<210> SEQ ID NO 260
<211> LENGTH: 12
<212> TYPE: PRT
<213> ORGANISM: Homo sapiens
<220> FEATURE:
<223> OTHER INFORMATION: Antibody 26

<400> SEQUENCE: 260

Gly Thr Trp Asp Thr Ser Thr Val Trp Glu Trp Pro
            5               10

<210> SEQ ID NO 261
<211> LENGTH: 348
<212> TYPE: DNA
<213> ORGANISM: Homo sapiens
<220> FEATURE:
<223> OTHER INFORMATION: Antibody 27

<400> SEQUENCE: 261
caggtccagc tggtgcagtc tggggctgag gtgaggaagc ctggggcctc agtgaaggtt     60
tcctgcaagg catctggata cgccttcacc agctactata tgcactgggc gcgacaggcc    120
cctggacaag gcttgagtg gatgggaata atcaaccta gtggtggtag cacaagctac      180
gcacagaagt tccagggcag agttaccatg accagggaca cgtccacgag cacggtctac    240
atggagctga gcagcctgag acctgaggac acggccgtgt attactgtgc gagaggaaag    300
tactggatgt acgactgggg caaaggcacc caggtcaccg tctcgagt               348

<210> SEQ ID NO 262
<211> LENGTH: 116
<212> TYPE: PRT
<213> ORGANISM: Homo sapiens
<220> FEATURE:
<223> OTHER INFORMATION: Antibody 27

<400> SEQUENCE: 262

Gln Val Gln Leu Val Gln Ser Gly Ala Glu Val Arg Lys Pro Gly Ala
                5               10                  15

Ser Val Lys Val Ser Cys Lys Ala Ser Gly Tyr Ala Phe Thr Ser Tyr
            20                  25                  30

Tyr Met His Trp Ala Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Pro Glu Asp Thr Ala Val Tyr Tyr Cys
                85                  90                  95

Ala Arg Gly Lys Tyr Trp Met Tyr Asp Trp Gly Lys Gly Thr Gln Val
            100                 105                 110

Thr Val Ser Ser
        115

<210> SEQ ID NO 263
<211> LENGTH: 5
<212> TYPE: PRT
<213> ORGANISM: Homo sapiens
<220> FEATURE:
<223> OTHER INFORMATION: Antibody 27

<400> SEQUENCE: 263

Ser Tyr Tyr Met His
                5

<210> SEQ ID NO 264
<211> LENGTH: 17
<212> TYPE: PRT
<213> ORGANISM: Homo sapiens
<220> FEATURE:
<223> OTHER INFORMATION: Antibody 27

<400> SEQUENCE: 264

Ile Ile Asn Pro Ser Gly Gly Ser Thr Ser Tyr Ala Gln Lys Phe Gln
                5                   10                  15
Gly

<210> SEQ ID NO 265
<211> LENGTH: 7
<212> TYPE: PRT
<213> ORGANISM: Homo sapiens
<220> FEATURE:
<223> OTHER INFORMATION: Antibody 27

<400> SEQUENCE: 265

Gly Lys Tyr Trp Met Tyr Asp
                5

<210> SEQ ID NO 266
<211> LENGTH: 333
<212> TYPE: DNA
<213> ORGANISM: Homo sapiens
<220> FEATURE:
<223> OTHER INFORMATION: Antibody 27

<400> SEQUENCE: 266
cagtctgtgt tgacgcagcc gcccttagtg tctgcggccc caggacagaa ggtcaccatc      60
tcctgctctg gaggcagctc aacattggga atagttatg tatcctggta ccagcgactc     120
ccaggaacag cccccaaact cctcatttac gacaataata agcgaccctc agggattcct     180
gaccgattct ctggctccaa gtctggcacg tcagccaccc tggccatcac cggactccag     240 actgggacg aggccgatta ttactgcgga acatgggata ccagcacggt gtgggagtgg     300
ccgttcggaa ctgggaccaa gctgaccgtc cta                                   333

<210> SEQ ID NO 267
<211> LENGTH: 111
<212> TYPE: PRT
<213> ORGANISM: Homo sapiens
<220> FEATURE:
<223> OTHER INFORMATION: Antibody 27

<400> SEQUENCE: 267

Gln Ser Val Leu Thr Gln Pro Pro Leu Val Ser Ala Ala Pro Gly Gln
                5                   10                  15

Lys Val Thr Ile Ser Cys Ser Gly Gly Ser Ser Asn Ile Gly Asn Ser
            20                  25                  30

Tyr Val Ser Trp Tyr Gln Arg Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Ala Ile Thr Gly Leu Gln
65                  70                  75                  80

Thr Gly Asp Glu Ala Asp Tyr Tyr Cys Gly Thr Trp Asp Thr Ser Thr
                85                  90                  95

Val Trp Glu Trp Pro Phe Gly Thr Gly Thr Lys Leu Thr Val Leu
            100                 105                 110

<210> SEQ ID NO 268
<211> LENGTH: 13
<212> TYPE: PRT
<213> ORGANISM: Homo sapiens
<220> FEATURE:

<223> OTHER INFORMATION: Antibody 27

<400> SEQUENCE: 268

Ser Gly Gly Ser Ser Asn Ile Gly Asn Ser Tyr Val Ser
                5                   10

<210> SEQ ID NO 269
<211> LENGTH: 7
<212> TYPE: PRT
<213> ORGANISM: Homo sapiens
<220> FEATURE:
<223> OTHER INFORMATION: Antibody 27

<400> SEQUENCE: 269

Asp Asn Asn Lys Arg Pro Ser
                5

<210> SEQ ID NO 270
<211> LENGTH: 12
<212> TYPE: PRT
<213> ORGANISM: Homo sapiens
<220> FEATURE:
<223> OTHER INFORMATION: Antibody 27

<400> SEQUENCE: 270

Gly Thr Trp Asp Thr Ser Thr Val Trp Glu Trp Pro
                5                   10

<210> SEQ ID NO 271
<211> LENGTH: 348
<212> TYPE: DNA
<213> ORGANISM: Homo sapiens
<220> FEATURE:
<223> OTHER INFORMATION: Antibody 28

<400> SEQUENCE: 271
caggtccagc tggtgcagtc tggggctgag gtgaagaagc ctggggcctc agtgaaggtt      60
tcctgcaagg catctggata cgccttcacc agctactata tgcactgggc gcgacaggcc     120
cctggacaag gcttgagtg gatgggaata atcaaccta gtggtggtag cacaagctac       180
gcacagaagt tccagggcag agtcaccatg accagggaca cgtccacgag cacagtctac     240
atggagctga gcagcctgag atctgaagac acggccgtgt attactgtgc gagaggaaag     300
tactggatgt acgactgggg caacggcacc ctggtcaccg tctcgagt                  348

<210> SEQ ID NO 272
<211> LENGTH: 116
<212> TYPE: PRT
<213> ORGANISM: Homo sapiens
<220> FEATURE:
<223> OTHER INFORMATION: Antibody 28

<400> SEQUENCE: 272

Gln Val Gln Leu Val Gln Ser Gly Ala Glu Val Lys Lys Pro Gly Ala
                5                   10                  15

Ser Val Lys Val Ser Cys Lys Ala Ser Gly Tyr Ala Phe Thr Ser Tyr
            20                  25                  30

Tyr Met His Trp Ala Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
            85                  90                  95

Ala Arg Gly Lys Tyr Trp Met Tyr Asp Trp Gly Asn Gly Thr Leu Val
            100                 105                 110

Thr Val Ser Ser
        115

<210> SEQ ID NO 273
<211> LENGTH: 5
<212> TYPE: PRT
<213> ORGANISM: Homo sapiens
<220> FEATURE:
<223> OTHER INFORMATION: Antibody 28

<400> SEQUENCE: 273

Ser Tyr Tyr Met His
              5

<210> SEQ ID NO 274
<211> LENGTH: 17
<212> TYPE: PRT
<213> ORGANISM: Homo sapiens
<220> FEATURE:
<223> OTHER INFORMATION: Antibody 28

<400> SEQUENCE: 274

Ile Ile Asn Pro Ser Gly Gly Ser Thr Ser Tyr Ala Gln Lys Phe Gln
                 5                  10                  15

Gly

<210> SEQ ID NO 275
<211> LENGTH: 7
<212> TYPE: PRT
<213> ORGANISM: Homo sapiens
<220> FEATURE:
<223> OTHER INFORMATION: Antibody 28

<400> SEQUENCE: 275

Gly Lys Tyr Trp Met Tyr Asp
             5

<210> SEQ ID NO 276
<211> LENGTH: 333
<212> TYPE: DNA
<213> ORGANISM: Homo sapiens
<220> FEATURE:
<223> OTHER INFORMATION: Antibody 28

<400> SEQUENCE: 276
ctgcctgtgt tgacgcagcc gccctcagtg tctgcggccc caggacagaa ggtcaccatc      60
tcctgctctg gaggcagctc cagcattggg aatagttatg tatcctggta ccagcaactc     120
ccaggagcag cccccaaact cctcatttac gacaacaata gcgaccctc agggattcct      180 gaccgattct ctggcttcag gtctggcacg tcagccaccc tggccatcac cggactccag     240
actggggacg aggccgatta ttactgcgga acatgggata ccagcccggt gtgggagtgg     300
ccgttcggaa ctgggaccaa gctgaccgtc cta                                  333

<210> SEQ ID NO 277
<211> LENGTH: 111
<212> TYPE: PRT
<213> ORGANISM: Homo sapiens
<220> FEATURE:
<223> OTHER INFORMATION: Antibody 28

<400> SEQUENCE: 277

Leu Pro Val Leu Thr Gln Pro Pro Ser Val Ser Ala Ala Pro Gly Gln
 1               5                  10                  15

Lys Val Thr Ile Ser Cys Ser Gly Gly Ser Ser Ile Gly Asn Ser
             20                  25                  30

Tyr Val Ser Trp Tyr Gln Gln Leu Pro Gly Ala Ala Pro Lys Leu Leu
             35                  40                  45

Ile Tyr Asp Asn Asn Lys Arg Pro Ser Gly Ile Pro Asp Arg Phe Ser
 50                  55                  60

Gly Phe Arg Ser Gly Thr Ser Ala Thr Leu Ala Ile Thr Gly Leu Gln
 65                  70                  75                  80

Thr Gly Asp Glu Ala Asp Tyr Tyr Cys Gly Thr Trp Asp Thr Ser Pro
                 85                  90                  95

Val Trp Glu Trp Pro Phe Gly Thr Gly Thr Lys Leu Thr Val Leu
            100                 105                 110

<210> SEQ ID NO 278
<211> LENGTH: 13
<212> TYPE: PRT
<213> ORGANISM: Homo sapiens
<220> FEATURE:
<223> OTHER INFORMATION: Antibody 28

<400> SEQUENCE: 278

Ser Gly Gly Ser Ser Ile Gly Asn Ser Tyr Val Ser
 1               5                  10

<210> SEQ ID NO 279
<211> LENGTH: 7
<212> TYPE: PRT
<213> ORGANISM: Homo sapiens
<220> FEATURE:
<223> OTHER INFORMATION: Antibody 28

<400> SEQUENCE: 279

Asp Asn Asn Lys Arg Pro Ser
 1               5

<210> SEQ ID NO 280
<211> LENGTH: 12
<212> TYPE: PRT
<213> ORGANISM: Homo sapiens
<220> FEATURE:
<223> OTHER INFORMATION: Antibody 28

<400> SEQUENCE: 280

Gly Thr Trp Asp Thr Ser Pro Val Trp Glu Trp Pro
 1               5                  10

<210> SEQ ID NO 281
<211> LENGTH: 348
<212> TYPE: DNA
<213> ORGANISM: Homo sapiens
<220> FEATURE:
<223> OTHER INFORMATION: Antibody 29

<400> SEQUENCE: 281
caggtccagc tggtgcagtc tggggctgag gtgaagaagc ctggggcctc agtgaaggtt      60
tcctgcaagg catctggata cgccttcacc agctactata tgcactgggc gcgacaggcc    120
cctggacaag ggcttgagtg gatgggaata atcaacccta gtggtggtag cacaagctac    180
gcacagaagt tccagggcag agtcaccatg accagggaca cgtccacgag cacagtctac    240

```
atggagctga gcagcctgag atctgaggac acggccgtgt attactgtgc gagaggaaag    300
tactggatgt acgactgggg caaaggcacc cgggtcaccg tctcgagt                 348
```

<210> SEQ ID NO 282
<211> LENGTH: 116
<212> TYPE: PRT
<213> ORGANISM: Homo sapiens
<220> FEATURE:
<223> OTHER INFORMATION: Antibody 29

<400> SEQUENCE: 282

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Ser Tyr
            20                  25                  30

Tyr Met His Trp Ala Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Lys Tyr Trp Met Tyr Asp Trp Gly Lys Gly Thr Arg Val
            100                 105                 110

Thr Val Ser Ser
        115

<210> SEQ ID NO 283
<211> LENGTH: 5
<212> TYPE: PRT
<213> ORGANISM: Homo sapiens
<220> FEATURE:
<223> OTHER INFORMATION: Antibody 29

<400> SEQUENCE: 283

Ser Tyr Tyr Met His
1               5

<210> SEQ ID NO 284
<211> LENGTH: 17
<212> TYPE: PRT
<213> ORGANISM: Homo sapiens
<220> FEATURE:
<223> OTHER INFORMATION: Antibody 29

<400> SEQUENCE: 284

Ile Ile Asn Pro Ser Gly Gly Ser Thr Ser Tyr Ala Gln Lys Phe Gln
1               5                   10                  15

Gly

<210> SEQ ID NO 285
<211> LENGTH: 7
<212> TYPE: PRT
<213> ORGANISM: Homo sapiens
<220> FEATURE:
<223> OTHER INFORMATION: Antibody 29

<400> SEQUENCE: 285

Gly Lys Tyr Trp Met Tyr Asp
1               5

<210> SEQ ID NO 286
<211> LENGTH: 333
<212> TYPE: DNA
<213> ORGANISM: Homo sapiens
<220> FEATURE:
<223> OTHER INFORMATION: Antibody 29

<400> SEQUENCE: 286

```
cagtctgtgt tgacgcagcc gccctcagtg tctgcggccc caggacagaa ggtcaccatc      60
tcctgctctg gaggcagctc caacattggg aatagttatg tatcctggta ccagcaactc     120
ccaggaacag cccccaaact cctcatttac gacaataata gcgaccctca agggattcct     180
gaccgattct ctggctccaa gtctggcacg tcagccaccc tggccatcac cggactccag     240
actggggacg aggccgatta ttactgcgga acatgggata ccagcccggt gtgggagtgg     300
ccgttcggaa ctgggaccaa gctgaccgtc cta                                   333
```

<210> SEQ ID NO 287
<211> LENGTH: 111
<212> TYPE: PRT
<213> ORGANISM: Homo sapiens
<220> FEATURE:
<223> OTHER INFORMATION: Antibody 29

<400> SEQUENCE: 287

Gln Ser Val Leu Thr Gln Pro Pro Ser Val Ala Ala Pro Gly Gln
                 5                  10                  15
Lys Val Thr Ile Ser Cys Ser Gly Gly Ser Ser Asn Ile Gly Asn Ser
             20                  25                  30
Tyr Val Ser Trp Tyr Gln Gln Leu Pro Gly Thr Ala Pro Lys Leu Leu
         35                  40                  45
Ile Tyr Asp Asn Asn Lys Arg Pro Ser Gly Ile Pro Asp Arg Phe Ser
     50                  55                  60
Gly Ser Lys Ser Gly Thr Ser Ala Thr Leu Ala Ile Thr Gly Leu Gln
 65                  70                  75                  80
Thr Gly Asp Glu Ala Asp Tyr Tyr Cys Gly Thr Trp Asp Thr Ser Pro
                 85                  90                  95
Val Trp Glu Trp Pro Phe Gly Thr Gly Thr Lys Leu Thr Val Leu
            100                 105                 110

<210> SEQ ID NO 288
<211> LENGTH: 13
<212> TYPE: PRT
<213> ORGANISM: Homo sapiens
<220> FEATURE:
<223> OTHER INFORMATION: Antibody 29

<400> SEQUENCE: 288

Ser Gly Gly Ser Ser Asn Ile Gly Asn Ser Tyr Val Ser
                 5                  10

<210> SEQ ID NO 289
<211> LENGTH: 7
<212> TYPE: PRT
<213> ORGANISM: Homo sapiens
<220> FEATURE:
<223> OTHER INFORMATION: Antibody 29

<400> SEQUENCE: 289

Asp Asn Asn Lys Arg Pro Ser
                 5

<210> SEQ ID NO 290

```
<211> LENGTH: 12
<212> TYPE: PRT
<213> ORGANISM: Homo sapiens
<220> FEATURE:
<223> OTHER INFORMATION: Antibody 29

<400> SEQUENCE: 290

Gly Thr Trp Asp Thr Ser Pro Val Trp Glu Trp Pro
                5                   10

<210> SEQ ID NO 291
<211> LENGTH: 348
<212> TYPE: DNA
<213> ORGANISM: Homo sapiens
<220> FEATURE:
<223> OTHER INFORMATION: Antibody 30

<400> SEQUENCE: 291
caggtccagc tggtgcagtc tggggctgag gtgaagaagc ctggggcctc agtgaaggtt     60
tcctgcaagg catctggata cgccttcacc agctactata tgcactgggc gcgacaggcc    120
cctggacaag ggcttgagtg gatggggata atcaaccctg gtggtggtag cacaagctac    180
gcacagaagt tccagggcag agtcaccatg accaggaca cgtccacgag cacagtctac     240
atggagctga gcagcctgag atctgaggac acggccgtgt attactgtgc gagaggaaag    300
tactggatgt acgactgggg caaaggcacc ctggtcaccg tctcgagt                 348

<210> SEQ ID NO 292
<211> LENGTH: 116
<212> TYPE: PRT
<213> ORGANISM: Homo sapiens
<220> FEATURE:
<223> OTHER INFORMATION: Antibody 30

<400> SEQUENCE: 292

Gln Val Gln Leu Val Gln Ser Gly Ala Glu Val Lys Lys Pro Gly Ala
                5                   10                  15

Ser Val Lys Val Ser Cys Lys Ala Ser Gly Tyr Ala Phe Thr Ser Tyr
            20                  25                  30

Tyr Met His Trp Ala Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Lys Tyr Trp Met Tyr Asp Trp Gly Lys Gly Thr Leu Val
            100                 105                 110

Thr Val Ser Ser
        115

<210> SEQ ID NO 293
<211> LENGTH: 5
<212> TYPE: PRT
<213> ORGANISM: Homo sapiens
<220> FEATURE:
<223> OTHER INFORMATION: Antibody 30

<400> SEQUENCE: 293

Ser Tyr Tyr Met His
                5
```

```
<210> SEQ ID NO 294
<211> LENGTH: 17
<212> TYPE: PRT
<213> ORGANISM: Homo sapiens
<220> FEATURE:
<223> OTHER INFORMATION: Antibody 30

<400> SEQUENCE: 294

Ile Ile Asn Pro Ser Gly Gly Ser Thr Ser Tyr Ala Gln Lys Phe Gln
                 5                  10                  15
Gly

<210> SEQ ID NO 295
<211> LENGTH: 7
<212> TYPE: PRT
<213> ORGANISM: Homo sapiens
<220> FEATURE:
<223> OTHER INFORMATION: Antibody 30

<400> SEQUENCE: 295

Gly Lys Tyr Trp Met Tyr Asp
                 5

<210> SEQ ID NO 296
<211> LENGTH: 333
<212> TYPE: DNA
<213> ORGANISM: Homo sapiens
<220> FEATURE:
<223> OTHER INFORMATION: Antibody 30

<400> SEQUENCE: 296
cagtctgtgt tgacgcagcc gccctcagtg tctgcggccc caggacagaa ggtcaccatc      60
tcctgctctg ggggcagctc caacattggg aatagttatg tatcctggta ccagcgactc     120
ccaggagcag cccccaaact cctcatttac gacaataata agcgaccctc agggattcct     180
gaccgattct ctggctccaa gtctggcacg tcagccaccc tggccatcac cggactccag     240
actggggacg aggccgatta ttactgcgga acatgggata ccagcacggt gtgggagtgg     300
ccgttcggaa ctgggaccaa gctgaccgtc cta                                  333

<210> SEQ ID NO 297
<211> LENGTH: 111
<212> TYPE: PRT
<213> ORGANISM: Homo sapiens
<220> FEATURE:
<223> OTHER INFORMATION: Antibody 30

<400> SEQUENCE: 297

Gln Ser Val Leu Thr Gln Pro Pro Ser Val Ser Ala Ala Pro Gly Gln
                 5                  10                  15

Lys Val Thr Ile Ser Cys Ser Gly Gly Ser Ser Asn Ile Gly Asn Ser
             20                  25                  30

Tyr Val Ser Trp Tyr Gln Arg Leu Pro Gly Ala Ala Pro Lys Leu Leu
         35                  40                  45

Ile Tyr Asp Asn Asn Lys Arg Pro Ser Gly Ile Pro Asp Arg Phe Ser
     50                  55                  60

Gly Ser Lys Ser Gly Thr Ser Ala Thr Leu Ala Ile Thr Gly Leu Gln
 65                  70                  75                  80

Thr Gly Asp Glu Ala Asp Tyr Tyr Cys Gly Thr Trp Asp Thr Ser Thr
                 85                  90                  95

Val Trp Glu Trp Pro Phe Gly Thr Gly Thr Lys Leu Thr Val Leu
            100                 105                 110
```

<210> SEQ ID NO 298
<211> LENGTH: 13
<212> TYPE: PRT
<213> ORGANISM: Homo sapiens
<220> FEATURE:
<223> OTHER INFORMATION: Antibody 30

<400> SEQUENCE: 298

Ser Gly Gly Ser Ser Asn Ile Gly Asn Ser Tyr Val Ser
                 5                  10

<210> SEQ ID NO 299
<211> LENGTH: 7
<212> TYPE: PRT
<213> ORGANISM: Homo sapiens
<220> FEATURE:
<223> OTHER INFORMATION: Antibody 30

<400> SEQUENCE: 299

Asp Asn Asn Lys Arg Pro Ser
                 5

<210> SEQ ID NO 300
<211> LENGTH: 12
<212> TYPE: PRT
<213> ORGANISM: Homo sapiens
<220> FEATURE:
<223> OTHER INFORMATION: Antibody 30

<400> SEQUENCE: 300

Gly Thr Trp Asp Thr Ser Thr Val Trp Glu Trp Pro
                 5                  10

<210> SEQ ID NO 301
<211> LENGTH: 348
<212> TYPE: DNA
<213> ORGANISM: Homo sapiens
<220> FEATURE:
<223> OTHER INFORMATION: Antibody 31

<400> SEQUENCE: 301
caggtccagc tggtgcagtc tggggctgag gtgaagaagc ctggggcctc agtgaaggtt      60
tcctgcaagg catctggata cgccttcacc agctactata tgcactgggc gcgacaggcc     120
cctggacaag gcttgagtg gatgggaata atcaaccta gtggtggtag cacaagctac      180
gcacagaagt tccagggcag agtcaccatg accagggaca cgtccacgag cacagtctac     240
atggagctga gcagcctgag atctgaggac acggccgtgt attactgtgc gagaggaaag     300
tactggatgt acgactgggg caaaggcacc ctggtcaccg tctcgagt                  348

<210> SEQ ID NO 302
<211> LENGTH: 116
<212> TYPE: PRT
<213> ORGANISM: Homo sapiens
<220> FEATURE:
<223> OTHER INFORMATION: Antibody 31

<400> SEQUENCE: 302

Gln Val Gln Leu Val Gln Ser Gly Ala Glu Val Lys Lys Pro Gly Ala
                 5                  10                  15

Ser Val Lys Val Ser Cys Lys Ala Ser Gly Tyr Ala Phe Thr Ser Tyr
            20                  25                  30

Tyr Met His Trp Ala Arg Gln Ala Pro Gly Gln Gly Leu Glu Trp Met
        35                  40                  45

```
Gly Ile Ile Asn Pro Ser Gly Gly Ser Thr Ser Tyr Ala Gln Lys Phe
     50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Gly Lys Tyr Trp Met Tyr Asp Trp Gly Lys Gly Thr Leu Val
            100                 105                 110

Thr Val Ser Ser
        115

<210> SEQ ID NO 303
<211> LENGTH: 5
<212> TYPE: PRT
<213> ORGANISM: Homo sapiens
<220> FEATURE:
<223> OTHER INFORMATION: Antibody 31

<400> SEQUENCE: 303

Ser Tyr Tyr Met His
                5

<210> SEQ ID NO 304
<211> LENGTH: 17
<212> TYPE: PRT
<213> ORGANISM: Homo sapiens
<220> FEATURE:
<223> OTHER INFORMATION: Antibody 31

<400> SEQUENCE: 304

Ile Ile Asn Pro Ser Gly Gly Ser Thr Ser Tyr Ala Gln Lys Phe Gln
                 5                  10                  15

Gly

<210> SEQ ID NO 305
<211> LENGTH: 7
<212> TYPE: PRT
<213> ORGANISM: Homo sapiens
<220> FEATURE:
<223> OTHER INFORMATION: Antibody 31

<400> SEQUENCE: 305

Gly Lys Tyr Trp Met Tyr Asp
                5

<210> SEQ ID NO 306
<211> LENGTH: 333
<212> TYPE: DNA
<213> ORGANISM: Homo sapiens
<220> FEATURE:
<223> OTHER INFORMATION: Antibody 31

<400> SEQUENCE: 306
cagtctgtgt tgacgcagcc gccctcagtg tctgcggccc caggacagaa ggtcaccatc      60
tcctgctctg gaggcagctc cagcattggg aatagttatg tatcctggta ccagcaactc     120
ccaggaacag cccccaaact cctcatttac gacaataata gcgaccctca gggattcct     180 gaccgattct ctggctccaa gtctggcacg tcagccaccc tggccatcac cggactccag     240
actggggacg aggccgatta ttactgcgga acatgggcta ccagcccggt gtgggagtgg     300
ccgttcggaa ctgggaccaa gctgaccgtc cta                                   333
```

```
<210> SEQ ID NO 307
<211> LENGTH: 111
<212> TYPE: PRT
<213> ORGANISM: Homo sapiens
<220> FEATURE:
<223> OTHER INFORMATION: Antibody 31

<400> SEQUENCE: 307

Gln Ser Val Leu Thr Gln Pro Pro Ser Val Ser Ala Ala Pro Gly Gln
                 5                  10                  15
Lys Val Thr Ile Ser Cys Ser Gly Gly Ser Ser Ile Gly Asn Ser
         20                  25                  30
Tyr Val Ser Trp Tyr Gln Leu Pro Gly Thr Ala Pro Lys Leu Leu
     35                  40                  45
Ile Tyr Asp Asn Asn Lys Arg Pro Ser Gly Ile Pro Asp Arg Phe Ser
 50                  55                  60
Gly Ser Lys Ser Gly Thr Ser Ala Thr Leu Ala Ile Thr Gly Leu Gln
 65                  70                  75                  80
Thr Gly Asp Glu Ala Asp Tyr Tyr Cys Gly Thr Trp Ala Thr Ser Pro
                 85                  90                  95
Val Trp Glu Trp Pro Phe Gly Gly Thr Lys Leu Thr Val Leu
            100                 105                 110

<210> SEQ ID NO 308
<211> LENGTH: 13
<212> TYPE: PRT
<213> ORGANISM: Homo sapiens
<220> FEATURE:
<223> OTHER INFORMATION: Antibody 31

<400> SEQUENCE: 308

Ser Gly Gly Ser Ser Ile Gly Asn Ser Tyr Val Ser
                 5                  10

<210> SEQ ID NO 309
<211> LENGTH: 7
<212> TYPE: PRT
<213> ORGANISM: Homo sapiens
<220> FEATURE:
<223> OTHER INFORMATION: Antibody 31

<400> SEQUENCE: 309

Asp Asn Asn Lys Arg Pro Ser
                 5

<210> SEQ ID NO 310
<211> LENGTH: 12
<212> TYPE: PRT
<213> ORGANISM: Homo sapiens
<220> FEATURE:
<223> OTHER INFORMATION: Antibody 31

<400> SEQUENCE: 310

Gly Thr Trp Ala Thr Ser Pro Val Trp Glu Trp Pro
                 5                  10

<210> SEQ ID NO 311
<211> LENGTH: 348
<212> TYPE: DNA
<213> ORGANISM: Homo sapiens
<220> FEATURE:
<223> OTHER INFORMATION: Antibody 32

<400> SEQUENCE: 311
caggtccagc tggtgcagtc tggggctgag gtgaagaagc ctggggcctc agtgaaggtt      60
```

```
tcctgcaagg catctggata cgccttcacc agctactata tgcactgggc gcgacaggcc    120
cctggacaag ggcttgagtg gatgggaata atcaacccta gtggtggtag cacaagctac    180
gcacagaagt tccagggcag agtcaccatg accagggaca cgtccacgag cacagtctac    240
atggagctga gcagcctgag atctgaggac acggccgtgt attactgtgc gagaggaaag    300
tactggatgt acgactgggg caaaggcacc ctggtcaccg tctcgagt               348
```

```
<210> SEQ ID NO 312
<211> LENGTH: 116
<212> TYPE: PRT
<213> ORGANISM: Homo sapiens
<220> FEATURE:
<223> OTHER INFORMATION: Antibody 32

<400> SEQUENCE: 312
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Ser Tyr
            20                  25                  30

Tyr Met His Trp Ala Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Lys Tyr Trp Met Tyr Asp Trp Gly Lys Gly Thr Leu Val
            100                 105                 110

Thr Val Ser Ser
        115

```
<210> SEQ ID NO 313
<211> LENGTH: 5
<212> TYPE: PRT
<213> ORGANISM: Homo sapiens
<220> FEATURE:
<223> OTHER INFORMATION: Antibody 32

<400> SEQUENCE: 313
```

Ser Tyr Tyr Met His
1               5

```
<210> SEQ ID NO 314
<211> LENGTH: 17
<212> TYPE: PRT
<213> ORGANISM: Homo sapiens
<220> FEATURE:
<223> OTHER INFORMATION: Antibody 32

<400> SEQUENCE: 314
```

Ile Ile Asn Pro Ser Gly Gly Ser Thr Ser Tyr Ala Gln Lys Phe Gln
1               5                   10                  15

Gly

```
<210> SEQ ID NO 315
<211> LENGTH: 7
<212> TYPE: PRT
<213> ORGANISM: Homo sapiens
<220> FEATURE:
<223> OTHER INFORMATION: Antibody 32
```

<400> SEQUENCE: 315

Gly Lys Tyr Trp Met Tyr Asp
                5

<210> SEQ ID NO 316
<211> LENGTH: 333
<212> TYPE: DNA
<213> ORGANISM: Homo sapiens
<220> FEATURE:
<223> OTHER INFORMATION: Antibody 32

<400> SEQUENCE: 316

```
cagtctgtgt tgacgcagcc gccctcagtg tctgcggccc caggacagaa ggtcaccatc    60
tcctgctctg gaggcagctc aacattggg aatagttatg tatcctggta ccagcaactc   120
ccaggaacag ccccccaaact cctcatttac gacaataata agcgaccctc agggattcct   180
gaccgattct ctggctccaa gtctggcacg tcagccaccc tggccatcac cggactccag   240
actggggacg aggccgatta tttctgcgga acatgggata ccagcacggc gtgggagtgg   300
ccgttcggaa ctgggaccaa gctgaccgtc cta                                333
```

<210> SEQ ID NO 317
<211> LENGTH: 111
<212> TYPE: PRT
<213> ORGANISM: Homo sapiens
<220> FEATURE:
<223> OTHER INFORMATION: Antibody 32

<400> SEQUENCE: 317

Gln Ser Val Leu Thr Gln Pro Pro Ser Val Ser Ala Ala Pro Gly Gln
                5                  10                  15
Lys Val Thr Ile Ser Cys Ser Gly Gly Ser Ser Asn Ile Gly Asn Ser
            20                  25                  30
Tyr Val Ser Trp Tyr Gln Gln Leu Pro Gly Thr Ala Pro Lys Leu Leu
        35                  40                  45
Ile Tyr Asp Asn Asn Lys Arg Pro Ser Gly Ile Pro Asp Arg Phe Ser
    50                  55                  60
Gly Ser Lys Ser Gly Thr Ser Ala Thr Leu Ala Ile Thr Gly Leu Gln
65                  70                  75                  80
Thr Gly Asp Glu Ala Asp Tyr Phe Cys Gly Thr Trp Asp Thr Ser Thr
                85                  90                  95
Ala Trp Glu Trp Pro Phe Gly Thr Gly Thr Lys Leu Thr Val Leu
            100                 105                 110

<210> SEQ ID NO 318
<211> LENGTH: 13
<212> TYPE: PRT
<213> ORGANISM: Homo sapiens
<220> FEATURE:
<223> OTHER INFORMATION: Antibody 32

<400> SEQUENCE: 318

Ser Gly Gly Ser Ser Asn Ile Gly Asn Ser Tyr Val Ser
                5                  10

<210> SEQ ID NO 319
<211> LENGTH: 7
<212> TYPE: PRT
<213> ORGANISM: Homo sapiens
<220> FEATURE:
<223> OTHER INFORMATION: Antibody 32

```
<400> SEQUENCE: 319

Asp Asn Asn Lys Arg Pro Ser
                 5

<210> SEQ ID NO 320
<211> LENGTH: 12
<212> TYPE: PRT
<213> ORGANISM: Homo sapiens
<220> FEATURE:
<223> OTHER INFORMATION: Antibody 32

<400> SEQUENCE: 320

Gly Thr Trp Asp Thr Ser Thr Ala Trp Glu Trp Pro
                 5                  10

<210> SEQ ID NO 321
<211> LENGTH: 348
<212> TYPE: DNA
<213> ORGANISM: Homo sapiens
<220> FEATURE:
<223> OTHER INFORMATION: Antibody 33

<400> SEQUENCE: 321
caggtccagc tggtgcagtc tggggctgag gagaagaagc ctggggcctc agtgaaggtt      60
tcctgcaagg catctggata cgccttcacc agctactata tgcactgggc gcgacaggcc     120
cctggacaag ggcttgagtg gatgggaata atcaaccta gtggtggtag cactagctac      180
gcacagaagt tccagggcag agtcaccatg accagggaca cgtccacgag cacagtctac     240
atggagctga gcagcctgag atctgaggac acggccgtgt attactgtgc gagaggaaag     300
tactggatgt acgactgggg caaaggcacc ctggtcaccg tctcgagt                  348

<210> SEQ ID NO 322
<211> LENGTH: 116
<212> TYPE: PRT
<213> ORGANISM: Homo sapiens
<220> FEATURE:
<223> OTHER INFORMATION: Antibody 33

<400> SEQUENCE: 322

Gln Val Gln Leu Val Gln Ser Gly Ala Glu Glu Lys Lys Pro Gly Ala
                 5                  10                  15

Ser Val Lys Val Ser Cys Lys Ala Ser Gly Tyr Ala Phe Thr Ser Tyr
             20                  25                  30

Tyr Met His Trp Ala Arg Gln Ala Pro Gly Gln Gly Leu Glu Trp Met
         35                  40                  45

Gly Ile Ile Asn Pro Ser Gly Gly Ser Thr Ser Tyr Ala Gln Lys Phe
     50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Gly Lys Tyr Trp Met Tyr Asp Trp Gly Lys Gly Thr Leu Val
            100                 105                 110

Thr Val Ser Ser
        115

<210> SEQ ID NO 323
<211> LENGTH: 5
<212> TYPE: PRT
<213> ORGANISM: Homo sapiens
<220> FEATURE:
```

<223> OTHER INFORMATION: Antibody 33

<400> SEQUENCE: 323

Ser Tyr Tyr Met His
              5

<210> SEQ ID NO 324
<211> LENGTH: 17
<212> TYPE: PRT
<213> ORGANISM: Homo sapiens
<220> FEATURE:
<223> OTHER INFORMATION: Antibody 33

<400> SEQUENCE: 324

Ile Ile Asn Pro Ser Gly Gly Ser Thr Ser Tyr Ala Gln Lys Phe Gln
                 5                  10                  15

Gly

<210> SEQ ID NO 325
<211> LENGTH: 7
<212> TYPE: PRT
<213> ORGANISM: Homo sapiens
<220> FEATURE:
<223> OTHER INFORMATION: Antibody 33

<400> SEQUENCE: 325

Gly Lys Tyr Trp Met Tyr Asp
                 5

<210> SEQ ID NO 326
<211> LENGTH: 333
<212> TYPE: DNA
<213> ORGANISM: Homo sapiens
<220> FEATURE:
<223> OTHER INFORMATION: Antibody 33

<400> SEQUENCE: 326
cagtctgcgt tgacgcagcc gccctcagtg tctgcggccc caggacagaa ggtcaccatc       60
tcctgctctg gaggcagctc aacattggg aatagttatg tatcctggta ccagcaactc      120
cctggaacag cccccaaact cctcatttac gacaataata agcgaccctc agggattcct      180
gaccgattct ctggctccaa gtctggcacg tcagccaccc tggccatcac cggactccag      240
actggggacg aggccgatta tttctgcgga acatgggata ccagcacggt gtgggagtgg      300
ccgttcggaa ccgggaccaa gctgaccgtc cta                                   333

<210> SEQ ID NO 327
<211> LENGTH: 111
<212> TYPE: PRT
<213> ORGANISM: Homo sapiens
<220> FEATURE:
<223> OTHER INFORMATION: Antibody 33

<400> SEQUENCE: 327

Gln Ser Ala Leu Thr Gln Pro Pro Ser Val Ser Ala Ala Pro Gly Gln
                 5                  10                  15

Lys Val Thr Ile Ser Cys Ser Gly Gly Ser Ser Asn Ile Gly Asn Ser
             20                  25                  30

Tyr Val Trp Tyr Gln Gln Leu Pro Gly Thr Ala Pro Lys Leu Leu
         35                  40                  45

Ile Tyr Asp Asn Asn Lys Arg Pro Ser Gly Ile Pro Asp Arg Phe Ser
     50                  55                  60

Gly Ser Lys Ser Gly Thr Ser Ala Thr Leu Ala Ile Thr Gly Leu Gln

```
                65                  70                  75                  80
Thr Gly Asp Glu Ala Asp Tyr Phe Cys Gly Thr Trp Asp Thr Ser Thr
                        85                  90                  95
Val Trp Glu Trp Pro Phe Gly Thr Gly Thr Lys Leu Thr Val Leu
            100                 105                 110

<210> SEQ ID NO 328
<211> LENGTH: 13
<212> TYPE: PRT
<213> ORGANISM: Homo sapiens
<220> FEATURE:
<223> OTHER INFORMATION: Antibody 33

<400> SEQUENCE: 328

Ser Gly Gly Ser Ser Asn Ile Gly Asn Ser Tyr Val Ser
                5                   10

<210> SEQ ID NO 329
<211> LENGTH: 7
<212> TYPE: PRT
<213> ORGANISM: Homo sapiens
<220> FEATURE:
<223> OTHER INFORMATION: Antibody 33

<400> SEQUENCE: 329

Asp Asn Asn Lys Arg Pro Ser
                5

<210> SEQ ID NO 330
<211> LENGTH: 12
<212> TYPE: PRT
<213> ORGANISM: Homo sapiens
<220> FEATURE:
<223> OTHER INFORMATION: Antibody 33

<400> SEQUENCE: 330

Gly Thr Trp Asp Thr Ser Thr Val Trp Glu Trp Pro
                5                   10

<210> SEQ ID NO 331
<211> LENGTH: 348
<212> TYPE: DNA
<213> ORGANISM: Homo sapiens
<220> FEATURE:
<223> OTHER INFORMATION: Antibody 34

<400> SEQUENCE: 331
caggtccagc tggtgcagtc tggggctgag gtgaagaagc ctggggcctc agtgaaggtt      60
tcctgcaagg catctggata cgccttcacc agctactata tgcactgggc gcgacaggcc     120
cctggacaag ggcttgagtg gatgggaata atcaacccta gtggtggtag cacaagctac     180
gcacagaagt tccagggcag agtctccatg accagggaca cgtccacgag cacagtctac     240
atggagctga gcagcctgag atctgaggac acggccgtgt attactgtgc gagaggaaag     300
tactggatgt acgactgggg caaaggcacc ctggtcaccg tctcgagt                   348

<210> SEQ ID NO 332
<211> LENGTH: 116
<212> TYPE: PRT
<213> ORGANISM: Homo sapiens
<220> FEATURE:
<223> OTHER INFORMATION: Antibody 34

<400> SEQUENCE: 332

Gln Val Gln Leu Val Gln Ser Gly Ala Glu Val Lys Lys Pro Gly Ala
```

```
                    5                  10                  15
Ser Val Lys Val Ser Cys Lys Ala Ser Gly Tyr Ala Phe Thr Ser Tyr
                20                  25                  30

Tyr Met His Trp Ala Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
    50                  55                  60

Gln Gly Arg Val Ser Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Lys Tyr Trp Met Tyr Asp Trp Gly Lys Gly Thr Leu Val
                100                 105                 110

Thr Val Ser Ser
        115

<210> SEQ ID NO 333
<211> LENGTH: 5
<212> TYPE: PRT
<213> ORGANISM: Homo sapiens
<220> FEATURE:
<223> OTHER INFORMATION: Antibody 34

<400> SEQUENCE: 333

Ser Tyr Tyr Met His
            5

<210> SEQ ID NO 334
<211> LENGTH: 17
<212> TYPE: PRT
<213> ORGANISM: Homo sapiens
<220> FEATURE:
<223> OTHER INFORMATION: Antibody 34

<400> SEQUENCE: 334

Ile Ile Asn Pro Ser Gly Gly Ser Thr Ser Tyr Ala Gln Lys Phe Gln
                5                   10                  15

Gly

<210> SEQ ID NO 335
<211> LENGTH: 7
<212> TYPE: PRT
<213> ORGANISM: Homo sapiens
<220> FEATURE:
<223> OTHER INFORMATION: Antibody 34

<400> SEQUENCE: 335

Gly Lys Tyr Trp Met Tyr Asp
            5

<210> SEQ ID NO 336
<211> LENGTH: 333
<212> TYPE: DNA
<213> ORGANISM: Homo sapiens
<220> FEATURE:
<223> OTHER INFORMATION: Antibody 34

<400> SEQUENCE: 336
cagtctgtgt tgacgcagcc gccctcagtg tccgcggccc caggacagaa ggtcaccatc     60
tcctgctctg gaggcagctc caacattggg aatagttatg tgtcctggta ccagcaactc    120
ccaggaacgg cccccaaact cctcatttac gacaataata gcgaccctc agggattcct    180
```

-continued

```
gaccgattct ctggctccaa gtctggcacg tcagccaccc tggccatcac cggactccag    240
actggggacg aggccgatta tttctgcgga acatgggata ccagcacggt gtgggagtgg    300
ccgttcggaa ctgggaccaa gctgaccgtc cta    333
```

<210> SEQ ID NO 337
<211> LENGTH: 111
<212> TYPE: PRT
<213> ORGANISM: Homo sapiens
<220> FEATURE:
<223> OTHER INFORMATION: Antibody 34

<400> SEQUENCE: 337

Gln Ser Val Leu Thr Gln Pro Pro Ser Val Ser Ala Ala Pro Gly Gln
1               5                   10                  15
Lys Val Thr Ile Ser Cys Ser Gly Gly Ser Ser Asn Ile Gly Asn Ser
            20                  25                  30
Tyr Val Ser Trp Tyr Gln Gln Leu Pro Gly Thr Ala Pro Lys Leu Leu
        35                  40                  45
Ile Tyr Asp Asn Asn Lys Arg Pro Ser Gly Ile Pro Asp Arg Phe Ser
    50                  55                  60
Gly Ser Lys Ser Gly Thr Ser Ala Thr Leu Ala Ile Thr Gly Leu Gln
65                  70                  75                  80
Thr Gly Asp Glu Ala Asp Tyr Phe Cys Gly Thr Trp Asp Thr Ser Thr
                85                  90                  95
Val Trp Glu Trp Pro Phe Gly Thr Gly Thr Lys Leu Thr Val Leu
            100                 105                 110

<210> SEQ ID NO 338
<211> LENGTH: 13
<212> TYPE: PRT
<213> ORGANISM: Homo sapiens
<220> FEATURE:
<223> OTHER INFORMATION: Antibody 34

<400> SEQUENCE: 338

Ser Gly Gly Ser Ser Asn Ile Gly Asn Ser Tyr Val Ser
1               5                   10

<210> SEQ ID NO 339
<211> LENGTH: 7
<212> TYPE: PRT
<213> ORGANISM: Homo sapiens
<220> FEATURE:
<223> OTHER INFORMATION: Antibody 34

<400> SEQUENCE: 339

Asp Asn Asn Lys Arg Pro Ser
1               5

<210> SEQ ID NO 340
<211> LENGTH: 12
<212> TYPE: PRT
<213> ORGANISM: Homo sapiens
<220> FEATURE:
<223> OTHER INFORMATION: Antibody 34

<400> SEQUENCE: 340

Gly Thr Trp Asp Thr Ser Thr Val Trp Glu Trp Pro
1               5                   10

<210> SEQ ID NO 341
<211> LENGTH: 348
<212> TYPE: DNA

```
<213> ORGANISM: Homo sapiens
<220> FEATURE:
<223> OTHER INFORMATION: Antibody 35

<400> SEQUENCE: 341
caggtccagc tggtgcagtc tgggctgag gtgaagaagc ctggggcctc agtgaaggtt      60
tcctgcaagg catctggata cgccttcacc agctactata tgcactgggc gcgacaggcc     120
cctggacaag gcttgagtg gatgggaata atcaaccta gtggtggtag cacaagctac     180
gcacagaagt tccagggcag agtcaccatg accagggaca cgtccacgag cacagtctac    240
atggagctga gcagcctgag atctgaggac acggccgtgt attactgtgc gagaggaaag    300
tactggatgt acgactgggg caaaggcacc ctggtcaccg tctcgagt                 348

<210> SEQ ID NO 342
<211> LENGTH: 116
<212> TYPE: PRT
<213> ORGANISM: Homo sapiens
<220> FEATURE:
<223> OTHER INFORMATION: Antibody 35

<400> SEQUENCE: 342

Gln Val Gln Leu Val Gln Ser Gly Ala Glu Val Lys Lys Pro Gly Ala
                5                  10                  15

Ser Val Lys Val Ser Cys Lys Ala Ser Gly Tyr Ala Phe Thr Ser Tyr
            20                  25                  30

Tyr Met His Trp Ala Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Lys Tyr Trp Met Tyr Asp Trp Gly Lys Gly Thr Leu Val
            100                 105                 110

Thr Val Ser Ser
        115

<210> SEQ ID NO 343
<211> LENGTH: 5
<212> TYPE: PRT
<213> ORGANISM: Homo sapiens
<220> FEATURE:
<223> OTHER INFORMATION: Antibody 35

<400> SEQUENCE: 343

Ser Tyr Tyr Met His
                5

<210> SEQ ID NO 344
<211> LENGTH: 17
<212> TYPE: PRT
<213> ORGANISM: Homo sapiens
<220> FEATURE:
<223> OTHER INFORMATION: Antibody 35

<400> SEQUENCE: 344

Ile Ile Asn Pro Ser Gly Gly Ser Thr Ser Tyr Ala Gln Lys Phe Gln
                5                  10                  15

Gly
```

<210> SEQ ID NO 345
<211> LENGTH: 7
<212> TYPE: PRT
<213> ORGANISM: Homo sapiens
<220> FEATURE:
<223> OTHER INFORMATION: Antibody 35

<400> SEQUENCE: 345

Gly Lys Tyr Trp Met Tyr Asp
            5

<210> SEQ ID NO 346
<211> LENGTH: 333
<212> TYPE: DNA
<213> ORGANISM: Homo sapiens
<220> FEATURE:
<223> OTHER INFORMATION: Antibody 35

<400> SEQUENCE: 346
cagtctgtgt tgacgcagcc gccctcagtg tctgcggccc caggacagaa ggtcaccatc     60
tcctgctctg gaggcagctc aacattggg aatagttatg tatcctggta ccagcaactc    120
ccaggaacag ccccccaaact cctcatttac gacaataata gcgaccctc agggattcct    180 gaccgattct ctggctccaa gtctggcacg tcagccaccc tggccatcac cggactccag    240
actggggacg aggccgatta ttactgcgga acatgggata ccagcccggt gtgggagtgg    300
ccgttcggaa ctgggaccaa gctgaccgtc cta                                  333

<210> SEQ ID NO 347
<211> LENGTH: 111
<212> TYPE: PRT
<213> ORGANISM: Homo sapiens
<220> FEATURE:
<223> OTHER INFORMATION: Antibody 35

<400> SEQUENCE: 347

Gln Ser Val Leu Thr Gln Pro Pro Ser Val Ser Ala Ala Pro Gly Gln
                5                   10                  15

Lys Val Thr Ile Ser Cys Ser Gly Gly Ser Ser Asn Ile Gly Asn Ser
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Ala Ile Thr Gly Leu Gln
65                  70                  75                  80

Thr Gly Asp Glu Ala Asp Tyr Tyr Cys Gly Thr Trp Asp Thr Ser Pro
                85                  90                  95

Val Trp Glu Trp Pro Phe Gly Thr Gly Thr Lys Leu Thr Val Leu
            100                 105                 110

<210> SEQ ID NO 348
<211> LENGTH: 13
<212> TYPE: PRT
<213> ORGANISM: Homo sapiens
<220> FEATURE:
<223> OTHER INFORMATION: Antibody 35

<400> SEQUENCE: 348

Ser Gly Gly Ser Ser Asn Ile Gly Asn Ser Tyr Val Ser
                5                   10

<210> SEQ ID NO 349
<211> LENGTH: 7
<212> TYPE: PRT
<213> ORGANISM: Homo sapiens
<220> FEATURE:
<223> OTHER INFORMATION: Antibody 35

<400> SEQUENCE: 349

Asp Asn Asn Lys Arg Pro Ser
                5

<210> SEQ ID NO 350
<211> LENGTH: 12
<212> TYPE: PRT
<213> ORGANISM: Homo sapiens
<220> FEATURE:
<223> OTHER INFORMATION: Antibody 35

<400> SEQUENCE: 350

Gly Thr Trp Asp Thr Ser Pro Val Trp Glu Trp Pro
                5                   10

<210> SEQ ID NO 351
<211> LENGTH: 348
<212> TYPE: DNA
<213> ORGANISM: Homo sapiens
<220> FEATURE:
<223> OTHER INFORMATION: Antibody 36

<400> SEQUENCE: 351
caggtccagc tggtgcagtc tggggctgag gtgaagaagc ctggggcctc agtgaaggtt      60
tcctgcaagg catctggata cgccttcacc agctactaca tgcactgggc gcgacaggcc     120
cctggacaag gcttgagtg gatgggaata atcaaccctaa gtggtggtag cgcaagctac     180
gcacagaagt tccagggcag agtcaccatg accagggaca cgtccacgag cacagtctac     240
atggagctga gcagcctgag atctgaggac acggccgtgt attactgtgc gagaggaaag     300
tactggatgt acgactgggg caaaggcacc ctggtcaccg tctcgagt                  348

<210> SEQ ID NO 352
<211> LENGTH: 116
<212> TYPE: PRT
<213> ORGANISM: Homo sapiens
<220> FEATURE:
<223> OTHER INFORMATION: Antibody 36

<400> SEQUENCE: 352

Gln Val Gln Leu Val Gln Ser Gly Ala Glu Val Lys Lys Pro Gly Ala
                5                   10                  15

Ser Val Lys Val Ser Cys Lys Ala Ser Gly Tyr Ala Phe Thr Ser Tyr
            20                  25                  30

Tyr Met His Trp Ala Arg Gln Ala Pro Gly Gln Gly Leu Glu Trp Met
        35                  40                  45

Gly Ile Ile Asn Pro Ser Gly Gly Ser Ala Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Lys Tyr Trp Met Tyr Asp Trp Gly Lys Gly Thr Leu Val
            100                 105                 110

Thr Val Ser Ser
        115

<210> SEQ ID NO 353
<211> LENGTH: 5
<212> TYPE: PRT
<213> ORGANISM: Homo sapiens
<220> FEATURE:
<223> OTHER INFORMATION: Antibody 36

<400> SEQUENCE: 353

Ser Tyr Tyr Met His
                 5

<210> SEQ ID NO 354
<211> LENGTH: 17
<212> TYPE: PRT
<213> ORGANISM: Homo sapiens
<220> FEATURE:
<223> OTHER INFORMATION: Antibody 36

<400> SEQUENCE: 354

Ile Ile Asn Pro Ser Gly Gly Ser Ala Ser Tyr Ala Gln Lys Phe Gln
                5                  10                 15

Gly

<210> SEQ ID NO 355
<211> LENGTH: 7
<212> TYPE: PRT
<213> ORGANISM: Homo sapiens
<220> FEATURE:
<223> OTHER INFORMATION: Antibody 36

<400> SEQUENCE: 355

Gly Lys Tyr Trp Met Tyr Asp
                 5

<210> SEQ ID NO 356
<211> LENGTH: 333
<212> TYPE: DNA
<213> ORGANISM: Homo sapiens
<220> FEATURE:
<223> OTHER INFORMATION: Antibody 36

<400> SEQUENCE: 356
cagtctgtgt tgacgcagcc gccctcagtg tctgcggccc caggacagaa ggtcaccatc      60
tcctgctctg gaggcagctc aacattggga atagttatg tatcctggta ccagcaactc     120
ccaggaacag cccccaaact cctcatttac gacaataata gcgaccctc agggattcct     180 gaccgattct ctggctccaa gtctggcacg tcagccaccc tggccatcac cggactccag     240 actgggacg aggccgatta ttactgcgga acatgggatt ccagcacggt gtgggagtgg     300
ccgttcggaa ctgggaccaa gctgaccgtc cta                                  333

<210> SEQ ID NO 357
<211> LENGTH: 111
<212> TYPE: PRT
<213> ORGANISM: Homo sapiens
<220> FEATURE:
<223> OTHER INFORMATION: Antibody 36

<400> SEQUENCE: 357

Gln Ser Val Leu Thr Gln Pro Pro Ser Val Ser Ala Ala Pro Gly Gln
                5                  10                 15

Lys Val Thr Ile Ser Cys Ser Gly Gly Ser Ser Asn Ile Gly Asn Ser
           20                  25                 30

-continued

```
Tyr Val Ser Trp Tyr Gln Gln Leu Pro Gly Thr Ala Pro Lys Leu Leu
         35                  40                  45
Ile Tyr Asp Asn Asn Lys Arg Pro Ser Gly Ile Pro Asp Arg Phe Ser
 50                  55                  60
Gly Ser Lys Ser Gly Thr Ser Ala Thr Leu Ala Ile Thr Gly Leu Gln
 65                  70                  75                  80
Thr Gly Asp Glu Ala Asp Tyr Tyr Cys Gly Thr Trp Asp Ser Ser Thr
                 85                  90                  95
Val Trp Glu Trp Pro Phe Gly Thr Gly Thr Lys Leu Thr Val Leu
            100                 105                 110
```

<210> SEQ ID NO 358
<211> LENGTH: 13
<212> TYPE: PRT
<213> ORGANISM: Homo sapiens
<220> FEATURE:
<223> OTHER INFORMATION: Antibody 36

<400> SEQUENCE: 358

```
Ser Gly Gly Ser Ser Asn Ile Gly Asn Ser Tyr Val Ser
              5                  10
```

<210> SEQ ID NO 359
<211> LENGTH: 7
<212> TYPE: PRT
<213> ORGANISM: Homo sapiens
<220> FEATURE:
<223> OTHER INFORMATION: Antibody 36

<400> SEQUENCE: 359

```
Asp Asn Asn Lys Arg Pro Ser
              5
```

<210> SEQ ID NO 360
<211> LENGTH: 12
<212> TYPE: PRT
<213> ORGANISM: Homo sapiens
<220> FEATURE:
<223> OTHER INFORMATION: Antibody 36

<400> SEQUENCE: 360

```
Gly Thr Trp Asp Ser Ser Thr Val Trp Glu Trp Pro
              5                  10
```

<210> SEQ ID NO 361
<211> LENGTH: 348
<212> TYPE: DNA
<213> ORGANISM: Homo sapiens
<220> FEATURE:
<223> OTHER INFORMATION: Antibody 37

<400> SEQUENCE: 361

```
caggtccagc tggtgcagtc tggggctgag gtgaagaagc ctggggcctc agtgaaggtt      60
tcctgcaagg catctggata cgccttcacc agctactata tgcactgggc gcgacaggcc     120
cctggacaag gcttgagtg gatgggaata tcaaccccta gaggtggtag cacaagctac     180
gcacagaagt tccagggcag agtcgccatg accagggaca cgtccacgag cacagtctac     240
atggagctga gcagcctgag acctgaggac acggccgtgt attactgtgc gagaggaaag     300
tactggatgt acgactgggg caaaggcacc ctggtcaccg tctcgagt                  348
```

<210> SEQ ID NO 362
<211> LENGTH: 116
<212> TYPE: PRT

```
<213> ORGANISM: Homo sapiens
<220> FEATURE:
<223> OTHER INFORMATION: Antibody 37

<400> SEQUENCE: 362

Gln Val Gln Leu Val Gln Ser Gly Ala Glu Val Lys Lys Pro Gly Ala
                 5                  10                  15

Ser Val Lys Val Ser Cys Lys Ala Ser Gly Tyr Ala Phe Thr Ser Tyr
             20                  25                  30

Tyr Met His Trp Ala Arg Gln Ala Pro Gly Gln Gly Leu Glu Trp Met
         35                  40                  45

Gly Ile Ile Asn Pro Arg Gly Gly Ser Thr Ser Tyr Ala Gln Lys Phe
     50                  55                  60

Gln Gly Arg Val Ala Met Thr Arg Asp Thr Ser Thr Ser Thr Val Tyr
 65                  70                  75                  80

Met Glu Leu Ser Ser Leu Arg Pro Glu Asp Thr Ala Val Tyr Tyr Cys
                 85                  90                  95

Ala Arg Gly Lys Tyr Trp Met Tyr Asp Trp Gly Lys Gly Thr Leu Val
            100                 105                 110

Thr Val Ser Ser
        115

<210> SEQ ID NO 363
<211> LENGTH: 5
<212> TYPE: PRT
<213> ORGANISM: Homo sapiens
<220> FEATURE:
<223> OTHER INFORMATION: Antibody 37

<400> SEQUENCE: 363

Ser Tyr Tyr Met His
                 5

<210> SEQ ID NO 364
<211> LENGTH: 17
<212> TYPE: PRT
<213> ORGANISM: Homo sapiens
<220> FEATURE:
<223> OTHER INFORMATION: Antibody 37

<400> SEQUENCE: 364

Ile Ile Asn Pro Arg Gly Gly Ser Thr Ser Tyr Ala Gln Lys Phe Gln
                 5                  10                  15

Gly

<210> SEQ ID NO 365
<211> LENGTH: 7
<212> TYPE: PRT
<213> ORGANISM: Homo sapiens
<220> FEATURE:
<223> OTHER INFORMATION: Antibody 37

<400> SEQUENCE: 365

Gly Lys Tyr Trp Met Tyr Asp
                 5

<210> SEQ ID NO 366
<211> LENGTH: 333
<212> TYPE: DNA
<213> ORGANISM: Homo sapiens
<220> FEATURE:
<223> OTHER INFORMATION: Antibody 37

<400> SEQUENCE: 366
```

```
cagtctgtgt tgacgcagcc gccctcagtg tcagcggccc caggacagaa ggtcaccatc      60
tcctgctctg gaggcggctc cagcattggg aatagctatg tatcctggta ccagcaactc     120
ccaggaacag cccccaaact cctcatctac gacaataata agcgaccctc aggggttcct     180
gaccgattct ctggctccaa gtctggcacg tcggccaccc tggccatcac cggactccag     240
actggggacg aggccgatta ttactgcgga acatgggata ccagcccggt gtgggagtgg     300
ccgttcggaa ctgggaccaa gctgaccgtc cta                                  333
```

<210> SEQ ID NO 367
<211> LENGTH: 111
<212> TYPE: PRT
<213> ORGANISM: Homo sapiens
<220> FEATURE:
<223> OTHER INFORMATION: Antibody 37

<400> SEQUENCE: 367

Gln Ser Val Leu Thr Gln Pro Pro Ser Val Ser Ala Ala Pro Gly Gln
                5                  10                  15
Lys Val Thr Ile Ser Cys Ser Gly Gly Gly Ser Ser Ile Gly Asn Ser
            20                  25                  30
Tyr Val Ser Trp Tyr Gln Gln Leu Pro Gly Thr Ala Pro Lys Leu Leu
        35                  40                  45
Ile Tyr Asp Asn Asn Lys Arg Pro Ser Gly Val Pro Asp Arg Phe Ser
    50                  55                  60
Gly Ser Lys Ser Gly Thr Ser Ala Thr Leu Ala Ile Thr Gly Leu Gln
65                  70                  75                  80
Thr Gly Asp Glu Ala Asp Tyr Tyr Cys Gly Thr Trp Asp Thr Ser Pro
                85                  90                  95
Val Trp Glu Trp Pro Phe Gly Thr Gly Thr Lys Leu Thr Val Leu
            100                 105                 110

<210> SEQ ID NO 368
<211> LENGTH: 13
<212> TYPE: PRT
<213> ORGANISM: Homo sapiens
<220> FEATURE:
<223> OTHER INFORMATION: Antibody 37

<400> SEQUENCE: 368

Ser Gly Gly Gly Ser Ser Ile Gly Asn Ser Tyr Val Ser
                5                  10

<210> SEQ ID NO 369
<211> LENGTH: 7
<212> TYPE: PRT
<213> ORGANISM: Homo sapiens
<220> FEATURE:
<223> OTHER INFORMATION: Antibody 37

<400> SEQUENCE: 369

Asp Asn Asn Lys Arg Pro Ser
                5

<210> SEQ ID NO 370
<211> LENGTH: 12
<212> TYPE: PRT
<213> ORGANISM: Homo sapiens
<220> FEATURE:
<223> OTHER INFORMATION: Antibody 37

<400> SEQUENCE: 370

```
Gly Thr Trp Asp Thr Ser Pro Val Trp Glu Trp Pro
                 5                  10
```

<210> SEQ ID NO 371
<211> LENGTH: 348
<212> TYPE: DNA
<213> ORGANISM: Homo sapiens
<220> FEATURE:
<223> OTHER INFORMATION: Antibody 38

<400> SEQUENCE: 371

```
caggtccagc tggtgcagtc tggggctgag gtgaagaagc ctggggcctc agtgaaggtt    60
tcctgcaagg catctggata cgccttcacc agctactata tgcactgggc gcgacaggcc   120
cctggacaag gcttgagtg gatgggaata atcaaccta gtggtggtag cgcaagctac    180
gcacagaagt tccagggcag agtcaccatg accaggaca cgtccacgag cacagtctac    240
atggagctga gcagcctgag atctgaggac acggccgtgt attactgtgc gagaggaaag   300
tactggatgt acgactgggg caaaggcacc ctggtcaccg tctcgagt               348
```

<210> SEQ ID NO 372
<211> LENGTH: 116
<212> TYPE: PRT
<213> ORGANISM: Homo sapiens
<220> FEATURE:
<223> OTHER INFORMATION: Antibody 38

<400> SEQUENCE: 372

```
Gln Val Gln Leu Val Gln Ser Gly Ala Glu Val Lys Lys Pro Gly Ala
                 5                  10                  15

Ser Val Lys Val Ser Cys Lys Ala Ser Gly Tyr Ala Phe Thr Ser Tyr
             20                  25                  30

Tyr Met His Trp Ala Arg Gln Ala Pro Gly Gln Gly Leu Glu Trp Met
         35                  40                  45

Gly Ile Ile Asn Pro Ser Gly Gly Ser Ala Ser Tyr Ala Gln Lys Phe
     50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Gly Lys Tyr Trp Met Tyr Asp Trp Gly Lys Gly Thr Leu Val
            100                 105                 110

Thr Val Ser Ser
        115
```

<210> SEQ ID NO 373
<211> LENGTH: 5
<212> TYPE: PRT
<213> ORGANISM: Homo sapiens
<220> FEATURE:
<223> OTHER INFORMATION: Antibody 38

<400> SEQUENCE: 373

```
Ser Tyr Tyr Met His
                 5
```

<210> SEQ ID NO 374
<211> LENGTH: 17
<212> TYPE: PRT
<213> ORGANISM: Homo sapiens
<220> FEATURE:
<223> OTHER INFORMATION: Antibody 38

```
<400> SEQUENCE: 374

Ile Ile Asn Pro Ser Gly Gly Ser Ala Ser Tyr Ala Gln Lys Phe Gln
                5                   10                  15
Gly

<210> SEQ ID NO 375
<211> LENGTH: 7
<212> TYPE: PRT
<213> ORGANISM: Homo sapiens
<220> FEATURE:
<223> OTHER INFORMATION: Antibody 38

<400> SEQUENCE: 375

Gly Lys Tyr Trp Met Tyr Asp
                5

<210> SEQ ID NO 376
<211> LENGTH: 333
<212> TYPE: DNA
<213> ORGANISM: Homo sapiens
<220> FEATURE:
<223> OTHER INFORMATION: Antibody 38

<400> SEQUENCE: 376
cagtctgtgt tgacgcagcc gccctcagtg tctgcggccc caggacagaa ggtcaccatc      60
tcctgctctg gaggcagctc caacattggg aatagttatg tatcctggta ccagcaactc     120
ccaggaacag cccccaaact cctcatttac gacaataata agcgaccctc agggattcct     180
gaccgattct ctggctccaa gtctggcacg tcagccaccc tggccatcac cggactccag     240
actggggacg aggccgatta tttctgcgga acatgggata ccagcacggt gtgggagtgg     300
ccgttcggaa ctgggaccaa gctgaccgtc cta                                  333

<210> SEQ ID NO 377
<211> LENGTH: 111
<212> TYPE: PRT
<213> ORGANISM: Homo sapiens
<220> FEATURE:
<223> OTHER INFORMATION: Antibody 38

<400> SEQUENCE: 377

Gln Ser Val Leu Thr Gln Pro Pro Ser Val Ala Ala Pro Gly Gln
                5                   10                  15

Lys Val Thr Ile Ser Cys Ser Gly Gly Ser Ser Asn Ile Gly Asn Ser
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Ala Ile Thr Gly Leu Gln
65                  70                  75                  80

Thr Gly Asp Glu Ala Asp Tyr Phe Cys Gly Thr Trp Asp Thr Ser Thr
                85                  90                  95

Val Trp Glu Trp Pro Phe Gly Thr Gly Thr Lys Leu Thr Val Leu
            100                 105                 110

<210> SEQ ID NO 378
<211> LENGTH: 13
<212> TYPE: PRT
<213> ORGANISM: Homo sapiens
<220> FEATURE:
<223> OTHER INFORMATION: Antibody 38
```

<400> SEQUENCE: 378

Ser Gly Gly Ser Ser Asn Ile Gly Asn Ser Tyr Val Ser
                5                   10

<210> SEQ ID NO 379
<211> LENGTH: 7
<212> TYPE: PRT
<213> ORGANISM: Homo sapiens
<220> FEATURE:
<223> OTHER INFORMATION: Antibody 38

<400> SEQUENCE: 379

Asp Asn Asn Lys Arg Pro Ser
                5

<210> SEQ ID NO 380
<211> LENGTH: 12
<212> TYPE: PRT
<213> ORGANISM: Homo sapiens
<220> FEATURE:
<223> OTHER INFORMATION: Antibody 38

<400> SEQUENCE: 380

Gly Thr Trp Asp Thr Ser Thr Val Trp Glu Trp Pro
                5                   10

<210> SEQ ID NO 381
<211> LENGTH: 348
<212> TYPE: DNA
<213> ORGANISM: Homo sapiens
<220> FEATURE:
<223> OTHER INFORMATION: Antibody 39

<400> SEQUENCE: 381
caggtccagc tggtgcagtc tggggctgag gtgaagaagc ctggggcctc agtgaaggtt      60
tcctgcaagg catctggata cgccttcacc agctactata tgcactgggc gcgacaggcc     120
cctggacaag gcttgagtg gatgggaata atcaacccta ggggtggtag cacaagctac      180
gcacagaagt tccagggcag agtcaccatg accaggaca cgtccacgag cacagtctac      240
atggagctga gcagcctgag atctgaggac acggccgtgt attactgtgc gagaggaaag    300
tactggatgt acgactgggg caaaggcacc ctggtcaccg tctcgagt                  348

<210> SEQ ID NO 382
<211> LENGTH: 116
<212> TYPE: PRT
<213> ORGANISM: Homo sapiens
<220> FEATURE:
<223> OTHER INFORMATION: Antibody 39

<400> SEQUENCE: 382

Gln Val Gln Leu Val Gln Ser Gly Ala Glu Val Lys Lys Pro Gly Ala
                5                   10                  15

Ser Val Lys Val Ser Cys Lys Ala Ser Gly Tyr Ala Phe Thr Ser Tyr
            20                  25                  30

Tyr Met His Trp Ala Arg Gln Ala Pro Gly Gln Gly Leu Glu Trp Met
        35                  40                  45

Gly Ile Ile Asn Pro Arg Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys

```
                    85                  90                  95

Ala Arg Gly Lys Tyr Trp Met Tyr Asp Trp Gly Lys Gly Thr Leu Val
            100                 105                 110

Thr Val Ser Ser
        115

<210> SEQ ID NO 383
<211> LENGTH: 5
<212> TYPE: PRT
<213> ORGANISM: Homo sapiens
<220> FEATURE:
<223> OTHER INFORMATION: Antibody 39

<400> SEQUENCE: 383

Ser Tyr Tyr Met His
                5

<210> SEQ ID NO 384
<211> LENGTH: 17
<212> TYPE: PRT
<213> ORGANISM: Homo sapiens
<220> FEATURE:
<223> OTHER INFORMATION: Antibody 39

<400> SEQUENCE: 384

Ile Ile Asn Pro Arg Gly Gly Ser Thr Ser Tyr Ala Gln Lys Phe Gln
                5                  10                  15

Gly

<210> SEQ ID NO 385
<211> LENGTH: 7
<212> TYPE: PRT
<213> ORGANISM: Homo sapiens
<220> FEATURE:
<223> OTHER INFORMATION: Antibody 39

<400> SEQUENCE: 385

Gly Lys Tyr Trp Met Tyr Asp
                5

<210> SEQ ID NO 386
<211> LENGTH: 333
<212> TYPE: DNA
<213> ORGANISM: Homo sapiens
<220> FEATURE:
<223> OTHER INFORMATION: Antibody 39

<400> SEQUENCE: 386
cagtctgtgt tgacgcagcc gccctcagtg tctgcggccc caggacagaa ggtcaccatc      60
tcctgctctg gaggcagctc caacattggg aatagttatg tatcctggta ccagcaactc     120
ccaggaacag cccccaaact cctcatttac gacaataata agcgaccctc aggattcct     180 gaccgattct ctggctccaa gtctggcacg tcagccaccc tggccatcac cggactccag     240
actggggacg aggccgatta ttactgcgga acatgggata ccagcacggc gtgggagtgg     300
ccgttcggaa ctgggaccaa gctgaccgtc cta                                  333

<210> SEQ ID NO 387
<211> LENGTH: 111
<212> TYPE: PRT
<213> ORGANISM: Homo sapiens
<220> FEATURE:
<223> OTHER INFORMATION: Antibody 39

<400> SEQUENCE: 387
```

-continued

```
Gln Ser Val Leu Thr Gln Pro Pro Ser Val Ser Ala Ala Pro Gly Gln
                  5                  10                  15
Lys Val Thr Ile Ser Cys Ser Gly Gly Ser Ser Asn Ile Gly Asn Ser
             20                  25                  30
Tyr Val Ser Trp Tyr Gln Gln Leu Pro Gly Thr Ala Pro Lys Leu Leu
         35                  40                  45
Ile Tyr Asp Asn Asn Lys Arg Pro Ser Gly Ile Pro Asp Arg Phe Ser
 50                  55                  60
Gly Ser Lys Ser Gly Thr Ser Ala Thr Leu Ala Ile Thr Gly Leu Gln
 65                  70                  75                  80
Thr Gly Asp Glu Ala Asp Tyr Tyr Cys Gly Thr Trp Asp Thr Ser Thr
                 85                  90                  95
Ala Trp Glu Trp Pro Phe Gly Gly Thr Lys Leu Thr Val Leu
            100                 105                 110

<210> SEQ ID NO 388
<211> LENGTH: 13
<212> TYPE: PRT
<213> ORGANISM: Homo sapiens
<220> FEATURE:
<223> OTHER INFORMATION: Antibody 39

<400> SEQUENCE: 388

Ser Gly Gly Ser Ser Asn Ile Gly Asn Ser Tyr Val Ser
                 5                  10

<210> SEQ ID NO 389
<211> LENGTH: 7
<212> TYPE: PRT
<213> ORGANISM: Homo sapiens
<220> FEATURE:
<223> OTHER INFORMATION: Antibody 39

<400> SEQUENCE: 389

Asp Asn Asn Lys Arg Pro Ser
             5

<210> SEQ ID NO 390
<211> LENGTH: 12
<212> TYPE: PRT
<213> ORGANISM: Homo sapiens
<220> FEATURE:
<223> OTHER INFORMATION: Antibody 39

<400> SEQUENCE: 390

Gly Thr Trp Asp Thr Ser Thr Ala Trp Glu Trp Pro
                 5                  10

<210> SEQ ID NO 391
<211> LENGTH: 348
<212> TYPE: DNA
<213> ORGANISM: Homo sapiens
<220> FEATURE:
<223> OTHER INFORMATION: Antibody 40

<400> SEQUENCE: 391
caggtccagc tggtgcagtc tggggctgag gtgaagaagc ctggggcctc agtgaaggtt      60
tcctgcaagg catctggata cgccttcacc agctactata tgcactgggc gcgacaggcc     120
cctggacaag gcttgagtg gatgggaata atcaaccta gtggtggtag cacaagctac      180
gcacagaagt tccagggcag agtcaccatg accagggaca cgtccacgag cacagtctac     240
atggagctga gcagcctgag atctgaggac acggccgtgt attactgtgc gagaggaaag     300
```
tactggatgt acgactgggg caaaggcacc ctggtcaccg tctcgagt      348

<210> SEQ ID NO 392
<211> LENGTH: 116
<212> TYPE: PRT
<213> ORGANISM: Homo sapiens
<220> FEATURE:
<223> OTHER INFORMATION: Antibody 40

<400> SEQUENCE: 392

Gln Val Gln Leu Val Gln Ser Gly Ala Glu Val Lys Lys Pro Gly Ala
                1               5                   10                  15

Ser Val Lys Val Ser Cys Lys Ala Ser Gly Tyr Ala Phe Thr Ser Tyr
            20                  25                  30

Tyr Met His Trp Ala Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Lys Tyr Trp Met Tyr Asp Trp Gly Lys Gly Thr Leu Val
            100                 105                 110

Thr Val Ser Ser
        115

<210> SEQ ID NO 393
<211> LENGTH: 5
<212> TYPE: PRT
<213> ORGANISM: Homo sapiens
<220> FEATURE:
<223> OTHER INFORMATION: Antibody 40

<400> SEQUENCE: 393

Ser Tyr Tyr Met His
                5

<210> SEQ ID NO 394
<211> LENGTH: 17
<212> TYPE: PRT
<213> ORGANISM: Homo sapiens
<220> FEATURE:
<223> OTHER INFORMATION: Antibody 40

<400> SEQUENCE: 394

Ile Ile Asn Pro Ser Gly Gly Ser Thr Ser Tyr Ala Gln Lys Phe Gln
                5                   10                  15

Gly

<210> SEQ ID NO 395
<211> LENGTH: 7
<212> TYPE: PRT
<213> ORGANISM: Homo sapiens
<220> FEATURE:
<223> OTHER INFORMATION: Antibody 40

<400> SEQUENCE: 395

Gly Lys Tyr Trp Met Tyr Asp
                5

<210> SEQ ID NO 396

<211> LENGTH: 333
<212> TYPE: DNA
<213> ORGANISM: Homo sapiens
<220> FEATURE:
<223> OTHER INFORMATION: Antibody 40

<400> SEQUENCE: 396
cagtctgtgt tgacgcagcc gccctcagtg tctgcggccc caggacagaa ggtcaccatc      60
tcctgctctg gaggcagctc caacattggg aatagttatg tatcctggta ccagcaactc     120
ccaggaacag cccccaaact cctcatttac gacaataata gcgaccctca aggattcct     180
gaccgattct ctggctccaa gtctggcacg tcagccaccc tggccatcac cggactccag     240
actggggacg aggccgatta ttactgcgga acatgggatt ccagcacggt gtgggagtgg     300
ccgttcggaa ctgggaccaa gctgaccgtc cta                                  333

<210> SEQ ID NO 397
<211> LENGTH: 111
<212> TYPE: PRT
<213> ORGANISM: Homo sapiens
<220> FEATURE:
<223> OTHER INFORMATION: Antibody 40

<400> SEQUENCE: 397

Gln Ser Val Leu Thr Gln Pro Pro Ser Val Ser Ala Ala Pro Gly Gln
                5                  10                  15
Lys Val Thr Ile Ser Cys Ser Gly Gly Ser Ser Asn Ile Gly Asn Ser
            20                  25                  30
Tyr Val Ser Trp Tyr Gln Gln Leu Pro Gly Thr Ala Pro Lys Leu Leu
        35                  40                  45
Ile Tyr Asp Asn Asn Lys Arg Pro Ser Gly Ile Pro Asp Arg Phe Ser
    50                  55                  60
Gly Ser Lys Ser Gly Thr Ser Ala Thr Leu Ala Ile Thr Gly Leu Gln
65                  70                  75                  80
Thr Gly Asp Glu Ala Asp Tyr Tyr Cys Gly Thr Trp Asp Ser Ser Thr
                85                  90                  95
Val Trp Glu Trp Pro Phe Gly Thr Gly Thr Lys Leu Thr Val Leu
            100                 105                 110

<210> SEQ ID NO 398
<211> LENGTH: 13
<212> TYPE: PRT
<213> ORGANISM: Homo sapiens
<220> FEATURE:
<223> OTHER INFORMATION: Antibody 40

<400> SEQUENCE: 398

Ser Gly Gly Ser Ser Asn Ile Gly Asn Ser Tyr Val Ser
                5                  10

<210> SEQ ID NO 399
<211> LENGTH: 7
<212> TYPE: PRT
<213> ORGANISM: Homo sapiens
<220> FEATURE:
<223> OTHER INFORMATION: Antibody 40

<400> SEQUENCE: 399

Asp Asn Asn Lys Arg Pro Ser
                5

<210> SEQ ID NO 400
<211> LENGTH: 12

```
<212> TYPE: PRT
<213> ORGANISM: Homo sapiens
<220> FEATURE:
<223> OTHER INFORMATION: Antibody 40

<400> SEQUENCE: 400

Gly Thr Trp Asp Ser Ser Thr Val Trp Glu Trp Pro
                5                  10

<210> SEQ ID NO 401
<211> LENGTH: 348
<212> TYPE: DNA
<213> ORGANISM: Homo sapiens
<220> FEATURE:
<223> OTHER INFORMATION: Antibody 41

<400> SEQUENCE: 401
caggtccagc tggtgcagtc tggggctgag gtgaggaagc ctggggcctc agtgaaggtt      60
tcctgcaagg catctggata cgccttcacc agctactata tgcactgggc gcgacaggcc     120
cctggacaag gcttgagtg gatgggaata atcaaccta gtggtggtag cacaagctac       180
gcacagaagt tccagggcag agtcaccatg accaggaca cgtccacgag cacagtctac      240
atggagctga gcagcctgag acctgaggac acggccgtgt attactgtgc gagaggaaag    300
tactggatgt acgactgggg caaaggcacc ctggtcaccg tctcgggt                  348

<210> SEQ ID NO 402
<211> LENGTH: 116
<212> TYPE: PRT
<213> ORGANISM: Homo sapiens
<220> FEATURE:
<223> OTHER INFORMATION: Antibody 41

<400> SEQUENCE: 402

Gln Val Gln Leu Val Gln Ser Gly Ala Glu Val Arg Lys Pro Gly Ala
                5                  10                  15

Ser Val Lys Val Ser Cys Lys Ala Ser Gly Tyr Ala Phe Thr Ser Tyr
            20                  25                  30

Tyr Met His Trp Ala Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Pro Glu Asp Thr Ala Val Tyr Tyr Cys
                85                  90                  95

Ala Arg Gly Lys Tyr Trp Met Tyr Asp Trp Gly Lys Gly Thr Leu Val
            100                 105                 110

Thr Val Ser Gly
        115

<210> SEQ ID NO 403
<211> LENGTH: 5
<212> TYPE: PRT
<213> ORGANISM: Homo sapiens
<220> FEATURE:
<223> OTHER INFORMATION: Antibody 41

<400> SEQUENCE: 403

Ser Tyr Tyr Met His
                5
```

```
<210> SEQ ID NO 404
<211> LENGTH: 17
<212> TYPE: PRT
<213> ORGANISM: Homo sapiens
<220> FEATURE:
<223> OTHER INFORMATION: Antibody 41

<400> SEQUENCE: 404

Ile Ile Asn Pro Ser Gly Gly Ser Thr Ser Tyr Ala Gln Lys Phe Gln
                 5                  10                  15
Gly

<210> SEQ ID NO 405
<211> LENGTH: 7
<212> TYPE: PRT
<213> ORGANISM: Homo sapiens
<220> FEATURE:
<223> OTHER INFORMATION: Antibody 41

<400> SEQUENCE: 405

Gly Lys Tyr Trp Met Tyr Asp
                 5

<210> SEQ ID NO 406
<211> LENGTH: 333
<212> TYPE: DNA
<213> ORGANISM: Homo sapiens
<220> FEATURE:
<223> OTHER INFORMATION: Antibody 41

<400> SEQUENCE: 406
cagtctgtgt tgacgcagcc gccctcagtg tctgcggccc caggacagaa ggtcaccatc      60
tcctgctctg gaggcagcac caacattggg aatagttatg tatcctggta ccagcgactc     120
ccaggaacag ccccaaaact cctcatttac gacaataata gcgaccccc agggattcct     180
gaccgattct ctggctccaa gtctggcacg tcagccaccc tggccatcac cggactccag     240
actggggacg aggccgatta ttactgcgga acatgggata ccagcacggt gtgggagtgg     300
ccgttcggaa ctgggaccaa gctgaccgtc cta                                  333

<210> SEQ ID NO 407
<211> LENGTH: 111
<212> TYPE: PRT
<213> ORGANISM: Homo sapiens
<220> FEATURE:
<223> OTHER INFORMATION: Antibody 41

<400> SEQUENCE: 407

Gln Ser Val Leu Thr Gln Pro Pro Ser Val Ser Ala Ala Pro Gly Gln
                 5                  10                  15
Lys Val Thr Ile Ser Cys Ser Gly Gly Ser Thr Asn Ile Gly Asn Ser
             20                  25                  30
Tyr Val Ser Trp Tyr Gln Arg Leu Pro Gly Thr Ala Pro Lys Leu Leu
         35                  40                  45
Ile Tyr Asp Asn Asn Lys Arg Pro Pro Gly Ile Pro Asp Arg Phe Ser
     50                  55                  60
Gly Ser Lys Ser Gly Thr Ser Ala Thr Leu Ala Ile Thr Gly Leu Gln
 65                  70                  75                  80
Thr Gly Asp Glu Ala Asp Tyr Tyr Cys Gly Thr Trp Asp Thr Ser Thr
                 85                  90                  95
Val Trp Glu Trp Pro Phe Gly Thr Gly Thr Lys Leu Thr Val Leu
                100                 105                 110
```

```
<210> SEQ ID NO 408
<211> LENGTH: 13
<212> TYPE: PRT
<213> ORGANISM: Homo sapiens
<220> FEATURE:
<223> OTHER INFORMATION: Antibody 41

<400> SEQUENCE: 408

Ser Gly Gly Ser Thr Asn Ile Gly Asn Ser Tyr Val Ser
                5                   10

<210> SEQ ID NO 409
<211> LENGTH: 7
<212> TYPE: PRT
<213> ORGANISM: Homo sapiens
<220> FEATURE:
<223> OTHER INFORMATION: Antibody 41

<400> SEQUENCE: 409

Asp Asn Asn Lys Arg Pro Pro
                5

<210> SEQ ID NO 410
<211> LENGTH: 12
<212> TYPE: PRT
<213> ORGANISM: Homo sapiens
<220> FEATURE:
<223> OTHER INFORMATION: Antibody 41

<400> SEQUENCE: 410

Gly Thr Trp Asp Thr Ser Thr Val Trp Glu Trp Pro
                5                   10

<210> SEQ ID NO 411
<211> LENGTH: 348
<212> TYPE: DNA
<213> ORGANISM: Homo sapiens
<220> FEATURE:
<223> OTHER INFORMATION: Antibody 42

<400> SEQUENCE: 411
caggtccagc tggtgcagtc tggggctgag gtgaagaagc ctggggcctc agtgaaggtt      60
tcctgcaagg catctggata cgcctttacc agctactata tgcactgggc gcgacaggcc     120
cctggacagg ggcttgagtg gtgggaata  atcaaccta  gcggtggtag cacaagctac     180
gcacagaagt tccagggcag agtcaccatg accaggaca  cgtccacgag cacagtctac     240
atggagctga gcagcctgag atctggggac acggccgtgt attactgtgc gagaggaaag     300
tactggatgt acgactgggg caaaggcacc ctggtcaccg tctcgagt                  348

<210> SEQ ID NO 412
<211> LENGTH: 116
<212> TYPE: PRT
<213> ORGANISM: Homo sapiens
<220> FEATURE:
<223> OTHER INFORMATION: Antibody 42

<400> SEQUENCE: 412

Gln Val Gln Leu Val Gln Ser Gly Ala Glu Val Lys Lys Pro Gly Ala
                5                   10                  15

Ser Val Lys Val Ser Cys Lys Ala Ser Gly Tyr Ala Phe Thr Ser Tyr
            20                  25                  30

Tyr Met His Trp Ala Arg Gln Ala Pro Gly Gln Gly Leu Glu Trp Val
        35                  40                  45
```

-continued

Gly Ile Ile Asn Pro Ser Gly Gly Ser Thr Ser Tyr Ala Gln Lys Phe
            50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Gly Asp Thr Ala Val Tyr Tyr Cys
                85                  90                  95

Ala Arg Gly Lys Tyr Trp Met Tyr Asp Trp Gly Lys Gly Thr Leu Val
            100                 105                 110

Thr Val Ser Ser
        115

<210> SEQ ID NO 413
<211> LENGTH: 5
<212> TYPE: PRT
<213> ORGANISM: Homo sapiens
<220> FEATURE:
<223> OTHER INFORMATION: Antibody 42

<400> SEQUENCE: 413

Ser Tyr Tyr Met His
              5

<210> SEQ ID NO 414
<211> LENGTH: 17
<212> TYPE: PRT
<213> ORGANISM: Homo sapiens
<220> FEATURE:
<223> OTHER INFORMATION: Antibody 42

<400> SEQUENCE: 414

Ile Ile Asn Pro Ser Gly Gly Ser Thr Ser Tyr Ala Gln Lys Phe Gln
                5                   10                  15

Gly

<210> SEQ ID NO 415
<211> LENGTH: 7
<212> TYPE: PRT
<213> ORGANISM: Homo sapiens
<220> FEATURE:
<223> OTHER INFORMATION: Antibody 42

<400> SEQUENCE: 415

Gly Lys Tyr Trp Met Tyr Asp
              5

<210> SEQ ID NO 416
<211> LENGTH: 333
<212> TYPE: DNA
<213> ORGANISM: Homo sapiens
<220> FEATURE:
<223> OTHER INFORMATION: Antibody 42

<400> SEQUENCE: 416
caggctgtgt tgacgcagcc gccctcagtg tctgcggccc caggacagaa ggtcaccatc      60
tcctgctctg gaggcagctc caacattggg aatagttatg tatcctgta ccagcgactc     120 ccaggagcag cccccaaact cctcatttac gacaataata agcgaccctc agggattcct     180
gaccgattct ctggctccaa gtctggcacg tcagccaccc tggccatcac cggactccag     240
actggggacg aggccgatta ttactgcgga acatgggata ccagcacggg gtgggagtgg     300
ccgttcggaa ctgggaccaa gctgaccgtc cta                                  333

<210> SEQ ID NO 417

```
<211> LENGTH: 111
<212> TYPE: PRT
<213> ORGANISM: Homo sapiens
<220> FEATURE:
<223> OTHER INFORMATION: Antibody 42

<400> SEQUENCE: 417

Gln Ala Val Leu Thr Gln Pro Pro Ser Val Ser Ala Ala Pro Gly Gln
                  5                  10                  15

Lys Val Thr Ile Ser Cys Ser Gly Gly Ser Ser Asn Ile Gly Asn Ser
             20                  25                  30

Tyr Val Ser Trp Tyr Gln Arg Leu Pro Gly Ala Ala Pro Lys Leu Leu
         35                  40                  45

Ile Tyr Asp Asn Asn Lys Arg Pro Ser Gly Ile Pro Asp Arg Phe Ser
     50                  55                  60

Gly Ser Lys Ser Gly Thr Ser Ala Thr Leu Ala Ile Thr Gly Leu Gln
 65                  70                  75                  80

Thr Gly Asp Glu Ala Asp Tyr Tyr Cys Gly Thr Trp Asp Thr Ser Thr
                 85                  90                  95

Gly Trp Glu Trp Pro Phe Gly Thr Gly Thr Lys Leu Thr Val Leu
            100                 105                 110

<210> SEQ ID NO 418
<211> LENGTH: 13
<212> TYPE: PRT
<213> ORGANISM: Homo sapiens
<220> FEATURE:
<223> OTHER INFORMATION: Antibody 42

<400> SEQUENCE: 418

Ser Gly Gly Ser Ser Asn Ile Gly Asn Ser Tyr Val Ser
                  5                  10

<210> SEQ ID NO 419
<211> LENGTH: 7
<212> TYPE: PRT
<213> ORGANISM: Homo sapiens
<220> FEATURE:
<223> OTHER INFORMATION: Antibody 42

<400> SEQUENCE: 419

Asp Asn Asn Lys Arg Pro Ser
                  5

<210> SEQ ID NO 420
<211> LENGTH: 12
<212> TYPE: PRT
<213> ORGANISM: Homo sapiens
<220> FEATURE:
<223> OTHER INFORMATION: Antibody 42

<400> SEQUENCE: 420

Gly Thr Trp Asp Thr Ser Thr Gly Trp Glu Trp Pro
                  5                  10

<210> SEQ ID NO 421
<211> LENGTH: 348
<212> TYPE: DNA
<213> ORGANISM: Homo sapiens
<220> FEATURE:
<223> OTHER INFORMATION: Antibody 24 PGL

<400> SEQUENCE: 421
caggtccagc tggtgcagtc tggggctgag gtgaagaagc ctggggcctc agtgaaggtt    60
```

```
tcctgcaagg catctggata cgccttcacc agctactata tgcactgggt gcgacaggcc    120
cctggacaag ggcttgagtg gatgggaata atcaaccctg aggtggtag cacaagctac     180 gcacagaagt tccagggcag agtcaccatg accagggaca cgtccacgag cacagtctac    240
atggagctga gcagcctgag atctgaggac acggccgtgt attactgtgc gagaggaaag    300
tactggatgt acgactgggg caaaggcacc ctggtcaccg tctcgagt                 348
```

<210> SEQ ID NO 422
<211> LENGTH: 116
<212> TYPE: PRT
<213> ORGANISM: Homo sapiens
<220> FEATURE:
<223> OTHER INFORMATION: Antibody 24 PGL

<400> SEQUENCE: 422

Gln Val Gln Leu Val Gln Ser Gly Ala Glu Val Lys Lys Pro Gly Ala
                1               5                   10                  15
Ser Val Lys Val Ser Cys Lys Ala Ser Gly Tyr Ala Phe Thr Ser Tyr
                20                  25                  30
Tyr Met His Trp Val Arg Gln Ala Pro Gly Gln Gly Leu Glu Trp Met
            35                  40                  45
Gly Ile Ile Asn Pro Arg Gly Gly Ser Thr Ser Tyr Ala Gln Lys Phe
        50                  55                  60
Gln Gly Arg Val Thr Met Thr Arg Asp Thr Ser Thr Ser Thr Val Tyr
    65                  70                  75                  80
Met Glu Leu Ser Ser Leu Arg Ser Glu Asp Thr Ala Val Tyr Tyr Cys
                85                  90                  95
Ala Arg Gly Lys Tyr Trp Met Tyr Asp Trp Gly Lys Gly Thr Leu Val
                100                 105                 110
Thr Val Ser Ser
            115

<210> SEQ ID NO 423
<211> LENGTH: 5
<212> TYPE: PRT
<213> ORGANISM: Homo sapiens
<220> FEATURE:
<223> OTHER INFORMATION: Antibody 24 PGL

<400> SEQUENCE: 423

Ser Tyr Tyr Met His
                5

<210> SEQ ID NO 424
<211> LENGTH: 17
<212> TYPE: PRT
<213> ORGANISM: Homo sapiens
<220> FEATURE:
<223> OTHER INFORMATION: Antibody 24 PGL

<400> SEQUENCE: 424

Ile Ile Asn Pro Arg Gly Gly Ser Thr Ser Tyr Ala Gln Lys Phe Gln
                5                   10                  15
Gly

<210> SEQ ID NO 425
<211> LENGTH: 7
<212> TYPE: PRT
<213> ORGANISM: Homo sapiens
<220> FEATURE:
<223> OTHER INFORMATION: Antibody 24 PGL

<400> SEQUENCE: 425

Gly Lys Tyr Trp Met Tyr Asp
              5

<210> SEQ ID NO 426
<211> LENGTH: 333
<212> TYPE: DNA
<213> ORGANISM: Homo sapiens
<220> FEATURE:
<223> OTHER INFORMATION: Antibody 24 PGL

<400> SEQUENCE: 426
cagtctgtgt tgacgcagcc gccctcagtg tctgcggccc caggacagaa ggtcaccatc      60
tcctgctctg gaggcagctc aacattggg aatagttatg tatcctggta ccagcaactc     120
ccaggaacag cccccaaaact cctcatttac gacaataata agcgaccctc agggattcct    180
gaccgattct ctggctccaa gtctggcacg tcagccaccc tgggcatcac cggactccag    240
actggggacg aggccgatta tttctgcgga acatgggata ccagcacggt gtgggagtgg    300
ccgttcggaa ctgggaccaa gctgaccgtc cta                                  333

<210> SEQ ID NO 427
<211> LENGTH: 111
<212> TYPE: PRT
<213> ORGANISM: Homo sapiens
<220> FEATURE:
<223> OTHER INFORMATION: Antibody 24 PGL

<400> SEQUENCE: 427

Gln Ser Val Leu Thr Gln Pro Pro Ser Val Ser Ala Ala Pro Gly Gln
                5                  10                  15

Lys Val Thr Ile Ser Cys Ser Gly Gly Ser Ser Asn Ile Gly Asn Ser
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Phe Cys Gly Thr Trp Asp Thr Ser Thr
                85                  90                  95

Val Trp Glu Trp Pro Phe Gly Thr Gly Thr Lys Leu Thr Val Leu
            100                 105                 110

<210> SEQ ID NO 428
<211> LENGTH: 13
<212> TYPE: PRT
<213> ORGANISM: Homo sapiens
<220> FEATURE:
<223> OTHER INFORMATION: Antibody 24 PGL

<400> SEQUENCE: 428

Ser Gly Gly Ser Ser Asn Ile Gly Asn Ser Tyr Val Ser
                5                  10

<210> SEQ ID NO 429
<211> LENGTH: 7
<212> TYPE: PRT
<213> ORGANISM: Homo sapiens
<220> FEATURE:
<223> OTHER INFORMATION: Antibody 24 PGL

<400> SEQUENCE: 429

Asp Asn Asn Lys Arg Pro Ser
            5

<210> SEQ ID NO 430
<211> LENGTH: 12
<212> TYPE: PRT
<213> ORGANISM: Homo sapiens
<220> FEATURE:
<223> OTHER INFORMATION: Antibody 24 PGL

<400> SEQUENCE: 430

Gly Thr Trp Asp Thr Ser Thr Val Trp Glu Trp Pro
            5                   10

<210> SEQ ID NO 431
<211> LENGTH: 348
<212> TYPE: DNA
<213> ORGANISM: Homo sapiens
<220> FEATURE:
<223> OTHER INFORMATION: Antibody 24 GL

<400> SEQUENCE: 431
caggtccagc tggtgcagtc tggggctgag gtgaagaagc ctggggcctc agtgaaggtt        60
tcctgcaagg catctggata cgccttcacc agctactata tgcactgggt gcgacaggcc       120
cctggacaag gcttgagtg gatgggaata atcaaccta gaggtggtag cacaagctac         180
gcacagaagt tccagggcag agtcaccatg accagggaca cgtccacgag cacagtctac       240
atggagctga gcagcctgag atctgaggac acggccgtgt attactgtgc gagaggaaag       300
tactggatgt acgactgggg caaaggcacc ctggtcaccg tctcgagt                    348

<210> SEQ ID NO 432
<211> LENGTH: 116
<212> TYPE: PRT
<213> ORGANISM: Homo sapiens
<220> FEATURE:
<223> OTHER INFORMATION: Antibody 24 GL

<400> SEQUENCE: 432

Gln Val Gln Leu Val Gln Ser Gly Ala Glu Val Lys Lys Pro Gly Ala
            5                   10                  15

Ser Val Lys Val Ser Cys Lys Ala Ser Gly Tyr Ala Phe Thr Ser Tyr
            20                  25                  30

Tyr Met His Trp Val Arg Gln Ala Pro Gly Gln Gly Leu Glu Trp Met
            35                  40                  45

Gly Ile Ile Asn Pro Arg Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Lys Tyr Trp Met Tyr Asp Trp Gly Lys Gly Thr Leu Val
            100                 105                 110

Thr Val Ser Ser
        115

<210> SEQ ID NO 433
<211> LENGTH: 5
<212> TYPE: PRT
<213> ORGANISM: Homo sapiens
<220> FEATURE:
<223> OTHER INFORMATION: Antibody 24 GL

<400> SEQUENCE: 433

Ser Tyr Tyr Met His
                5

<210> SEQ ID NO 434
<211> LENGTH: 17
<212> TYPE: PRT
<213> ORGANISM: Homo sapiens
<220> FEATURE:
<223> OTHER INFORMATION: Antibody 24 GL

<400> SEQUENCE: 434

Ile Ile Asn Pro Arg Gly Gly Ser Thr Ser Tyr Ala Gln Lys Phe Gln
                5                  10                  15
Gly

<210> SEQ ID NO 435
<211> LENGTH: 7
<212> TYPE: PRT
<213> ORGANISM: Homo sapiens
<220> FEATURE:
<223> OTHER INFORMATION: Antibody 24 GL

<400> SEQUENCE: 435

Gly Lys Tyr Trp Met Tyr Asp
                5

<210> SEQ ID NO 436
<211> LENGTH: 333
<212> TYPE: DNA
<213> ORGANISM: Homo sapiens
<220> FEATURE:
<223> OTHER INFORMATION: Antibody 24 GL

<400> SEQUENCE: 436
cagtctgtgt tgacgcagcc gccctcagtg tctgcggccc caggacagaa ggtcaccatc        60
tcctgctctg gaggcagctc caacattggg aatagttatg tatcctggta ccagcaactc       120
ccaggaacag cccccaaact cctcatttac gacaataata gcgaccctca gggattcct        180 gaccgattct ctggctccaa gtctggcacg tcagccaccc tgggcatcac cggactccag       240
actggggacg aggccgatta ttactgcgga acatgggata ccagcacggt gtgggagtgg       300
ccgttcggaa ctgggaccaa gctgaccgtc cta                                    333

<210> SEQ ID NO 437
<211> LENGTH: 111
<212> TYPE: PRT
<213> ORGANISM: Homo sapiens
<220> FEATURE:
<223> OTHER INFORMATION: Antibody 24 GL

<400> SEQUENCE: 437

Gln Ser Val Leu Thr Gln Pro Pro Ser Val Ser Ala Ala Pro Gly Gln
                5                  10                  15

Lys Val Thr Ile Ser Cys Ser Gly Gly Ser Ser Asn Ile Gly Asn Ser
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Thr Ser Thr
            85                  90                  95

Val Trp Glu Trp Pro Phe Gly Thr Gly Thr Lys Leu Thr Val Leu
            100                 105                 110

<210> SEQ ID NO 438
<211> LENGTH: 13
<212> TYPE: PRT
<213> ORGANISM: Homo sapiens
<220> FEATURE:
<223> OTHER INFORMATION: Antibody 24 GL

<400> SEQUENCE: 438

Ser Gly Gly Ser Ser Asn Ile Gly Asn Ser Tyr Val Ser
            5                   10

<210> SEQ ID NO 439
<211> LENGTH: 7
<212> TYPE: PRT
<213> ORGANISM: Homo sapiens
<220> FEATURE:
<223> OTHER INFORMATION: Antibody 24 GL

<400> SEQUENCE: 439

Asp Asn Asn Lys Arg Pro Ser
            5

<210> SEQ ID NO 440
<211> LENGTH: 12
<212> TYPE: PRT
<213> ORGANISM: Homo sapiens
<220> FEATURE:
<223> OTHER INFORMATION: Antibody 24 GL

<400> SEQUENCE: 440

Gly Thr Trp Asp Thr Ser Thr Val Trp Glu Trp Pro
            5                   10

<210> SEQ ID NO 441
<211> LENGTH: 348
<212> TYPE: DNA
<213> ORGANISM: Homo sapiens
<220> FEATURE:
<223> OTHER INFORMATION: Antibody 37 GL

<400> SEQUENCE: 441
caggtccagc tggtgcagtc tggggctgag gtgaagaagc ctggggcctc agtgaaggtt      60
tcctgcaagg catctggata cgccttcacc agctactata tgcactgggt gcgacaggcc     120
cctggacaag gcttgagtg gatgggaata atcaaccta gaggtggtag cacaagctac       180
gcacagaagt tccagggcag agtcaccatg accagggaca cgtccacgag cacagtctac     240
atggagctga gcagcctgag atctgaggac acggccgtgt attactgtgc gagaggaaag     300
tactggatgt acgactgggg caaaggcacc ctggtcaccg tctcgagt                  348

<210> SEQ ID NO 442
<211> LENGTH: 116
<212> TYPE: PRT
<213> ORGANISM: Homo sapiens
<220> FEATURE:
<223> OTHER INFORMATION: Antibody 37 GL

<400> SEQUENCE: 442

Gln Val Gln Leu Val Gln Ser Gly Ala Glu Val Lys Lys Pro Gly Ala
            5                   10                  15

```
Ser Val Lys Val Ser Cys Lys Ala Ser Gly Tyr Ala Phe Thr Ser Tyr
          20                  25                  30

Tyr Met His Trp Val Arg Gln Ala Pro Gly Gln Gly Leu Glu Trp Met
         35                  40                  45

Gly Ile Ile Asn Pro Arg Gly Gly Ser Thr Ser Tyr Ala Gln Lys Phe
 50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Gly Lys Tyr Trp Met Tyr Asp Trp Gly Lys Gly Thr Leu Val
            100                 105                 110

Thr Val Ser Ser
        115

<210> SEQ ID NO 443
<211> LENGTH: 5
<212> TYPE: PRT
<213> ORGANISM: Homo sapiens
<220> FEATURE:
<223> OTHER INFORMATION: Antibody 37 GL

<400> SEQUENCE: 443

Ser Tyr Tyr Met His
              5

<210> SEQ ID NO 444
<211> LENGTH: 17
<212> TYPE: PRT
<213> ORGANISM: Homo sapiens
<220> FEATURE:
<223> OTHER INFORMATION: Antibody 37 GL

<400> SEQUENCE: 444

Ile Ile Asn Pro Arg Gly Gly Ser Thr Ser Tyr Ala Gln Lys Phe Gln
                 5                  10                  15

Gly

<210> SEQ ID NO 445
<211> LENGTH: 7
<212> TYPE: PRT
<213> ORGANISM: Homo sapiens
<220> FEATURE:
<223> OTHER INFORMATION: Antibody 37 GL

<400> SEQUENCE: 445

Gly Lys Tyr Trp Met Tyr Asp
              5

<210> SEQ ID NO 446
<211> LENGTH: 333
<212> TYPE: DNA
<213> ORGANISM: Homo sapiens
<220> FEATURE:
<223> OTHER INFORMATION: Antibody 37 GL

<400> SEQUENCE: 446
cagtctgtgt tgacgcagcc gccctcagtg tcagcggccc caggacagaa ggtcaccatc      60
tcctgctctg gaggcggctc cagcattggg aatagctatg tatcctggta ccagcaactc     120
ccaggaacag ccccc aaact cctcatctac gacaataata gcgaccctc agggattcct     180 gaccgattct ctggctccaa gtctggcacg tcagccaccc tgggcatcac cggactccag     240
```
actggggacg aggccgatta ttactgcgga acatgggata ccagcccggt gtgggagtgg    300
ccgttcggaa ctgggaccaa gctgaccgtc cta                                 333

<210> SEQ ID NO 447
<211> LENGTH: 111
<212> TYPE: PRT
<213> ORGANISM: Homo sapiens
<220> FEATURE:
<223> OTHER INFORMATION: Antibody 37 GL

<400> SEQUENCE: 447

Gln Ser Val Leu Thr Gln Pro Pro Ser Val Ala Ala Pro Gly Gln
                 5                  10                  15

Lys Val Thr Ile Ser Cys Ser Gly Gly Gly Ser Ser Ile Gly Asn Ser
             20                  25                  30

Tyr Val Ser Trp Tyr Gln Gln Leu Pro Gly Thr Ala Pro Lys Leu Leu
         35                  40                  45

Ile Tyr Asp Asn Asn Lys Arg Pro Ser Gly Ile Pro Asp Arg Phe Ser
     50                  55                  60

Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp Thr Ser Pro
                 85                  90                  95

Val Trp Glu Trp Pro Phe Gly Thr Gly Thr Lys Leu Thr Val Leu
            100                 105                 110

<210> SEQ ID NO 448
<211> LENGTH: 13
<212> TYPE: PRT
<213> ORGANISM: Homo sapiens
<220> FEATURE:
<223> OTHER INFORMATION: Antibody 37 GL

<400> SEQUENCE: 448

Ser Gly Gly Gly Ser Ser Ile Gly Asn Ser Tyr Val Ser
                 5                  10

<210> SEQ ID NO 449
<211> LENGTH: 7
<212> TYPE: PRT
<213> ORGANISM: Homo sapiens
<220> FEATURE:
<223> OTHER INFORMATION: Antibody 37 GL

<400> SEQUENCE: 449

Asp Asn Asn Lys Arg Pro Ser
                 5

<210> SEQ ID NO 450
<211> LENGTH: 12
<212> TYPE: PRT
<213> ORGANISM: Homo sapiens
<220> FEATURE:
<223> OTHER INFORMATION: Antibody 37 GL

<400> SEQUENCE: 450

Gly Thr Trp Asp Thr Ser Pro Val Trp Glu Trp Pro
                 5                  10

<210> SEQ ID NO 451
<211> LENGTH: 96
<212> TYPE: DNA
<213> ORGANISM: Artificial

```
<220> FEATURE:
<223> OTHER INFORMATION: Cyno IL4R primer 1

<400> SEQUENCE: 451
ggggacaagt tgtacaaaa aagcaggctt ctttaacttt aagaaggaga tataaccatg    60
gggtggcttt gctctgggct cctgttgcct gtgagc                            96

<210> SEQ ID NO 452
<211> LENGTH: 63
<212> TYPE: DNA
<213> ORGANISM: Artificial
<220> FEATURE:
<223> OTHER INFORMATION: Cyno IL4R primer 2

<400> SEQUENCE: 452
ggggaccact ttgtacaaga aagctgggtc ctgctcgaag ggctccctgt aggagttgta    60
cca                                                                63

<210> SEQ ID NO 453
<211> LENGTH: 32
<212> TYPE: DNA
<213> ORGANISM: Artificial
<220> FEATURE:
<223> OTHER INFORMATION: I75V oligonucleotide mutation primer

<400> SEQUENCE: 453
gaagcccaca cgtgtgccct gagaacaacg ga                                32

<210> SEQ ID NO 454
<211> LENGTH: 478
<212> TYPE: PRT
<213> ORGANISM: Homo sapiens

<400> SEQUENCE: 454
```

Met Gly Trp Leu Cys Ser Gly Leu Leu Phe Pro Val Ser Cys Leu Val
1               5                   10                  15

Leu Leu Gln Val Ala Ser Ser Gly Asn Met Lys Val Leu Gln Glu Pro
            20                  25                  30

Thr Cys Val Ser Asp Tyr Met Ser Ile Ser Thr Cys Glu Trp Lys Met
        35                  40                  45

Asn Gly Pro Thr Asn Cys Ser Thr Glu Leu Arg Leu Leu Tyr Gln Leu
    50                  55                  60

Val Phe Leu Leu Ser Glu Ala His Thr Cys Ile Pro Glu Asn Asn Gly
65                  70                  75                  80

Gly Ala Gly Cys Val Cys His Leu Leu Met Asp Asp Val Val Ser Ala
                85                  90                  95

Asp Asn Tyr Thr Leu Asp Leu Trp Ala Gly Gln Gln Leu Leu Trp Lys
            100                 105                 110

Gly Ser Phe Lys Pro Ser Glu His Val Lys Pro Arg Ala Pro Gly Asn
        115                 120                 125

Leu Thr Val His Thr Asn Val Ser Asp Thr Leu Leu Leu Thr Trp Ser
    130                 135                 140

Asn Pro Tyr Pro Pro Asp Asn Tyr Leu Tyr Asn His Leu Thr Tyr Ala
145                 150                 155                 160

Val Asn Ile Trp Ser Glu Asn Asp Pro Ala Asp Phe Arg Ile Tyr Asn
                165                 170                 175

Val Thr Tyr Leu Glu Pro Ser Leu Arg Ile Ala Ala Ser Thr Leu Lys
            180                 185                 190

Ser Gly Ile Ser Tyr Arg Ala Arg Val Arg Ala Trp Ala Gln Cys Tyr

```
                  195                 200                 205
Asn Thr Thr Trp Ser Glu Trp Ser Pro Ser Thr Lys Trp His Asn Ser
210                 215                 220

Tyr Arg Glu Pro Phe Asp Pro Ala Phe Leu Tyr Lys Val Val Gly Ala
225                 230                 235                 240

Ala Pro Lys Ser Cys Asp Lys Thr His Thr Cys Pro Pro Cys Pro Ala
                    245                 250                 255

Pro Glu Leu Leu Gly Gly Pro Ser Val Phe Leu Phe Pro Pro Lys Pro
                260                 265                 270

Lys Asp Thr Leu Met Ile Ser Arg Thr Pro Glu Val Thr Cys Val Val
            275                 280                 285

Val Asp Val Ser His Glu Asp Pro Glu Val Lys Phe Asn Trp Tyr Val
290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                    325                 330                 335

Asp Trp Leu Asn Gly Lys Glu Tyr Lys Cys Lys Val Ser Asn Lys Ala
                340                 345                 350

Leu Pro Ala Pro Ile Glu Lys Thr Ile Ser Lys Ala Lys Gly Gln Pro
            355                 360                 365

Arg Glu Pro Gln Val Tyr Thr Leu Pro Pro Ser Arg Asp Glu Leu Thr
370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                    405                 410                 415

Lys Thr Thr Pro Pro Val Leu Asp Ser Asp Gly Ser Phe Phe Leu Tyr
                420                 425                 430

Ser Lys Leu Thr Val Asp Lys Ser Arg Trp Gln Gln Gly Asn Val Phe
            435                 440                 445

Ser Cys Ser Val Met His Glu Ala Leu His Asn His Tyr Thr Gln Lys
450                 455                 460

Ser Leu Ser Leu Ser Pro Gly Lys His His His His His His
465                 470                 475
```

<210> SEQ ID NO 455
<211> LENGTH: 693
<212> TYPE: DNA
<213> ORGANISM: Macaca fascicularis
<220> FEATURE:
<223> OTHER INFORMATION: Cynomolgus monkey IL-4Ra cDNA nucleotide

<400> SEQUENCE: 455

```
atgggtggc tttgctctgg gctcctgttg cctgtgagct gcctggtcct gctgcaggtg      60
gcaagctctg ggagcatgaa ggtcctgcag gagcccacct gcgtctccga ctacatgagc    120
atctctacct gtgagtggaa gatgggcggt cccaccaatt gcagcgccga gctccgtctg    180
ttgtaccagc tggttttttca gtcctccgaa acccacacgt gtgtccccga gaacaacggc    240
ggtgtggggt gcgtgtgcca cctgctcatg gatgatgtgg tcagtatgga caactatacg    300
ctggacctgt gggctggaca gcagctgctg tggaagggcc cttcaagcc cagcgagcat    360 gtgaaaccca gggccccagg aaacctcacg gttcacacca tgtctccga cactgtgctg    420 ctgacctgga gcaacccata tcccctgac aattacctgt ataatgatct cacctatgca    480
gtcaacattt ggagtgaaaa cgacccggca tattccagaa tccataacgt gacctaccta    540
```

```
aaacccaccc tccgcatccc agccagcacc ctgaagtctg gaatttccta cagggcacgg      600
gtgagggcct gggctcagca ctataacacc acctggagtg agtggagccc cagcaccaag      660
tggtacaact cctacaggga gcccttcgag cag                                   693
```

<210> SEQ ID NO 456
<211> LENGTH: 1428
<212> TYPE: DNA
<213> ORGANISM: Macaca fascicularis
<220> FEATURE:
<223> OTHER INFORMATION: Cynomolgus monkey IL-4Ra/Fc cDNA nucleotide

<400> SEQUENCE: 456

```
atggggtggc tttgctctgg gctcctgttg cctgtgagct gcctggtcct gctgcaggtg       60
gcaagctctg ggagcatgaa ggtcctgcag gagcccacct gcgtctccga ctacatgagc      120
atctctacct gtgagtggaa gatgggcggt cccaccaatt gcagcgccga gctccgtctg      180
ttgtaccagc tggttttttca gtcctccgaa acccacacgt gtgtccccga gaacaacggc     240
ggtgtggggt gcgtgtgcca cctgctcatg gatgatgtgg tcagtatgga caactatacg      300
ctggacctgt gggctggaca gcagctgctg tggaagggct ccttcaagcc cagcgagcat      360
gtgaaaccca gggccccagg aaacctcacg gttcacacca atgtctccga cactgtgctg      420
ctgacctgga gcaacccata tccccctgac aattacctgt ataatgatct cacctatgca      480
gtcaacattt ggagtgaaaa cgacccggca tattccagaa tccataacgt gacctaccta      540
aaacccaccc tccgcatccc agccagcacc ctgaagtctg gaatttccta cagggcacgg      600
gtgagggcct gggctcagca ctataacacc acctggagtg agtggagccc cagcaccaag      660
tggtacaact cctacaggga gcccttcgag caggacccag ctttcttgta caaagtggtt      720
cgattcgagg agcccaaatc tagcgacaaa actcacacat gcccaccgtg cccagcacct      780
gaactcctgg ggggaccgtc agtcttcctc ttccccccaa aacccaagga caccctcatg      840
atctcccgga cccctgaggt cacatgcgtg gtggtggacg tgagccacga agaccctgag      900
gtcaagttca actggtacgt ggacggcgtg gaggtgcata atgccaagac aaagccgcgg      960
gaggagcagt acaacagcac gtaccgtgtg gtcagcgtcc tcaccgtcct gcaccaggac     1020
tggctgaatg gcaaggagta caagtgcaag gtctccaaca aagccctccc agcccccatc     1080
gagaaaacca tctccaaagc caaagggcag ccccgagaac acaggtgta cacccctgccc     1140 ccatcccggg atgagctgac caagaaccag gtcagcctga cctgcctggt caaaggcttc     1200
tatcccagcg acatcgccgt ggagtgggag agcaatgggc agccggagaa caactacaaa     1260
accacgcctc ccgtgctgga ctccgacggc tccttcttcc tctacagcaa gctcaccgtg     1320
gacaagagca ggtggcagca ggggaacgtc ttctcatgct ccgtgatgca tgaggctctg     1380
cacaaccact acacgcagaa gagcctctcc ctgtctccgg gtaaatga               1428
```

<210> SEQ ID NO 457
<211> LENGTH: 475
<212> TYPE: PRT
<213> ORGANISM: Macaca fascicularis
<220> FEATURE:
<223> OTHER INFORMATION: Cynomolgus monkey IL-4Ra/Fc protein

<400> SEQUENCE: 457

```
Met Gly Trp Leu Cys Ser Gly Leu Leu Leu Pro Val Ser Cys Leu Val
1               5                   10                  15

Leu Leu Gln Val Ala Ser Ser Gly Ser Met Lys Val Leu Gln Glu Pro
            20                  25                  30
```

```
Thr Cys Val Ser Asp Tyr Met Ser Ile Ser Thr Cys Glu Trp Lys Met
            35                  40                  45

Gly Gly Pro Thr Asn Cys Ser Ala Glu Leu Arg Leu Leu Tyr Gln Leu
 50                  55                  60

Val Phe Gln Ser Ser Glu Thr His Thr Cys Val Pro Glu Asn Asn Gly
 65                  70                  75                  80

Gly Val Gly Cys Val Cys His Leu Leu Met Asp Asp Val Val Ser Met
                 85                  90                  95

Asp Asn Tyr Thr Leu Asp Leu Trp Ala Gly Gln Gln Leu Leu Trp Lys
            100                 105                 110

Gly Ser Phe Lys Pro Ser Glu His Val Lys Pro Arg Ala Pro Gly Asn
            115                 120                 125

Leu Thr Val His Thr Asn Val Ser Asp Thr Val Leu Leu Thr Trp Ser
            130                 135                 140

Asn Pro Tyr Pro Pro Asp Asn Tyr Leu Tyr Asn Asp Leu Thr Tyr Ala
145                 150                 155                 160

Val Asn Ile Trp Ser Glu Asn Asp Pro Ala Tyr Ser Arg Ile His Asn
                165                 170                 175

Val Thr Tyr Leu Lys Pro Thr Leu Arg Ile Pro Ala Ser Thr Leu Lys
            180                 185                 190

Ser Gly Ile Ser Tyr Arg Ala Arg Val Arg Ala Trp Ala Gln His Tyr
            195                 200                 205

Asn Thr Thr Trp Ser Glu Trp Ser Pro Ser Thr Lys Trp Tyr Asn Ser
210                 215                 220

Tyr Arg Glu Pro Phe Glu Gln Asp Pro Ala Phe Leu Tyr Lys Val Val
225                 230                 235                 240

Arg Phe Glu Glu Pro Lys Ser Ser Asp Lys Thr His Thr Cys Pro Pro
                245                 250                 255

Cys Pro Ala Pro Glu Leu Leu Gly Gly Pro Ser Val Phe Leu Phe Pro
            260                 265                 270

Pro Lys Pro Lys Asp Thr Leu Met Ile Ser Arg Thr Pro Glu Val Thr
            275                 280                 285

Cys Val Val Val Asp Val Ser His Glu Asp Pro Glu Val Lys Phe Asn
            290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Glu Tyr Lys Cys Lys Val Ser
            340                 345                 350

Asn Lys Ala Leu Pro Ala Pro Ile Glu Lys Thr Ile Ser Lys Ala Lys
            355                 360                 365

Gly Gln Pro Arg Glu Pro Gln Val Tyr Thr Leu Pro Pro Ser Arg Asp
            370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
            435                 440                 445

Asn Val Phe Ser Cys Ser Val Met His Glu Ala Leu His Asn His Tyr
```

Thr Gln Lys Ser Leu Ser Leu Ser Pro Gly Lys
465                 470                 475

<210> SEQ ID NO 458
<211> LENGTH: 1422
<212> TYPE: DNA
<213> ORGANISM: Homo sapiens
<220> FEATURE:
<223> OTHER INFORMATION: Human I75V IL-4Ra/Fc cDNA nucleotide

<400> SEQUENCE: 458

```
atggggtggc tttgctctgg gctcctgttc cctgtgagct gcctggtcct gctgcaggtg     60
gcaagctctg gaacatgaa ggtcttgcag gagcccacct gcgtctccga ctacatgagc    120
atctctactt gcgagtggaa gatgaatggt cccaccaatt gcagcaccga gctccgcctg    180
ttgtaccagc tggttttct gctctccgaa gcccacacgt gtgtccctga gaacaacgga    240
ggcgcgggt gcgtgtgcca cctgctcatg atgacgtgg tcagtgcgga taactataca    300
ctggacctgt gggctgggca gcagctgctg tggaagggct ccttcaagcc cagcgagcat    360
gtgaaaccca gggccccagg aaacctgaca gttcacacca atgtctccga cactctgctg    420
ctgacctgga gcaacccgta tccccctgac aattacctgt ataatcatct cacctatgca    480
gtcaacattt ggagtgaaaa cgacccggca gatttcagaa tctataacgt gacctaccta    540
gaaccctccc tccgcatcgc agccagcacc ctgaagtctg gatttcctag gggcacgg    600
gtgagggcct gggctcagtg ctataacacc acctggagtg agtggagccc cagcaccaag    660
tggcacaact cctacaggga gcccttcgac ccagctttct tgtacaaagt ggttcgattc    720
gaggagccca atctagcga caaaactcac acatgcccac cgtgcccagc acctgaactc    780
ctggggggac cgtcagtctt cctcttcccc ccaaaaccca aggacaccct catgatctcc    840
cggacccctg aggtcacatg cgtggtggtg gacgtgagcc acgaagaccc tgaggtcaag    900
ttcaactggt acgtggacgg cgtggaggtg cataatgcca agacaaagcc gcgggaggag    960
cagtacaaca gcacgtaccg tgtggtcagc gtcctcaccg tcctgcacca ggactggctg   1020
aatggcaagg agtacaagtg caaggtctcc aacaaagccc tcccagcccc catcgagaaa   1080
accatctcca aagccaaagg gcagccccga gaaccacagg tgtacaccct gcccccatcc   1140
cgggatgagc tgaccaagaa ccaggtcagc ctgacctgcc tggtcaaagg cttctatccc   1200
agcgacatcg ccgtggagtg ggagagcaat gggcagccgg agaacaacta caaaaccacg   1260
cctcccgtgc tggactccga cggctccttc ttcctctaca gcaagctcac cgtggacaag   1320
agcaggtggc agcaggggaa cgtcttctca tgctccgtga tgcatgaggc tctgcacaac   1380
cactacacgc agaagagcct ctccctgtct ccgggtaaat ga                      1422
```

<210> SEQ ID NO 459
<211> LENGTH: 473
<212> TYPE: PRT
<213> ORGANISM: Homo sapiens
<220> FEATURE:
<223> OTHER INFORMATION: Human I75V IL-4Ra/Fc protein

<400> SEQUENCE: 459

Met Gly Trp Leu Cys Ser Gly Leu Leu Phe Pro Val Ser Cys Leu Val
1               5                   10                  15

Leu Leu Gln Val Ala Ser Ser Gly Asn Met Lys Val Leu Gln Glu Pro
            20                  25                  30

Thr Cys Val Ser Asp Tyr Met Ser Ile Ser Thr Cys Glu Trp Lys Met

```
                35                  40                  45
Asn Gly Pro Thr Asn Cys Ser Thr Glu Leu Arg Leu Leu Tyr Gln Leu
 50                  55                  60
Val Phe Leu Leu Ser Glu Ala His Thr Cys Val Pro Glu Asn Asn Gly
 65                  70                  75                  80
Gly Ala Gly Cys Val Cys His Leu Leu Met Asp Asp Val Val Ser Ala
                     85                  90                  95
Asp Asn Tyr Thr Leu Asp Leu Trp Ala Gly Gln Leu Leu Trp Lys
                100                 105                 110
Gly Ser Phe Lys Pro Ser Glu His Val Lys Pro Arg Ala Pro Gly Asn
            115                 120                 125
Leu Thr Val His Thr Asn Val Ser Asp Thr Leu Leu Leu Thr Trp Ser
        130                 135                 140
Asn Pro Tyr Pro Pro Asp Asn Tyr Leu Tyr Asn His Leu Thr Tyr Ala
145                 150                 155                 160
Val Asn Ile Trp Ser Glu Asn Asp Pro Ala Asp Phe Arg Ile Tyr Asn
                165                 170                 175
Val Thr Tyr Leu Glu Pro Ser Leu Arg Ile Ala Ala Ser Thr Leu Lys
            180                 185                 190
Ser Gly Ile Ser Tyr Arg Ala Arg Val Arg Ala Trp Ala Gln Cys Tyr
        195                 200                 205
Asn Thr Thr Trp Ser Glu Trp Ser Pro Ser Thr Lys Trp His Asn Ser
    210                 215                 220
Tyr Arg Glu Pro Phe Asp Pro Ala Phe Leu Tyr Lys Val Val Arg Phe
225                 230                 235                 240
Glu Glu Pro Lys Ser Ser Asp Lys Thr His Thr Cys Pro Pro Cys Pro
                245                 250                 255
Ala Pro Glu Leu Leu Gly Gly Pro Ser Val Phe Leu Phe Pro Pro Lys
            260                 265                 270
Pro Lys Asp Thr Leu Met Ile Ser Arg Thr Pro Glu Val Thr Cys Val
        275                 280                 285
Val Val Asp Val Ser His Glu Asp Pro Glu Val Lys Phe Asn Trp Tyr
    290                 295                 300
Val Asp Gly Val Glu Val His Asn Ala Lys Thr Lys Pro Arg Glu Glu
305                 310                 315                 320
Gln Tyr Asn Ser Thr Tyr Arg Val Val Ser Val Leu Thr Val Leu His
                325                 330                 335
Gln Asp Trp Leu Asn Gly Lys Glu Tyr Lys Cys Lys Val Ser Asn Lys
            340                 345                 350
Ala Leu Pro Ala Pro Ile Glu Lys Thr Ile Ser Lys Ala Lys Gly Gln
        355                 360                 365
Pro Arg Glu Pro Gln Val Tyr Thr Leu Pro Pro Ser Arg Asp Glu Leu
    370                 375                 380
Thr Lys Asn Gln Val Ser Leu Thr Cys Leu Val Lys Gly Phe Tyr Pro
385                 390                 395                 400
Ser Asp Ile Ala Val Glu Trp Glu Ser Asn Gly Gln Pro Glu Asn Asn
                405                 410                 415
Tyr Lys Thr Thr Pro Pro Val Leu Asp Ser Asp Gly Ser Phe Phe Leu
            420                 425                 430
Tyr Ser Lys Leu Thr Val Asp Lys Ser Arg Trp Gln Gln Gly Asn Val
        435                 440                 445
Phe Ser Cys Ser Val Met His Glu Ala Leu His Asn His Tyr Thr Gln
    450                 455                 460
```

```
Lys Ser Leu Ser Leu Ser Pro Gly Lys
465                 470
```

<210> SEQ ID NO 460
<211> LENGTH: 261
<212> TYPE: PRT
<213> ORGANISM: Homo sapiens
<220> FEATURE:
<223> OTHER INFORMATION: Human IL-4Ra/HIS tag polypeptide

<400> SEQUENCE: 460

```
Met Gly Trp Leu Cys Ser Gly Leu Leu Phe Pro Val Ser Cys Leu Val
1               5                   10                  15

Leu Leu Gln Val Ala Ser Ser Gly Asn Met Lys Val Leu Gln Glu Pro
            20                  25                  30

Thr Cys Val Ser Asp Tyr Met Ser Ile Ser Thr Cys Glu Trp Lys Met
        35                  40                  45

Asn Gly Pro Thr Asn Cys Ser Thr Glu Leu Arg Leu Leu Tyr Gln Leu
    50                  55                  60

Val Phe Leu Leu Ser Glu Ala His Thr Cys Ile Pro Glu Asn Asn Gly
65                  70                  75                  80

Gly Ala Gly Cys Val Cys His Leu Leu Met Asp Asp Val Val Ser Ala
                85                  90                  95

Asp Asn Tyr Thr Leu Asp Leu Trp Ala Gly Gln Gln Leu Leu Trp Lys
            100                 105                 110

Gly Ser Phe Lys Pro Ser Glu His Val Lys Pro Arg Ala Pro Gly Asn
        115                 120                 125

Leu Thr Val His Thr Asn Val Ser Asp Thr Leu Leu Leu Thr Trp Ser
    130                 135                 140

Asn Pro Tyr Pro Pro Asp Asn Tyr Leu Tyr Asn His Leu Thr Tyr Ala
145                 150                 155                 160

Val Asn Ile Trp Ser Glu Asn Asp Pro Ala Asp Phe Arg Ile Tyr Asn
                165                 170                 175

Val Thr Tyr Leu Glu Pro Ser Leu Arg Ile Ala Ala Ser Thr Leu Lys
            180                 185                 190

Ser Gly Ile Ser Tyr Arg Ala Arg Val Arg Ala Trp Ala Gln Cys Tyr
        195                 200                 205

Asn Thr Thr Trp Ser Glu Trp Ser Pro Ser Thr Lys Trp His Asn Ser
    210                 215                 220

Tyr Arg Glu Pro Phe Asn Pro Ala Phe Leu Tyr Lys Val Val Gly Ala
225                 230                 235                 240

Ala Asp Tyr Lys Asp Asp Asp Lys Ala Ala His His His His His His
                245                 250                 255

His His His His His
            260
```

<210> SEQ ID NO 461
<211> LENGTH: 262
<212> TYPE: PRT
<213> ORGANISM: Mus musculus
<220> FEATURE:
<223> OTHER INFORMATION: Murine IL-4Ra/HIS tag polypeptide

<400> SEQUENCE: 461

```
Met Gly Arg Leu Cys Thr Lys Phe Leu Thr Ser Val Gly Cys Leu Ile
1               5                   10                  15

Leu Leu Leu Val Thr Gly Ser Gly Ser Ile Lys Val Leu Gly Glu Pro
            20                  25                  30
```

-continued

```
Thr Cys Phe Ser Asp Tyr Ile Arg Thr Ser Thr Cys Glu Trp Phe Leu
         35                  40                  45

Asp Ser Ala Val Asp Cys Ser Ser Gln Leu Cys Leu His Tyr Arg Leu
     50                  55                  60

Met Phe Phe Glu Phe Ser Glu Asn Leu Thr Cys Ile Pro Arg Asn Ser
65               70                  75                  80

Ala Ser Thr Val Cys Val Cys His Met Glu Met Asn Arg Pro Val Gln
                 85                  90                  95

Ser Asp Arg Tyr Gln Met Glu Leu Trp Ala Glu His Arg Gln Leu Trp
             100                 105                 110

Gln Gly Ser Phe Ser Pro Ser Gly Asn Val Lys Pro Leu Ala Pro Asp
         115                 120                 125

Asn Leu Thr Leu His Thr Asn Val Ser Asp Glu Trp Leu Leu Thr Trp
     130                 135                 140

Asn Asn Leu Tyr Pro Ser Asn Asn Leu Leu Tyr Lys Asp Leu Ile Ser
145                 150                 155                 160

Met Val Asn Ile Ser Arg Glu Asp Asn Pro Ala Glu Phe Ile Val Tyr
                 165                 170                 175

Asn Val Thr Tyr Lys Glu Pro Arg Leu Ser Phe Pro Ile Asn Ile Leu
             180                 185                 190

Met Ser Gly Val Tyr Tyr Thr Ala Arg Val Arg Val Arg Ser Gln Ile
         195                 200                 205

Leu Thr Gly Thr Trp Ser Glu Trp Ser Pro Ser Ile Thr Trp Tyr Asn
     210                 215                 220

His Phe Gln Leu Pro Leu Asn Pro Ala Phe Leu Tyr Lys Val Val Gly
225                 230                 235                 240

Ala Ala Asp Tyr Lys Asp Asp Asp Lys Ala Ala His His His His His
             245                 250                 255

His His His His His His
             260
```